US011246928B2

(12) United States Patent
Estelles et al.

(10) Patent No.: US 11,246,928 B2
(45) Date of Patent: Feb. 15, 2022

(54) ANTIBODIES USEFUL IN PASSIVE INFLUENZA IMMUNIZATION, AND COMPOSITIONS, COMBINATIONS AND METHODS FOR USE THEREOF

(71) Applicants: CONTRAFECT CORPORATION, Yonkers, NY (US); TRELLIS BIOSCIENCE, LLC, South San Francisco, CA (US)

(72) Inventors: Angeles Estelles, Belmont, CA (US); Lawrence M. Kauvar, San Francisco, CA (US); Adam Vigil, Yonkers, NY (US); Michael Wittekind, Yonkers, NY (US)

(73) Assignees: CONTRAFECT CORPORATION, Yonkers, NY (US); TRELLIS BIOSCIENCE, LLC, Menlo Park, CA (US)

( * ) Notice: Subject to any disclaimer, the term of this patent is extended or adjusted under 35 U.S.C. 154(b) by 0 days.

(21) Appl. No.: 16/674,149

(22) Filed: Nov. 5, 2019

(65) Prior Publication Data
US 2020/0054749 A1    Feb. 20, 2020

Related U.S. Application Data

(62) Division of application No. 15/116,106, filed as application No. PCT/US2015/014521 on Feb. 4, 2015, now Pat. No. 10,639,370.
(Continued)

(51) Int. Cl.
A61K 39/42    (2006.01)
C07K 16/10    (2006.01)
A61K 39/00    (2006.01)

(52) U.S. Cl.
CPC .......... *A61K 39/42* (2013.01); *C07K 16/1018* (2013.01); *A61K 2039/505* (2013.01);
(Continued)

(58) Field of Classification Search
None
See application file for complete search history.

(56) References Cited

U.S. PATENT DOCUMENTS

| 4,625,015 A | 11/1986 | Green et al. |
| 6,235,708 B1 | 5/2001 | Holloway et al. |

(Continued)

FOREIGN PATENT DOCUMENTS

| JP | 62175426 A | 8/1987 |
| WO | 2004/080403 A2 | 9/2004 |

(Continued)

OTHER PUBLICATIONS

Baker et al., Protein Structure Predication and Structural Genomics, Science (2001) vol. 294, No. 5540, pp. 93-96 (Year: 2001).*
(Continued)

*Primary Examiner* — Michelle S Horning
(74) *Attorney, Agent, or Firm* — MH2 Technology Law Group, LLP

(57) ABSTRACT

Antibodies, compositions and methods are provided for treatment and prophylaxis of influenza virus. Antibodies and antigen-binding fragments are provided that hind near the $HA_0$ maturation cleavage site consensus sequence of influenza hemagglutinin A. Antibody compositions, combinations and methods for effective passive immunization across influenza A and B strains are also provided.

35 Claims, 26 Drawing Sheets

Specification includes a Sequence Listing.

Related U.S. Application Data

(60) Provisional application No. 62/051,630, filed on Sep. 17, 2014, provisional application No. 61/935,746, filed on Feb. 4, 2014.

(52) U.S. Cl.
CPC .. *A61K 2039/507* (2013.01); *A61K 2039/543* (2013.01); *C07K 2317/33* (2013.01); *C07K 2317/34* (2013.01); *C07K 2317/55* (2013.01); *C07K 2317/76* (2013.01); *C07K 2317/92* (2013.01); *C07K 2317/94* (2013.01)

(56) References Cited

U.S. PATENT DOCUMENTS

| | | |
|---|---|---|
| 7,262,270 B2 | 8/2007 | Weissenhorn et al. |
| 7,696,330 B2 | 4/2010 | Meulen et al. |
| 8,192,927 B2 | 6/2012 | Van Den Brink et al. |
| 8,288,090 B2 | 10/2012 | Fomsgaard |
| 2003/0100096 A1 | 5/2003 | Holloway |
| 2009/0092620 A1 | 4/2009 | Moste et al. |
| 2009/0203538 A1 | 8/2009 | Sugioka et al. |
| 2009/0311183 A1 | 12/2009 | Devy et al. |
| 2009/0311265 A1 | 12/2009 | Van Den Brink et al. |
| 2010/0086555 A1 | 4/2010 | Lanzavecchia |
| 2011/0027270 A1 | 2/2011 | Garcia-Sastre et al. |
| 2011/0319600 A1 | 12/2011 | Kuta et al. |
| 2012/0020971 A1 | 1/2012 | Kauvar et al. |
| 2012/0039899 A1 | 2/2012 | Olsen et al. |
| 2012/0128671 A1 | 5/2012 | Horowitz et al. |
| 2016/0083456 A1 | 3/2016 | Wittekind et al. |

FOREIGN PATENT DOCUMENTS

| | | |
|---|---|---|
| WO | 2007/134327 A2 | 11/2007 |
| WO | 2008/028946 A2 | 3/2008 |
| WO | 2008/110937 A2 | 9/2008 |
| WO | 2009/053604 A2 | 4/2009 |
| WO | 2009/079259 A2 | 6/2009 |
| WO | 2009/121004 A2 | 10/2009 |
| WO | 2010/010466 A2 | 1/2010 |
| WO | 2010/010467 A2 | 1/2010 |
| WO | 2010/022120 A1 | 2/2010 |
| WO | 2010/027818 A2 | 3/2010 |
| WO | 2010/074656 A1 | 7/2010 |
| WO | 2010/130636 A1 | 11/2010 |
| WO | 2011/117848 A1 | 9/2011 |
| WO | 2011/126370 A1 | 10/2011 |
| WO | 2011/160083 | 12/2011 |
| WO | 2012/045001 A2 | 4/2012 |
| WO | 2013/007770 A1 | 1/2013 |
| WO | 2013/086052 | 6/2013 |
| WO | 2013/114885 A1 | 8/2013 |
| WO | 2013/132007 A1 | 9/2013 |
| WO | 2014/152841 A1 | 9/2014 |

OTHER PUBLICATIONS

Attwood, T. The Babel of Bioinformatics, Science (2000) vol. 290, No. 5491, pp. 471-473 (Year: 2000).*
Indian Office Action issued in corresponding Indian Application No. 201627030111 dated Dec. 11, 2019, pp. 1-8.
European Office Action issued in corresponding European Application No. 15 704 447.0 dated Dec. 19, 2019, pp. 1-6.
Chinese Office Action issued in corresponding Chinese Application No. 201580018794.7 dated Dec. 25, 2019, pp. 1-11, with English translation.
Office Action issued in corresponding Israel Patent Application No. 268431 dated May 21, 2020 and partial English language translation (5 pages).
Altshuler, E.P. et al, Generation of Recombinant Antibodies and Means for Increasing Their Affinity, Biochemistry, 2010, vol. 50, pp. 203-258.
Ehrenmann, F. et al, IMGT/3Dstructure-DB and IMGT/DomainGapAlign: a database and a tool for immunoglobulins or antibodies, T cell receptors, MHC, IgSF and MhcSF, Nucleic Acids Research, 2010, vol. 38, pp. D301-307.
Feng, J. et al, Complement component C1q enhances the biological activity of influenza virus hemagglutinin-specific antibodies depending on their fine antigen specificity and heavy chain isotype, Journal of Virology, 2002, vol. 76, pp. 1369-1378.
Friesen et al, New Class of Monoclonal Antibodies against Severe Influenza: Prophylactic and Therapeutic Efficacy in Ferrets, PLoS ONE, 2010, vol. 5, No. 2, p. EL906.
Huber V.C. et al, Fc receptor-mediated phagocytosis makes a significant contribution to clearance of influenza virus infections, Journal of Immunology, 2001, vol. 166, pp. 7381-7738.
Jegerlehner, A. et al, Influenza A vaccine based on the extracellular domain of M2: weak protection mediated via antibody-dependent NK cell activity, Journal of Immunology, 2004, vol. 172, pp. 5598-5605.
Mozdzanowska, K. et al, Enhancement of neutralizing activity of influenza virus-specific antibodies by serum components, Virology, 2006, vol. 352, pp. 418-426.
Newsome, B.W. et al, The clinical pharmacology of therapeutic monoclonal antibodies in the treatment of malignancy; have magic bullets arrived?, The Journal of Clinical Pharmacology, 2008, vol. 66, No. 1, pp. 6-19.
Tan, G.S et al., A Pan-H1 Anti-Hemagglutinin Monoclonal Antibody with Potent Broad-Spectrum Efficacy In Vivo, Journal of Virology, 2012, vol. 86, No. 11, pp. 6179-6188.
Communication from the European Patent Office issued in European Patent Application No. 15 704 447 dated Jun. 21, 2018, pp. 1-10.
Communication from the European Patent Office issued in European Patent Application No. 15 704 447 dated Feb. 21, 2018, pp. 1-6.
English-language translation of Japanese Office Action issued in Japanese Patent Application No. 2016-550714 dated Jan. 15, 2019, pp. 1-7.
English-language translation of Japanese Office Action issued in Japanese Patent Application No. 2016-550714 dated Oct. 8, 2019, pp. 1-9.
English-language translation of Russian Office Action issued in Russian Patent Application No. 2016132419/10(050278) dated Oct. 31, 2018, pp. 1-3.
Australian Office Action issued in Australian Patent Application No. 2015214146 dated Sep. 3, 2019, pp. 1-6.
Office Action issued in corresponding Mexican Patent Application No. MX/a/2016/010059 dated Jul. 16, 2020 and partial English language translation (9 pages).
Office Action issued in corresponding Chinese Patent Application No. 201580018794.7 dated Jul. 23, 2020 and English language translation (18 pages).
Office Action issued in corresponding Brazilian Patent Application No. 112016018082-8 dated Oct. 20, 2020 and English language translation (6 pages).
Yasugi et al., "Human Monoclonal Antibodies Broadly Neutralizing against Influenza B Virus" Plos Pathogens, 2013, vol. 9, No. 2: e1003150. https://doi.org/10.1371/journal.ppat.1003150, pp. 1-11.
Min Dai et al., "Long-lasting Complete Regression of Established Mouse Tumors by Counteracting Th2 Inflammation", Journal of Immunotherapy, 2013, vol. 36, No. 4, doi:10.1097/CJI.0b013e3182943549, pp. 248-257.
Wei et al., "Combinatorial PD-1 Blockade and CD137 Activation Has Therapeutic Efficacy in Murine Cancer Models and Synergizes with Cisplatin", Plos One, 2013, vol. 8, No. 12, doi:10.1371/journal.pone.0084927, p. e84927, pp. -10.
J. Duraiswamy et al., "Therapeutic PD-1 Pathway Blockade Augments with Other Modalities of Immunotherapy T-Cell Function to Prevent Immune Decline in Ovarian Cancer", Cancer Research, 2013, vol. 73, No. 23, 6900-6912, doi:10.1158/0008-5472.CAN-13-1550.
Murphy, M., Office Action issued in corresponding Canadian Patent Application No. 2,938,726 dated Jan. 19, 2021 (4 pages).

(56) References Cited

OTHER PUBLICATIONS

Saku, T., Office Action issued in corresponding Japanese Patent Application No. 2020-019359 dated Apr. 6, 2021 (11 pages).
Office Action issued in corresponding Mexican Patent Application No. MX/a/2016/010059 dated Apr. 13, 2021, 14 pages (with English language translation).
Russian Patent Office Action issued in corresponding Russian patent application No. 2016132419 dated Jul. 8, 2019, pp. 1-3, with English translation.
Yarilin, A. A., "Fundamentals of Immunology," Meditsyna (1999) Moscow, pp. 172-174, with English translation.
Pache, Umberto, Israeli Office Action issued in corresponding Israeli patent application No. 247075, dated Apr. 7, 2019, pp. 1-6.
Clementi, N., et al., "Broad-range neutralizing anti-influenza A human monoclonal antibodies: new perspectives in therapy and prophylaxis," New Microbiologica, 2012, vol. 35, pp. 399-406.
Kalenik, B., et al. "Influenza prevention and treatment by passive immunization," Acta Biochimica Polonica, 2014, vol. 61, No. 3, pp. 573-587.
Rudikoff, S. et al., "Single amino acid substitution altering antigen-binding specificity," Proc. Natl. Acad. Sci. USA, 1982, vol. 79, pp. 1979-1983.
Baker et al., Protein Structure Predication and Structural Genomics, Science, 2001, vol. 294, No. 5540, pp. 93-96.
Attwood, T., The Babel of Bioinformatics, Science, 2000, vol. 290, No. 5491, pp. 471-473.
Abrahamson, M. et al., "Identification of the Probable Inhibitory Reactive Sites of the Cysteine Proteinase Inhibitors Human Cystatin C and Chicken Cystatin," The Journal of Biological Chemistry, 1987, vol. 262, No. 20, pp. 9688-9694.
Bianchi et al., "Universal influenza B vaccine based on the maturational cleavage site of the hemagglutinin precursor." J Virol (2005) 79(12): 7380-7388.
Bright et al., "Cross-clade protective immune responses to influenza viruses with H5N1 HA and NA elicited by an influenza virus-like particle." PLoS One (Jan. 30, 2008), 3(1):e1501.
Carragher et al. "A Novel Role for Non-Neutralizing Antibodies against Nucleoprotein in Facilitating Resistance to Influenza Virus." J Immunol 2008; 181 :4168-4176.
Corti et al., "A neutralizing antibody selected from plasma cells that binds to group 1 and D qroup 2 influenza A hemaaalutinins." Science (2011) 333(6044): 850-856.
Donis et al. "Distinct Lineages of Influenza Virus H4 Hemagglutinin Genes in Different Regions of the World." Virology (1989) 169:408-417.
Doyle et al. "A monoclonal antibody targeting a highly conserved epitope in influenza B neuraminidase provides protection against drug-resistant strains," Biochemical and Biophysical Res. Communications, vol. 441, No. 1, Oct. 16, 2013, pp. 226-229.
Dreyfus, et al., "Highly conserved protective epitopes on influenza B viruses," 22, Science, vol. 337, No. 6100, Sep. 14, 2012, pp. 1343-1348. XP002693350, American Association for the Advancement of Science, US ISSN: 1095-9203, DOI: 10.1126/SCIENCE. 1222908 [retrieved on Aug. 9, 2012], p. 1345.
Ekiertet al. "A highly conserved neutralizing epitope on group 2 influenza A viruses." Science (2011) 333 (6044): 843-850.
Ekiert et al. "Antibody Recognition of a Highly Conserved Influenza Virus Epitope." Science (2009) 324: 246-251.
Grandea et al., "Human antibodies reveal a protective epitope that is highly conserved among human and nonhuman influenza A viruses," Proc. Natl. Acad. Sci. USA (2010), vol. 107, No. 28, pp. 12658-12663.
International Preliminary Report on Patentability and Written Opinion for International Patent Application No. PCT/US2012/068037, dated Jun. 10, 2014, 14 pages.
International Search Report and Written Opinion for International Patent Application No. PCT/US2015/014521 dated Aug. 11, 2015, 17 pages.
International Search Report and Written Opinion for International Patent Application No. PCT/US2012/068037, dated Jun. 12, 2013, 14 pages.
International Search Report and Written Opinion for International Patent Application No. PCT/US2011/040982, dated Nov. 25, 2011, 11 pages.
International Search Report and Written Opinion for International Patent Application No. PCT/US2014/027939, dated Aug. 28, 2014, 14 pages.
Kostolansky et al., "Antibody Response to Hidden Epitope of Influenza A Haemagglutinin Elicited by Anti-Idiotypic Antibodies," Acta vifologica (1994) 38:215-222.
Krause et al., "A Broadly Neutralizing Human Monoclonal Antibody That Recognizes a Conserved, Novel Epitope on the Globular Head of the Influenza H1N1 Virus Hemagglutinin," Journal of Virology, vol. 85, No. 20, Oct. 15, 2011, pp. 10905-10908, XP055044176, ISSN: 0022-538X, DOI: 10.1128/JVI.00700-11.
Kuboto-Koketsu et al., "Broad neutralizing human monoclonal antibodies against influenza virus from vaccinated healthy donors." Biochem Biophys Res Commun (Sep. 11, 2009), 387(1): 180-5.
McCutcheon et al. "Multiplexed screening of natural humeral immunity identifies antibodies at fine specificity for oomplex and dynamic viral targets", MABS (Jan. 8, 2014), 6(2):460-473.
Mottet et al. "Characterization of Sendai virus M protein mutants that can partially interfere with virus particle productionm" Journal of Virology, 1999, vol. 80, pp. 2977-2986.
Prabhu et al., "Monoclonal Antibodies against the Fusion Peptide of Hemagglutinin Protect Mice from Lethal Influenza A Virus H5N 1 Infection," Journal of Virology (2009) 83(6):2553-2562.
Schoofs et al., "Epitopes of an influenza viral peptide recognized by antibody at single amino acid resolution," Journal of Immunology, 1988, vol. 140 pp. 611-616.
Song, G. et al.,"Progesterone and Interferon Regulate Cystatin C in the Endometrium," Endocrinology, 2006, vol. 147, pp. 3478-3483.
Steel et al. "Influenza virus vaccine based on the conserved hemagglutinin stalk domain," Mbio (Apr. 2010), 1(1): 1-9.
Sui et al., "Structural and functional bases for broad-spectrum neutralization of avian and human influenza A viruses," Nat Struct Mol Biol (2009) 16(3):265-273.
Sui et al. "Wide Prevalence of Heterosubtypic Broadly Neutralizing Human Anti-Influenza A Antibodies," Clinical Infectious Diseases (Apr. 15, 2011), 52(8):1003-1009.
Supplementary European Search Report for European Patent Application No. 12854682.7, dated Aug. 7, 2015, 8 pages.
Supplementary European Search Report for European Patent Application No. EP 11796555.8, dated Oct. 22, 2013, 17 pages.
Throsby et al., "Heterosubtypic neutralizing monoclonal antibodies cross-protective against H5N1 and H1 N1 recovered from human IgM+ memory B cells," PLoS One (2008) 3(12):e3942.
Usinger et al., "Human monoclonal antibody 53 shows unique cross-clade neutralization of influenza," American Society of Virology (Jul. 16-20, 2011), Abstract only.
Wagner et al, "Bispecific antibody generated with sortase and click chemistry has broad antiinfluenza virus activity," Proceedings of the National Academy of Sciences (Nov. 10, 2014), 111 (47):16820-16825.
Wang et al., "Broadly Protective Monoclonal Antibodies against H3 Influenza Viruses following Sequential Immunization With Different Hemagglutinins." PLoS (Feb. 2010), 6(2):e1000796.
Weltzin et al., "Intranasal Antibody Prophylaxis for Protection Against Viral Disease." Clinical Microbiology Reviews, Washington, D.C., US, vol. 12, No. 3, Jul. 1, 1999 (Jul. 1, 1999), pp. 383-393.
Yasugi et al. "Human monoclonal antibodies broadly neutralizing against influenza B virus." PLoS Pathogens (Feb. 2013), 9(2):1-12.
Ye et al., "Intranasal Delivery of an IgA Monoclonal Antibody Effective against Sublethal H5N1 Influenza Virus Infection in Mice," Clinical and Vaccine Immunology, Sep. 2010, pp. 1363-1370.
Yoshida et al., "Cross-protective potential of a novel monoclonal antibody directed against antigenic site B of the hemagglutinin of influenza A viruses," PLoS Pathog (2009) 5(3):e1000350.

(56) References Cited

OTHER PUBLICATIONS

Zanin et al., "An Anti-H5N1 Influenza Virus FcDart Antibody is a Highly Efficacious Therapeutic Agent and Prophylactic against H5N1 Influenza Virus Infection," Journal of Virology (Feb. 11, 2015), 89(8):4549-4561.

Ziegler et al., "Type- and Subtype-Specific Detection of Influenza Viruses in Clinical Specimens by Rapid Culture Assay," Journal of Clinical Microbiology (1995) 33(2):318-321.

Office Action issued in corresponding Israel Patent Application No. 268431 dated Aug. 31, 2021 and partial English language translation (5 pages).

Office Action issued in corresponding Japanese Patent Application No. 2020-019359 dated Sep. 22, 2021 and English language translation (4 pages).

Office Action issued in corresponding Mexican Patent Application No. MX/a/2016/010059 dated Nov. 1, 2021 and partial English language translation (11 pages).

Damschroder, M. et al. "Framework shuffling of antibodies to reduce immunogenicity and manipulate functional and biophysical properties", Molecular Immunology, 2007, vol. 44, pp. 3049-3060.

McConnell, A. et al. "An integrated approach to extreme thermostabilization and affinity maturation of an antibody", Protein Engineering, Design & Selection, 2013, vol. 26, No. 2, pp. 151-163.

Canadian Office Action issued in corresponding Canadian Patent Application No. 2,938,726 dated Nov. 29, 2021 (4 pages).

\* cited by examiner

Table 7.

| | B/Brisbane/08 (Vic lineage) | B/Florida/06 (Yam lineage) | B/Malaysia/04 (Vic lineage) | B/Mass/12 (Yam lineage) | B/Victoria/87 (Vic lineage) | B/Wisconsin/10 (Yam lineage) | A/Sydney/97 (H3) | A/California/09 (H1) | PBS |
|---|---|---|---|---|---|---|---|---|---|
| TRL809 | 25.6 | 25.6 | 25.6 | 25.6 | 25.6 | 25.6 | 1.2 | 1.3 | 1.0 |
| TRL812 | 25.6 | 25.6 | 25.6 | 25.6 | 25.6 | 25.6 | 1.2 | 1.1 | 1.0 |
| TRL813 | 25.6 | 25.6 | 25.6 | 25.6 | 25.6 | 25.6 | 1.1 | 1.6 | 1.0 |
| TRL832 | 25.6 | 25.6 | 25.6 | 25.6 | 25.3 | 25.6 | 1.0 | 1.1 | 1.0 |
| TRL841 | 25.6 | 25.6 | 25.6 | 25.6 | 25.6 | 25.6 | 1.1 | 1.1 | 0.9 |
| TRL842 | 25.6 | 25.6 | 25.6 | 25.6 | 25.6 | 25.6 | 1.1 | 1.0 | 1.0 |
| TRL845 | 25.6 | 25.6 | 25.6 | 25.6 | 25.6 | 25.6 | 1.1 | 1.4 | 1.0 |
| TRL846 | 25.6 | 25.6 | 25.6 | 25.6 | 25.6 | 25.6 | 1.0 | 1.5 | 1.0 |
| TRL847 | 25.6 | 25.6 | 25.6 | 25.6 | 25.6 | 25.6 | 1.1 | 1.1 | 0.9 |
| TRL848 | 25.6 | 25.6 | 25.6 | 25.6 | 25.6 | 25.6 | 1.1 | 1.0 | 1.0 |
| TRL849 | 25.6 | 25.6 | 25.6 | 25.6 | 25.6 | 25.6 | 1.3 | 1.2 | 1.0 |
| TRL854 | 25.6 | 25.6 | 25.6 | 25.6 | 25.6 | 25.6 | 1.3 | 1.2 | 0.9 |
| TRL856 | 24.1 | 25.6 | 25.6 | 25.6 | 25.6 | 2.8 | 1.0 | 25.6 | 1.0 |
| CF401 | 1.0 | 1.1 | 1.6 | 1.0 | 1.5 | 1.0 | 25.6 | 1.0 | 0.9 |
| CF402 | 1.0 | 1.0 | 1.1 | 3.2 | 1.1 | 0.9 | 1.0 | 1.5 | 0.9 |
| pbs | 0.9 | 1.0 | 1.0 | 0.9 | 0.9 | 0.9 | 1.0 | 1.1 | 1.0 |
| pbs | 0.9 | 1.1 | 1.0 | 1.1 | 0.9 | 0.9 | 1.0 | | |

FIG. 3

Table 8. Neutralization Data, IC$_{50}$ (ug/ml)

| Strain | TRL845 | TRL848 | TRL849 | TRL854 | TRL832 | TRL809 |
|---|---|---|---|---|---|---|
| B/Yamagata/16/1988 | 0.99 | 0.95 | 0.98 | 0.70 | 0.95 | 0.96 |
| B/Victoria/2/1987 | 0.64 | 0.72 | 0.76 | 0.71 | 0.82 | 0.93 |

FIG. 4

Epitope Mapping Results (PepScan™)

>AAA43700 B/Lee/40 1940// HA

MKAIIVLLMVVTSNADRICTGITSSNSPHVVKTATQGEVNVTGVIPLTTTPTKSHFANLKGTETRGKLCPKCLNCTD
TDVALGRPKCTGNIPSARVSILHEVRPVTSGCFPIMHDRTKIRQLPNLLRGYEHIRLSTSNVINTETAPGGSY
EIKCTGSCFYRDGALLRNKSDQSIVDSWTGFNSSLQKNIQEFWPNFHDQDFRTPRPNMDLYAGMPCDGSMPS
KFTSSANGVTHTVSGFPNDTGKTPGTPTTEDTGLKGSSEIVADIMTVKGQKQEGKTGTTVKQRSITLLPWTCSSGAVTNGS
LPPKKPTNSSMKLCRPVRMGSTKKKATRVKEITHPEKKTTEHIGIKGGHEKNPEEKKTTRHATESETVSPRIHPTVAEVSS
PFDSNTVTRAGLMDRGDNTTLVYSAAASLAVTIMAIFVWMHSRHVSSTCL

Highlighted are the residues that have been used to generate the peptide arrays: aa_15-65, aa_300-359, aa_362-481.

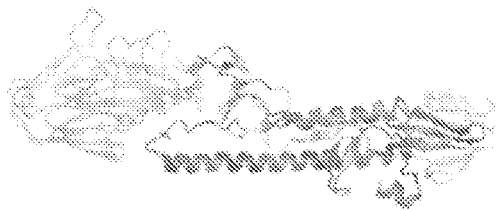

Table 9

| Antibody | Epitope |
|---|---|
| 5A7 | $_{333}$GNCPIWVK$_{338}$, $_{342}$LKLAN$_{346}$, $_{457}$IELAVLL$_{463}$ |
| TRL845 | $_{455}$SQIELAVLL$_{463}$ |
| TRL848 | $_{64}$SHFANLK$_{71}$, $_{336}$PIWVKTPLKLANG$_{348}$, $_{424}$RLSG$_{428}$ |
| TRL849 | $_{317}$LNKSKPY$_{323}$, $_{344}$KLANTGT$_{349}$, $_{378}$MIAGWH$_{383}$ |
| TRL854 | $_{457}$IELAVLL$_{463}$ |

FIG. 8

| | Tm1 | Tm2 |
|---|---|---|
| TRL845 | 58.3 | 68.7 |
| TRL847 | 70.3 | |
| TRL848 | 70.1 | |
| TRL849 | 70 | 81.8 |
| TRL854 | 59.7 | 68.9 |
Table 10
FIG. 10B
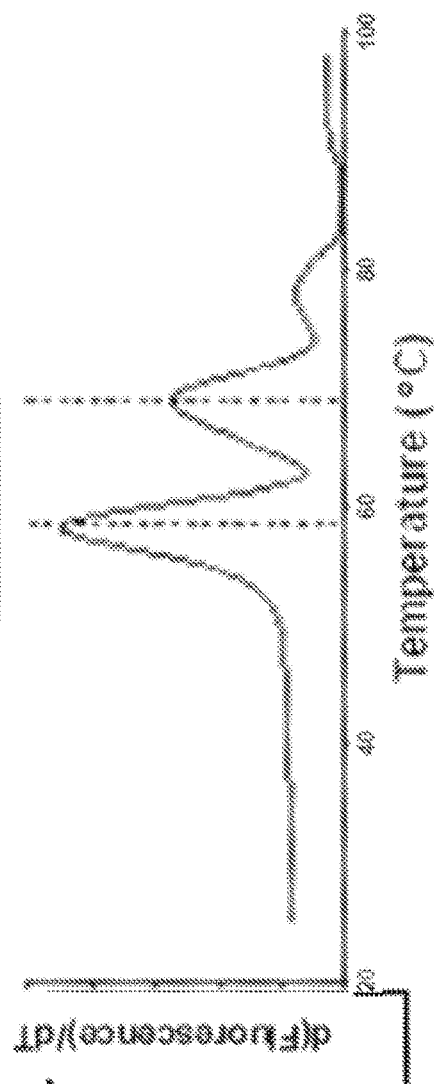
FIG. 10A
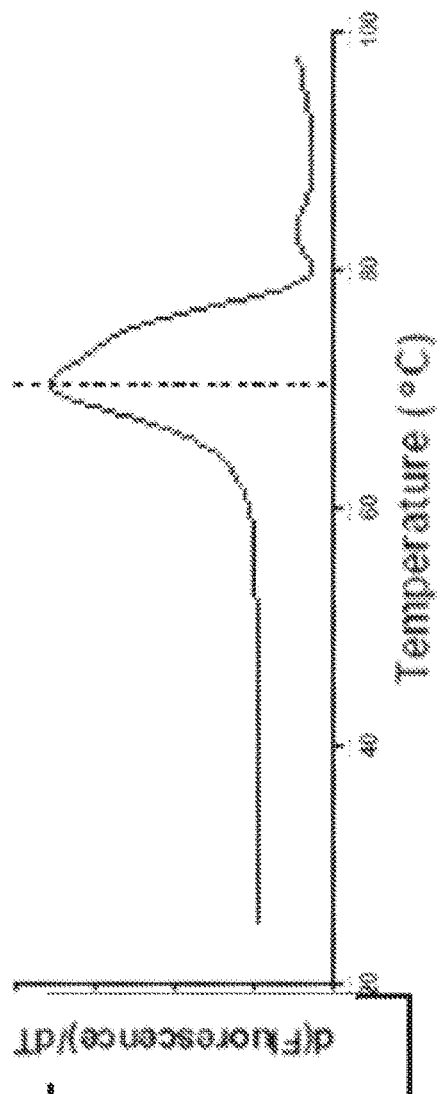
FIG. 10C

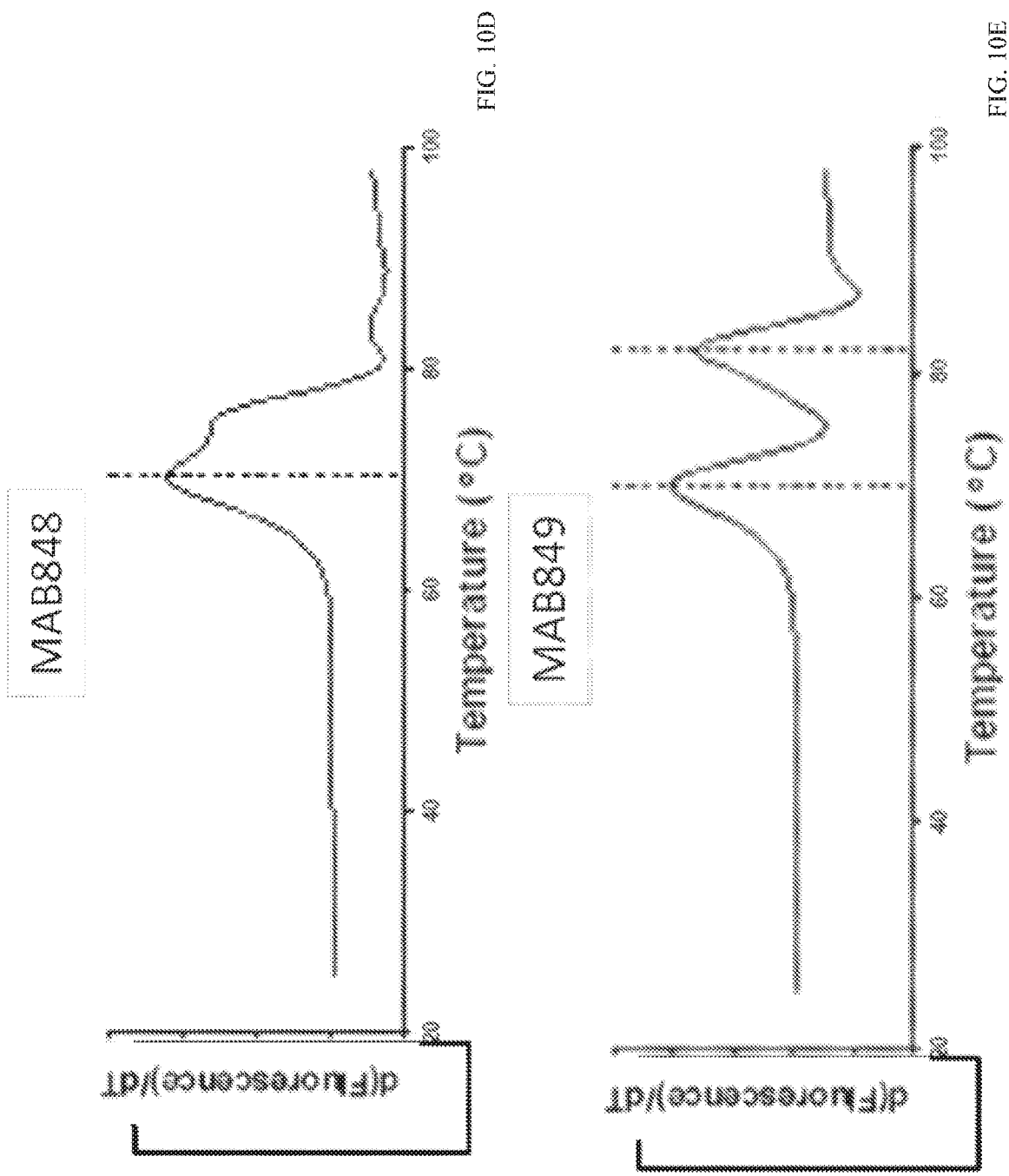

Table 11

In vivo

Lowest recorded body weight observed post infection

| | mAb name | HI activity B/Vic | HI activity B/Yam | HI and western blot predicted binding site | In vitro neut B/Vic | In vitro neut B/Yam | In vivo B/Mal (Vic) min weight | In vivo B/Flo (Yam) min weight | In vivo B/Mal (Vic) min weight | In vivo B/Flo (Yam) min weight | In vivo B/Mal (Vic) min weight | In vivo B/Flo (Yam) min weight |
|---|---|---|---|---|---|---|---|---|---|---|---|---|
| 1 | TRL809 | yes | yes | head | yes | yes | 100% | 98% | | | 97% | 96% |
| 3 | TRL832 | yes | yes | head | yes | yes | 100% | 98% | 98% | 99% | | |
| 14 | TRL846 | no | no | stem | No (egress) | No (egress) | | | | | 98 | 95 |
| 16 | TRL845 | no | no | Stem | yes | yes | | | 98 | 99 | | |
| 17 | TRL847 | no | no | Stem | yes | yes | | | 96 | 97 | 96 | 97 |
| 18 | TRL848 | no | no | Stem | yes | yes | | | 98 | 99 | 97 | 98 |
| 19 | TRL849 | no | no | Stem | yes | yes | | | 98 | 98 | 98 | 98 |
| 20 | TRL854 | no | no | stem | yes | yes | | | | | 97 | 98 |

FIG. 16

Table 12

| mAb name | Isoelectric Point | Affinity B/Florida Ag (nM) | Affinity B/Malaysia Ag (nM) |
|---|---|---|---|
| TRL809 | 8.01 | 0.18 | 0.2 |
| TRL832 | 7.79 | 1.7 | 0.2 |
| TRL846 | 8.36 | 0.85 | <1 |
| TRL845 | 8.54 | 0.19 | <1 |
| TRL847 | 8.55 | 0.7 | <1 |
| TRL848 | 6.87 | 1.7 | <1 |
| TRL849 | 7.94 | 0.2 | <1 |
| TRL854 | 7.19 | 8.8 | <1 |

ANTIBODIES USEFUL IN PASSIVE INFLUENZA IMMUNIZATION, AND COMPOSITIONS, COMBINATIONS AND METHODS FOR USE THEREOF

CROSS-REFERENCES TO RELATED APPLICATIONS

This application is a divisional application of U.S. patent application Ser. No. 15/116,106, filed Aug. 2, 2016, which is a national phase application of International Patent Application No. PCT/US2015/014521, filed Feb. 4, 2015, and which and claims the benefit of priority to United States Provisional Application No. 61/935,746, filed Feb. 4, 2014, and United States Provisional Application No. 62/051,630, filed Sep. 17, 2014, the entire contents of each of which are incorporated by reference herein.

REFERENCE TO SEQUENCE LISTING SUBMITTED BY EFS-WEB

The entire content of the following electronic submission of the sequence listing via the USPTO-EFS-WEB server, as authorized and set forth in MPEP 1730 II.B.2(a)C), is incorporated herein by reference in its entirety for all purposes. The sequence listing is identified on the electronically filed text file as follows:

| File Name | Date of Creation | Size (bytes) |
| --- | --- | --- |
| 9079004_1.txt | Feb. 4, 2015 | 285.473 |

TECHNICAL FIELD

Antibodies, compositions and methods are provided for treatment and prophylaxis of influenza virus. Antibodies and antigen-binding fragments are provided that bind near the $HA_0$ maturation cleavage site consensus sequence of influenza hemagglutinin A. Antibody compositions, combinations and methods for effective passive immunization across influenza A and B strains are also provided.

BACKGROUND

Influenza is a leading cause of death and illness and affects the upper and lower respiratory tracts. There are three types of influenza viruses, influenza A, B and C. Human influenza A and B viruses cause seasonal epidemics of disease. Influenza type C infections cause a mild respiratory illness and are not thought to cause epidemics. Influenza A viruses are divided into subtypes based on two proteins on the surface of the virus: the hemagglutinin (H) and the neuraminidase (N). There are 17 different hemagglutinin subtypes and 10 different neuraminidase subtypes. Influenza A viruses can be further broken down into different strains. Current subtypes of influenza A viruses commonly found in people are influenza A (H1N1) and influenza A (H3N2) viruses. Influenza B viruses are not divided into subtypes, but are classified into two different lineages: B/Victoria/2/87-like and B/Yamagata/16/88-like. Influenza A (e.g. H1N1), A (e.g. H3N2), and influenza B viruses are included in each year's influenza vaccine.

At varying frequencies, five kinds of clinically relevant influenza viruses are circulating in the human population at the present time, three of influenza A and also two of influenza B. Influenza A type virus is divided into two distinct phylogenetic groups 1 and 2. Group 1 includes hemagglutinin subtypes H1, H2, H5, H6, H8, H9. H11, H13 and H16. Group 2 includes H3, H4, H7, H10, H15 and H14. Currently relevant circulating influenza A viruses of group 1 are of subtype H1, which is further divided into those of human and swine origin, and group 2 relevant circulating viruses are presently of subtype H3. Influenza A viruses are responsible for the bulk of seasonal disease, with H3 viruses dominating eight of the past twelve influenza seasons in the United States (CDC Seasonal flu; United States Surveillance Data). In 1968, an H3 virus caused one of the three major influenza pandemics of the twentieth century and H3 viruses have persisted since that time as a significant agent of human disease. In addition to humans, H3 influenza viruses commonly infect birds, swine, and horses. Influenza B viruses have been circulating in humans for more than 100 years, with current strains divided into two lineages, the Yamagata lineage and Victoria lineage. Recently the trivalent influenza vaccine has expanded to a quadrivalent antigen-containing vaccine covering both lineages of influenza B, as well as an H1 virus and H3 virus.

Current prevention and treatments for influenza are not adequate and can be ineffective. Despite widespread vaccination, susceptibility to influenza remains. The factors contributing to susceptibility include (1) incomplete vaccination coverage such as with the 2009 H1N1 pandemic, when vaccine shortages were widespread, (2) years such as 2008 when the vaccine formulation poorly represented the strains in circulation, (3) reduced efficacy of vaccination in the elderly, as the average efficacy ranges from 40-50% at age 65, and only 15-30% past age 70, and (4) the emergence of pandemic strains not represented in seasonal vaccines, with H5N1 being of particular concern. Further, drug resistance against the anti-viral therapeutics currently available for the treatment of influenza has become a serious problem. Resistance to adamantanes (amantidine and rimantadine), drugs that act on the M2 protein and inhibit viral fusion, increased from 1.9% in 2004 to 14.5% during the first 6 months of the 2004-2005 flu season, and currently has surpassed 90% (Sheu, T. G. et al (2011) J Infect Dis 203:13-17). Resistance to oseltamivir phosphate (Tamiflu®), an antiviral drug that inhibits the influenza neuraminidase protein, dramatically increased from 1-2% of H1N1 viruses during the 2006-2007 flu season, to 12% by 2007-2008, and exceeded 99% of the seasonal H1N1 viruses in 2009. Fortunately, the pandemic H1N1 strain of 2009 was sensitive to Tamiflu which likely resulted in fewer deaths. As such there is an overwhelming need for new influenza prophylactic/therapeutic approaches.

Unfortunately, diagnostics to determine flu strain typically require a 12-24 hour turnaround time which results in an unfavorable delay in treatment if determination of strain is needed for selecting the appropriate therapy. Thus there remains a need for antibodies that bind multiple clades and show enhanced affinity thereto. In particular, a passive vaccine that comprises antibodies effective against both influenza A and influenza B and is broadly immunoreactive with multiple strains is desirable in order to avoid the need to characterize an infective virus in detail prior to administering the antibody or antibody mixture. Broadly reactive antibodies and compositions effective against all strains of both influenza A and B are desirable, particularly because prior strain diagnosis is not necessary prior to treatment. High potency is further desirable to facilitate both manufacturing and administration of the agents.

SUMMARY

In some embodiments, recombinant human antibodies, or antigen binding fragments thereof, are provided that are reactive with both major influenza B lineages-Yamagata and Victoria clades.

In some embodiments, monoclonal antibodies are provided that bind trimers representative of influenza B, with high affinity.

In some embodiments, antibodies are provided that are able to confer passive immunity in the event of an infection caused, for example, by a previously unidentified influenza B strain or a strain against which protection is not conferred by the seasonal vaccines which fail to include the actual strain in circulation about once every 2-3 years: Monto, A. A., et al., *Vaccine* (2009) 27:5043-5053.

In some embodiments, antibodies are provided that bind across many strains, indicative of targeting an essential site, and as such are likely to bind even previously unencountered strains. Such antibodies are also useful to ameliorate or prevent infection or attenuate its virulence in subjects for whom vaccination failed to produce a fully protective response or who are at high risk due to underlying compromised bronchial function as in chronic obstructive pulmonary disease patients or a weak immune system (e.g., the very young, the elderly, transplant patients, and cancer- or HIV-chemotherapy-treated patients).

In some embodiments, compositions are provided comprising mixtures of mAbs that confer broad passive immunization.

In some embodiments, compositions are provided comprising (1) one or more binding moieties, monoclonal antibodies, or immunoreactive fragments thereof, that are reactive with both major influenza B lineages, and (2) one or more binding moieties, monoclonal antibodies, or immunoreactive fragments thereof, that are reactive with influenza A virus of Group 1 including H1, H2, H5, H6, H8, H9, H11, H13, H16 and/or Group 2 including H3 and H7 as type specimens, including those that show cross-Group reactivity. In some embodiments, the antibodies provided herein bind to an epitope contained in the $HA_0$ protein specifically and recognize the native trimeric form of HA, as well as the proteolytically activated form.

In another embodiment, binding moieties are provided that are selected from bispecific and multispecific antibodies and fragments thereof which are able to enhance the range of viral types and clades that can be bound specifically, as well as compositions containing two or more binding moieties that react with multiple strains characteristic both of influenza A and influenza B.

In some embodiments, an isolated human antibody, or antigen-binding fragment thereof, is provided that exhibits a binding affinity (KD) of 10 nM or tighter, or 3 nM or tighter, to one or more strains of each of influenza B Yamagata and influenza B Victoria clades. In some embodiments, the antibody of fragment is a recombinant antibody or fragment thereof.

In some embodiments, an antibody or antigen-binding fragment is an engineered monospecific antibodies or multispecific human monoclonal antibodies.

In some embodiments, an antibody or antigen-binding fragment is provided that neutralizes infection in a cell by one or more strains of influenza B Yamagata and influenza B Victoria clades.

In some embodiments, an isolated human antibody, or antigen-binding fragment thereof, is provided comprising amino acid sequences of (a) a heavy chain complementarity determining region 1 (HCDR1), (b) a heavy chain complementarity determining region 2 (HCDR2); and (c) a heavy chain complementarity determining region 3 (HCDR3), HCDR1/HCDR2/HCDR3, selected from the group consisting of SEQ ID NO: 31/32/33; 41/42/43; 51/52/53; 61/62/63; 71/72/73; 81/82/83; 91/92/93; 101/102/103; 111/112/113; 121/122/123; 131/132/133; 141/142/143; 151/152/153; 161/162/163; 171/172/173; 181/182/183; 191/192/193; 201/202/203; 211/212/213; 221/222/223; 231/232/233; 241/242/243; 251/252/253; 261/262/263; 271/272/273 and 281/282/283, or highly homologous variants thereof comprising 1 to 3 amino acid substitutions in one or more CDR domain sequences, said variants and said antibody or fragment having the property of binding to and/or inhibiting influenza virus.

In some embodiments, an isolated human antibody, or antigen-binding fragment thereof, is provided comprising (a) a light chain complementarity determining region 1 (LCDR1), (b) a light chain complementarity determining region 2 (LCDR2); and (c) a light chain complementarity determining region 3 (LCDR3), LCDR1/CDR2/LCDR3, selected from the group consisting of SEQ ID NO: 34/35/36; 44/45/46; 54/55/56; 64/65/66; 74/75/76; 84/85/86; 104/105/106; 114/115/16; 124/125/126; 134/135/136; 144/145/146; 154/155/156; 164/165/166; 174/175/176; 184/185/186; 194/195/196; 204/205/206; 214/215/216; 224/225/226; 234/235/236; 244/245/246; 254/255/256; 264/265/266; 274/275/276; and 284/285/286, or highly homologous variants thereof comprising 1 to 3 amino acid substitutions in one or more CDR domain sequences, said variants and said antibody or fragment having the property of binding to and/or inhibiting influenza virus.

In some embodiments, an isolated human antibody, or antigen-binding fragment thereof, is provided comprising heavy and light chain CDR sequences, HCDR1/HCDR2/HCDR3/LCDR1/LCDR2/LCDR3, are selected from the group consisting of SEQ ID NO: 31/32/33/34/35/36; 41/42/43/44/45/46; 51/52/53/54/55/56; 61/62/63/64/65/66; 71/72/73/74/75/76; 81/82/83/84/85/86; 91/92/93/94/95/96; 101/102/103/104/105/106; 111/112/113/114/115/116; 121/122/123/124/125/126; 131/132/133/134/135/136; 141/142/143/144/145/146; 151/152/153/154/155/156; 161/162/163/164/165/166; 171/172/173/174/175/176; 181/182/183/184/185/186; 191/192/193/194/195/196; 201/202/203/204/205/206; 211/212/213/214/215/216; 221/222/223/224/225/226; 231/232/233/234/235/236; 241/242/243/244/245/246; 251/252/253/254/255/256; 261/262/263/264/265/266; 271/272/273/274/275/276; and 281/282/283/284/285/286, or a highly homologous variant thereof comprising 1 to 3 amino acid substitutions in one or more CDR domain sequences; said variant and said antibody or fragment having the property of binding to and/or inhibiting influenza virus.

In some embodiments, an isolated human antibody or antigen binding-fragment thereof is provided that specifically binds to one or more strains of each of both influenza B Yamagata and influenza B Victoria clades and comprises a heavy chain variable region (HCVR) comprising an amino acid sequence selected from the group consisting of SEQ ID NO: 39, 49, 59, 69, 79, 89, 99, 109, 119, 129, 139, 149, 159, 169, 179, 189, 199, 209, 219, 229, 239, 249, 259, 269, 279, and 289, or a homologous variant thereof having at least 80% sequence identity with said HCVR; said variant and said antibody or fragment having the property of binding to and/or inhibiting influenza virus.

In some embodiments, an isolated human antibody or antigen binding-fragment thereof is provided comprising a light chain variable sequence (LCVR) comprising an amino acid sequence selected from the group consisting of SEQ ID NO: 40, 50, 60, 70, 80, 90, 100, 110, 120, 130, 140, 150, 160, 170, 180, 190, 200, 210, 220, 230, 240, 250, 260, 270, 280, and 290, or a homologous variant thereof having at least 80% sequence identity with said LCVR, said variant and said antibody or fragment having the property of binding to and/or inhibiting influenza virus.

In some embodiments, an isolated human antibody or antigen binding-fragment thereof is provided comprising a HCVR/LCVR sequence pair selected from the group consisting of 39/40, 49/50, 59/60, 69/70, 79/80, 89/90, 99/100, 109/110, 119/120, 129/130, 139/140, 149/150, 159/160, 169/170, 179/180, 189/190, 199/200, 209/210, 219/220, 229/230, 239/240, 249/250, 259/260, 269/270, 279/280, and 289/290, or homologous variants thereof having at least 80% sequence identity of said HCVR and/or LCVR; said variant and said antibody having the property of binding to and/or inhibiting influenza virus.

In some embodiments, an isolated human antibody or antigen binding-fragment thereof is provided comprising an HCVR/LCVR pair selected from the group consisting of SEQ ID NO: 79/80, 129/130, 219/220, 229/230, 239/240, 249/250, and 269/270, or homologous variants thereof having at least 80% sequence identity of said HCVR and or LCVR; said variant and said antibody having the property of binding to and/or inhibiting influenza virus.

In some embodiments, an isolated human antibody or antigen binding-fragment thereof is provided that binds to one or more epitopes selected from the group consisting of SEQ ID NO: 307, 308, 309, 310, 311, 312, and 313, or a discontinuous epitope thereof.

In some embodiments, an isolated human antibody or antigen binding-fragment thereof is provided that competes for binding to one or more strains of each of influenza B Yamagata and influenza B Victoria clades, as an antibody or fragment of the disclosure by displacing at least 50% of the latter when present in an excess less than 100-fold.

In some embodiments, an isolated codon optimized nucleic acid molecule is provided encoding an antibody or fragment of the disclosure. In some embodiments, an expression vector comprising a nucleic acid molecule is provided encoding an antibody or fragment of the disclosure.

In some embodiments, a host cell for expression of a recombinant polypeptide comprising an expression vector comprising a nucleic acid molecule is provided encoding an antibody or fragment of the disclosure.

In some embodiments, a method of producing an anti-influenza B antibody or antigen-binding fragment thereof is provided, comprising growing a host cell under conditions permitting production of the antibody or fragment thereof, and recovering the antibody or fragment thereof so produced.

In some embodiments, a pharmaceutical composition is provided comprising an antibody or antigen-binding fragment that exhibits a binding affinity (KD) of 10 nM or tighter, or 3 nM or tighter, to one or more strains of each of influenza B Yamagata and influenza B Victoria clades, and a pharmaceutically acceptable carrier.

In some embodiments a pharmaceutical composition is provided comprising an antibody or antigen-binding fragment comprising amino acid sequences of HCDR1/HCDR2/HCDR3, selected from SEQ ID NO: 31/32/33; 41/42/43; 51/52/53; 61/62/63; 71/72/73; 81/82/83; 91/92/93; 101/102/103; 111/112/113; 121/122/123; 131/132/133; 141/142/143; 151/152/153; 161/162/163; 171/172/173; 181/182/183; 191/192/193; 201/202/203; 211/212/213; 221/222/223; 231/232/233; 241/242/243; 251/252/253; 261/262/263; 271/272/273 and 281/282/283, or highly homologous variants thereof comprising 1 to 3 amino acid substitutions in one or more CDR domain sequences, said variants and said antibody or fragment having the property of binding to and/or inhibiting influenza virus, and a pharmaceutically acceptable carrier, wherein said antibody or fragment exhibits a first melting temperature (Tm1) as measured in PBS of greater than or equal to 55° C.

In some embodiments, a composition is provided comprising one or more human antibodies or antigen-binding fragments thereof with binding specificity to at least one strain of influenza A. In some aspects, the antibody or antigen-binding fragment with specificity to influenza A includes specificity to one or more strains of both Group 1 and Group 2.

In some embodiments, a pharmaceutical composition is provided comprising (a) a first antibody or antigen-binding fragment thereof comprising a heavy chain amino acid sequence comprising a heavy chain variable region (HCVR) comprising HCDR1/HCDR2/HCDR3 of SEQ ID NOS: 11, 12, 13 and a light chain amino acid sequence comprising a light chain variable region (LCVR) comprising LCDR1/LCDR2/LCDR3 of SEQ ID NOS: 14, 15, 16, or highly homologous variants thereof comprising 1 to 3 amino acid substitutions in one or more CDR domain sequences, said variants capable of binding to and/or inhibiting influenza virus, (b) a second antibody or antigen-binding fragment thereof comprising a heavy chain amino acid sequence comprising a heavy chain variable region (HCVR) comprising HCDR1/HCDR2/HCDR3 of SEQ ID NOS: 21, 22, 23 and a light chain amino acid sequence comprising a light chain variable region (LCVR) comprising CDR domain sequences LCDR1/LCDR2/LCDR3 of SEQ ID NOS: 24, 25, 26, or highly homologous variants thereof comprising 1 to 3 amino acid substitutions in one or more CDR domain sequences, said variants capable of binding to and/or inhibiting influenza virus; and (c) a third antibody or antigen-binding fragment thereof comprising a heavy chain amino acid sequence comprising a heavy chain variable region (HCVR) comprising HCDR1/HCDR2/HCDR3, and a light chain amino acid sequence comprising a light chain variable region (LCVR) comprising light chain CDR domain sequences. LCDR1/LCDR2/LCDR3, respectively, selected from:

(i) SEQ ID NOS: 71, 72, 73, and SEQ ID NOS: 74, 75, 76;
(ii) SEQ ID NOS: 91, 92, 93, and SEQ ID NOS: 94, 95, 96;
(iii) SEQ ID NOS: 101, 102, 103, and SEQ ID NOS: 104, 105, 106;
(iv) SEQ ID NOS: 121, 122, 123, and SEQ ID NOS: 124, 125, 126;
(v) SEQ ID NOS: 181, 182, 183, and SEQ ID NOS: 184, 185, 186;
(vi) SEQ ID NOS: 191, 192, 193, and SEQ ID NOS: 194, 195, 196;
(vii) SEQ ID NOS: 201, 202, 203, and SEQ ID NOS: 204, 205, 206;
(viii) SEQ ID NOS: 211, 212, 213, and SEQ ID NOS: 214, 215, 216;
(ix) SEQ ID NOS: 221, 222, 223, and SEQ ID NOS: 224, 225, 226;
(x) SEQ ID NOS: 231, 232, 233, and SEQ ID NOS: 234, 235, 236;
(xi) SEQ ID NOS: 241, 242, 243, and SEQ ID NOS: 244, 245, 246;

(xii) SEQ ID NOS: 261; 262, 263, and SEQ ID NOS: 264, 265, 266; or (xiii) SEQ ID NOS: 271, 272, 273, and SEQ ID NOS: 274, 275, 276, or highly homologous variants thereof comprising 1 to 3 amino acid substitutions in one or more CDR domain sequences, said variants and said antibody or fragment capable of binding to and/or inhibiting influenza virus.

In some embodiments, said first antibody or fragment comprises a HCVR/LCVR pair of SEQ ID NO: 19/20, or highly homologous variants thereof comprising at least 80% sequence identity in one or both HCVR or LCVR domain sequences; said variant and said antibody or fragment having the property of binding to and/or inhibiting influenza virus.

In some embodiments, said second antibody or fragment comprises a HCVR/LCVR pair of SEQ ID NO:29/30, or highly homologous variants thereof comprising at least 80% sequence identity in one or both HCVR or LCVR domain sequences; said variants and said antibody or fragment having the property of binding to and/or inhibiting influenza virus.

In some embodiments, said third antibody or fragment comprises a HCVR/LCVR pair selected from the group consisting of SEQ ID NO: 79/80, 99/100. 109/110, 129/130, 189/190, 199/200, 209/210, 219/220, 229/230, 239/240, 249/250, 269/270, and 279/280, or highly homologous variants thereof comprising at least 80% sequence identity in one or both HCVR or LCVR domain sequences; said variants and said antibody or fragment having the property of binding to and/or inhibiting influenza virus.

In some embodiments, said third antibody or fragment comprises a HCVR/LCVR pair selected from the group consisting of SEQ ID NO: 79/80, 129/130, 219/220, 229/230, 239/240, 249/250, and 269/270, or highly homologous variants thereof comprising at least 80% sequence identity in one or both HCVR or LCVR domain sequences said variant and said antibody or fragment having the property of binding to and/or inhibiting influenza virus. In some embodiments, a composition is provided comprising said first, second and third antibodies or fragments exhibit isoelectric points (pI) all within a 2 pI point range.

In a specific embodiment, a composition is provided comprising a first antibody that is TRL053/Mab53 comprising HC/LC amino acid sequences of SEQ ID NO: 17/18, a second antibody that is antibody TRL579/Mab579 comprising a HC/LC amino acid sequences of SEQ ID NO: 27/28, and a third antibody that is selected from the group consisting of TRL847, TRL845, TRL849, TRL848, TRL846, TRL854, TRL809 and TRL832, comprising HC/LC amino acid sequences selected from the group consisting of 227/228, 207/208, 247/248, 237/238, 217/218, 267/268, 77/78, and 127/128, respectively, or highly homologous variants thereof comprising at least 80% sequence identity in one or both HC or LC domain sequences; said variants and said antibody or fragment having the property of binding to and/or inhibiting influenza virus.

In a specific embodiment, a composition is provided comprising each of said first, second and third antibodies or fragments of the disclosure are formulated in a single dose in an effective amount for treating or preventing influenza A and influenza B infection or disease in a subject in need thereof.

In a specific embodiment, a composition is provided comprising a first, second and third antibodies or fragments of the disclosure in an amount of 100 mg/kg or less of each of said first, second and third antibodies or fragments per dose; in an amount of 10 mg/kg or less of each of said first, second and third antibodies or fragments per dose; or in an amount of 1 mg/kg or less of each of said first, second and third antibodies or fragments per dose. In some embodiments, each of said first, second and third antibodies or fragments are each present in the composition in an amount of total antibody or antibody fragment of 10 mg/kg or less per dose.

In specific embodiments, a composition is provided comprising a carrier, diluent and/or excipient for nasal or pulmonary delivery.

In some embodiments, a composition is provided comprising an antibody or fragment of the disclosure and further comprising one or more of an antiviral therapeutic, viral replication inhibitor, protease inhibitor, polymerase inhibitor, hemagglutinin inhibitor, bronchodilator, or inhaled corticosteroid. In some embodiments, the immune modulator is Interferon beta 1a; the antiviral therapeutic is a neuraminidase inhibitor selected from the group consisting of Oseltamivir, Zanamivir, Peramivir, and Laninamivir; the antiviral therapeutic is an RNA polymerase inhibitor selected from the group consisting of Favipiravir (T-705) and VX 787; the antiviral therapeutic is a host-cell targeting therapeutic selected from the group consisting of Fludase (Das181) and AB-103 (p2TA); the antiviral therapeutic is an ion channel inhibitor selected from the group consisting of Ramantadine and Amantadine; and the bronchodilator is selected from albuterol, levalbuterol, or salmeterol.

In some embodiments, a composition is provided comprising each of said first, second and third antibodies or fragments of the disclosure in an effective amount for treating or preventing influenza A and influenza B infection or disease in a subject in need thereof wherein one or more of said antibodies or antigen binding fragments thereof is an antibody fragment selected from Fab, Fab', and F(ab')$_2$, scFv, dAb, or a multispecific antibody, comprising HCDR1/HCDR2/HCDR3 amino acid sequences selected from the group consisting of 11/12/13, 21/22/23, 71/72/73, 74/75/76, 91/92/93, 101/102/103, 121/122/123, 181/182/183, 191/192/193, 201/202/203, 211/212/213, 221/222/223, 231/232/233, 241/242/243, 261/262/263, and 271/272/273, or highly homologous variants thereof comprising 1 to 3 amino acid substitutions in one or more CDR domain sequences, said variants and said antibody having the property of binding to and/or inhibiting influenza virus.

In some embodiments, a method is provided for the treatment or prophylaxis of influenza infection in a subject which method comprises administering to a subject (a) a first antibody or antigen-binding fragment thereof comprising a heavy chain amino acid sequence comprising a heavy chain variable region (HCVR) comprising HCDR1/HCDR2/HCDR3 of SEQ ID NOS: 11, 12, 13 and a light chain amino acid sequence comprising a light chain variable region (LCVR) comprising LCDR1/LCDR2/LCDR3 of SEQ ID NOS: 14, 15, 16, or highly homologous variants thereof comprising 1 to 3 amino acid substitutions in one or more CDR domain sequences, said variants and said antibody or fragment capable of binding to and/or inhibiting influenza virus; (b) a second antibody or antigen-binding fragment thereof comprising a heavy chain amino acid sequence comprising a heavy chain variable region (HCVR) comprising HCDR1/HCDR2/HCDR3 of SEQ ID NOS: 21, 22, 23 and a light chain amino acid sequence comprising a light chain variable region (LCVR) comprising CDR domain sequences LCDR1/LCDR2/LCDR3 of SEQ ID NOS: 24, 25, 26, or highly homologous variants thereof comprising 1 to 3 amino acid substitutions in one or more CDR domain sequences, said variants and said antibody or fragment capable of binding to and/or inhibiting influenza virus; and (c) a third antibody or antigen-binding fragment thereof comprising a heavy chain amino acid sequence comprising a heavy chain variable region (HCVR) comprising HCDR1/ HCDR2/HCDR3, and a light chain amino acid sequence comprising a light chain variable region (LCVR) comprising light chain CDR domain sequences, LCDR1/LCDR2/ LCDR3, respectively, selected from: (i) SEQ ID NOS: 71, 72, 73, and SEQ ID NOS: 74, 75, 76; (ii) SEQ ID NOS: 91, 92, 93, and SEQ ID NOS: 94, 95, 96; (iii) SEQ ID NOS: 101, 102, 103, and SEQ ID NOS: 104, 105, 106; (iv) SEQ ID NOS: 121, 122, 123, and SEQ ID NOS: 124, 125, 126; (v) SEQ ID NOS: 181, 182, 183, and SEQ ID NOS: 184, 185, 186; (vi) SEQ ID NOS: 191, 192, 193, and SEQ ID NOS: 194, 195, 196; (vii) SEQ ID NOS: 201, 202, 203, and SEQ ID NOS: 204, 205, 206; (viii) SEQ ID NOS: 211, 212, 213, and SEQ ID NOS: 214, 215, 216; (ix) SEQ ID NOS: 221, 222, 223, and SEQ ID NOS: 224, 225, 226; (x) SEQ ID NOS: 231, 232, 233, and SEQ ID NOS: 234, 235, 236; (xi) SEQ ID NOS: 241, 242, 243, and SEQ ID NOS: 244, 245, 246; (xii) SEQ ID NOS: 261; 262, 263, and SEQ ID NOS: 264, 265, 266; or (xiii) SEQ ID NOS: 271, 272, 273, and SEQ ID NOS: 274, 275, 276, or highly homologous variants thereof comprising 1 to 3 amino acid substitutions in one or more CDR domain sequences, said variants and said antibody or fragment capable of binding to and inhibiting influenza virus. In some embodiments, each of the first, second and third antibodies or fragments are administered simultaneously, or sequentially.

In some embodiments, an anti-influenza composition of the disclosure is administered to a subject wherein the influenza infection status of said subject is determined without the need for detailed viral strain determination.

In some embodiments, an anti-influenza composition of the disclosure is administered to a subject, wherein the subject is protected against influenza infection or disease.

As is well understood in the art, non-immunoglobulin based proteins may have similar epitope recognition properties as antibodies and can also provide suitable embodiments, including binding agents based on fibronectin, transferrin or lipocalin. Nucleic acid based moieties, such as aptamers also have these binding properties.

In other embodiments, the invention is directed to pharmaceutical compositions and formulations comprising the binding moieties of the invention, in particular to those wherein the binding moieties are associated with red blood cells either covalently or non-covalently in a manner that promotes partitioning from the blood into the lungs, to methods for use of the binding moieties of the invention for passively inhibiting viral infection in subjects as a preventive in normal populations or in subjects that may have been already exposed to the virus, or as a therapeutic in subjects that are already infected. The invention is also directed to recombinant materials and methods to produce antibodies or fragments, including use of these to generate antibodies or fragments in situ in a subject.

In some embodiments, a combination of binding molecules is provided, particularly human monoclonal antibodies or fragments thereof, that bind and are effective against influenza virus, wherein the combination is effective against Group 1 influenza A viruses. Group 2 influenza A viruses, and influenza B viruses. The combination of antibodies is effective in treatment or prophylaxis against influenza A and B viruses, thus providing an effective agent against all relevant and circulating influenza viruses in a single composition or dose.

In some embodiments, a combination composition is provided comprising monoclonal antibodies, each binding to influenza with low nM or sub-nM affinity. A combination composition is provided including an antibody or binding fragment directed particularly against Group 1 influenza A viruses, an antibody or binding fragment directed particularly against Group 2 influenza A viruses, and an antibody or binding fragment directed particularly against influenza B viruses, including both Yamagata and Victoria B lineages.

In some embodiments, a combination of antibodies is provided comprising a first antibody directed against Group 1 influenza A, and in more specific embodiments particularly at least H1 influenza viruses, a second antibody directed against Group 2 influenza A, and in more specific embodiments particularly at least H3 influenza viruses, and a third antibody directed against influenza B virus, and in more specific embodiments particularly against both Yamagata and Victoria lineages.

In some embodiments, a composition is provided comprising or consisting of a combination of influenza monoclonal antibodies or fragments thereof, which are effective in combination for treatment or prophylaxis of influenza A and influenza B.

In one embodiment, the invention comprises an antibody or antigen-binding fragment of an antibody comprising a heavy chain variable region (HCVR) selected from the group consisting of SEQ ID NO: 39, 49, 59, 69, 79, 89, 99, 109, 119, 129, 139, 149, 159, 169, 179, 189, 199, 209, 219, 229, 239, 249, 259, 269, 279, and 289, or a homologous sequence thereof having at least 80%, at least 90%, at least 95%, at least 98% or at least 99% sequence identity. In another embodiment, the antibody or an antigen-binding fragment thereof comprises an HCVR having an amino acid sequence selected from the group consisting of SEQ ID NO: 79, 99, 109, 129, 189, 199, 209, 219, 229, 239, 249, 269 and 279. In yet another embodiment, the antibody or fragment thereof comprises an HCVR comprising SEQ ID NO:209, 229, 239, 249, or 269.

In one embodiment, the invention comprises an antibody or antigen-binding fragment of an antibody comprises a light chain variable region (LCVR) selected from the group consisting of SEQ ID NO: 40, 50, 60, 70, 80, 90, 100, 110, 120, 130, 140, 150, 160, 170, 180, 190, 200, 210, 220, 230, 240, 250, 260, 270, 280, and 290, or a substantially homologous sequence thereof having at least 80%, at least 90%, at least 95%, at least 98% or at least 99% sequence identity. In another embodiment, the antibody or antigen-binding portion of an antibody comprises an LCVR having an amino acid sequence selected from the group consisting of SEQ ID NO: 80, 100, 110, 130, 190, 200, 210, 220, 230, 240, 250, 270, or 280. In yet another embodiment, the antibody or fragment thereof comprises an LCVR comprising SEQ ID NO: 210, 230, 240, 250, or 270.

In one embodiment, the invention comprises a composition comprising an antibody or antigen-binding fragment comprising a heavy chain variable region (HCVR) selected from the group consisting of one or more of SEQ ID NO: 39, 49, 59, 69, 79, 89, 99, 109, 119, 129, 139, 149, 159, 169, 179, 189, 199, 209, 219, 229, 239, 249, 259, 269, 279, and 289, or a homologous sequence thereof having at least 80%, at least 90%, at least 95%, at least 98% or at least 99% sequence identity. In another embodiment, the composition comprises an antibody or an antigen-binding fragment thereof comprises an HCVR having an amino acid sequence selected from the group consisting of SEQ ID NO: 79, 99, 109, 129, 189, 199, 209, 219, 229, 239, 249, 269 and 279. In yet another embodiment, the composition comprises an antibody or fragment thereof comprising an HCVR comprising SEQ ID NO:209, 229, 239, 249, or 269.

In one embodiment, the invention comprises a composition comprising an antibody or antigen-binding fragment of an antibody comprises a light chain variable region (LCVR) selected from the group consisting SEQ ID NO: 40, 50, 60, 70, 80, 90, 100, 110, 120, 130, 140, 150, 160, 170, 180, 190, 200, 210, 220, 230, 240, 250, 260, 270, 280, and 290, or a homologous sequence thereof having at least 80%, at least 90%, at least 95%, at least 98% or at least 99% sequence identity. In another embodiment, the composition comprises an antibody or antigen-binding portion of an antibody comprising an LCVR having an amino acid sequence selected from the group consisting of SEQ ID NO: 80, 100, 110, 130, 190, 200, 210, 220, 230, 240, 250, 270, or 280. In yet another embodiment, the composition comprises an antibody or fragment thereof comprises an LCVR comprising SEQ ID NO: 210, 230, 240, 250, or 270.

In one embodiment, the invention comprises a composition comprising a B antibody (anti-B type) or fragment as provided herein and an antibody or antigen-binding fragment comprising a heavy chain variable region (HCVR) selected from the group consisting of one or more of SEQ ID NO: 19 and 29 or a homologous sequence thereof having at least 80%, at least 90%, at least 95%, at least 98% or at least 99% sequence identity.

In one embodiment, the invention comprises a composition comprising a B antibody or fragment as provided herein and an antibody or antigen-binding fragment of an antibody comprises a light chain variable region (LCVR) selected from the group consisting SEQ ID NO: 20 and 30, or a homologous sequence thereof having at least 80%, at least 90%, at least 95%, at least 98% or at least 99% sequence identity.

In more specific embodiments compositions comprising at least one B antibody and at least one or at least two A antibodies.

In some embodiments, an antibody or antigen binding fragment is provided comprising HC and LC variable region amino acid sequences wherein the HCVR comprises HCDR1/HCDR2/HCDR3 amino acid sequences selected from any of SEQ ID NO: 31/32/33; 41/42/43; 51/52/53; 61/62/63; 71/72/73; 81/82/83; 91/92/93; 101/102/103; 111/112/113; 121/122/123; 131/132/133; 141/142/143; 151/152/153; 161/162/163; 171/172/173; 181/182/183; 191/192/193; 201/202/203; 211/212/213; 221/222/223; 231/232/233; 241/242/243; 251/252/253; 261/262/263; 2711272/273 and 281/282/283, or highly homologous variants thereof comprising 1 to 3 amino acid substitutions in one or more CDR domain sequences, and the LCVR comprises LCDR1/LCDR2/LCDR3 amino acid sequences selected from any of SEQ ID NO: 34/35/36; 44/45/46; 54/55/56; 64/65/66; 74/75/76; 84/85/86; 104/105/106; 114/115/16; 124/125/126; 134/135/136; 144/145/146; 154/155/156; 164/165/166; 174/175/176; 184/185/186; 194/195/196; 204/205/206; 214/215/216; 224/225/226; 234/235/236; 244/245/246; 254/255/256; 264/265/266; 274/275/276; and 284/285/286, or highly homologous variants thereof comprising 1 to 3 amino acid substitutions in one or more CDR domain sequences.

In some embodiments, an antibody or antigen binding fragment is provided comprising Fc modifications to extend serum half-life. Such modifications are disclosed in Xencor XTEND™ antibody engineering technology (Xencor, Melbourne, AU). In some aspects, the antibody or fragment comprising Fc modifications exhibits an amino acid sequence having greater than 80%, greater than 90%, greater than 95% or greater than 99% sequence identity with SEQ ID NO: 297, 17, 27, 37, 47, 57, 67, 77, 87, 97, 107, 117, 127, 137, 147, 157, 167, 177, 187, 197, 207, 217, 227, 237, 247, 257, 267, 277, or 287.

In some embodiments, without being bound by theory, because a model Fab works in the inhaled formulation, an antigen-binding fragment is provided that is an scFv. Such engineered antibodies are not present in Nature. In some embodiments, an engineered antibody or binding fragment is provided comprising HCDR1/HCDR2/HCDR3 amino acid sequences selected from any of SEQ ID NO: 31/32/33; 41/42/43; 51/52/53; 61/62/63; 71/72/73; 81/82/83; 91/92/93; 101/102/103; 111/112/113; 121/122/123; 131/132/133; 141/142/143; 151/152/153; 161/162/163; 171/172/173; 181/182/183; 191/192/193; 201/202/203; 211/212/213; 221/222/223; 231/232/233; 241/242/243; 251/252/253; 261/262/263; 271/272/273 and 281/282/283, or highly homologous variants thereof comprising 1 to 3 amino acid substitutions in one or more CDR domain sequences.

In some embodiments, a codon optimized nucleic acid is provided for expression of the antibodies and fragments provided herein. In some embodiments, such non-naturally occurring nucleic acids are employed to produce higher expression levels. In some embodiments, codon optimized nucleic acid molecules are employed in the production of recombinant antibodies and fragments provided herein.

In some embodiments, an antibody or antigen binding fragment is provided comprising HC and LC variable region amino acid sequences wherein the HCVR comprises HCDR1/HCDR2/HCDR3 amino acid sequences selected from any of SEQ ID NO: 31/32/33; 41/42/43; 51/52/53; 61/62/63; 71/72/73; 81/82/83; 91/92/93; 101/102/103; 111/112/113; 121/122/123; 131/132/133; 141/142/143; 151/152/153; 161/162/163; 171/172/173; 181/182/183; 191/192/193; 201/202/203; 211/212/213; 221/222/223; 231/232/233; 241/242/243; 251/252/253; 261/262/263; 271/272/273 and 281/282/283, or highly homologous variants thereof comprising 1 to 3 amino acid substitutions in one or more CDR domain sequences, and the LCVR comprises LCDR1/LCDR2/LCDR3 amino acid sequences selected from any of SEQ ID NO: 34/35/36; 44/45/46; 54/55/56; 64/65/66; 74/75/76; 84/85/86; 104/105/106; 114/115/16; 124/125/126; 134/135/136; 144/145/146; 154/155/156; 164/165/166; 174/175/176; 184/185/186; 194/195/196; 204/205/206; 214/215/216; 224/225/226; 234/235/236; 244/245/246; 254/255/256; 264/265/266; 274/275/276; and 284/285/286, or highly homologous variants thereof comprising 1 to 3 amino acid substitutions in one or more CDR domain sequences.

In some embodiments, an antibody or antigen binding fragment is provided comprising Fc modifications to extend serum half-life. Such modifications are disclosed in Xencor Xtend™ antibody engineering technology (Xencor, Melbourne, AU). In some aspects, the antibody or fragment comprising Fc modifications exhibits an amino acid sequence having greater than 80%, greater than 90%, greater than 95% or greater than 99% sequence identity with SEQ ID NO: 297, 17, 27, 37, 47, 57, 67, 77, 87, 97, 107, 117, 127, 137, 147, 157, 167, 177, 187, 197, 207, 217, 227, 237, 247, 257, 267, 277, or 287.

In some embodiments, an engineered antibody or binding fragment is provided comprising HCDR1/HCDR2/HCDR3 amino acid sequences selected from any of SEQ ID NO: 31/32/33; 41/42/43; 51/52/53; 61/62/63; 71/72/73; 81/82/83; 91/92/93; 101/102/103; 111/112/113; 121/122/123; 131/132/133; 141/142/143; 151/152/153; 161/162/163; 171/172/173; 181/182/183; 191/192/193; 201/202/203; 211/212/213; 221/222/223; 231/232/233; 241/242/243; 251/252/253; 261/262/263; 271/272/273 and 281/282/283, or highly homologous variants thereof comprising 1 to 3 amino acid substitutions in one or more CDR domain sequences.

In some embodiments, a codon optimized nucleic acid is provided for expression of the antibodies and fragments provided herein. In some embodiments, such non-naturally occurring nucleic acids are employed to produce higher expression levels. In some embodiments, codon optimized nucleic acid molecules are employed in the production of recombinant antibodies and fragments provided herein.

BRIEF DESCRIPTION OF THE DRAWINGS

FIG. 3 shows Table 7 with recombinant HA ELISA data illustrating reactivity of several anti-influenza B mAbs and two anti-influenza A mAbs to influenza A and B strains. Recombinant HA ELISAs were performed in triplicate and the average fold reactivity (relative fluorescent units) over background is shown. FIG. 3 shows each of the anti-B mAbs TRL809, TRL812, TRL813; TRL832, TRL841, TRL842, TRL845, TRL846, TRL847, TRL848, TRL849, TRL854, and TRL856 are broadly cross-reactive against both lineages of influenza B viruses including B/Florida/06, B/Mass/12, and B/Wisconsin/10 of the Yamagata clade, and B/Brisbane/08, B/Malaysia/04, and B/Victoria %87 of the Victoria clade. The anti-influenza A mAbs CF401 (mAb 53) and CF402 (mAb 579) are reactive to members of the influenza A H1 (A/California/09) and H3 (A/Sydney/97) subtypes, but not to the influenza B strains.

FIG. 4 shows Table 8 with neutralization IC50 data for anti-influenza B antibodies TRL845, TRL848, TRL849, TRL854, TRL832 and TRL809 against representative strains B/Yamagata/16/1988 and B/Victoria/2/1987.

FIG. 6A shows 1 mg/kg of mAbs TRL845, TRL847, TRL 848, TRL849, and 5A7 by IN mute provides protection from disease in mice infected with B/Malaysia/2506/04, representative of the Victoria clade.

FIG. 6B shows 1 mg/kg of mAbs TRL845, TRL847, TRL 848, TRL849, and 5A7 by IN route provides protection from disease in mice infected with B/Florida/04/2006, representative of the Yamagata clade.

FIG. 6C shows 1 mg/kg of mAbs TRL849, TRL846, TRL854, TRL 856, TRL847, and 5A7 by IN route provides protection from disease in mice infected with B/Malaysia/2506/04, representative of the Victoria clade.

FIG. 6D shows 1 mg/kg of mAbs TRL849, TRL846, TRL854, TRL 856, TRL847, and 5A7 by IN route provides protection from disease in mice infected with B/Florida/04/2006, representative of the Yamagata clade.

FIGS. 7A-7D together demonstrate that the cocktail will provide the expected level of protection without interference from the other mabs in the cocktail against representative strains from all seasonal influenza subtypes (H1N1, H3N2, and both lineages of B).

FIG. 7A shows in vivo protection of mice infected with 10×LD50 H1N1 and treated 24 hpi with 3 mg/kg triple mAb cocktail comprised of anti-H1 CF-401, anti-H3 CF-402, and either anti-B TRL845 (Cocktail 1), anti-B TRL847 (Cocktail 2), or anti-B TRL849 (Cocktail 3).

FIG. 7B shows in vivo protection of mice infected with 10×LD50 H3N2 and treated 24 hpi with 3 mg/kg triple mAb cocktail comprised of anti-H1 CF-401, anti-H3 CF-402, and either anti-B TRL845 (Cocktail 1), anti-B TRL847 (Cocktail 2), or anti-B TRL849 (Cocktail 3).

FIG. 7C shows in vivo protection of mice infected with 10×LD50 B/Yamagata lineage and treated 24 hpi with 3 mg/kg triple mAb cocktail comprised of anti-H1 CF-401, anti-H3 CF-402, and either anti-B TRL845 (Cocktail 1), anti-B TRL847 (Cocktail 2), or anti-B TRL849 (Cocktail 3).

FIG. 7D shows in vivo protection of mice infected with 10×LD50 B/Victoria lineage and treated 24 hpi with 3 mg/kg triple mAb cocktail comprised of anti-H1 CF-401, anti-H3 CF-402, and either anti-B TRL845 (Cocktail 1), anti-B TRL847 (Cocktail 2), or anti-B TRL849 (Cocktail 3).

FIG. 8 shows the CLIPS™ peptide array that was made by PEPSCAN Inc. of B/Lee/1940/HA protein (SEQ ID NO: 291) (upper panel). Shaded regions of B/Lee/1940/HA protein correspond to residues used to generate peptide arrays from aa_15-65 (SEQ ID NO: 292), aa_300-359 (SEQ ID NO:293), and aa_362-481 (SEQ ID NO: 294). The Table 9 (lower panel) shows mAb 5A7 epitope 1-aa_333-338 (SEQ ID NO: 304), epitope 2-aa_342-346 (SEQ ID NO: 305), and epitope 3-aa_457-463 (SEQ ID NO:306); mAb TRL845 epitope-aa_455-463 (SEQ ID NO:307); TRL848 epitope 1-aa_64-71 (SEQ ID NO: 308); epitope 2-aa_336-348 (SEQ ID NO: 309); epitope 3-aa_424-428 (SEQ ID NO: 310); mAb 849 epitope 1-aa_317-323 (SEQ ID NO: 311), epitope 2-aa_344-349312), epitope 3-aa_378-383 (SEQ ID NO: 313); mAb 854 epitope 1-aa_457-463 (SEQ ID NO: 314). The drawing at lower right shows the region mapped out onto the stalk of the HA in dark grey.

FIGS. 10A-10F show melting curve assays for mAbs TRL845, TRL847, TRL848, TRL849, and TRL854. Each mAb exhibited high thermal stability.

FIG. 10A shows melting curve for TRL845 exhibiting two melting temperatures (Tm1, Tm2), at 58.3° C. and 68.7° C., respectively.

FIG. 10B shows Table 10 with melting temperatures (Tms) for mAbs TRL845, TRL847, TRL848, TRL849, and TRL854, as shown in FIGS. 10A and 10C-10F, respectively.

FIG. 10C shows melting curve for TRL847, exhibiting a melting temperature (Tm1) of 70.3° C.

FIG. 10D shows melting curve for TRL848, exhibiting a melting temperature (Tm1) of 70.1° C.

FIG. 10E shows melting curve for TRL849 exhibiting two melting temperatures (Tm1, Tm2), at 70° C. and 81.8° C., respectively.

FIG. 10F shows melting curve for TRL854 exhibiting two melting temperatures (Tm1, Tm2), at 59.7° C. and 68.9° C.

FIG. 13 demonstrates IN administration up to 4 days prior to infection (−4 dpi) (assessed at 0.1 mg/kg) protected mice from virus challenge. IP administration 3 or 4 days prior to infection at the same dose (0.1 mg/kg) was completely ineffective. IP administration at 3 or 4 days pre-infection was effective at 1 mg/kg. On comparing the IN (0.1 mg/kg) and IP (1 mg/kg) administrations at −3 dpi and −4 dpi, in both instances, the tenfold lower IN dose was more effective than IP.

FIG. 16 shows Table 11 with assessment of monoclonal anti-influenza B antibodies in hemagglutination inhibition, B/Victoria and B/Yamagata lineage neutralization in vitro, predicted binding site (head, stem) and efficacy in vivo. In vivo results are provided as a summary of three different studies in each instance, evaluating percent of original body weight in animals inoculated with 10×LD50 of virus and administered denoted TRL antibody IN at 1 mg/kg 24 hpi. Animal body weight was observed for 14 days and the lowest body weight observed is indicated. Results are shown for antibodies TRL 809, TRL832, TRL846, TRL845, TRL847, TRL848, TRL849 and TRL854. Each of TRL809, TRL832, TRL846, TRL845, TRL847, TRL848, TRL849 and TRL854 were effective to maintain at least 95% of original animal body weight throughout efficacy evaluations in vivo. Each of TRL845, TRL847, TRL848, TRL849 and TRL854 were effective to maintain at least 96% of original animal body weight throughout efficacy evaluations in vivo. Although TRL846 did not exhibit neutralization in a traditional in vitro assay, it did exhibit egress inhibition and thus is considered to be neutralizing.

FIG. 17 shows Table 12 with characterization of B antibodies for isoelectric point and affinity ($K_D$ in nM) to B/Florida (Yamagata lineage) and B/Malaysia (Victoria lineage) influenza virus strains. The affinity of B antibodies for influenza virus was evaluated to serve as an indicator aspect of relative efficacy. Affinity of each of TRL845, TRL847, TRL848, TRL849 and TRL854 for B/Malaysia was sub-nM (<1.0 nM) in each instance (data not shown).

FIG. 23 provides evidence that antibody cocktail administered as a single mixed dose 24 hours post infection with 10×LD50 virus exhibited efficacy against infection with each or any of H1 virus, H3 virus, B/Yamagata lineage virus and B/Victoria lineage virus

DETAILED DESCRIPTION

Figures 1, 2:
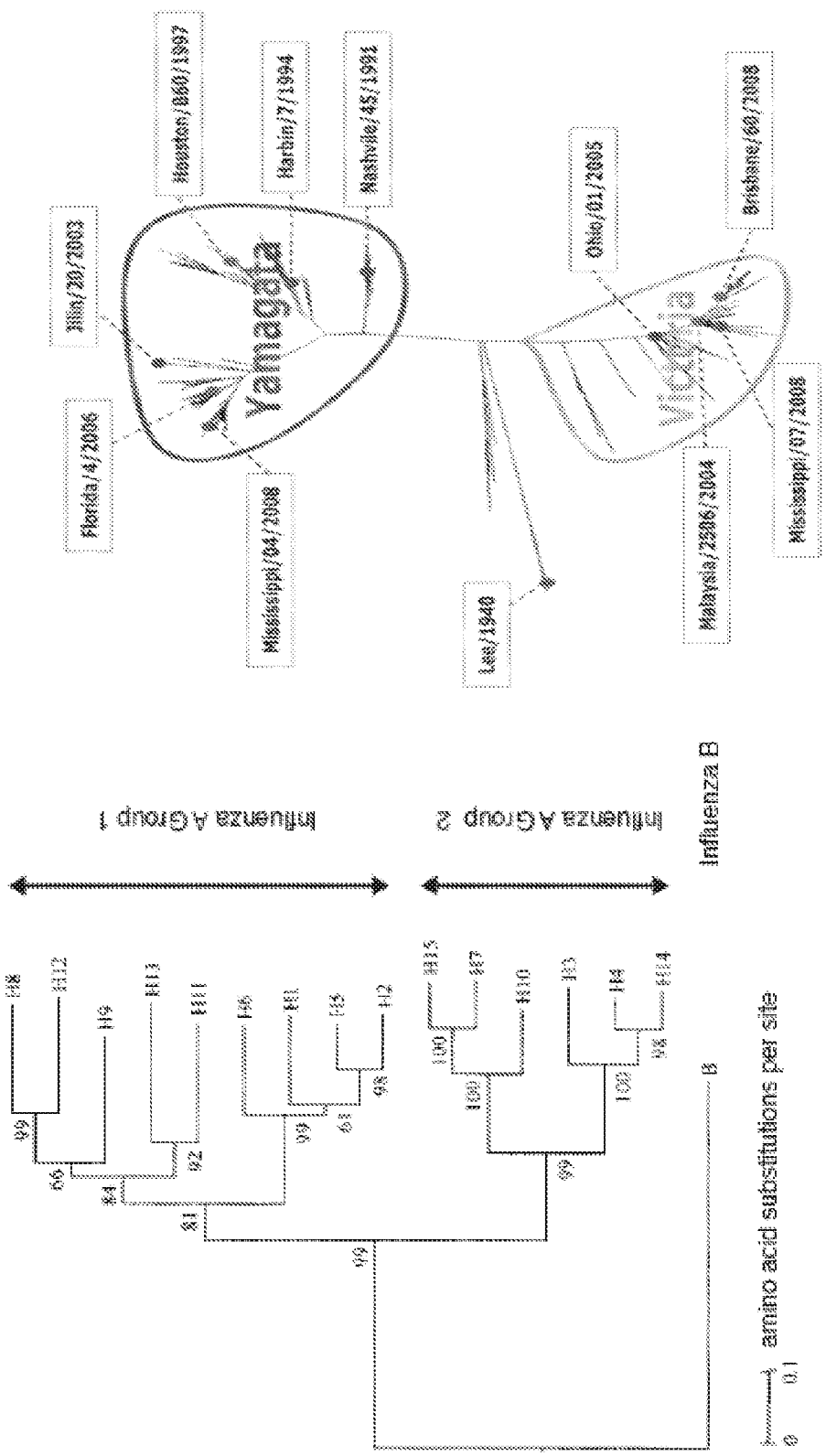
FIG. 1 shows the art-known classification of influenza A and B virus into groups of significant clades, adapted from Suzuki, Y., et al., *Mol. Biol. Evol.* (2002) 19:501-509.
FIG. 2 shows representative strains within the two influenza B clades, Yamagata and Victoria, drawn from Dreyfus, C., et al., *Science* (2012) 337:1343-1348. Representative Yamagata clades include Mississippi/04/2008; Florida/4/2006; Jilin/20/2003; Houston/B60/1997; Harbin/7/1994; and Nashville/45/1991. Representative Victoria clades include Malaysia2506/2004; Mississippi/07/2008; Brisbane/60/2008; and Ohio/01/2005.

Life-threatening seasonal and pandemic influenza infections remain a serious disease that kills 40,000 people in the U.S. alone. The availability of seasonal vaccines has failed to eliminate influenza as a significant clinical problem. There is only one approved drug for influenza that is used in practice, Tamiflu®, however, influenza has demonstrated a strong propensity for developing resistance to Tamiflu® and other neuraminidase inhibitors. Further, Tamiflu® is known to lose efficacy substantially if given after 48 hours of symptom onset.

Antibodies targeting influenza provide an alternative to vaccines and can be rapidly effective in treating or preventing infection, whereas vaccines normally take several weeks to induce effective anti-viral activity. Particularly attractive are monoclonal antibodies reactive with the principal protein, hemagglutinin, on the surface of influenza at a region referred to as the hemagglutinin stalk, which is genetically stable and does not vary significantly or at all from one season to another.

Numerous antibodies have been characterized and are in development as therapeutic antibodies for influenza, including based on conserved epitopes of the virus. Some cross-reactive antibodies target the hemagglutinin (HA) glycoprotein, which elicits the most robust neutralizing antibodies during vaccination or natural infection. HA comprises two subunits HA1 and HA2 which are critical components in virus infection. MAb CR6261 is a well characterized antibody that is said to bind to H1 viruses and other subtypes (H5) within group 1 and binds on the HA2 subunit (Throsby M et al (2008) PL0S ONE 3:e3942; Eckert D C et al (2009) Science 324:246-251; Friesen RHE et al (2010) PLoS ONE 5(2):e1906; U.S. Pat. No. 8,192,927). MAb CR8020 is said to bind to the membrane-proximal region of HA2 on both H3 and another subtype (H7) viruses which are group 2 viruses (Eckert D C et al (2011) Science 333:843-850). The antibody FI6v3 from researchers in Switzerland is said to have the ability to bind to an epitope present on both group 1 (H1) and 2 (H3) viruses, however FI6 has shown limited efficacy in mice (Corti D et al (2011) Science 333:850-856). Palese and colleagues have reported broadly protective monoclonal antibodies against H3 influenza viruses using sequential immunization in mice with different hemagglutinins (Wang T T et al (2010) PLoS Pathog 6(2):e1000796; US Application 20110027270). Using this approach, an H1 antibody said to be broadly reactive was isolated (Tan G S et al (2012) J Virol 86(11):6179-6188).

Therapeutic treatment of influenza with monoclonal antibodies to HA is dose dependent, and also requires higher doses if administered at later times post infection. Typical therapeutic doses given IP or IV of broadly-reactive HA specific antibodies require doses ranging from 2 mg/kg to 50 mg/kg in order to see protection from lethal challenges. At later times post infection the same effect requires dosing in ranges that are above >10 mg/kg. An average adult in North America is approximately 80.7 kg and would require 807 mgs of antibody if given 10 mg/kg. Two current phase 1 studies of influenza monoclonal antibodies CR6261 and CR8020 by Crucell Holland BV are assessing safety and tolerability in single doses escalating from 1 mg/kg to 50 mg/kg (trials NCT01406418 and NCT01756950 respectively; clinical trials.gov). In mice, these antibodies required 15 mg/kg to protect mice from death (Friesen, R H E et al (2010) PLoS ONE 5(2):e1906); Ekiert D C et al (2011) Science 333:843-850). Based on these IP or IV dosing amounts, near or at gram amounts of a single antibody per patient will be required based on the weight of a human (about 70 kg). This is compounded by the need, in any therapy directed at multiple influenza subtypes, for more than one antibody to treat the three different subtypes of influenza that are in circulation (influenza A H3, influenza A H1 and influenza B) and may thus require a total of on the order of 3 grams of antibody, assuming about a gram of each antibody. This large amount of antibody becomes cost prohibitive and is difficult to administer and presents a major hurdle in the development of therapeutic antibodies for influenza.

We have identified a solution to reduce the amount of antibody significantly, by more than 10 fold, while remarkably retaining and even improving efficacy. We have found that intranasal or more generally by-inhalation delivery of antibodies provides a marked and significant improvement in efficacy compared to IV or IP route. Effective airway administration of influenza monoclonal antibodies is described in U.S. Ser. No. 61/782,661 and PCT/US2014/27939, incorporated herein by reference.

Remarkably, intranasal (IN) delivery of neutralizing antibodies can dramatically increase therapeutic efficacy by more than 10 fold compared to intraperitoneal (IP) or intravenous (IV) route of delivery, using an accepted and known influenza mouse model. Comparable efficacy can be achieved using less than one tenth of the same dose when given IN instead of by IV or IP routes. Current therapeutic designs for treating influenza utilize intravenous delivery as the standard (ClinicalTrials.gov Identifier: NCT01390025, NCT01756950, NCT01406418). This delivery approach is the standard in the field as the ability to capitalize on the neutralization characteristics of an antibody are not known. The vast majority of research on antibody therapeutics utilizes IV or IP delivery, and fails to recognize that IN delivery of neutralizing antibodies to influenza will improve the efficacy compared to IV or IP delivery.

Previous reports of IN delivery have evaluated polyclonal sera gamma globulin IVIG or the IgA class of antibodies (IgA antibodies are inherently common for the lung) (Akerfeldt S et al (1973) Biochem Pharmacol 22:2911-2917; Ramisse F et al (1998) Clin Exp Immmunol 111:583-587; Ye J et al (2010) Clin Vaccine Immunol 17(9):1363). One group tested an ascites fluid preparation of an antibody (C179) by IN route and described that protective IN delivery (pre-challenge) was comparable to IP (Sakabe S et al (2010) Antiviral Res 88(3):249-255). C179 exhibits low neutralizing activity against the 2009 pandemic H1N1 virus, but was reported to protect the mice from infection.

Contrary to this, the present inventors have found that importantly the increased efficacy does not simply accompany any cross-reactive anti-influenza antibodies regardless of the mode of administration. Generally, antibodies that do not neutralize when given IN do not exhibit efficacy against influenza. To the best of our knowledge, earlier studies have failed to recognize that this effect can be applied more broadly to antibodies that exhibit in vitro neutralization activity, irrespective of their viral epitope or protein target. Furthermore, antibodies do not need to be cross-reactive against HA, as strain specific antibodies that neutralize will exhibit increased efficacy when given IN. We have found that neutralizing antibodies (and not simply cross-reactive anti-HA antibodies) are essential for significantly reducing the amount of antibody needed to achieve comparable efficacy depending on the route of administration. In fact we have found that the inverse occurs when using cross-reactive anti-HA antibodies that are not neutralizing. Therapeutic use of these cross-reactive non-neutralizing anti-HA antibodies results in a marked reduction in therapeutic efficacy when treating mice intranasally; yet, when administered by IP or IV route, these antibodies exhibit substantial efficacy.

Without being bound by theory, a possible mechanism behind this phenomenon resides in the fact that intranasal delivery achieves a level of IgG antibody in the airway mucosa that can utilize the neutralizing capabilities of an antibody antigen combining site, whereas IV or IP delivery of the antibody is Fc dependent. In the airway the inhibitory mechanism relies on the neutralizing characteristics of the antibody and the Fc dependent effect is severely limited. When giving IgG antibody by IP or IV, the amount of antibody that reaches this space in the airway is too low to capitalize on the neutralizing effect of the antibody. For example, when neutralizing antibodies are administered by IP or IV the therapeutic effect that is observed primarily comes from the antibody effector function. We have found comparable levels of efficacy of neutralizing or non-neutralizing antibodies when given IP or IV, but not by IN. To further illustrate that this effect is dependent on neutralization, antibodies against the M2 protein do not exhibit in vitro neutralization and are only capable of exhibiting Fc mediated effects. Previous work using antibodies directed to the M2 ion channel (a more genetically conserved molecule than HA) has shown promise in preclinical models, and has completed phase I studies (TCN-032 from Theraclone; NCT01390025, NCT01719874; Grandea A G et al (2010) Proc Natl Acad Sci USA 107(28):12658-12663). Antibodies against M2 protein cannot neutralize the virus, but can have well documented therapeutic efficacy mediated through effector function (Wang, R. et al. (2008) Antiviral research 80:168-177; Grandea, A. G., 3rd et al. (2010) Proc Natl Acad Sci USA 107(28):12658-12663). We believe that both neutralizing and non-neutralizing antibodies when given IP or IV function primarily through effector function similar to M2 targeted antibodies. The M2 protein is significantly less abundant than HA, and also does not protrude from the surface. Antibodies against HA can neutralize the virus offering the potential for further improved efficacy. As such, typically antibodies to HA are more therapeutically effective than anti-M2 antibodies. Nonetheless antibodies that are not neutralizers and still target HA can exhibit comparable levels of efficacy as neutralizing antibodies when given IP, suggesting that this route of delivery fails to capitalize on the potent effect that can be harnessed when given IN. Furthermore, delivery of neutralizing Fabs through IN but not IP result in therapeutic efficacy. Non-neutralizing Fabs given IN do not exhibit therapeutic efficacy. Altogether, only neutralizing antibodies given IN exhibit this increased efficacy. Extending this observation, this phenomenon, enhanced efficacy through pulmonary delivery, may occur for neutralizing antibodies that target other influenza proteins (e.g., neuraminidase) and to neutralizing antibodies against other respiratory pathogens (e.g., palivizumab for RSV). This enhanced efficacy, or the level of enhanced efficacy, may be dependent on apical replication life cycles of this subset of respiratory pathogens, where in the apical space these viruses are susceptible to the neutralizing capabilities of these antibodies. As delivery of antibodies both by the IN and IP/IV routes can be effective in different ways on their own, it is possible that the use of both routes in combination will harness the maximum therapeutic potential of a neutralizing antibody. This approach will allow maximal efficacy by utilizing the increased neutralization activity through the IN route, and increased Fc dependent activity by IP/IV route.

The present examples demonstrate intranasal efficacy at low doses for neutralizing antibodies, including known antibodies and newly isolated antibodies. Intranasal efficacy is provided for numerous distinct and known antibodies as exemplary antibodies, including antibodies CR6261, CR8020, CR9114, 5A7, mAb53(TRL053), mAb579 (TRL579), TRL845, TRL846, TRL847, TRL848, TRL849, TRL854, TRL809 and TRL832. Such activity and efficacy has not been previously demonstrated, this despite numerous studies for example of CR6261 and CR8020, including preclinical trials. Numerous distinct antibodies, including known and newly isolated antibodies, are assessed herein and are efficacious with airway administration.

Figure 25:
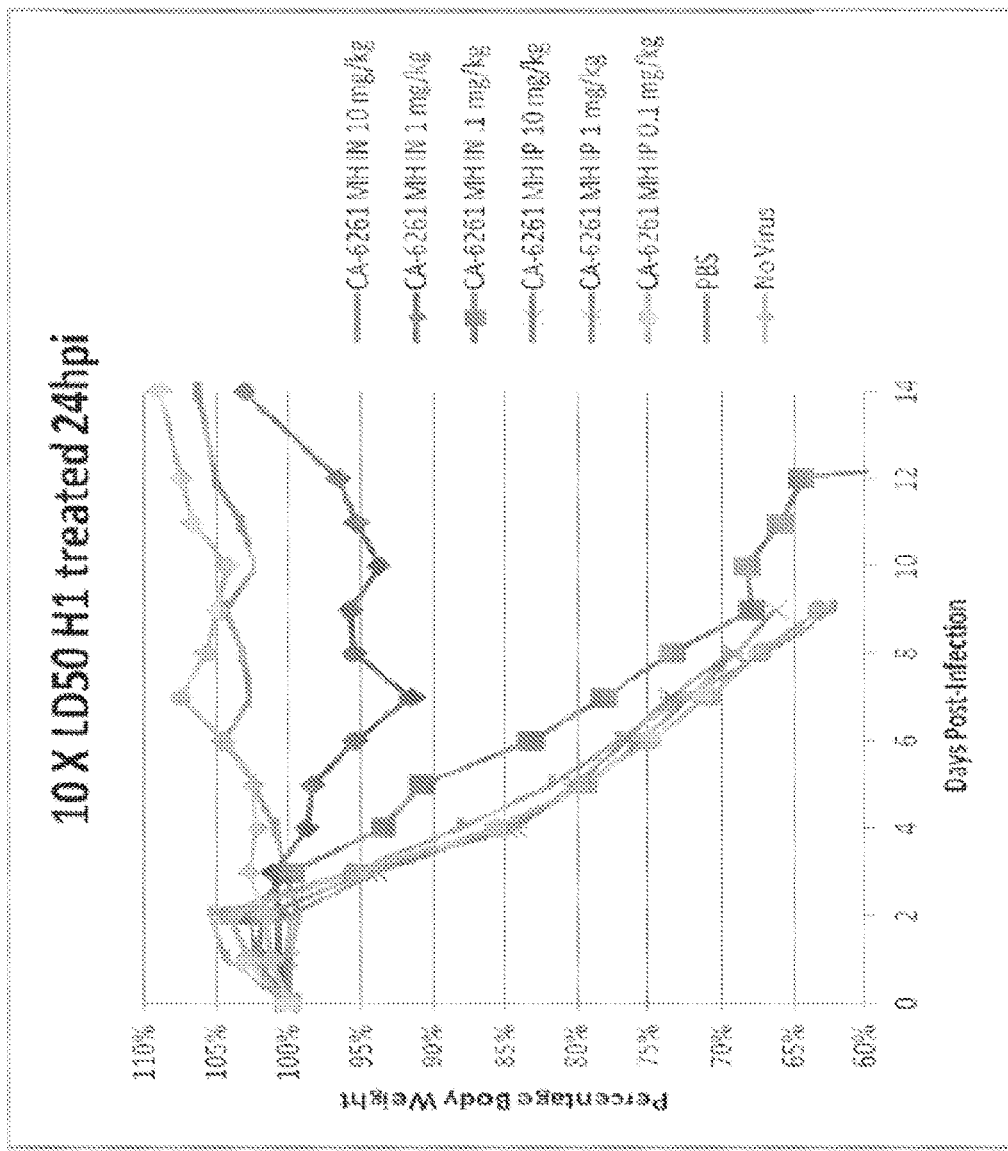
FIG. 25 provides results comparing IN versus IP administration of a model antibody fragment Fab of CA6261 antibody in therapeutic efficacy against H1 virus. Animals were inoculated with 10×LD50 of H1 influenza virus and treated 24 hpi with 10 mg/kg, 1 mg/kg and 0.1 mg/kg of neutralizing CA6261 Fab administered IN or IP, with PBS treatment and no virus as controls. Animals were monitored for body weight daily for 14 days post infection and percent body weight of original day 0 weight is plotted. All doses of Fab CA6261 antibody administered IN demonstrated greater efficacy that any IP dose. Administration of neutralizing Fab IP did not demonstrate detectable efficacy even at the highest dose, 10 mg/kg.

The present invention is directed to a novel and unique combination of antibodies which are effective against influenza A and B viruses and can be manufactured and administered in concert without untoward interactions and with remarkable formulation efficiency. The antibodies of the combination in accordance with the present invention are directed to distinct but all clinically relevant subtypes, including subtypes H1, H3, H5 of influenza A virus and also influenza B Yamagata and Victoria lineages. Thus, the invention provides a generally applicable antibody combination and cocktail, wherein a unique combination or cocktail of antibodies capable of neutralizing relevant circulating influenza viruses can be utilized in methods and compositions for airway administration and treatment or prevention of influenza virus, influenza infection and/or transmission by administering the antibody combination or cocktail of the invention via the airway, such as intranasally or delivery to the lung or bronchial mucosa. Because of the unique and useful effectiveness of the antibody combination or cocktails of the invention, clinical evaluation or specific diagnosis of influenza virus or subtype is not necessary or required prior to administration or use. Antibody fragments, derivatives or variants are contemplated. Antibody fragments, including Fabs, are demonstrated herein to be effective in accordance with the present disclosure. In one aspect of the presently disclosed embodiments, antibody Fab fragments are active and efficacious when administered via airway route (e.g., intranasally or via inhalation), and are ineffective when administered IP or IV. A model Fab is effective in vivo in the inhaled formulation, as shown in FIG. 25. In some embodiments, an antigen-binding fragment is provided that is an scFv.

In some embodiments, antibodies, antigen-binding fragments, compositions and methods for use in passive immunization against influenza are provided. In some embodiments, antibody combinations, compositions, and methods for treatment or prophylaxis of influenza virus are provided. In some aspects, compositions are provided comprising monoclonal antibodies directed against influenza A and B that are suitable for administration systemically or directly to the respiratory tract, including by airway administration such as by intranasal or inhalation administration. Compositions and methods are provided for treatment or prophylaxis via airway administration of antibody(ies) or combining intranasal or inhalation administration with intraperitoneal or intravenous administration of antibodies.

Conserved epitopes within the hemagglutinin (HA) molecule have recently been discovered. There have been several reports of the isolation and characterization of human monoclonal antibodies (MAb) capable of recognizing and neutralizing a diverse number of influenza A virus subtypes. Many of these are targeted to the hemagglutinin (HA) glycoprotein, which elicits the most robust neutralizing antibodies during vaccination or natural infection. HA comprises two subunits HA1 and HA2 which are critical components in virus infection. HA1 is involved in attachment to the host cell receptor sialic acid and HA2 mediates fusion of viral and endosome membranes.

Current antibody therapy doses are well-established to be multiple mg/kg per dose, based on research and clinical experience to date with numerous recombinant antibodies, including the over twenty monoclonal antibodies that have been clinically approved in the United States (Newsome B W and Ernstoff M S (2008) Br J Clin Pharmacol 66(1):6-19). For example, panitumumab, an anti-EGFR fully human antibody approved for colorectal cancer, is administered intravenously at 6 mg/kg over 1-1½ hours every 2 weeks. Using an average human weight of 70 kg, this amounts to 420 mg of antibody per dose.

No monoclonal antibody has yet been clinically approved for influenza. Reports of studies with influenza antibodies in animals demonstrate that the effective dose range of these antibodies when given intravenously or intraperitoneally for therapeutic or prophylactic purposes require ranges from 1 mg/kg up to 100 mg/kg. Phase I clinical trials in the US with some of these antibodies (CR6261, CR8020, TCN-032) use a dose escalation in safety and tolerance studies from 2 mg/kg up to 50 mg/kg (clinicaltrials.gov; NCT01390025, NCT01406418, NCT01756950). Subsequent Phase IIa studies with these antibodies were performed at the highest Phase I doses (e.g. 30 mg/kg or 50 mg/kg). This large amount of material presents a major hurdle in the development of this new line of antibody therapeutics. Specifically, systemic doses in this range result in a significant cost of material and also entails time, space and personnel costs associated with infusions. As such there is an imperative need to either increase efficacy and/or reduce the amount of material needed for antibody therapy or prophylaxis against influenza to be a viable alternative.

Although influenza B is somewhat less common than influenza A, it is still a serious health problem. Generally, influenza B viruses are classified into two lineages: B/Victoria/2/87-like and B/Yamagata/16/88-like. Influenza B viruses differ from influenza A viruses because they lack a protein called basic 1-F2 (PB1-F2) but have additional proteins that are absent in influenza A, such as the glycoprotein B (NB). There are additional differences as well. However, the HA proteins of influenza B strains are as homologous to some influenza A HA's as they are to each other.

The hemagglutinin protein (HA) of influenza virus has a globular head domain which is highly heterogeneous among flu strains and a stalk region containing a fusion site which is needed for entry into the cells. HA is present as a trimer on the viral envelope. The uncleaved form of hemagglutinin protein ($HA_0$) is activated by cleavage by trypsin into $HA_1$ and $HA_2$ portions to permit the fusion site to effect virulence. The two cleaved portions remain coupled using disulfide bonds but undergo a conformational change in the low pH environment of the host cell endosomal compartment which leads to fusion of the viral and host cell membranes.

The cleavage site contains a consensus sequence that is shared by the various strains of both influenza A and B. The uncleaved hemagglutinin protein trimer ($HA_0$) is referred to as the inactivated form, whereas when cleaved into $HA_1$ and $HA_2$ portions, the hemagglutinin protein is referred to as being in the activated form.

Bianchi, E., et al., *J. Virol.* (2005) 79:7380-7388 describe a "universal" influenza B vaccine based on the consensus sequence of this cleavage site wherein a peptide comprising this site was able to raise antibodies in mice when conjugated to the outer membrane protein complex of *Neisseria meningitidis*. Monoclonal antibodies (mAbs) which appear to bind to the consensus sequence were also described. In addition, successful passive transfer of antiserum was observed in mice. Other prior art vaccines, such as those described in WO2004/080403 comprising peptides derived from the M2 and/or HA proteins of influenza induce antibodies that are either of weak efficacy or are not effective across strains.

Antibodies described in the art which bind the HA stalk region include those developed by Crucell, such as CR6261 and CR8020 described in WO2008/028946 ('946); in Throsby, M., et al., *PLoS One* (2008) 3:e3942; in Ekiert, D. C., et al., *Science* (2011) 333:843-850; and in Sui, J., et al., *Nat. Struct. Mol. Biol.* (2009) 16:265-273. According to the above-mentioned PCT publication '946, these antibodies bind not only to H5N1, but also to H2, H6, H9 and H1. An mAb has also been developed against the conserved M2E antigen as described by Grandea, A. G., et al., *PNAS USA* (2010) 107:12658-12663. M2E is a viral encoded protein that appears on the surface of infected cells and is also the target of amantadine and rimantadine. Drug resistance has become widespread against these antiviral agents which suggests that this target does not serve an essential function.

An additional prior art antibody has been described by the Lanzavecchia Group: Corti, D., et al., *Science* (2011) 333: 850-856 which binds and neutralizes both Group 1 and Group 2 strains of influenza A, but the potency is not as high as those described herein. In addition, an mAb that is immunoreactive against the stalk region of both influenza A and B is described in Dreyfus, C., et al., *Science* (2012) 337:1343-1348 but it has no detectable neutralizing potency. The same authors described two mAbs that bind the head group of HA, one of which has high variability in affinity and potency on strains from the two clades of influenza B and the other of which is ~1 nM affinity. These results establish that a broadly neutralizing mAb for influenza B is difficult to achieve.

PCT application publication No. WO2011/160083, incorporated herein by reference, describes monoclonal antibodies that are derived from human cells and useful in passive vaccines. The antibodies show high affinities of binding to influenza viral clade H1, which is in Group 1, and some of the antibodies also show high affinities to H9, also in Group 1 and/or to H7 in Group 2 and/or H2 in Group 1. Some of the antibodies disclosed bind only the inactivated trimer form, presumably at the consensus cleavage region, while others are able to bind activated hemagglutinin protein which has already been cleaved.

PCT publication No. WO2013/086052, incorporated herein by reference, discloses a group of antibodies, including bispecific antibodies, that bind to an epitope in this consensus region and bind to a large number of influenza A viruses of both Group 1 and Group 2, including H1, H2, H5, H6, H8, H9, H11, H13 and H16 in Group 1 and H3 and H7 of Group 2. In addition, a recent publication by Yasugi, M., et al., *PLoS Pathogens* (2013) 9: published online as e1003150, pages 1-12, describes human mAbs that neutralize influenza B virus, in particular, an mAb designated 5A7 which is said to have therapeutic efficacy in mice even when it was administered 72 hours post-infection. The $K_D$ of 5A7 was reported to be 5 nM against the only strain tested, with the epitope identified as in the highly conserved C terminal stalk region; potency reported was comparable on all strains of influenza B. This result establishes that a high affinity (sub-nM) mAb against influenza B is difficult to achieve.

In some embodiments, antibodies or analogous binding moieties are provided that are useful for both prophylaxis and therapy. Thus, they may be used to protect a subject against infection by the virus as well as for treatment of subjects that are already exposed or infected with influenza B. The subjects of most ultimate interest are human subjects and for use in human subjects, human forms or humanized forms of the binding moieties, which are traditional natural antibodies or immunoreactive fragments thereof, are preferred. However, the antibodies containing appropriate binding characteristics as dictated by the complementarity-determining regions (CDR) when used in studies in laboratory animals may retain non-human characteristics. The antibodies employed in the studies of the examples below, although the studies are done in mice, nevertheless contain both variable and constant regions which are human.

Definitions

In accordance with the present disclosure there may be employed conventional molecular biology, microbiology, and recombinant DNA techniques within the skill of the art. Such techniques are explained fully in the literature. See, e.g., Sambrook et al, "Molecular Cloning: A Laboratory Manual" (1989); "Current Protocols in Molecular Biology" Volumes I-III [Ausubel, R. M., ed. (1994)]; "Cell Biology: A Laboratory Handbook" Volumes I-III [J. E. Cells, ed. (1994))]; "Current Protocols in Immunology" Volumes 1-III [Coligan, J. E., ed. (1994)]; "Oligonucleotide Synthesis" (M J. Gait ed. 1984); "Nucleic Acid Hybridization" [B. D. Hames & S J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

Therefore, if appearing herein, the following terms shall have the definitions set out below unless the context clearly requires otherwise.

As used herein, the term "antibody", or "binding moiety", refers to antibodies, immunoreactive fragments, or antigen-binding fragments, thereof, as well as monospecific monoclonal antibodies, multispecific antibodies such as bi-specific monoclonal antibodies or tri-specific monoclonal antibodies, isolated monoclonal antibodies, recombinant monoclonal antibodies, and isolated human or humanized monoclonal antibodies, orantigen-binding fragments thereof. molecule comprising two immunoglobulin heavy chains and two immunoglobulin light chains, and also includes immunoreactive fragments, or antigen-binding fragments, of traditional antibodies even if, on occasion, "fragments" are mentioned redundantly. The antibodies, thus, include Fab fragments, F, single-chain antibodies which contain substantially only variable regions, bispecific or trispecific antibodies and their various fragmented forms that still retain immunospecificity and proteins in general that mimic the activity of "natural" antibodies by comprising amino acid sequences or modified amino acid sequences (i.e., pseudopeptides) that approximate the activity of variable regions of more traditional naturally occurring antibodies. Thus, this term covers antibody fragments, derivatives, functional equivalents and homologues of antibodies, including any polypeptide comprising an immunoglobulin binding domain, whether natural or wholly or partially synthetic such as recombinant or otherwise engineered. Chimeric molecules comprising an immunoglobulin binding domain, or equivalent, fused to another polypeptide are therefore included. Cloning and expression of chimeric antibodies are described in EP-A-0120694 and EP-A-0125023 and U.S. Pat. Nos. 4,816,397 and 4,816,567.

The term "antibody" also includes an immunoglobulin whether natural or partly or wholly synthetically produced. The term also covers any polypeptide or protein having a binding domain which is, or is homologous to, an antibody binding domain. CDR grafted antibodies are also contemplated by this term. An "antibody" is any immunoglobulin, including antibodies and fragments thereof, that binds a specific epitope. The term encompasses polyclonal, monoclonal, and chimeric antibodies, the last mentioned described in further detail in U.S. Pat. Nos. 4,816,397 and 4,816,567. The term "antibody(ies)" includes a wild type immunoglobulin (Ig) molecule, generally comprising four full length polypeptide chains, two heavy (H) chains and two light (L) chains, or an equivalent Ig homologue thereof (e.g., a camelid nanobody, which comprises only a heavy chain); including full length functional mutants, variants, or derivatives thereof, which retain the essential epitope binding features of an Ig molecule, and including dual specific, bispecific, multispecific, and dual variable domain antibodies; Immunoglobulin molecules can be of any class (e.g., IgG, IgE, IgM, IgD, IgA, and IgY), or subclass (e.g., IgG1, IgG2, IgG3, IgG4, IgA1, and IgA2). Preferred antibodies are of the IgG class.

An "antibody combining site" is that structural portion of an antibody molecule comprised of heavy and light chain variable and hypervariable regions that specifically binds antigen.

The phrase "antibody molecule" in its various grammatical forms as used herein contemplates both an intact immunoglobulin molecule and an immunologically active portion of an immunoglobulin molecule.

The term "monoclonal antibody" as used herein refers to an antibody obtained from a population of substantially homogeneous antibodies, i.e., the individual antibodies comprising the population are identical and/or bind the same epitope (or epitopes), except for possible variant antibodies, e.g., containing naturally occurring mutations or arising during production of a monoclonal antibody preparation, such variants generally being present in minor amounts. A monoclonal antibody is an antibody having one species of antibody combining site capable of immunoreacting with a particular antigen. A monoclonal antibody thus typically displays a single binding affinity for any antigen with which it immunoreacts. In contrast to polyclonal antibody preparations, which typically include different antibodies directed against different determinants (epitopes), each monoclonal antibody of a monoclonal antibody preparation is directed against a single determinant on an antigen. However, a monoclonal antibody may be multiply specific if it contains an antibody molecule having a plurality of antibody combining sites, each immunospecific for a different antigen; e.g., a bispecific (chimeric) monoclonal antibody. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present disclosure may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

The term "antigen-binding fragment", used synonymously with "immunoreactive fragment", "binding fragment", and "antibody fragment", refers to an enzymatically obtainable, synthetic, or recombinant "engineered" polypeptide or glycoprotcin that specifically binds an antigen to form a complex. An "antibody fragment" refers to a molecule other than an intact antibody that comprises a portion of an intact antibody that binds the antigen to which the intact antibody binds. Examples of "engineered" antibody fragments include but are not limited to Fv, Fab', Fab'-SH, F(ab')$_2$; diabodies; linear antibodies; single-chain antibody molecules (e.g. scFv); and multispecific antibodies formed from antibody fragments. In addition, antibody fragments comprise single chain polypeptides having the characteristics of a VH domain, namely being able to assemble together with a VL domain, or of a VL domain, namely being able to assemble together with a VH domain to a functional antigen binding site and thereby providing the antigen binding property of full length antibodies. An "antibody fragment" includes a molecule comprising at least one polypeptide chain that is not full length, including (i) a Fab fragment, which is a monovalent fragment consisting of the variable light (VL), variable heavy (VH), constant light (CL) and constant heavy 1 (CH1) domains; (ii) a F(ab')2 fragment, which is a bivalent fragment comprising two Fab fragments linked by a disulfide bridge at the hinge region; (iii) a heavy chain portion of an Fab (Fd) fragment, which consists of the VH and CH1 domains; (iv) a variable fragment (Fv) fragment, which consists of the VL and VH domains of a single arm of an antibody, (v) a domain antibody (dAb) fragment, which comprises a single variable domain (Ward, E. S. et al., Nature 341, 544-546 (1989)); (vi) a camelid antibody; (vii) an isolated complementarity determining region (CDR); (viii) a Single Chain Fv Fragment wherein a VH domain and a VL domain are linked by a peptide linker which allows the two domains to associate to form an antigen binding site (Bird et al, Science, 242, 423-426, 1988; Huston et al, PNAS USA, 85, 5879-5883, 1988); (ix) a diabody, which is a bivalent, bispecific antibody in which VH and VL domains are expressed on a single polypeptide chain, but using a linker that is too short to allow for pairing between the two domains on the same chain, thereby forcing the domains to pair with the complementarity domains of another chain and creating two antigen binding sites (WO94/13804; P. Holliger et al Proc. Natl. Acad. Sci. USA 90 6444-6448, (1993)); and (x) a linear antibody, which comprises a pair of tandem Fv segments (VH-CH1—VH-CH1) which, together with complementarity light chain polypeptides, form a pair of antigen binding regions; (xi) multivalent antibody fragments (scFv dimers, trimers and/or tetramers (Power and Hudson, J Immunol. Methods 242: 193-204 9 (2000)); (xii) a minibody, which is a bivalent molecule comprised of scFv fused to constant immunoglobulin domains, CH3 or CH4, wherein the constant CH3 or CH4 domains serve as dimerization domains (Olafsen T et al (2004) Prot Eng Des Sel 17(4): 315-323; Hollinger P and Hudson P J (2005) Nature Biotech 23(9):1126-1136); and (xiii) other non-full length portions of heavy and/or light chains, or mutants, variants, or derivatives thereof, alone or in any combination. Single chain Fabs (scFAb) are known and described including in US20070274985.

Antigen-binding fragments include Fab fragments F(ab')$_2$ fragments; Fd fragments; Fv fragments; single-chain Fv (scFv) molecules; dAb fragments; and minimal recognition units consisting of the amino acid residues that mimic the hypervariable region of an antibody (CDRs). Other engineered molecules, such as diabodies, triabodies, tetrabodies and minibodies, are also encompassed within the expression "antigen-binding fragment," as used herein.

The antibodies used and referred to herein in combinations, other than the antibodies first described herein and constituting new polypeptidic entities, may include those having the amino acid sequences as reported and publicly known and include antibodies, proteins, polypeptides having modifications to the known or public amino acid sequence and retaining or displaying substantially equivalent activity, including target neutralization or recognition and binding activity. Accordingly, proteins displaying substantially equivalent or altered activity are likewise contemplated. These modifications may be deliberate, for example, such as modifications obtained through site-directed mutagenesis, or may be accidental, such as those obtained through mutations in hosts that are producers of the complex or its named subunits. The antibodies are intended to include within their scope proteins specifically recited herein as well as all substantially homologous analogs and allelic variations such as sequences having at least 80%, at least 90%, at least 95%, at least 98% or at least 99% sequence identity with a specifically disclosed or publicly reported antibody.

The amino acid residues described herein are preferred to be in the "L" isomeric form. However, residues in the "D" isomeric form can be substituted for any L-amino acid residue, as long as the desired functional property of immunoglobulin-binding is retained by the polypeptide. $NH_2$ refers to the free amino group present at the amino terminus of a polypeptide. COOH refers to the free carboxy group present at the carboxy terminus of a polypeptide. In keeping with standard polypeptide nomenclature. *J. Biol. Chem.,* 243:355259 (1969), abbreviations for amino acid residues are shown in the following Table 1 of Correspondence:

TABLE 1 OF CORRESPONDENCE SYMBOL AMINO ACID

| 1-Letter | 3-Letter | Amino Acid |
|---|---|---|
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |

It should be noted that all amino-acid residue sequences are represented herein by formulae whose left and right orientation is in the conventional direction of amino-terminus to carboxy-terminus. Table 1 is presented to correlate the three-letter and one-letter notations which may appear alternately herein.

The following are examples of various groupings of amino acids: Amino acids with nonpolar R groups: Alanine, Valine, Leucine, Isoleucine, Proline, Phenylalanine, Tryptophan, Methionine; Amino acids with uncharged polar R groups: Glycine, Serine, Threonine, Cysteine, Tyrosine, Asparagine, Glutamine; Amino acids with charged polar R groups (negatively charged at Ph 6.0): Aspartic acid, Glutamic acid; Basic amino acids (positively charged at pH 6.0): Lysine, Arginine, Histidine (at pH 6.0): Another grouping may be those amino acids with phenyl groups: Phenylalanine, Tryptophan, Tyrosine.

Another grouping may be according to molecular weight (i.e., size of R groups):

| | |
|---|---|
| Glycine | 75 |
| Alanine | 89 |

| | |
|---|---|
| Serine | 105 |
| Proline | 115 |
| Valine | 117 |
| Threonine | 119 |
| Cysteine | 121 |
| Leucine | 131 |
| Isoleucine | 131 |
| Asparagine | 132 |
| Aspartic acid | 133 |
| Glutamine | 146 |
| Lysine | 146 |
| Glutamic acid | 147 |
| Methionine | 149 |
| Histidine (at pH 6.0) | 155 |
| Phenylalanine | 165 |
| Arginine | 174 |
| Tyrosine | 181 |
| Tryptophan | 204 |

Particularly preferred conservative amino acid substitutions are:

Lys for Arg and vice versa such that a positive charge may be maintained;

Glu for Asp and vice versa such that a negative charge may be maintained;

Ser for Thr such that a free —OH can be maintained; and

Gln for Asn such that a free $NH_2$ can be maintained.

Amino acid substitutions may also be introduced to substitute an amino acid with a particularly preferable property. For example, a Cys may be introduced a potential site for disulfide bridges with another Cys. A His may be introduced as a particularly "catalytic" site (i.e., His can act as an acid or base and is the most common amino acid in biochemical catalysis). Pro may be introduced because of its particularly planar structure, which induces beta-turns in the protein's structure.

Two amino acid sequences are "substantially homologous" when at least about 70% of the amino acid residues (preferably at least about 80%, and in more specific embodiments at least about 90 or 95% at least about 98% or at least about 99% sequence identity) are identical, or represent conservative substitutions. In some embodiments, a substantially homologous sequence is provided having one or more conservative amino acid substitutions.

Nucleic acids encoding antibodies used in accordance with the present disclosure may be used in preparation and/or production of antibodies or active fragments thereof of use in presently disclosed embodiments. Vectors comprising such nucleic acids may be used in expression or isolation of antibodies as provided or of use herein.

A "replicon" is any genetic element (e.g., plasmid, chromosome, virus) that functions as an autonomous unit of DNA replication in vivo; i.e., capable of replication under its own control.

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA).

An "origin of replication" refers to those DNA sequences that participate in DNA synthesis.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A "promoter sequence" or "promoter" is a DNA regulatory region capable of binding RNA polymerase in a cell and initiating transcription of a downstream (3' direction) coding sequence. For purposes of defining presently disclosed embodiments, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the −10 and −35 consensus sequences.

An "expression control sequence" is a form of a regulatory sequence and is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

A cell has been "transformed" by exogenous or heterologous DNA when such DNA has been introduced inside the cell. The transforming DNA may or may not be integrated (covalently linked) into chromosomal DNA making up the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

Two DNA sequences are "substantially homologous" when at least about 75% (preferably at least about 80%, and most preferably at least about 90 or 95%) of the nucleotides match over the defined length of the DNA sequences.

Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

It should be appreciated that also within the scope of the present disclosure are DNA sequences encoding antibodies of or of use in the present disclosure which code for an antibody, polypeptide or active fragment thereof having the same amino acid sequence, but which are degenerate to the original or known encoding sequence. By "degenerate to" is meant that a different three-letter codon is used to specify a particular amino acid. It is well known in the art that the following codons can be used interchangeably to code for each specific amino acid:

| | |
|---|---|
| Phenylalanine (Phe or F) | UUU or UUC |
| Leucine (Leu or L) | UUA or UUG or CUU or CUC or CUA or CUG |
| Isoleucine (Ile or I) | AUU or AUC or AUA |
| Methionine (Met or M) | AUG |
| Valine (Val or V) | GUU or GUC of GUA or GUG |
| Serine (Ser or S) | UCU or UCC or UCA or UCG or AGU or AGC |
| Proline (Pro or P) | CCU or CCC or CCA or CCG |
| Threonine (Thr or T) | ACU or ACC or ACA or ACG |
| Alanine (Ala or A) | GCU or GCG or GCA or GCG |
| Tyrosine (Tyr or Y) | UAU or UAC |
| Histidine (His or H) | CAU or CAC |
| Glutamine (Gln or Q) | CAA or CAG |
| Asparagine (Asn or N) | AAU or AAC |
| Lysine (Lys or K) | AAA or AAG |
| Aspartic Acid (Asp or D) | GAU or GAC |
| Glutamic Acid (Glu or E) | GAA or GAG |
| Cysteine (Cys or C) | UGU or UGC |
| Arginine (Arg or R) | CGU or CGC or CGA or CGG or AGA or AGG |
| Glycine (Gly or G) | GGU or GGC or GGA or GGG |
| Tryptophan (Trp or W) | UGG |
| Termination codon | UAA (ochre) or UAG (amber) or UGA (opal) |

It should be understood that the codons specified above are for RNA sequences. The corresponding codons for DNA have a T substituted for U.

Mutations can be made in antibody or active fragment encoding sequences such that a particular codon is changed to a codon which codes for a different amino acid. Such a mutation is generally made by making the fewest nucleotide changes possible. A substitution mutation of this sort can be made to change an amino acid in the resulting protein in a "non-conservative" manner (i.e., by changing the codon from an amino acid belonging to a different grouping of amino acids having a particular size or characteristic to an amino acid belonging to another grouping) or in a "conservative" manner (i.e., by changing the codon from an amino acid belonging to a grouping of amino acids having a particular size or characteristic to an amino acid belonging to the same grouping). Such a conservative change generally leads to less change in the structure and function of the resulting protein. A non-conservative change is more likely to alter the structure, activity or function of the resulting protein. Certain embodiments are considered to include sequences containing conservative changes or substitutions in amino acid sequences in one, two, three, four, five, six or seven amino acid residues which do not significantly alter the activity or binding characteristics of the resulting protein.

As mentioned above, a DNA sequence encoding an antibody, polypeptide or active fragment thereof can be prepared synthetically rather than cloned. The DNA sequence can be designed with the appropriate codons for the antibody or fragment amino acid sequence. In general, one will select preferred codons for the intended host if the sequence will be used for expression. The complete sequence is assembled from overlapping oligonucleotides prepared by standard methods and assembled into a complete coding sequence. See, e.g., *Edge. Nature,* 292:756 (1981); Nambair et al., *Science,* 223:1299 (1984); Jay et al., *J. Biol. Chem.,* 259: 6311 (1984). Synthetic DNA sequences allow convenient construction of genes which will express analogs or "muteins". Alternatively, DNA encoding muteins can be made by site-directed mutagenesis of native genes or cDNAs, and muteins can be made directly using conventional polypeptide synthesis.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologous coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

A DNA sequence is "operatively linked" to an expression control sequence when the expression control sequence controls and regulates the transcription and translation of that DNA sequence. The term "operatively linked" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence. If a gene that one desires to insert into a recombinant DNA molecule does not contain an appropriate start signal, such a start signal can be inserted in front of the gene.

The term "standard hybridization conditions" refers to salt and temperature conditions substantially equivalent to 5×SSC and 65° C. for both hybridization and wash. However, one skilled in the art will appreciate that such "standard hybridization conditions" are dependent on particular conditions including the concentration of sodium and magnesium in the buffer, nucleotide sequence length and concentration, percent mismatch, percent formamide, and the like. Also important in the determination of"standard hybridization conditions" is whether the two sequences hybridizing are RNA-RNA, DNA-DNA or RNA-DNA. Such standard hybridization conditions are easily determined by one skilled in the art according to well-known formulae, wherein hybridization is typically 10-20° C. below the predicted or determined $T_m$ with washes of higher stringency, if desired.

The term "binding affinity" for antibodies and fragments is described herein as KD (the equilibrium dissociation constant between the antibody and its antigen), that can be determined by various methods known in the art. In some embodiments, the antibodies, or antigen-binding fragments exhibit the following binding affinity for influenza A virus, influenza B virus or HA proteins derived therefrom, such as recombinant HA proteins. In one embodiment the binding affinity is between about $5\times10^{-8}$ M and about $5\times10^{-12}$ M, in some embodiments the binding affinity is about $5\times10^{-9}$ M to about $5\times10^{-11}$ M, in some embodiments the binding affinity is about $3\times10^{-9}$ M to about $5\times10^{-11}$ M, in some embodiments the binding affinity is about $5\times10^{-10}$ M to about $5\times10^{-11}$ M. In some embodiments, antibodies and antigen-binding fragments are provided that exhibit a KD of less than 10 nM, less than 3 nM, or less than 1 nM or tighter for recombinant HA protein. In some embodiments, antibodies and fragments are provided exhibiting KDs of between 10 nM and 0.1 pM. In some embodiments, antibodies and fragments are provided exhibiting KDs of between 3 nM and 1 pM. As used herein, the term "tighter" indicates the referred KD value or less (lower KD value), as the more intense or tighter the affinity the lower the KD value. In some embodiments, the KD is measured by determining oblique-incidence reflectivity difference (OI-RD) by, for example, by use of a microarray or fluidic system, e.g., by ABCAM®, see Landry et al., 2012, Assay and Drug Dev Technol 10(3), 250-259, or by BIACORE® (i.e., surface plasmon resonance) or competitive binding assays.

Antibody mediated neutralization of virus is defined herein as defined or accepted in the art and as referred to and utilized herein can be tested in various conventional or recognized neutralization assays. Examples of neutralization assays include conventional neutralization assays based on the inhibition of a virus cytopathic effect (CPE) on cells in culture. For example, influenza neutralization may be tested by reducing or blocking formation of CPE in MDCK cells infected with influenza. Virus and neutralizing agent may be premixed before addition to cells, followed by measuring blocking of virus entry. Hemagglutinin inhibition (H1) may be tested in vitro and can detect the blocking of a viruses ability to bind to red blood cells. An exemplary known and accepted neutralization assay is provided in the WHO Manual on Animal Influenza (who/cds/csr/ncs/2002.5, pages 48-54). Antibodies that block the sialic acid receptor binding site will neutralize virus binding to cells, thereby blocking infection. Conversely neutralization assays can detect blocking of virus egress, as in the case of neuraminidase inhibitors like Tamiflu®. Recently, neutralizing antibodies have been identified that function in a similar manner by preventing viral egress, this example of neutralization includes the CR9114 antibody on influenza B viruses (Dreyfus et al (2012) Science 337:1343-1348). Also, microneutralization assays are utilized wherein virus nucleoprotein (NP) is detected in infected cells using microtiter plates in combination with ELISA. Quantitative PCR assays have been described to measure viral proteins (Dreyfus C et al (2012) Emerging Inf Diseases 19(10:1685-1687). In some embodiments, an antibody or fragment is provided that does not appear to be a neutralizing antibody in another conventional in vitro neutralization assay, but does exhibit egress inhibition neutralization, and thus is effective by IN administration. Thus a "neutralizing" antibody as defined herein will refer to an antibody exhibiting neutralization in a conventional in vitro neutralization assay and/or an antibody that exhibits egress inhibition. Thus, in one sense of the term an egress inhibitor is neutralizing as it inhibits propagation of an influenza infection A "non-neutralizing" antibody, or nonneutralizing antibody, may bind to virus but does not inhibit the virus or viral replication in a recognized neutralizing assay or in a conventional evaluative assessment. Binding to virus can inhibit the virus by preventing its effective interaction with cells, cellular receptors or cellular targets. Non-neutralizing antibodies may bind to conserved proteins or epitopes on proteins in a virus. For example the M2 antibody in clinical trials TCN-032 can bind to a broad range of influenza A viruses, but does not demonstrate neutralization in conventional neutralization assays. Similarly, antibodies that do not neutralize can be identified that bind to HA.

As used herein, "Fab fragment" refers to an antibody fragment comprising a light chain fragment comprising a VL domain and a constant domain of a light chain (CL), and a VH domain and a first constant domain (CH1) of a heavy chain. Fab and $F(ab')_2$ portions of antibody molecules may be prepared by the proteolytic reaction of papain and pepsin, respectively, on substantially intact antibody molecules by methods that are well-known or may be prepared synthetically or recombinantly. Fab' antibody molecule portions are also well-known and may be produced from $F(ab')_2$ portions followed by reduction of the disulfide bonds linking the two heavy chain portions as with mercaptoethanol, and followed by alkylation of the resulting protein mercaptan with a reagent such as iodoacetamide.

The term "Fc domain" herein is used to define a C-terminal region of an immunoglobulin heavy chain that contains at least a portion of the constant region. For example in natural antibodies, the Fc domain is composed of two identical protein fragments, derived from the second and third constant domains of the antibody's two heavy chains in IgG, IgA and IgD isotypes; IgM and IgE Fe domains contain three heavy chain constant domains ($C_H$ domains 2-4) in each polypeptide chain.

Exemplary antibody molecules are intact immunoglobulin molecules, substantially intact immunoglobulin molecules and those portions of an immunoglobulin molecule that contains the paratope, including those portions known in the art as Fab, Fab', $F(ab')_2$ and F(v), which portions are preferred for use in the therapeutic methods described herein.

In certain instances as taught in the present disclosure, some level or amount of neutralizing activity is required and a necessary feature of an antibody for use, particularly for intranasal or inhalation administration. Therefore, any fragment, variant, derivative, synthetic or antibody portion for use intranasally in accordance with the present disclosure need retain neutralization capability and activity against target virus or pathogen, in an aspect influenza virus. On the other hand, an antibody that will be administered via alternative systemic routes, including intraperitoneally or intravenously must bind or recognize target virus or pathogen, in an aspect influenza virus, however, neutralization is not required. Thus, as an example, Fab fragments of antibody(ies), which retain neutralization, may be utilized intranasally. Effector functions, mediated via Fc are not required for intranasally efficacy and neutralization. Conversely, systemically delivered antibodies will mediate their efficacy significantly through effector function.

The term "antigen binding domain" refers to the part of an antigen binding molecule that comprises the area which specifically binds to and is complementary to part or all of an antigen. Where an antigen is large, an antigen binding molecule may only bind to a particular part of the antigen, which part is termed an epitope. An antigen binding domain may be provided by, for example, one or more antibody variable domains (also called antibody variable regions). Preferably, an antigen binding domain comprises an antibody light chain variable region (VL) and an antibody heavy chain variable region (VH).

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. Kuby Immunology, 6th ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., J. Immunol. 150:880-887 (1993); Clarkson et al., Nature 352:624-628 (1991).

The term "antigen-binding site of an antibody" when used herein refer to the amino acid residues of an antibody which are responsible for antigen-binding. The antigen-binding portion of an antibody comprises amino acid residues from the "complementary determining regions" or "CDRs". "Framework" or "FR" regions are those variable domain regions other than the hypervariable region residues as herein defined. Therefore, the light and heavy chain variable domains of an antibody comprise from N- to C-terminus the domains FR1, CDR1, FR2, CDR2, FR3, CDR3, and FR4. Especially, CDR3 of the heavy chain is the region which contributes most to antigen binding and defines the antibody's properties. Antibodies may be sufficiently defined in amino acid sequence in accordance with their heavy and light chain CDRs. and may particularly be described and characterized in accordance with their heavy chain variable region CDR1, CDR2, and CDR3 sequences and their light chain variable region CDR1, CDR2, and CDR3 sequences. An antibody may be defined or characterized as an antibody or fragment comprising a heavy and light chain, wherein the heavy chain variable region comprises specific CDR1, CDR2, and CDR3 sequences and the light chain variable region comprises specific CDR1, CDR2, and CDR3 sequences. CDR and FR regions of an antibody may be determined in accordance with standard methods and analyses available and known to one of skill in the art. Thus, CDR and FR regions may be determined according to the standard definition of Kabat et al., Sequences of Proteins of Immunological Interest, 5th ed., Public Health Service, National Institutes of Health, Bethesda, Md. (1991), or in accordance with the International ImmunoGeneTics information system (IMGT) (imgt.org; LeFranc, M-P (1999) Nucl Acids Res 27:209-212; LeFranc, M-P (2005) Nucl Acids Res 33:D539-D579).

By "substantially as set out" it is meant that that variable region sequences, and/or particularly the CDR sequences, of the antibodies of the present disclosure will be either identical or highly homologous to the specified sequences provided herein in the accompanying sequence listing. Wherein Xaa appears in the sequence listing, it represents any naturally occuring amino acid residue.

By "highly homologous" it is contemplated that only a few substitutions, preferably from 1 to 8, preferably from 1 to 5, preferably from 1 to 4, or from 1 to 3, or 1 or 2 substitutions may be made in the variable region sequence and/or in the CDR sequences. The term substantially set out as includes particularly conservative amino acid substitutions which do not materially or significantly affect the specificity and/or activity of the instant antibodies. Conservative amino acid substitutions are contemplated for the CDR region sequences. Exemplary CDR substitutions and variants are contemplated and provided herein. In some aspects, substitutions may be made in the variable region sequence outside of the CDRs so as to retain the CDR sequences. Thus, changes in the variable region sequence or alternative non-homologous or veneered variable region sequences may be introduced or utilized, such that the CDR sequences are maintained and the remainder of the variable region sequence may be substituted.

The term "epitope" includes any polypeptide determinant capable of specific binding to an antibody. In certain embodiments, epitope determinant include chemically active surface groupings of molecules such as amino acids, sugar side chains, phosphoryl, or sulfonyl, and, in certain embodiments, may have specific three dimensional structural characteristics, and or specific charge characteristics. An epitope is a region of an antigen that is bound by an antibody.

Methods and methodology for making monoclonal antibodies by hybridomas or other means and approaches is well known. Panels of monoclonal antibodies produced against pathogen, viral or influenza peptides can be screened for various properties; i.e., neutralization, isotype, epitope, affinity, etc. Of particular interest are monoclonal antibodies that neutralize the activity of the virus or its subunits. Such monoclonals can be readily identified in neutralization activity assays. High affinity antibodies are also useful for effective binding and/or neutralization or when immunoaffinity purification of native or recombinant virus is desired or of interest.

A monoclonal antibody useful in practicing presently disclosed embodiments can be produced by initiating a monoclonal hybridoma culture comprising a nutrient medium containing a hybridoma that secretes antibody molecules of the appropriate antigen specificity. The culture is maintained under conditions and for a time period sufficient for the hybridoma to secrete the antibody molecules into the medium. The antibody-containing medium is then collected. The antibody molecules can then be further isolated by well-known techniques.

Media useful for the preparation of these compositions are both well-known in the art and commercially available and include synthetic culture media, inbred mice and the like. An exemplary synthetic medium is Dulbecco's minimal essential medium (DMEM; Dulbecco et al., *Virol.* 8:396 (1959)) supplemented with 4.5 gm/l glucose, 20 mm glutamine, and 20% fetal calf serum. An exemplary inbred mouse strain is the Balb/c.

Methods for producing monoclonal anti-viral antibodies are also well-known in the art. See Niman et al., *Proc. Natl. Acad. Sci. LISA,* 80:4949-4953 (1983). Typically, the virus, viral protein, or a peptide analog is used either alone or conjugated to an immunogenic carrier, as the immunogen for producing monoclonal antibodies. The hybridomas are screened for the ability to produce an antibody that immunoreacts with the virus, protein or peptide analog.

Antibodies may also be bispecific or multispecific, for example wherein one binding domain of the antibody is a viral neutralizing antibody of use the invention, and the other binding domain has a different specificity, e.g. to bind or associate with apical surface of cells, to bind airway epithelial cells etc. Bispecific antibodies of the present invention include wherein one binding domain of the antibody is a neutralizer of use in the present invention, including a fragment thereof, and the other binding domain is a distinct antibody or fragment thereof, including that of a distinct anti-viral specific antibody, including an alternative neutralizing antibody or a non-neutralizing antibody. The other binding domain may be an antibody that recognizes or targets a particular cell type, as in a lung epithelial, alveolar macrophage, neural or glial cell-specific antibody. In the bispecific antibodies of the present invention the one binding domain of the antibody of the invention may be combined with other binding domains or molecules which recognize particular cell receptors and/or modulate cells in a particular fashion, as for instance an immune modulator (e.g., interleukin(s)), a growth modulator or cytokine or a toxin (e.g., ricin) or anti-mitotic or apoptotic agent or factor. Thus, the antibodies of the invention may be utilized to direct or target agents, labels, other molecules or compounds or antibodies in indications such as infection, inflammation, etc.

Bispecific antibodies of use in the invention may comprise at least two Fab fragments, in one example wherein either the variable regions or the constant regions of the heavy and light chain of the second Fab fragment are exchanged. Due to the exchange of either the variable regions or the constant regions, said second Fab fragment is also referred to as "cross-Fab fragment" or "xFab fragment" or "crossover Fab fragment". Such bispecifics are described in US2013006011.

In a particular and further aspect, combined or serial administration of neutralizing antibody IN, along with administration of antibody IP or IV, provides an effective and enhanced synergistic means for treatment and/or prophylaxis of virus infection. The antibody administered systemically, including IP or IV, may be neutralizing or non-neutralizing, and thereby may be the same antibody as administered IN, or may be a modified antibody, or a distinct antibody. Thus, the antibody for intranasal delivery, a neutralizing antibody, may be a distinct or different antibody from the antibody used in combination therewith for delivery via another means, particularly systemic delivery including IP or IV delivery.

The present disclosure demonstrates that Fc function and Fc portions of neutralizing antibodies, thus effector function, is not required for intranasal enhanced efficacy. Thus, antibodies and fragments such as Fab fragments, or antibodies lacking Fc or lacking effector function, are effective intranasally. In contrast, Fab fragments of antibodies (neutralizing or non-neutralizing), or antibodies lacking Fc or lacking effector function, are not effective IP or IV.

In some embodiments, immunoconjugates or antibody fusion proteins are provided, wherein the antibodies, antibody molecules, or fragments thereof, of use in the present invention are conjugated or attached to other molecules or agents further include, but are not limited to such antibodies, molecules, or fragments conjugated to a chemical ablation agent, toxin, immunomodulator, cytokine, cytotoxic agent, chemotherapeutic agent, antiviral agent, antimicrobial agent or peptide, cell wall and/or cell membrane disrupter, or drug. In an aspect, the immunoconjugates or antibody fusions may include antibodies, molecules, or fragments conjugated to an antiviral agent, particularly and anti-influenza agent. An anti-influenza agent may be a neuraminidase inhibitor. The anti-influenza agent may be selected from Tamiflu and Relenza. An anti-influenza agent may be an M2 inhibitor, such as amantadine or rimantadine. An anti-influenza agent may be a viral replication inhibitor.

The "subjects" or "subject" for which the antibodies, fragments, and compositions thereof, including antibodies of the invention are useful in therapy and prophylaxis include, in addition to humans, any subject that is susceptible to infection by flu. Thus, various mammals, such as bovine, porcine, ovine and other mammalian subjects including horses and household pets, as well as seals, will benefit from the prophylactic and therapeutic use of these binding moieties. In some cases, antibodies adapted to the subject species are used. In addition, influenza is known to infect avian species which will also benefit from compositions containing the antibodies of the invention, again possibly adapted to the subject species.

A "therapeutically effective amount" or "effective amount" of an antibody or fragment is a predetermined amount which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect or physician observes a change). An effective amount of each antibody in the composition may range from about 0.001 mg/kg to about 100 mg/kg, about 0.01 mg/kg to about 10 mg/kg, about 0.05 mg/Kg to about 1 mg/kg. The effect contemplated herein includes both medical therapeutic and/or prophylactic treatment, as appropriate. The specific dose of an antibody or fragment administered according to this disclosure to obtain therapeutic and/or prophylactic effects will, of course, be determined by the particular circumstances surrounding the case, including, for example, the compound administered, the route of administration, the co-administration of other active ingredients, the condition being treated, the specific composition employed, the age, body weight, general health, sex and diet of the patient; the time of administration, route of administration, and rate of excretion of the specific compound employed and the duration of the treatment. The effective amount administered may be determined by the physician in the light of the foregoing relevant circumstances and the exercise of sound medical judgment. 'Therapeutically effective amount' means that amount of a drug, compound, antimicrobial, antibody, or pharmaceutical agent that will elicit the biological or medical response of a subject that is being sought by a medical doctor or other clinician. In particular, with regard to viral infections and proliferation of virus, the term "effective amount" is intended to include an effective amount of a compound or agent that will bring about a biologically meaningful decrease in the amount of or extent of virus replication or pathogenesis and or decrease in length of illness (fever, joint pains, discomfort) in a subject, or a reduction in loss of body weight in an infected individual. The phrase "therapeutically effective amount" is used herein to mean an amount sufficient to reduce, and preferably prevent virus load, virus replication, virus transmission, or other feature of pathology such as for example, fever or increased white cell count as may attend its viral presence and activity.

In certain embodiments, an "effective amount" in the context of administration of a therapy to a subject refers to the amount of a therapy which is sufficient to achieve one, two, three, four, or more of the following effects: (i) reduction or amelioration the severity of an Influenza virus infection, an Influenza virus disease or a symptom associated therewith; (ii) reduction in the duration of an Influenza virus infection, an Influenza virus disease or a symptom associated therewith; (iii) prevention of the progression of an Influenza virus infection, an Influenza virus disease or a symptom associated therewith; (iv) regression of an Influenza virus infection, an Influenza virus disease or a symptom associated therewith; (v) prevention of the development or onset of an Influenza virus infection, an Influenza virus disease or a symptom associated therewith; (vi) prevention of the recurrence of an Influenza virus infection, an Influenza virus disease or a symptom associated therewith; (vii) reduction or prevention of the spread of an Influenza virus from one cell to another cell, one tissue to another tissue, or one organ to another organ; (viii) prevention or reduction of the spread/transmission of an Influenza virus from one subject to another subject; (ix) reduction in organ failure associated with an Influenza virus infection or Influenza virus disease; (x) reduction in the hospitalization of a subject; (xi) reduction in the hospitalization length; (xii) an increase in the survival of a subject with an Influenza virus infection or a disease associated therewith; (xiii) elimination of an Influenza virus infection or a disease associated therewith; (xiv) inhibition or reduction in Influenza virus replication; (xv) inhibition or reduction in the binding or fusion of Influenza virus to a host cell(s); (xvi) inhibition or reduction in the entry of an Influenza virus into a host cell(s); (xvii) inhibition or reduction of replication of the Influenza virus genome; (xviii) inhibition or reduction in the synthesis of Influenza virus proteins; (xix) inhibition or reduction in the assembly of Influenza virus particles; (xx) inhibition or reduction in the release of Influenza virus particles from a host cell(s); (xxi) reduction in Influenza virus titer, (xxii) the reduction in the number of symptoms associated with an Influenza virus infection or an Influenza virus disease; (xxiii) enhancement, improvement, supplementation, complementation, or augmentation of the prophylactic or therapeutic effect(s) of another therapy; (xxiv) prevention of the onset or progression of a secondary infection associated with an Influenza virus infection; (xxv) prevention of the onset or diminution of disease severity of bacterial pneumonias occurring secondary to Influenza virus infections; and/or (xxvi) change in the immune response to influenza including cytokines, chemokines, complement, cellular responses, etc. In some embodiments, the "effective amount" of a therapy has a beneficial effect but does not cure an Influenza virus infection or a disease associated therewith. In certain embodiments, the "effective amount" of a therapy may encompass the administration of multiple doses of a therapy at a certain frequency to achieve an amount of the therapy that has a prophylactic and/or therapeutic effect. In other situations, the "effective amount" of a therapy may encompass the administration of a single dose of a therapy at a certain amount.

A "symptom" or "symptoms" associated with virus infection, including particularly influenza infection, disease or exposure, may include, but not be limited to fever of 100° F. or higher, feeling feverish, cough and/or sore throat, runny or stuffy nose, headache and/or body aches, chills, fatigue, generalized weakness, nausea, vomiting and/or diarrhea, aches and pains in the joints and muscles and/or around the eyes.

The term 'preventing' or 'prevention' refers to a reduction in risk of acquiring or developing a disease or disorder (i.e., causing at least one of the clinical symptoms of the disease not to develop) in a subject that may be exposed to a disease-causing agent, or predisposed to the disease in advance of disease onset.

The term 'prophylaxis' is related to and encompassed in the term 'prevention', and refers to a measure or procedure the purpose of which is to prevent, rather than to treat or cure a disease. The term 'treating' or 'treatment' of any disease or infection refers, in one embodiment, to ameliorating the disease or infection (i.e., arresting the disease or growth of the infectious agent or virus or reducing the manifestation, extent or severity of at least one of the clinical symptoms thereof). In another embodiment 'treating' or 'treatment' refers to ameliorating at least one physical parameter, which may not be discernible by the subject. In yet another embodiment, 'treating' or 'treatment' refers to modulating the disease or infection, either physically, (e.g., stabilization of a discernible symptom), physiologically, (e.g., stabilization of a physical parameter), or both. In a further embodiment, 'treating' or 'treatment' relates to slowing the progression of a disease, transmission of disease, or reducing an infection.

As used herein, "pg" means picogram, "ng" means nanogram, "ug" or "µg" mean microgram, "mg" means milligram, "ul" or "µl" mean microliter, "ml" means milliliter, "l" means liter.

Methods of use for prophylaxis and therapy are conventional and generally well known. The antibodies or other binding moieties are typically provided by injection, but oral vaccines are also understood to be effective. Dosage levels and timing of administration are easily optimized and within the skill of the art. In an alternative, recombinant materials for generating the antibodies in situ may be administered. Technology is now available to express antibody genes in the cells of an animal subject, including lymphocytes or muscle cells for example (see, e.g., Johnson, P. R., et al., *Nature Medicine* (2009) 15:901-907). Such in situ production of antibodies can reduce the cost of manufacturing of the medicament, and simplifies administration. Administration of the antibodies of the invention by such methods is another aspect of the invention.

Human cells (or cells from any designated species) that secrete useful antibodies can be identified using, in particular, the CELLSPOT™ method described in U.S. Pat. No. 7,413,868, the contents of which are incorporated herein by reference. Briefly, the method is able to screen individual cells obtained from human (or other) subjects in high throughput assays taking advantage of labeling with particulate labels and microscopic observation. In one illustrative embodiment, even a single cell can be analyzed for antibodies it secretes by allowing the secreted antibodies to be adsorbed on, or coupled to, a surface and then treating the surface with desired antigens each coupled to a distinctive particulate label. The footprint of a cell can therefore be identified with the aid of a microscope. Using this technique, millions of cells can be screened for desirable antibody secretions and even rare antibodies, such as those herein desirable for passive influenza immunization across strains can be recovered. Since human subjects have existing antibodies to at least some influenza strains, and since the antibodies obtained by the method of the invention bind a conserved sequence, these antibodies serve the purpose of addressing new strains as well as strains with which human populations have experience.

Methods to obtain suitable antibodies are not limited to the CELLSPOT™ technique, nor are they limited to human subjects. Cells that produce suitable antibodies can be identified by various means and the cells may be those of laboratory animals such as mice or other rodents. The nucleic acid sequences encoding these antibodies can be isolated and a variety of forms of antibodies produced, including chimeric and humanized forms of antibodies produced by non-human cells. In addition, recombinantly produced antibodies or fragments include single-chain antibodies or Fab or $Fab_2$ regions of them. Human antibodies may also be obtained using hosts such as the XENOMOUSE® with a humanized immune system. Means for production of antibodies for screening for suitable binding characteristics are well known in the art.

Similarly, means to construct RNA aptamers with desired binding patterns are also known in the art.

As noted above, antibodies or other binding moieties may bind the activated form, the inactivated form or both of the hemagglutinin protein. It is advantageous in some instances that the epitope is at the cleavage site of this protein as it is relatively conserved across strains, but preferably the binding moiety binds both the trimer and the activated form.

The cleavage site for various strains of influenza A and influenza B is known. For example, the above cited article by Bianchi, et al., shows in Table 2 the sequence around the cleavage site of several such strains:

TABLE 2

Consensus sequence of the solvent-exposed region of the influenza A and B virus maturational cleavage sites.

| Virus/subtype | Strain | Sequence[a] |
|---|---|---|
| A/H3/HA$_0$ | Consensus | NVPEKQTR ↓ GIFGAIAGFIE |
| | | (SEQ ID NO: 51) (SEQ ID NO: 52) |
| A/H1/HA$_0$ | Consensus | NIPSIQSR ↓ GLFGAIAGFIE |
| | | (SEQ ID NO: 53) (SEQ ID NO: 54) |
| B/HA$_0$ | Consensus[b] | PAKLLKER ↓ GFFGAIAGFLE |
| | | (SEQ ID NO: 55) (SEQ ID NO: 56) |

[a]The position of cleavage between HA$_1$ and HA$_2$ is indicated by the arrow.
[b]The consensus is the same for both the Victoria and Yamagata lineages.

As indicated, strict consensus occurs starting with the arginine residue upstream of the cleavage site and thus preferred consensus sequences included in the test peptides of the invention have the sequence RGI/L/F FGAIAGFLE (SEQ ID NO:57). It may be possible to use only a portion of this sequence in the test peptides.

As noted above, once cells that secrete the desired antibodies have been identified, it is straightforward to retrieve the nucleotide sequences encoding them and to produce the desired antibodies on a large scale recombinantly. This also enables manipulation of the antibodies so that they can be produced, for example, as single-chain antibodies or in terms of their variable regions only, or as bispecific antibodies.

The retrieved nucleic acids may be physically stored and recovered for later recombinant production and/or the sequence information as to the coding sequence for the antibody may be retrieved and stored to permit subsequent synthesis of the appropriate nucleic acids. The availability of the information contained in the coding sequences and rapid synthesis and cloning techniques along with known methods of recombinant production permits rapid production of needed antibodies in the event of a pandemic or other emergency.

For reference, the sequences of human constant regions of both heavy and light chains have been described and are set forth herein as SEQ ID NOS:33-35. In the above-referenced WO2011/160083, and WO2013/086052 various monoclonal antibodies with variable regions of determined amino acid sequence and corresponding nucleotide coding sequences have been recovered that bind with varying degrees of affinity to HA protein of various strains of influenza. These antibodies include mAb53 and mAb579. mAb53 binds with particular affinity to H1; further, mAb53 binds tightly to H5, H7 and H9. mAb579 binds H3 and H7. The affinities are in the low to sub-nanomolar range. Reactivity to native trimer of HA was verified using HA expressed on the surface of HEK293 cells. Antibody binding was measured by flow cytometry. HA-encoding plasmid was provided by S. Galloway and D. Steinhauer of Emory University, and, the trimer displayed on the cell surface of the various clades was recognized by the mAbs of the present invention.

Multiple technologies now exist for making a single antibody-like molecule that incorporates antigen specificity domains from two separate antibodies (bispecific antibody). Thus, a single antibody with very broad strain reactivity can be constructed using the Fab domains of individual antibodies with broad reactivity to Group 1 and Group 2 respectively, or of one of these groups in combination with binding influenza B. Suitable technologies have been described by Macrogenics (Rockville, Md.), Micromet (Bethesda, Md.) and Merrimac (Cambridge, Mass.). (See, e.g., Orcutt, K. D., et al., "A modular IgG-scFv bispecific antibody topology," Protein Eng Des Sel. (2010) 23:221-228; Fitzgerald, J., et al., "Rational engineering of antibody therapeutics targeting multiple oncogene pathways," MAbs. (2011) 1:3(3); and Baeuerle, P. A., et al., "Bispecific T-cell engaging antibodies for cancer therapy," Cancer Res. (2009) 69:4941-4944.)

Thus, it is particularly useful to provide antibodies or other binding moieties which bind to multiple types of hemagglutinin protein by constructing bispecific antibodies. Particularly useful combinations are those that combine the binding specificity of mAb53 (H1, H5 and H9) with mAb579 (H3 and H7).

While mAb53 binds with high affinity to HA$_0$, it does not bind HA$_1$ implying binding to the complementary HA$_2$ fragment, which binding was confirmed. As mAb53 does not bind to HA$_0$ when tested by Western blot, it is assumed that the dominant epitope is at least in part conformational.

Table 3 and Table 4 provide KDs and IC$_{50}$s for various strains of influenza A hemagglutinin protein shown by mAbs 53 and 579.

TABLE 3

KDs of mAb 53 and 579 values for various flu strain monomeric and trimeric HA.

| | Group 1 mAb 53 | | | Group 2 mAb 579 | | |
|---|---|---|---|---|---|---|
| Influenza A strain | KD(nM) | Ka (1/Ms) | Kd (1/s) | KD (nM) | Ka (1/Ms) | Kd (1/s) |
| InfA HA Monomer Kinetic Binding | | | | | | |
| H1 California/07/2009 | 0.1 | 1.9E5 | 3.9E−5 | — | — | — |
| H2 Japan/305/1957 | 12.3 | 5.5E3 | 6.8E−5 | — | — | — |
| H5 Vietnam/1194/2004 | 0.5 | 3.8E4 | 1.9E−5 | — | — | — |
| H7 Netherlands/219/03 | 1.2 | 5.5E4 | 6.7E−5 | — | — | — |
| H9 HongKong/1073/99 | 0.2 | 9.8E4 | 1.6E−5 | — | — | — |
| H3 Perth/16/2009 | — | — | — | 3.9 | 1.7E5 | 6.4E−4 |
| InfA HA Trimer Kinetic Binding | | | | | | |
| H1 California 07/09 | 0.2 | 1.7E5 | 2.8E−5 | — | — | — |
| H5 Vietnam/1203/2004 | 0.5 | 9.2E4 | 4.5E−5 | — | — | — |

TABLE 3-continued

KDs of mAb 53 and 579 values for various flu strain monomeric and trimeric HA.

| | Group 1 mAb 53 | | | Group 2 mAb 579 | | |
|---|---|---|---|---|---|---|
| Influenza A strain | KD(nM) | Ka (1/Ms) | Kd (1/s) | KD (nM) | Ka (1/Ms) | Kd (1/s) |
| H3 Hong Kong/8/68 | — | — | — | 0.2 | 2.5E5 | 5.8E−5 |
| H7 Netherlands/219/03 | — | — | — | 0.4 | 1.0E5 | 4.0E−5 |

TABLE 4

$IC_{50}$s of mAb 53 and 579 values for various flu strain

| mAb | Subtype | Strain | $IC_{50}$ (ug/ml) |
|---|---|---|---|
| 53 | H1 | A/CA/04/09 | 0.9 |
| 53 | H2 | A/mallard/MN/AI08-3881/08 | 0.3 |
| 53 | H5 | A/VNH5N1-PR8/CDC-RG | 10.7 |
| 53 | H9 | A/Mallard/MN/182753/98 | 0.1 |
| 579 | H3 | A/Perth/16/2009 | 0.2 |
| 579 | | A/Philippines/2/82 x-79 | 0.9 |
| 579 | | A/Udorn/307/1976 | 1.9 |
| 579 | | A/New York/55/2004* | 1.1 |
| 579 | | A/Wisconsin/67/2005 | 1.0 |
| 579 | | A/HongKong/68 | 2.8 |
| 579 | | A/SW/MN/02719 | 3.9 |
| 579 | H4 | A/Bufflehead | 15.5 |
| 579 | H7 | A/Canada/rv444/04 | 1.6 |
| 579 | | A/Netherlands/219/03 | 0.6 |
| 579 | H10 | A/Northern Shoveler | 0.8 |

These values were obtained in the MDCK monolayer microneutralization assay.

The present invention supplies a multiplicity of new mAbs that have specificities that complement those referenced above, e.g., mAb53 and mAb579 that include mAbs that recognize influenza B. The availability of these additional mAbs provides an opportunity to prepare passive vaccines that are effective over a wide range of influenza strains, thus mitigating the need for accurate determination or diagnosis of the infective agent strain prior to treatment.

With respect to those binding moieties of the present disclosure that are indeed mAbs, as is well known, the specificity is essentially determined by the complementarity-determining regions (CDR) that are present in the variable regions of the light and heavy chains. The influence of the heavy chain CDR is understood to be more important while the light chain identities are more flexible. Thus, the overall specificity of an mAb or a fragment is typically determined by the nature of the CDR of the heavy chain while the CDR present in the light chain are subject to more variation while leaving the specificity of the antibody substantially the same.

In addition to bispecific antibodies per se, the present disclosure contemplates the use of the heavy chain only in constructs for neutralization of viral infection, such antibodies may also be bispecific. Since it is understood in the art that specificity is mostly conferred by the heavy chain variable regions in some stances, heavy chains alone have been and are herein successful, as active ingredients in vaccines. Alternatively, the heavy chain of appropriate specificity may be associated with various forms of light chain to enhance the affinity or ability to neutralize virus.

As noted, the specificities of the binding of the binding moieties of the invention are defined by the CDR mostly those of the heavy chain, but complemented by those of the light chain as well. Therefore, the binding moieties of the invention may contain the three CDR of a heavy chain and optionally the three CDR of a light chain that matches it. The invention also includes binding moieties that bind to the same epitopes as those that actually contain these CDR. Thus, for example, also included are aptamers that have the same binding specificity—i.e., bind to the same epitopes as do the binding moieties that actually contain the CDR. Because binding affinity is also determined by the manner in which the CDR are arranged on a framework, the binding moieties of the invention may contain complete variable regions of the heavy chain containing the three relevant CDR as well as, optionally, the complete light chain variable region comprising the three CDR associated with the light chain complementing the heavy chain in question. This is true with respect to the binding moieties that are immunospecific for a single epitope as well as for bispecific antibodies or binding entities that are able to bind two separate epitopes.

Thus, with respect to binding moieties that are derived from variable regions of antibodies of suitable affinity, the important amino acid sequences are the CDR sequences arranged on a framework which framework can vary without necessarily affecting specificity or decreasing affinity to an unacceptable level. Definition of these CDR is accomplished by art-known methods. Specifically, the most commonly used method for identifying the relevant CDR is that of Kabat as disclosed in Wu, T. T., et al., *J. Exp. Med.* (1970) 132:211-250 and in the book Kabat, E. A., et al. (1983) *Sequence of Proteins of Immunological Interest*, Bethesda National Institute of Health, 323 pages. Another similar and commonly employed method is that of Chothia, published in Chothia, C., et al., *J. Mol. Biol.* (1987) 196:901-917 and in Chothia, C., et al., *Nature* (1989) 342:877-883. An additional modification has been suggested by Abhinandan, K. R., et al., *Mol. Immunol.* (2008) 45:3832-3839. The present invention includes the CDR as defined by any of these systems.

Some criticism has been leveled at both systems by various workers; therefore, it is understood that the CDR as designated herein and in the claims may vary slightly. As long as the resulting variable regions retain their binding ability, the precise location of the CDR is not significant, and those regions designated in the claims are to be considered to include CDR identified by any accepted system.

The antibodies or other binding moieties of the invention can be administered as passive vaccines using standard procedures and formulations. Typically, such vaccines are administered by injection, usually intramuscular or subcutaneous, but other modes of administration are by no means excluded including intravenous. By proper design, vaccines may also be administered orally. As noted above, technology under development promises to allow production of mAbs in situ in human muscle or lymphocytes, for example, and the antibodies of the present invention are also suitable for this method of production.

As to formulation, typical passive antibody vaccine formulation excipients are employed, or the binding moieties may be administered in carriers such as liposomes, micelles, nanoparticles and the like. A particularly interesting method included within the scope of the invention is to attach the binding moiety to red blood cells through adsorption of nanoparticles made from the mAb as described in Anselmo, A. C., et al., in *ACS Nano*. and published online in 2013 as 10.1021/NN404853Z. According to this technique, by adsorbing either carrier particles or medicaments or both onto red blood cells, preferential delivery to the lung is obtained thus preventing a shortened half-life through processing in the liver and spleen and providing a higher concentration in the lungs. This is particularly appropriate with regard to influenza passive vaccines and various methods to attach the binding moieties to the red blood cells can be employed. According to the article, however, simple adsorption is all that is required. Other methods for enhancing partitioning of the mAbs to the lungs can also be used to enhance the potency of the passive vaccine, such as aerosolized product delivered by inhalation.

In some embodiments, the invention provides a method and means for effective treatment and prophylaxis of influenza virus and influenza virus infection, by simultaneous or combined administration of antibodies directed against Group 1 and Group 2 influenza A virus and influenza B virus. In accordance with the invention, a combination of broadly neutralizing antibodies are administered comprising antibody or active fragment broadly directed against Group 1 influenza A virus, an antibody or active fragment broadly directed against Group 2 influenza A viruses, and an antibody or active fragment broadly directed against influenza B viruses.

In some embodiments, a passive vaccine, antibody composition, or antibody combination is provided that comprises antibodies effective against both influenza A and influenza B and is broadly reactive with multiple strains. This will provide an anti-influenza agent effective in a single dose and could be administered upon development of initial symptoms, or after exposure to influenza. Also, this will circumvent the need to characterize an infective virus in detail prior to administering an antibody or antibody mixture. Diagnostics to determine influenza strain necessitate available clinical laboratory facilities and typically require a 12-24 hour minimum turnaround time, resulting in unfavorable delay in treatment if determination of flu strain is needed before selecting the appropriate directed therapy. With a broadly reactive composition against influenza A and B strains, prior strain diagnosis is not necessary prior to treatment.

In some embodiments, a novel method and means for effective treatment and prophylaxis of influenza virus is provided, by administration of a combination of antibodies or combined antibody composition directly to the respiratory tract or airways, including by intranasal or inhalation administration. The present invention demonstrates that direct delivery of neutralizing antibody or a combination of antibodies to the respiratory tract, including airway delivery, such as by inhalation (IH) and/or intranasal (IN) delivery and administration, is superior, more efficacious and effective at lower doses than systemic administration (IV or IP) of the same antibody or combination of antibodies in the same amounts. Treatment or prophylaxis with IN or IH delivered antibody before or even after virus exposure or infection is effective.

In some embodiments, compositions for airway administration are provided, particularly inhalation or intranasal compositions, particularly antibody combination compositions, effective for treatment or prophylaxis of viral infection in a mammal comprising antibody or active fragment broadly directed against Group 1 influenza A virus, an antibody or active fragment broadly directed against Group 2 influenza A viruses, and an antibody or active fragment broadly directed against influenza B viruses. In a first aspect, the invention provides inhalation or intranasal compositions effective for treatment or prophylaxis of influenza virus infection in a mammal comprising a combination of virus neutralizing monoclonal antibodies in a single unit dose, wherein each antibody is included in the dose in an administration amount of 1 mg/kg or less. The invention provides inhalation or intranasal compositions effective for treatment or prophylaxis of influenza virus infection in a mammal comprising a combination of neutralizing monoclonal antibodies in a single unit dose, wherein each antibody is administered in an effective amount of 10 mg/kg or less. The invention provides inhalation or intranasal compositions effective for treatment or prophylaxis of influenza virus in a mammal comprising a combination of influenza neutralizing monoclonal antibodies, each in a single unit dose of less than 1 mg/kg. The invention provides inhalation or intranasal compositions effective for treatment or prophylaxis of influenza virus in a mammal comprising a combination of influenza neutralizing monoclonal antibodies, each in a single unit dose of less than 0.5 mg/kg. The invention provides inhalation or intranasal compositions effective for treatment or prophylaxis of influenza virus in a mammal comprising a combination of antibodies wherein each is administered at a dose of less than 0.1 mg/kg.

In a further aspect, the invention provides inhalation or intranasal compositions effective for treatment, prophylaxis or reduction of transmission of influenza virus in a mammal comprising a combination of influenza neutralizing antibodies directed against circulating influenza virus strains. In an aspect the invention provides compositions for intranasal administration consisting of a combination of influenza neutralizing antibodies directed against circulating influenza virus strains, particularly consisting of an influenza A anti-H1 antibody, an influenza A anti-H3 antibody and an anti-influenza B antibody. In one aspect, the composition includes an influenza A antibody effective against or further effective against other influenza strains, including but not limited to H2, H5, and H7 strains.

The compositions are suitable and applicable for use and for treatment or prophylaxis of influenza virus. In a particular aspect, the compositions are suitable for reducing transmission of influenza virus.

In a specific embodiment, a composition is provided comprising a combination of antibodies comprising antibody Mab53(TRL053), antibody Mab579(TRL579), antibody fragments thereof or bispecific antibodies based thereon, and one or more influenza antibody against influenza B virus selected from TRL847, TRL845, TRL849, TRL848, TRL846, TRL854, TRL809 and TRL832.

In some embodiments, a pharmaceutical composition is provided comprising (a) a first antibody or antigen-binding fragment thereof comprising a heavy chain amino acid sequence comprising a heavy chain variable region (HCVR) comprising HCDR1/HCDR2/HCDR3 of SEQ ID NOS: 11, 12, 13 and a light chain amino acid sequence comprising a light chain variable region (LCVR) comprising LCDR1/LCDR2/LCDR3 of SEQ ID NOS: 14, 15, 16; (b) a second antibody or antigen-binding fragment thereof comprising a heavy chain amino acid sequence comprising a heavy chain variable region (HCVR) comprising HCDR1/HCDR2/HCDR3 of SEQ ID NOS: 21, 22, 23 and a light chain amino acid sequence comprising a light chain variable region (LCVR) comprising CDR domain sequences LCDR1/

LCDR2/LCDR3 of SEQ ID NOS: 24, 25, 26; and (c) one or more influenza virus neutralizing antibodies directed against influenza B, particularly against Yamagata lineage and/or Victoria lineage, wherein the antibody or fragment thereof is selected from an antibody or fragment thereof comprising a heavy chain amino acid sequence and a light chain amino acid sequence comprising a heavy chain complementarity determining region 1 (HCDR1), a heavy chain complementarity determining region 2 (HCDR2); and a heavy chain complementarity determining region 3 (HCDR3), HCDR1/HCDR2/HCDR3, selected from the group consisting of SEQ ID NO: 31/32/33; 41/42/43; 51/52/53; 61/62/63; 71/72/73; 81/82/83; 91/92/93; 101/102/103; 111/112/113; 121/122/123; 131/132/133; 141/142/143; 151/152/153; 161/162/163; 171/172/173; 181/182/183; 191/192/193; 201/202/203; 211/212/213; 221/222/223; 231/232/233; 241/242/243; 251/252/253; 261/262/263; 271/272/273 and 281/282/283, or highly homologous variants thereof comprising 1 to 3 amino acid substitutions in one or more CDR domain sequences, said variants and said antibody having the property of binding to and inhibiting influenza virus.

In some embodiments, a pharmaceutical composition is provided comprising (a) a first antibody or antigen-binding fragment thereof comprising a heavy chain amino acid sequence comprising a heavy chain variable region (HCVR) comprising HCDR1/HCDR2/HCDR3 of SEQ ID NOS: 11, 12, 13 and a light chain amino acid sequence comprising a light chain variable region (LCVR) comprising LCDR1/LCDR2/LCDR3 of SEQ ID NOS: 14, 15, 16; (b) a second antibody or antigen-binding fragment thereof comprising a heavy chain amino acid sequence comprising a heavy chain variable region (HCVR) comprising HCDR1/HCDR2/HCDR3 of SEQ ID NOS: 21, 22, 23 and a light chain amino acid sequence comprising a light chain variable region (LCVR) comprising CDR domain sequences LCDR1/LCDR2LCDR3 of SEQ ID NOS: 24, 25, 26; and (c) one or more influenza virus neutralizing antibodies directed against influenza B, particularly against Yamagata lineage and/or Victoria lineage, wherein the antibody or fragment thereof is selected from an antibody or fragment thereof comprising a heavy chain amino acid sequence and a light chain amino acid sequence comprising a light chain complementarity determining region 3 (LCDR3), LCDR1/LCDR2/LCDR3, selected from the group consisting of SEQ ID NO: 34/35/36; 44/45/46; 54/55/56; 64/65/66; 74/75/76; 84/85/86; 104/105/106; 114/115/16; 124/125/126; 134/135/136; 144/145/146; 154/155/156; 164/165/166; 174/175/176; 184/185/186; 194/195/196; 204/205/206; 214/215/216; 224/225/226; 234/235/236; 244/245/246; 254/255/256; 264/265/266; 274/275/276; and 284/285/286, or highly homologous variants thereof comprising 1 to 3 amino acid substitutions in one or more CDR domain sequences, said variants capable of binding to and inhibiting influenza virus.

In some embodiments, compositions are provided comprising (a) a first antibody or antigen-binding fragment thereof comprising a heavy chain amino acid sequence comprising a heavy chain variable region (HCVR) comprising HCDR1/HCDR2/HCDR3 of SEQ ID NOS: 11, 12, 13 and a light chain amino acid sequence comprising a light chain variable region (LCVR) comprising LCDR1/LCDR2/LCDR3 of SEQ ID NOS: 14, 15, 16; (b) a second antibody or antigen-binding fragment thereof comprising a heavy chain amino acid sequence comprising a heavy chain variable region (HCVR) comprising HCDR1/HCDR2/HCDR3 of SEQ ID NOS: 21, 22, 23 and a light chain amino acid sequence comprising a light chain variable region (LCVR) comprising CDR domain sequences LCDR1/LCDR2/LCDR3 of SEQ ID NOS: 24, 25, 26; and (c) one or more influenza virus neutralizing antibodies or fragments directed against influenza B, particularly against Yamagata lineage and/or Victoria lineage, wherein the antibody or fragment thereof is selected from an antibody or fragment thereof comprising a heavy chain amino acid sequence and a light chain amino acid sequence comprising heavy and light chain CDR sequences, HCDR1/HCDR2/HCDR3/LCDR1/LCDR2/LCDR3, selected from die group consisting of SEQ ID NO: 31/32/33/34/35/36; 41/42/43/44/45/46; 51/52/53/54/55/56; 61/62/63/64/65/66; 71/72/73/74/75/76; 81/82/83/84/85/86; 91/92/93/94/95/96; 101/102/103/104/105/106; 111/112/113/114/115/116; 121/122/123/124/125/126; 131/132/133/134/135/136; 141/142/143/144/145/146; 151/152/153/154/155/156; 161/162/163/164/165/166; 171/172/173/174/175/176; 181/182/183/184/185/186; 191/192/193/194/195/196; 201/202/203/204/205/206; 211/212/213/214/215/216; 221/222/223/224/225/226; 231/232/233/234/235/236; 241/242/243/244/245/246; 251/252/253/254/255/256; 261/262/263/264/265/266; 271/272/273/274/275/276; and 281/282/283/284/285/286, or highly homologous variants thereof comprising 1 to 3 amino acid substitutions in one or more CDR domain sequences, said variants capable of binding to and inhibiting influenza virus.

In some embodiments, a pharmaceutical composition is provided comprising (a) a first antibody or antigen-binding fragment thereof comprising a heavy chain amino acid sequence comprising a heavy chain variable region (HCVR) comprising HCDR1/HCDR2/HCDR3 of SEQ ID NOS: 11, 12, 13 and a light chain amino acid sequence comprising a light chain variable region (LCVR) comprising LCDR1/LCDR2/LCDR3 of SEQ ID NOS: 14, 15, 16; (b) a second antibody or antigen-binding fragment thereof comprising a heavy chain amino acid sequence comprising a heavy chain variable region (HCVR) comprising HCDR1/HCDR2/HCDR3 of SEQ ID NOS: 21, 22, 23 and a light chain amino acid sequence comprising a light chain variable region (LCVR) comprising CDR domain sequences LCDR1/LCDR2/LCDR3 of SEQ ID NOS: 24, 25, 26; and (c) one or more influenza virus neutralizing antibodies or fragments directed against influenza B, particularly against Yamagata lineage and/or Victoria lineage, wherein the antibody or fragment thereof is selected from an antibody or fragment thereof comprising a heavy chain amino acid sequence and a light chain amino acid sequence comprising an HCVR/LCVR sequence pair selected from the group consisting of 39/40, 49/50, 59/60, 69/70, 79/80, 89/90, 99/100, 109/110, 119/120, 129/130, 139/140, 149/150, 159/160, 169/170, 179/180, 189/190, 199/200, 209/210, 219/220, 229/230, 2391240, 249/250, 259/260, 269/270, 279/280, and 289/290.

In some embodiments, the neutralizing antibodies useful for airway, such as IN delivery and administration may be combined with non-neutralizing antibodies. The present application demonstrates that IN administration can be combined with alternative routes of administration, including IP or IV administration, to give overall and combination enhanced efficacy. As provided herein, combined IN and IP administration of an antibody gives enhanced synergistic activity and efficacy versus either IN or IP alone. In addition to providing a replacement or alternative administration or treatment method, the invention provides an enhanced combination approach to antibody-mediated therapy and prophylaxis wherein pulmonary administration is combined with systemic administration for superlative efficacy.

In some embodiments, alternative means of antibody dosing via pulmonary administration allows for lower dosing, lower dose formulations, and efficacious broad-spectrum anti-influenza antibody combination compositions.

In some embodiments, a combination of binding molecules, particularly human monoclonal antibodies or fragments thereof, that neutralize and are effective against influenza virus, wherein the combination is effective against Group 1 influenza A viruses, Group 2 influenza A viruses, and influenza B viruses. The combination of antibodies is effective in treatment or prophylaxis against influenza A and B viruses, thus providing an effective agent against all relevant and circulating influenza viruses in a single composition or dose.

The invention provides a composition comprising or consisting of a combination of influenza monoclonal antibodies or fragments thereof, which are effective in combination for treatment or prophylaxis of influenza A and influenza B.

The combination composition may be administered to be effective against an uncharacterized and undefined influenza infection. In a particular aspect of the invention, the combination composition is administered directly to the airway, including by intranasal or inhalation administration. Particularly, the antibody combination or cocktail is administered in a single dose, or can be administered in multiple rounds of dosing, or in sequential administrations of each antibody. Thus, the cocktail of antibodies is as effective against any unknown or undefined circulating influenza virus as a single specifically selected antibody is against a defined target influenza. For example, administration of the cocktail is as effective against any given Group 1 H1 virus as is a single specific anti-H virus antibody.

In some embodiments, antibodies in the combination have certain features and aspects which make them effective and particularly applicable and useful in combination. In specific aspects, the antibodies of the instant combinations each and all demonstrate significant binding and affinity to influenza virus.

In some embodiments, the antibodies in the combination may be co-formulated, mixed, or administered sequentially with other antibodies to treat a broad range of influenza-like illness, including pathogens such as RSV, PAIV, or MPV.

In some embodiments, each of the antibodies in the effective combination demonstrate nM or sub nM affinity to multiple influenza strains. This is an aspect which is distinct and particularly useful and applicable versus other known or existing antibodies. For example Mab53 and Mab579 demonstrate nM or sub nM affinity to various H1 (and also H5) or H3 (and also H7) strains respectively, showing significantly greater binding affinity versus CR6261 and CR8020 (WO2013/086052). The anti-influenza B antibodies of the instant combination similarly demonstrate nM or sub nM binding affinity to influenza B strains of both Yamagata and Victoria clades.

In some embodiments, the antibodies of the combination aspects of the present disclosure are designed and selected to have similar biophysical properties, including isoelectric point (pI). In some embodiments, the antibodies selected for combining into a composition each exhibit pIs within ±2 pI points of each other, within ±1.5 pI points, within ±1.0 pI points, or ±0.5 pI points of each other.

In some embodiments, antibodies of the combination aspects of the present disclosure are designed and selected to have similar biophysical properties, such as robust thermal stability. In some aspects, antibodies are provided that exhibit a first melting temperature (Tm1) in a melting curve assay when performed in PBS of ≥50° C., ≥55° C., ≥60° C., ≥65° C., or ≥70° C.

In some embodiments, the antibodies are preferably designed and expressed with similar or comparable constant region sequences and are preferably of the same IgG, selected from human IgG1, IgG2, IgG2, IgG3, or IgG4. Modified Fc sequences to provide longer half-life in circulation are also known in the art.

In some embodiments, anti-influenza B antibodies are provided comprising a human IgG1 constant region amino acid sequence. In some embodiments, anti-influenza B antibodies are provided comprising a human IgG1 constant region amino acid sequence of SEQ ID NO: 297. In some embodiments, anti-influenza B antibodies are provided comprising a human light chain kappa constant region of SEQ ID NO: 295 or a human light chain lambda constant region of SEQ ID NO: 296.

In some embodiments, antibody compositions are provided comprising anti-influenza B antibodies comprising a human IgG1 constant region of SEQ ID NO: 297. In some embodiments, antibody compositions are provided comprising anti-influenza B antibodies comprising a human light chain kappa constant region of SEQ ID NO: 295 or a human light chain lambda constant region of SEQ ID NO: 296.

In some embodiments, a composition is provided comprising a combination of one or more anti-influenza A antibodies and one or more anti-influenza B antibodies. In some aspects, the antibodies in the combination exhibit one or more properties selected from low to no antibody aggregation, absence of intermolecular association, and/or absence of competition binding. These aspects are demonstrated and exemplified in antibodies of the instant combinations.

The present invention concerns the identification of a novel method, protocol and means for effective treatment and prophylaxis of influenza virus infections, by administration of the instant cocktail of antibodies to the airways or respiratory tract, such as by intranasal or inhalation administration of neutralizing antibody(ies). Intranasal or inhalation administration of influenza virus neutralizing antibodies, is more effective to treat or block virus therapeutically or prophylactically than alternative means of administration, such as IP administration. Inhalation and/or intranasal delivery and administration is superior, more efficacious and effective at lower doses than systemic administration (IV or IP) of the same antibody or combination of antibodies in the same amounts. Treatment or prophylaxis with IN delivered antibody(ies) before or even after virus exposure or infection is effective.

Methods or protocols combining a pulmonary dose of antibody with a systemic dose of antibody are particularly effective therapeutically or prophylactically against influenza virus. Such methods or protocols include wherein one or more intranasal or inhalation dose of antibody is combined with one or more IP or IV dose of antibody. The intranasal or inhalation dose may be administered before, after, simultaneously or in sequence with the IP or IV dose. One or more intranasal, inhalation, IP or IV dose(s) may be administered. Intranasal administered antibody may be an antibody fragment lacking Fc or effector function, such as a Fab, whereas IP administered antibody may have effector function or enhanced effector function.

In accordance with the present disclosure, neutralizing antibody is administered to the airways or respiratory tract for enhanced efficacy against virus, particularly influenza virus. Administration to the airways or respiratory tract may be by any recognized or known means and may include inhalation administration or intranasal administration. For enhanced effectiveness, the antibody is delivered to one or more of the upper respiratory tract and the lower respiratory tract, and may include the nasal cavity, nose, sinus, throat, pharynx, larynx, trachea, bronchi and the lungs.

"Inhalation" refers to taking in, particularly in the context of taking in or administering/being administered an agent or compound, including an antibody or active fragment thereof, or a composition comprising such, whereby the agent, compound, antibody, fragment, including as comprised in the composition, is delivered to all or part of the respiratory tract. The respiratory tract may include the upper and/or lower respiratory tract. The upper respiratory tract comprises the nose, nasal cavity, sinuses, larynx, trachea. The lower respiratory tract comprises the lungs, airways (bronchi and bronchioles) and air sacs (alveoli). Inhalation may occur via the nose or via the mouth, or via direct administration to the lower respiratory tract as in intratracheal administration. Thus, inhalation may include nose only or primarily, intranasal, inhaling via the mouth, oral inhalation, intratracheal inhalation, intratracheal instillation. Thus inhalation provides for and contemplates any means of administration whereby drug, agent, composition, antibody, fragment, reaches or is deposited at or in the respiratory tract exclusively, specifically or preferentially, including the upper and/or lower respiratory tract.

The term "intranasal" as used herein includes, but is not limited to, administering, administration or occurring within or via the nose or nasal structures or airway delivery, for example by inhalation. The term intranasal as used herein and as exemplified as an embodiment in the examples in not intended to be limited to or to imply limitation to administration directly or specifically or solely via the nose or nasal cavity, particularly in serving to exclude other means of administration whereby drug, agent, antibody, fragment, composition is delivered or otherwise provided to, deposited in or at or otherwise distributed to the respiratory tract.

Devices for administration or delivery to the respiratory tract or airway(s) are known and recognized in the skilled art and in clinical or medical practice and are applicable in the methods, protocols and compositions of the present invention. Devices include the metered dose inhaler, metered spray pumps, hand-bulb atomizer, small or large volume nebulizers, ultrasonic nebulizer and dry powder inhaler.

The embodiments disclosed herein have application and use in treatment or prophylaxis particularly of agents or pathogens which target, infect, or affect the respiratory tract. These viruses may exhibit apical replication allowing for susceptibility to be neutralized by pulmonary delivered mAb or fragments thereof, which may then result in improved efficacy compared to systemic delivery. Thus, the present embodiments have application and use in treatment or prophylaxis of respiratory infections, particularly respiratory viruses, and of agents which are associated with or causally related to respiratory illness. Common viral respiratory diseases are illnesses caused by a variety of viruses that have similar traits and affect the upper respiratory tract. The viruses involved may be the influenza viruses, respiratory syncytial virus (RSV), parainfluenza viruses, and respiratory adenoviruses. Parainfluenza viruses are the major cause of croup in young children and can cause bronchitis, pneumonia, and bronchiolitis. Adenoviruses invade primarily the respiratory and gastrointestinal tracts, and the conjunctiva of the eyes. The adenoviruses can cause a variety of illnesses from pharyngitis to pneumonia, conjunctivitis, and diarrhea. Symptoms can appear from 1-10 days after exposure to the viruses.

Clinical administration of antibodies for treatment or alleviation of conditions (cancer, inflammatory conditions, antivirals, anti-infectives) has used systemic administration exclusively, and generally IV administration, which require large and costly amounts of antibody, assistance of medical personnel, and significant time for administration (typical IV dose is for 2 hours). While other means of administration, such as intranasal, may be mentioned, particularly in patents or applications covering these antibodies, intranasal administration is deemed an equivalent alternative at best, ignored entirely, or not pursued, perhaps because it is less understood, thought to be less attractive or less efficacious, and deemed to invoke the immunological system indirectly or less directly than IP or IV administration routes. However, the present invention and remarkable studies provided herein demonstrate that intranasal administration is indeed a preferred and more efficacious alternative, particularly for neutralizing antibodies. In particular, neutralizing antibodies that can act at the site or location of initial pathogen insult or exposure are more effective than alternative modes of administration. As such, neutralizing antibodies targeting influenza exhibit dramatic differences in efficacy brought about in part through different mechanisms of action when administered through the pulmonary route compared to systemic route.

Airway administration provides for the unique opportunity to deliver an effective low dose and low cost therapy that would therefore not require confirmation by a diagnostic assay. Presentation of symptoms during the influenza season would be sufficient for physicians to administer this low dose cocktail, for example as a dry-powder inhaler or as a nebulizer or via other airway delivery method. This diagnostic-free standard of care is the current practice for Tamiflu and Relenza, but would not be possible with expensive intravenous antibody therapy, which would not be practical and is cost prohibitive. Upon follow-up with diagnosis, administration of high dose antibody could be administered either through systemic, such as intravenous route, or through the airway, and could be composed as a cocktail or as a stand-alone specific antibody that is specific for the influenza type.

Thus in accordance with the present invention, pulmonary delivery of antibodies provides a marked and significant improvement in efficacy compared to systemic routes such as IV or IP routes. Furthermore, enhanced intranasal efficacy is demonstrated by antibodies that are neutralizing. Non-neutralizing antibodies, particularly antibodies which do not demonstrate direct inhibition or blocking of influenza virus, using accepted or known assays of neutralization or virus blocking, exhibit impaired efficacy when delivered intranasally versus systemic or IP administration. The present studies demonstrate that intranasal (IN) delivery of neutralizing antibodies can dramatically increase therapeutic and prophylactic efficacy by more than 10 fold compared to intraperitoneal (IP) or intravenous (IV) route of delivery, using an accepted and known influenza mouse model. Comparable efficacy can be achieved using less than one tenth of the same dose when given IN instead of by IV or IP routes. Neutralizing antibodies administered to the airway, such as intranasally, can dramatically increase therapeutic efficacy by orders of magnitude, particularly 10 to 100 fold or at least 10 to 100 fold. Neutralizing antibodies administered intranasally can dramatically increase therapeutic efficacy by at least 10 fold, at least 50 fold, more than 10 fold, more than 50 fold, more than 100 fold, up to 100 fold, compared to intraperitoneal (IP) administration of the same antibody under similar conditions. Intranasal administration of neutralizing antibodies provides a novel and unexpected approach to prophylaxis and treatment of infection, particularly including influenza infection. IN administration can now be implemented effectively and combined with other forms of administration to provide more effective and less costly approaches to treatment and prophylaxis. Airway administration, including IN administration, enables efficacy of a combination or cocktail of antibodies in a single dose against any anticipated influenza virus.

Compositions

In accordance with the present disclosure, antibody combination compositions are provided for use and effectiveness against influenza. The antibody combination compositions are effective at low doses when administered directly to the airway, such as intranasally. The compositions particularly comprise a combination of antibodies, particularly neutralizing antibodies, particularly monoclonal antibody or an active fragment thereof, particularly antiviral antibody, particularly influenza antibody. The neutralizing antibody(ies) may neutralize more than one type or subtype of influenza are combined with antibodies neutralizing distinct types or Groups of influenza. A composition of the invention particularly comprises a combination of influenza neutralizing antibodies directed against circulating influenza virus strains. Composition(s) particularly comprise a combination of influenza neutralizing antibodies directed against circulating influenza virus strains, particularly anti-influenza A and anti-influenza B antibody. Composition(s) particularly comprise a combination of influenza neutralizing antibodies which combination is collectively directed against the appropriate and relevant circulating influenza virus strains, particularly directed collectively against influenza A H1 and H3 subtypes and against influenza B of the Yamagata and Victoria lineages. The composition(s) may comprise three or more neutralizing antibodies, provided that influenza viruses A and B are neutralized by the combination or antibodies.

Composition(s) particularly may comprise a combination of influenza neutralizing antibodies directed against circulating influenza virus strains, particularly an influenza A anti-H1 antibody, an influenza A anti-H3 antibody and an anti-influenza B antibody. Composition(s) may include influenza A antibody effective against or further effective against influenza H5 and H7 strains. The influenza antibody may be strain specific or non specific or pan-specific and may neutralize influenza A, including H1 subtype and/or H3 subtype and/or H5 and/or H7 or other influenza A strains or subtypes, and/or may neutralize influenza B, including Yamagata and/or Victoria lineages. The compositions may have identical components or distinct or additive components as alternative administration compositions, such as IV or IP, of the antibody.

In some embodiments, a composition is provided comprising a neutralizing antibody or fragment thereof, including a Fab fragment. A composition of the invention may comprise a combination of influenza virus neutralizing antibodies particularly a Group 1 antibody TRL053Mab53, a Group 2 antibody TRL579/Mab579 and a B antibody selected from TRL847, TRL845, TRL849, TRL848, TRL846, TRL854, TRL809 and TRL832, fragments thereof, synthetic or recombinant derivatives thereof, humanized or chimerized versions thereof, and antibodies having the heavy and light chain CDRs thereof.

The virus neutralizing antibody may particularly be an antibody fragment capable of neutralization. In an aspect, the antibody fragment lacks the Fc and/or lacks or has reduced effector function. The antibody fragment may be selected from Fab, Fab', and $F(ab')_2$. The virus neutralizing antibody or fragment may be derived from recombinant protein, may be recombinantly expressed, including as an active fragment, or may be derived or generated by other means or methods, including means or methods to provide neutralizing antibody or fragment(s) within the airway or respiratory tract, including by way of genetic material or DNA or DNA vector expression, such as by delivering DNA or RNA encoding neutralizing antibody or fragment(s) thereof.

A composition of the invention may further comprise a pharmaceutically acceptable excipient, carrier or diluent. The composition may comprise an excipient, carrier, diluents or additive suitable or appropriate for nasal or pulmonary delivery and for intranasal or inhalation administration. The composition may comprise an excipient, carrier, diluents or additive suitable or appropriate to stimulate or enhance immunological response and/or antibody-mediated cellular or system effects. The composition may comprise an immunological mediator or stimulator of the immune response.

The invention provides methods for treatment, prophylaxis or reduction or inhibition of transmission of virus, particularly influenza virus. The invention provides a method for treatment or prophylaxis of viral infection in a mammal exposed to, having contracted, or suffering from influenza virus comprising administering to the airway of the mammal, such as intranasally (IN) or via inhalation to said mammal, a combination of antibodies as provide in the invention. In a particular aspect, the combination comprises a Group 1 antibody TRL053/Mab53, a Group 2 antibody TRL579/Mab579 and a B antibody selected from TRL847, TRL845, TRL849, TRL848, TRL846, TRL854, TRL809 and TRL832, fragments thereof, synthetic or recombinant derivatives thereof, humanized or chimerized versions thereof, and antibodies having the heavy and light chain CDRs thereof.

In an aspect of the method, the monoclonal antibodies in the composition combination are all of the same IgG subtype and have identical or near identical constant region sequences. In a particular aspect, all antibodies in the combination are IgG1 antibodies.

In accordance with the method, the antibody combination can be administered post infection or after presumed infection, exposure or manifestation of clinical symptoms. In an aspect thereof, the antibody combination can be administered in a time period up to 8 hours post infection. Alternatively, the antibody combination is administered in a time period up to 24 hours post infection. In a further alternative, the antibody combination is administered in a time period up to 48 hours post infection. In a still further alternative, the antibody combination is administered in a time period up to 72 hours post infection. Antibody combination may be administered, including as a single dose or in multiple sequential doses, up to 8 hours post infection (8 hpi), 12 hpi, 18 hpi, 24 hpi, 36 hpi, 48 hpi, 72 hpi, 1 day post infection, 2 days post infection, 3 days post infection, 4 days post infection, 5 days post infection, 6 days post infection 7 days post infection, a week post infection, 10 days post infection, 2 weeks post infection, 3 weeks post infection, 4 weeks post infection, a month post infection, months post infection.

The antibody combination is administered in a single dose or three separate doses simultaneously or nearly simultaneously, so as to ensure that any one antibody as necessitated in the combination is effective on administration.

In some embodiments, a composition is provided comprising a combination of two, three, four, five, six, seven, eight, nine, ten, or more antibodies in any ratio. In some embodiments, a composition is provided comprising from 2-10, or 3-5, antibodies or fragments on per weight basis of approximately 10-80 wt %; 20-50 wt %; 25-40 wt %, of each antibody or fragment per total antibody or fragment weight in the composition. In a specific embodiment, a composition is provided comprising a substantially equal dose or ratio of a first, second and third antibody or fragment at approximately 33 wt %/±3 wt % of each of first, second and third antibodies or fragments per total wt of antibody or fragment in the composition. In a particular preferred aspect the antibodies in the combination are administered in a substantially equal dose ratio, at the same dosage amount or in a 1:1:1 wt. ratio or equal ratio.

In some embodiments, a composition comprising from 2-10 antibodies is provided wherein a single dose effective amount of each antibody in the combination may be of less than 10 mg/kg body weight, of less than 5 mg/kg body weight, of less than 2 mg/kg body weight, of 1 mg/kg body weight or less. The single dose amount of each antibody in the combination may be of less than 1 mg/kg body weight, of less than 0.5 mg/kg, of less than 0.1 mg/kg, of less than 0.05 mg/kg. Multiple doses or the antibody combination may be administered. Each combination dose may be the same or the doses may differ, such as an initial higher dose, followed by lower doses, or an initial lower dose, followed by higher doses. The single dose or doses or any dose may be of less than 1 mg/kg body weight, of less than 0.5 mg/kg, of less than 0.1 mg/kg, of less than 0.05 mg/kg. The initial dose may be greater than 1 mg/kg and further or subsequent doses may be lower or may be less than 1 mg/kg.

Antibody may be administered to the airway, such as intranasally or via inhalation, in multiple doses, wherein each antibody in each individual combination dose is of less than 1 mg/kg per dose. In such an aspect, the multiple doses may be administered at least 2 hours apart and up to 72 hours or later after presumed infection, exposure or manifestation of clinical symptoms. Thus the antibody doses may be administered minutes or hours or days apart. The antibody doses may be administered post infection or post presumed infection or exposure hours or days apart. The antibody doses may be administered post infection or post presumed infection or exposure and up to 2, 4, 6, 8, 12, 24, 36, 48 or 72 hours after.

The administration protocol or method of the invention may particularly comprise a first administration of antibody to the airway or respiratory tract, particularly by inhalation or intranasal administration of antibody, combined with or followed by a second or one or more additional administration(s) which is or are not via the inhalation or intranasal route, for example systemic delivery, such as IP or IV administration(s). Thus the method may comprise additional administration IP or IV of a virus specific monoclonal antibody wherein the antibody additionally administered is a neutralizing or non-neutralizing antibody. In this instance, initial dose may be with the combination of antibodies of the invention, followed by a single antibody directed to the virus subtype of the infection, including as determined by clinical or diagnostic assays. Thus, the first dose of the combination of antibodies is initially effective, irrespective of the influenza virus type. Once virus type is determined, a second or additional dose(s) of the combination, an altered ratio of combination, a single directed antibody may be administered. The second or additional dose(s) may be administered to the airway, such as IH or IN, or may be administered systemically. The antibody additionally administered systemically, such as IP or IV, may be the same antibody as administered IN or via inhalation or may be a different or altered antibody as administered IN or via inhalation. The antibody additionally administered, for example via IP or IV, may be administered simultaneously, sequentially, or subsequently to the IN or inhalation administered antibody. Any such subsequent administration may be hours later and may be 2, 4, 6, 8, 12 or up to 24 hours later. Subsequent administration may be days later and may be 1 day, 2 days, or 3 days later. Subsequent administration may be days later and may be up to 7 days later, a week later, or weeks later. Subsequent administration may be in a single dose or multiple doses hours and/or days and/or weeks later.

In a further aspect, the invention provides a protocol for administration of a combination of antibodies directed against influenza A and influenza B virus, comprising administering a first airway dose, such as intranasal or inhalation dose, of the combination of antibodies provided in the invention, and subsequently or simultaneously administering a second dose, or one or more additional dose(s), of antibody which is not administered to the airway or respiratory tract, and may be administered intraperitoneally or intravenously, wherein the antibody of the second dose or additional dose(s) is the same or a different antibody as an antibody in the combination of the first dose. The antibody of the second dose or additional dose(s) may be an altered or modified antibody which is altered or modified to be more effective or efficacious IV or IP. In an aspect, the antibody of the first dose may lack effector function, such as an Fab antibody, and the antibody of the second dose may have effector function, have Fc, or may be modified to have enhanced effector function.

The protocol may include multiple doses of the antibody combination of the invention via the inhalation or intranasal route and may include multiple doses of the same combination, one or more antibody of the combination, or an alternative antibody via the IP or IV route. In an aspect of the protocol, the subject or patient being administered antibody may be monitored, such as for clinical manifestation of disease or viral infection, and the dose or doses may be altered, reduced or enhanced or administered closer or further apart depending on the status of the patient or subject and of the infection or illness.

In an aspect of the protocol, the influenza virus may be influenza A or influenza B or an unknown or undetermined influenza virus. The antibody of the second dose, which is not administered to the respiratory tract, may be a neutralizing or a non-neutralizing antibody, and may have effector function or enhanced effector function.

In an aspect of the protocol, the first intranasal or inhalation dose may comprise the combination antibodies of the present invention, each less than 1 mg/kg, less than 0.5 mg/kg, less than 0.1 mg/kg. The second or additional IP or IV dose is particularly administered at a higher dose than the first intranasal or inhalation dose. The second or additional IP or IV dose is particularly administered at a dose at least 10 fold higher of amount of each or any antibody than the first intranasal or inhalation dose. The second or additional IP or IV dose may be at least 1 mg/kg, at least 5 mg/kg, at least 10 mg/kg, at least 15 mg/kg, or greater than 10 mg/kg, or greater than 20 mg/kg, or greater than 50 mg/kg.

In a further aspect of the protocol, the first intranasal or inhalation dose may be less than 1 mg/kg of each antibody in the combination and the second IP or IV dose at least 10 fold higher in mg/kg than the first intranasal dose. In a further aspect of the protocol, the first intranasal or inhalation dose may be less than 1 mg/kg or each antibody in the combination and the second IP or IV dose at least 50 fold higher in mg/kg than the first intranasal dose. In an additional aspect, the first intranasal or inhalation dose may be less than 0.5 mg/kg of each antibody in the combination and the second IP or IV dose at least 5 mg/kg.

The dose of each antibody in the combination in the first intranasal or inhalation dose may be 10 mg/kg or less than 10 mg/kg and administered within 24 hours after presumed infection, exposure or manifestation of clinical symptoms. The dose of each antibody in the combination in the first intranasal or inhalation dose may be 10 mg/kg or less than 10 mg/kg and administered within 48 hours after presumed infection, exposure or manifestation of clinical symptoms. The dose of each antibody in the combination in the first intranasal or inhalation dose may be 10 mg/kg or less than 10 mg/kg and administered within 72 hours after presumed infection, exposure or manifestation of clinical symptoms.

Another aspect of the invention is a method for inhibiting transmission of respiratory virus comprising administering the combination of antibodies of the present invention to the airway, such as intranasally or via inhalation, to a subject exposed to, at risk of exposure to or showing clinical signs of influenza virus infection the instant combination of antibodies wherein each antibody is administered at a unit dose of 1 mg/kg or less. The unit dose of each antibody in the combination may be less than 10 mg/kg or less than 1 mg/kg. The unit dose of the method may be less than 0.5 mg/kg or less than 0.1 mg/kg or less than 0.05 mg/kg.

The invention provides antibody combination compositions, or compositions of a combination of antibodies, particularly influenza antibodies and particularly monoclonal influenza antibodies, suitable or selected for pulmonary administration wherein the combination of antibodies comprises, includes or consists of antibodies directed against the circulating virus strains consisting of seasonal and pandemic subtypes. For example in as much as seasonal influenza circulating strains are currently influenza B (Yamagata lineage), influenza B (Victoria lineage), influenza A H1 subtype and influenza A H3 subtype, a combination composition of the invention is provided having or comprising antibody(ies) directed against each of Influenza B (Yamagata), influenza B (Victoria), influenza A H1 subtype and influenza A H3 subtype. The invention includes the incorporation of other antibodies into a cocktail to provide additional specific coverage to other subtypes, for example the H7 subtype.

In some embodiments, a composition is provided comprising a combination of a Group 1 antibody TRL053/Mab53, a Group 2 antibody TRL579/Mab579 and one or more anti-influenza B antibodies selected from TRL784, TRL794, TRL798, TRL799, TRL809, TRL811, TRL812, TRL813, TRL823, TRL832, TRL833, TRL834, TRL835, TRL837, TRL839, TRL841, TRL842, TRL845, TRL846, TRL847, TRL848, TRL849, TRL851, TRL854, TRL856, and TRL858, immunoreactive fragments thereof, synthetic or recombinant derivatives thereof, humanized or chimerized versions thereof, and antibodies having the heavy and light chain CDRs thereof.

In some embodiments, a pharmaceutical composition is provided comprising a combination a Group 1 antibody TRL053/Mab53, a Group 2 antibody TRL579/Mab579 and a B antibody selected from TRL845, TRL846, TRL847, TRL848, TRL849, and TRL854, or fragments thereof, synthetic or recombinant derivatives thereof, humanized or chimerized versions thereof, and antibodies having the heavy and light chain CDRs thereof.

In some embodiments, a pharmaceutical composition is provided comprising a combination a Group 1 antibody TRL053/Mab53, a Group 2 antibody TRL579/Mab579 and a B antibody selected from TRL845, TRL847, and TRL849, or fragments thereof, synthetic or recombinant derivatives thereof, humanized or chimerized versions thereof, and antibodies having the heavy and light chain CDRs thereof. In some embodiments, an anti-influenza composition is provided comprising a combination of influenza monoclonal antibodies or binding fragments thereof comprising: (a) an antibody or fragment thereof comprising a heavy chain amino acid sequence comprising CDR domain sequences HCDR1/HCDR2/HCDR3 of SEQ ID NOS: 11, 12, 13 and a light chain amino acid sequence comprising CDR domain sequences LCDR1/LCDR2/LCDR3 of SEQ ID NOS: 14, 15, 16; (b) an antibody or fragment thereof comprising a heavy chain amino acid sequence comprising CDR domain sequences HCDR1/HCDR2/HCDR3 of SEQ ID NOS: 21, 22, 23 and a light chain amino acid sequence comprising CDR domain sequences LCDR1/LCDR2/LCDR3 of SEQ ID NOS: 24, 25, 26; and (c) an antibody or fragment thereof comprising a heavy chain amino acid sequence and a light chain amino acid sequence comprising heavy and light chain CDR domain sequences, HCDR1/HCDR2HCDR3, and LCDR1/LCDR2/LCDR3, respectively, selected from:

(i) SEQ ID NOS: 71, 72, 73, and SEQ ID NOS: 74, 75, 76;
(ii) SEQ ID NOS: 91, 92, 93, and SEQ ID NOS: 94, 95, 96;
(iii) SEQ ID NOS: 101, 102, 103, and SEQ ID NOS: 104, 105, 106;
(iv) SEQ ID NOS: 121, 122, 123, and SEQ ID NOS: 124, 125, 126;
(v) SEQ ID NOS: 181, 182, 183, and SEQ ID NOS: 184, 185, 186;
(vi) SEQ ID NOS: 191, 192, 193, and SEQ ID NOS: 194, 195, 196;
(vii) SEQ ID NOS: 201, 202, 203, and SEQ ID NOS: 204, 205, 206;
(viii) SEQ ID NOS: 211, 212, 213, and SEQ ID NOS: 214, 215, 216;
(ix) SEQ ID NOS: 221, 222, 223, and SEQ ID NOS: 224, 225, 226;
(x) SEQ ID NOS: 231, 232, 233, and SEQ ID NOS: 234, 235, 236;
(xi) SEQ ID NOS: 241, 242, 243, and SEQ ID NOS: 244, 245, 246;
(xii) SEQ ID NOS: 261; 262, 263, and SEQ ID NOS: 264, 265, 266; and
(xiii) SEQ ID NOS: 271, 272, 273, and SEQ ID NOS: 274, 275, 276, respectively.

The present invention contemplates and exemplifies highly homologous variants thereof comprising 1 to 3 amino acid substitutions in one or more CDR domain sequence, said variants capable of binding to and inhibiting influenza virus, wherein the composition is effective against Group 1 and 2 influenza A viruses and influenza B viruses.

In specific embodiments, compositions are provided comprising a combination of antibodies selected from: (a) an antibody or fragment thereof comprising a heavy chain and light chain CDR sequences, HCDR1/HCDR2/HCDR3, and LCDR1/LCDR2/LCDR3, respectively, of SEQ ID NOS: 11, 12, 13 and SEQ ID NOS: 14, 15, 16; an antibody or fragment thereof comprising HCDR1/HCDR2/HCDR3, and LCDR1/LCDR2/LCDR3, respectively, of SEQ ID NOS: 21, 22, 23 and SEQ ID NOS: 24, 25, 26, and an antibody or fragment thereof comprising HCDR1/HCDR2/HCDR3, and LCDR1/LCDR2/LCDR3, respectively, of SEQ ID NOS: 201, 202, 203 and SEQ ID NOS: 204, 205, 206; (b) an antibody or fragment thereof comprising a heavy chain and light chain CDR sequences, HCDR1/HCDR2/HCDR3, and LCDR1/LCDR2/LCDR3, respectively, of SEQ ID NOS: 11, 12, 13 and SEQ ID NOS: 14, 15, 16; an antibody or fragment thereof comprising HCDR1/HCDR2/HCDR3, and LCDR1/LCDR2/LCDR3, respectively, of SEQ ID NOS: 21, 22, 23 and SEQ ID NOS: 24, 25, 26, and an antibody or fragment thereof comprising HCDR1/HCDR2/HCDR3, and LCDR1/LCDR2/LCDR3, respectively, of SEQ ID NOS: 221, 222, 223 and SEQ ID NOS: 224, 225, 226; (c) an antibody or fragment thereof comprising a heavy chain and light chain CDR sequences, HCDR1/HCDR2/HCDR3, and LCDR1/LCDR2/LCDR3, respectively, of SEQ ID NOS: 11, 12, 13 and SEQ ID NOS: 14, 15, 16; an antibody or fragment thereof comprising HCDR1/HCDR2/HCDR3, and LCDR1/LCDR2/LCDR3, respectively, of SEQ ID NOS: 21, 22, 23 and SEQ ID NOS: 24, 25, 26, and an antibody or fragment thereof comprising HCDR1/HCDR2/HCDR3, and LCDR1/LCDR2/LCDR3, respectively, of SEQ ID NOS: 231, 232, 233 and SEQ ID NOS: 234, 235, 236; (d) an antibody or fragment thereof comprising a heavy chain and light chain CDR sequences, HCDR1/HCDR2/HCDR3, and LCDR1/LCDR2/LCDR3, respectively, of SEQ ID NOS: 11, 12, 13 and SEQ ID NOS: 14, 15, 16; an antibody or fragment thereof comprising HCDR1/HCDR2/HCDR3, and LCDR1/LCDR2/LCDR3, respectively, of SEQ ID NOS: 21, 22, 23 and SEQ ID NOS: 24, 25, 26, and an antibody or fragment thereof comprising HCDR1/HCDR2/HCDR3, and LCDR1/LCDR2/LCDR3, respectively, of SEQ ID NOS: 241, 242, 243 and SEQ ID NOS: 244, 245, 246; or (e) an antibody or fragment thereof comprising a heavy chain and light chain CDR sequences, HCDR1/HCDR2/HCDR3, and LCDR1/LCDR2/LCDR3, respectively, of SEQ ID NOS: 11, 12, 13 and SEQ ID NOS: 14, 15, 16; an antibody or fragment thereof comprising HCDR1/HCDR2/HCDR3, and LCDR1/LCDR2/LCDR3, respectively, of SEQ ID NOS: 21, 22, 23 and SEQ ID NOS: 24, 25, 26, and an antibody or fragment thereof comprising HCDR1/HCDR2/HCDR3, and LCDR1/LCDR2/LCDR3, respectively, of SEQ ID NOS: 261, 262, 263 and SEQ ID NOS: 264, 265, 266.

In some embodiments, antibodies in the combination may be directed against more than one influenza strain or subtype, such as indicated in FIG. 3 and demonstrated herein. Antibody Mab53 is effective against influenza A H1, H9, H7 and H5 subtypes of Group 1 and 2. Antibody Mab579 is effective against H3 and H7 subtypes. Thus, while the presently circulating influenza strains are H1, H3 and B types, combinations having efficacy against additional strains and subtypes, including subtypes which may arise and emerge in a new or single flu season, can be generated and are herein provided.

The compositions may particularly be formulated or contain lower doses or amounts of antibody than any alternative dosage or administration form, such as IP or IV. Thus, compositions of use in the present invention may comprise a 5 fold, 10 fold, 20 fold, 50 fold, 100 fold, greater than 10 fold, greater than 100 fold reduced amount of neutralizing antibody versus or in comparison to compositions thereof for alternative administration, particularly IP or IV administration.

In some embodiments, compositions are provided comprising a dose of each antibody that is intended for pulmonary administration, particularly intranasal administration, in an amount less than 1 mg/kg on the basis of the body weight of a mammal. In some embodiments, compositions are provided comprising antibody amounting to administration of less than 10 mg/kg, less than 5 mg/kg, or less than 1 mg/kg on the basis of the body weight of a human. Compositions of the present invention may particularly comprise a dose of antibody that is intended for administration, particularly intranasally, in an amount less than 1 mg/kg, less than 0.5 mg/kg, less than 0.1 mg/kg, less than 0.05 mg/kg, less than 0.01 mg/kg, less than 0.005 mg/kg, less than 0.0025 mg/kg, less than 0.001 mg/kg on the basis of the body weight of a mammal, including a clinically relevant mammal, such as a mouse, dog, horse, cat or a human. In some embodiments, a therapeutically effective dose is selected from about 100 mg/kg, 50 mg/kg, 10 mg/kg, 3 mg/kg, 1 mg/kg, or 1 mg/kg. In some aspects, an effective prophylactic dose or post-exposure prophylactic dose is selected from about 1 mg/kg/0.1 mg/kg or about 0.01 mg/kg.

One of skill in the art can determine, including on the basis of efficacy in animal models and in consideration of clinical and physiological response, viral load and viral transmission rates, the appropriate and efficacious dose in a mammal, including a human. Thus, the invention and dosing parameters are not limited by the examples provided herein or the specific doses exemplified. The present invention demonstrates that inhalation or intranasal dosing is a preferred alternative in terms of efficacy and in reducing, limiting or blocking the clinically manifested effects of a virus infection, including influenza virus infection. Inhalation or intranasal administration of neutralizing antibodies provides improved and enhanced efficacy versus other routes of administration, including IP or IV, which would not have been expected or predicted. The enhanced efficacy through pulmonary delivery permits the feasibility of incorporating multiple mAbs into a cocktail, enabling the development of a cocktail for all influenza types/subtypes. The amounts and timing of dosing via IN or inhalation routes can be further assessed and determined by one of skill in the art. The studies provided herein demonstrate that IN or inhalation administration is more efficacious at lower doses versus IP or IV and that administration can occur days following infection and still retain efficacy.

Doses and dose ranges applied and demonstrated herein in mouse models may be converted or applied as appropriate and using parameters known in the art by the skilled artisan or clinical or medical professional. Thus, mg/kg dosing in a mouse can be extrapolated to comparable or reasonably equivalent dosing to a human or other animal. For example, the average weight of a laboratory mouse is 20 g whereas the average weight of a human is 70 kg.

It is routine practice in clinical research to convert animal doses into human doses, and that the skilled person would have a strong expectation that such converted dose(s) would be successful in humans. Interspecies scaling and predicting pharmacokinetic parameters in humans have been described (for example, Mahmood et al. (2003) J Clin Pharmacol 43: 692-697; Mordenti (1986) Journal of Pharmaceutical Sciences, 75:1028-1040). For example, therapeutic levels are often assumed to parallel toxicity, and so the conversion factors applied to converting animal toxicity to human toxicity are commonly used to convert minimum effective doses in animals to minimum effective doses in humans. Further, the FDA provides a "Guidance for Industry" which provides conversion factors for estimating the maximum safe starting dose in clinical trials for therapeutics, including factors used to convert animal (mouse) doses to human doses (such as in one instance multiply the mouse dose by 0.08).

The phrase "pharmaceutically acceptable" refers to molecular entities and compositions that are physiologically tolerable and do not typically produce an allergic or similar untoward reaction, such as gastric upset, dizziness and the like, when administered to a human.

The present invention further contemplates therapeutic compositions useful in practicing the therapeutic methods of this invention. A subject therapeutic composition includes, in admixture, a pharmaceutically acceptable excipient (carrier) and one or more of an antibody or active fragment thereof, particularly a neutralizing antibody, polypeptide analog thereof or fragment thereof, as described herein as an active ingredient. In a preferred embodiment, the composition comprises an antibody or fragment capable of neutralizing virus, particularly influenza virus, within a target cell or in a subject or patient.

The preparation of therapeutic compositions which contain antibodies, polypeptides, analogs or active fragments as active ingredients is well understood in the art. Typically, such compositions are prepared for administration either as liquid solutions or suspensions, however, solid forms suitable for solution in, or suspension in, liquid prior to administration can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents which enhance the effectiveness of the active ingredient.

An antibody, polypeptide, analog or active fragment can be formulated into the therapeutic composition as neutralized pharmaceutically acceptable salt forms. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The therapeutic antibody-, polypeptide-, analog- or active fragment-containing compositions are conventionally administered, as by administration of a unit dose, for example. The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i.e., carrier, or vehicle.

In some embodiments, the carrier is selected from any carrier known in the art suitable for pulmonary administration. In some embodiments, the carrier is selected appropriate carriers for intranasal administration, for example, as disclosed in Csaba et al., Adv Drug Deliv Rev. 2009, 61(2):140-157, which is incorporated herein by reference. In some embodiments, the carrier is a nano- or micro-particulate system. In some embodiments, the carrier is selected from, or comprises, one or more of degradable starch, soluble starch, polystyrene, dextran, chitosan, microcrystalline cellulose (MCC), hydroxypropyl cellulose (HPC), hydroxypropylmethycellulose (HPMC), carbomer, Carbopol® 974P, maltodextran wax-like maize starch, alginate, Sephadex®, poly(vinyl alcohol), gelatin polymers, polylactic acid nanoparticles coated with a hydrophilic polyethyleneglycol coating (PEG-PLA nanoparticles) (Vila et al., J Aerosol Med 2004; 17(2):174-185); low molecular weight chitosan nanoparticles (Vila et al., Eur J Pharm Biopharm 2004 January; 67(l):123-131); polyacrylate polymer-based particulates (Zaman et al., Curr Drug Deliv 2010 April; 7(2):118-124). In some embodiments, the carrier is phosphate buffered saline (PBS). Intranasal delivery systems are described in Ozsoy et al., Molecules 2009, 14, 3754-3779, incorporated herein by reference.

In some embodiments, said nanoparticles are delivered to the lungs while avoiding liver and spleen through adsorption on red blood cells by the technique of Anselmo et al., ACSNano 2013, published online 10.1021/nn404853z. In this method, nanoparticles (e.g. spherical nanoparticles, e.g. 200 nm or 500 nm in diameter), for example, are attached to RBCs by incubation at varying particle/RBC ratios up to 100/1.

In some embodiments, the potency and activity of the antibody or fragment is formulated in a solution, powder or suspension that can be stabilized without excipients or with excipients that do not affect the potency of the active ingredient(s) and that are not toxic to the lungs. Antibodies may denature to oxidative or hydrolytic conditions. In some embodiments, aqueous formulations for delivery of antibodies by nasal sprays or by injection are provided with chelation agents, or complexing agents, such as caffeine, dextran or cyclodextrans, or as otherwise provided herein, to stabilize the antibody or fragment in solution. Further details of such excipients and aerosolized or nebulized compositions can be found for example in WO 2005/025506; Maillet, A. et al 2008 Phar, Res. 25(6):1318-1326; Hatcha, J et al, Am. J. Respir. Cell. Mol. Biol. 2012 47(5):709-717, all incorporated by reference.

Some stabilization agents are incompatible with pulmonary delivery because such stabilization agents cause local inflammation or are acutely toxic. In some embodiments, to further inhibit the degradation of active ingredient solutions, the antibody or fragment formulations are sealed in darkglass vials that must be opened with a specialized opener, filtered to remove glass shards, and transferred to injector or spray applicator just before use.

In other embodiments, the active ingredient solution can be prepared just prior to use by mixing active ingredient powder with injection fluid such as in a biphasic autoinjector format (powder portion is mixed with the liquid within a glass vial, syringe or blister package (such as the Pozen MT300). Such extemporaneous formulation approaches could be attempted to generate a solution for pulmonary delivery by jet or ultrasonic nebulization. However, any of the known nebulization processes used to generate inhalation aerosols from aqueous solutions expose the active ingredient to sufficient heat and oxygen concentrations to cause immediate, variable changes in potency and activity. Because of these intrinsic difficulties in obtaining or aerosolizing a stable formulation, active ingredient has not been suitable for administration via pulmonary inhalation. Another method of aerosol deliver uses the pressurized metered dose inhaler (pMDI) wherein a halocarbon propellant forces a solution or suspension of the antibody or fragment through a small orifice generating a fine inhalable mist consisting of the antibody or fragment within the propellant droplets. To make stable pMDI formulations, the antibody or fragment must be able to form solutions or fine particle suspensions that are stable in and physicochemically compatible with the propellant and the pMDI valve apparatus. Solution stability and lung toxicity issues described above for nasal or injection solutions are equally applicable to pMDI formulations, and the added requirement of propellant compatibility prohibits the use of accepted lung compatible reagents such as water or alcohol. For suspensions, fine particles of less than approximately 5.8 microns (mass median aerodynamic diameter necessary for deep lung penetration) are required, and the particle must be stable in the suspension. Such particles are generated from the bulk antibody or fragment by attrition processes such as grinding, micronizing, milling, or by multiphase precipitation processes such as spray drying, solution precipitation, or lyophilization to yield powders that can be dispersed in the propellant. These processes often directly alter the physicochemical properties of the antibody or fragment through thermal or chemical interactions. As some active ingredients can be unstable, these process have not proven suitable for generating powders that can be redispersed in the propellant, or if the powder is initially dispersible, the particles grow in size over time, or change their chemical composition on exposure to the formulation over time. This instability caused changes in potency, activity, or increases the particle size above 3.0 microns making pMDI suspension formulation approaches unsuitable for active ingredient aerosol delivery. An additional method to generate respirable aerosols is to use dry powder inhalers wherein a powdered formulation of the antibody or fragment is dispersed in the breath of the user and inhaled into the lungs. The difficulties described above for pMDI suspension formulations are equally applicable to generating stable dry powder formulation. Clearly, the art is lacking a suitable formulation for inhalation delivery of active ingredient. The present disclosure describes novel, stable formulations of active ingredient, or pharmaceutically acceptable salts thereof, to administer dry powders and propellant suspensions via pulmonary aerosol or nasal spray inhalation. Such formulations may be used for the treatment of various disease states and conditions, including, but not limited to, migraine headaches. In addition, methods of producing the novel formulations of active ingredient, or pharmaceutically acceptable salts thereof, are also described.

Active components which are administered by inhalation must penetrate deep into the lungs in order to show topical, or alternatively, systemic action. In order to achieve this, the particles of the active antibody or fragment must have a diameter which does not exceed approximately 0.5-5.8 µm mass mean aerodynamic diameter (MMAD). Particles of this optimal size range are rarely produced during the crystallization step, and secondary processes are required to generate particles in the 0.5-5.8 µm range. Such secondary processes include, but are not limited to, attrition by jet milling, micronization and mechanical grinding, multiphase precipitation such as solution precipitation, spray drying, freeze-drying or lyophilization. Such secondary processes involve large thermal and mechanical gradients which can directly degrade the potency and activity of active antibody or fragment, or cause topological imperfections or chemical instabilities that change the size, shape or chemical composition of the particles on further processing or storage. These secondary processes also impart a substantial amount of free energy to the particles, which is generally stored at the surface of the particles. This free energy stored by the particles produces a cohesive force that causes the particles to agglomerate to reduce this stored free energy.

Agglomeration processes can be so extensive that respirable, active antibody or fragment particles are no longer present in the particulate formulation or can no longer be generated from the particulate formulation due to the high strength of the cohesive interaction. This process is exacerbated in the case of inhalation delivery since the particles must be stored in a form suitable for delivery by an inhalation device. Since the particles are stored for relatively long periods of time, the agglomeration process may increase during storage. The agglomeration of the particles interferes with the re-dispersion of the particles by the inhaler device such that the respirable particles required for pulmonary delivery and nasal delivery cannot be generated. Additionally, most of the pharmaceutically customary methods used to overcome the agglomeration effect, such as the use of carriers and/or excipients, cannot be used in pharmaceutical forms for inhalation, as the pulmonary toxicological profile of these substances is undesirable.

The present disclosure describes novel, stable formulations of active ingredient, or pharmaceutically acceptable salts thereof. (referred to herein as DHE) to administer dry powders and propellant suspensions via pulmonary aerosol inhalation or nasal spray inhalation. In one embodiment, DHE is used as the mesylate salt. The DHE powder is generated using a supercritical fluid processes. Supercritical fluid processes offer significant advantages in the production of DHE particles for inhalation delivery. Importantly, supercritical fluid processes produce respirable particles of the desired size in a single step, eliminating the need for secondary processes to reduce particle size. Therefore, the respirable particle produced using supercritical fluid processes have reduced surface free energy, which results in a decreased cohesive forces and reduced agglomeration. The particles produced also exhibit uniform size distribution. In addition, the particles produced have smooth surfaces and reproducible crystal structures which also tend to reduce agglomeration. Such supercritical fluid processes may include rapid expansion (RES), solution enhanced diffusion (SEDS), gas-anti solvent (GAS), supercritical antisolvent (SAS), precipitation from gas-saturated solution (PGSS), precipitation with compressed antisolvent (PCA), aerosol solvent extraction system (ASES), or any combinations of the foregoing. The technology underlying each of these supercritical fluid processes is well known in the art and will not be repeated in this disclosure. In one specific embodiment, the supercritical fluid process used is the SEDS method as described by Palakodaty et al. in US Application 20030109421. The supercritical fluid processes produce dry particulates which can be used directly by premetering into a dry powder inhaler (DPI) format, or the particulates may be suspended/dispersed directly into a suspending media, such as a pharmaceutically acceptable propellant, in a metered dose inhaler (MDI) format. The particles produced may be crystalline or may be amorphous depending on the supercritical fluid process used and the conditions employed (for example, the SEDS method is capable of producing amorphous particles). As discussed above, the particles produced have superior properties as compared to particles produced by traditional methods, including but not limited to, smooth, uniform surfaces, low energy, uniform particle size distribution and high purity. These characteristics enhance physicochemical stability of the particles and facilitate dispersion of the particles, when used in either DPI format or the MDI format. The particle size should be such as to permit inhalation of the DHE particles into the lungs on administration of the aerosol particles. In one embodiment, the particle size distribution is less than 20 microns. In an alternate embodiment, the particle size distribution ranges from about 0.050 microns to 10.000 microns MMAD as measured by cascade impactors; in yet another alternate embodiment, the particle size distribution ranges from about and preferably between 0.400 and 3.000 microns MMAD as measured by cascade impactors. The supercritical fluid processes discussed above produce particle sizes in the lower end of these ranges. In the DPI format the DHE particles can be electrostatically, cryometrically, or traditionally metered into dosage forms as is known in the art. The DHE particle may be used alone (neat) or with one or more pharmaceutically acceptable excipients, such as carriers or dispersion powders including, but not limited to, lactose, mannose, maltose, etc., or surfactant coatings. In one prefened formulation, the DHE particles are used without additional excipients. One convenient dosage form commonly used in the art is the foil blister packs. In this embodiment, the DHE particles are metered into foil blister packs without additional excipients for use with a DPI. Typical doses metered can range from about 0.050 milligrams to 2.000 milligrams, or from about 0.250 milligrams to 0.500 milligrams. The blister packs are burst open and can be dispersed in the inhalation air by electrostatic, aerodynamic, or mechanical forces, or any combination thereof, as is known in the art. In one embodiment, more than 25% of the premetered dose will be delivered to the lungs upon inhalation; in an alternate embodiment, more 50% of the premetered dose will be delivered to the lungs upon inhalation; in yet another alternate embodiment, more than 80% of the premetered dose will be delivered to the lungs upon inhalation. The respirable fractions of DHE particles (as determined in accordance with the United States Pharmacopoeia, chapter 601) resulting from delivery in the DPI format range from 25% to 90%, with residual particles in the blister pack ranging from 5% or the premetered dose to 55% of the premetered dose. In the MDI format the particles can be suspended/dispersed directly into a suspending media, such as a pharmaceutically acceptable propellant. In one particular embodiment, the suspending media is the propellant. It is desirable that the propellant not serve as a solvent to the DHE particles. Suitable propellants include Ct_4 hydrofluoroalkane, such as, but not limited to 1,1,1,2-tetrafluoroethane (HFA 134a) and 1,1,1,2,3,3,3-heptafuoro-n-propane (HFA 227) either alone or in any combination. Carbon dioxide and alkanes, such as pentane, isopentane, butane, isobutane, propane and ethane, can also be used as propellants or blended with the C\ hydrofluoroalkane propellants discussed above. In the case of blends, the propellant may contain from 0-25% of such carbon dioxide and 0-50% alkanes. In one embodiment, the DHE particulate dispersion is achieved without surfactants. In an alternate embodiment, the DHE particulate dispersion may contain surfactants if desired, with the surfactants present in mass ratios to the DHE ranging from 0.001 to 10. Typical surfactants include the oleates, stearates, myristates, alkylethers, alklyarylethers, sorbates and other surfactants used by those skilled in the art of formulating antibody or fragment s for delivery by inhalation, or any combination of the foregoing. Specific surfactants include, but are not limited to, sorbitan monooleate (SPAN-80) and isopropyl myristate. The DHE particulate dispersion may also contain polar solvents in small amounts to aid in the solubilization of the surfactants, when used. Suitable polar s include C2-6 alcohols and polyols, such as ethanol, isopropanol, polypropylene glycol and any combination of the foregoing. The polar antibody or fragment s may be added at mass ratios to the propellant ranging from 0.0001% to 4%. Quantities of polar solvents in excess of 4% may react with the DHE or solubilize the DHE. In one particular embodiment, the polar antibody or fragment is ethanol used at a mass ratio to the propellant from 0.0001 to 1%. No additional water or hydroxyl containing antibody or fragment s are added to the DHE particle formulations other than is in equilibrium with pharmaceutically acceptable propellants and surfactants. The propellants and surfactants (if used) may be exposed to water of hydroxyl containing antibody or fragment s prior to their use so that the water and hydroxyl containing antibody or fragment s are at their equilibrium points. Standard metering valves (such as from Neotechnics, Valois, or Bespak) and canisters (such as from PressPart or Gemi) can be utilized as is appropriate for the propellant/surfactant composition. Canister fill volumes from 2.0 milliliters to 17 milliliters may be utilized to achieve dose counts from one (1) to several hundred actuations. A dose counter with lockout mechanism can optionally be provided to limit the specific dose count irrespective of the fill volume. The total mass of DHE in the propellant suspension will typically be in the range of 0.100 milligram to 2.000 milligram of DHE per 100 microliters of propellant. Using standard MDI metering valves ranging from 50 to 100 microliters dosing will result in metered doses ranging from 0.050 micrograms to 1.000 microgram per actuation. An actuator with breath actuation can preferably be used to maximize inhalation coordination, but it is not mandatory to achieve therapeutic efficacy. The respirable fraction of such MDIs would range from 25% to 75% of the metered dose (as determined in accordance with the United States Pharmacopoeia, chapter 601).

As provided herein, the unit dose of neutralizing antibody for intranasal administration effective and useful for treatment or prophylaxis of virus, particularly influenza virus, is comparatively reduced versus that indicated or required for alternative administration, such as that required for IP or IV administration. Thus in an aspect hereof is provided an antibody composition for administration, particularly intranasal administration, wherein the unit dose is reduced by orders of magnitude, particularly several or multiple orders of magnitude versus that indicated or required for alternative administration, such as that required for IP or IV administration. Thus in an aspect hereof is provided an antibody composition for administration, particularly intranasal administration, wherein the unit dose is at least 10 fold, 10 fold, 20 fold, 25 fold, 50 fold, at least 100 fold, 100 fold, 500 fold, up to 1000 fold reduced. In particular the composition is thus reduced in comparison to an equivalent unit dose for IP or IV administration, particularly for the same or comparable indication or effect and/or activity. The IN unit dose may be combined with IP or IV dose for improved efficacy.

The compositions are administered in a manner compatible with the dosage formulation, and in a therapeutically effective amount. The quantity to be administered depends on the subject to be treated, capacity of the subject's immune system to utilize the active ingredient, and degree of inhibition or neutralization of virus desired. Precise amounts of active ingredient required to be administered depend on the judgment of the practitioner and are peculiar to each individual. However, suitable dosages may range from about 0.001 to 10, preferably about 0.005 to about 1, less than 1, less than 0.5, less than 0.1, less than 0.05, less than 0.01, and more preferably below one, below 0.5, blow 0.1, milligrams of active ingredient per kilogram body weight of individual per dose for intranasal administration. Suitable regimes for initial administration and follow-on administration are also variable. In one regime there is an initial administration followed by repeated subsequent dose(s), a single or multiple subsequent doses, at one or more hour intervals by a subsequent injection or other administration.

Initial administration IN may be followed by administration of higher doses of antibody IP or IV or by other suitable route. In an aspect of the disclosure a novel dosing approach or parameter is provided wherein a patient or subject is administered neutralizing antibody intranasally, and either concomitantly, subsequently or later administered a neutralizing or non-neutralizing antibody by IP or IV administration.

Additional Combinations

In an aspect of the present embodiments, a virus binding antibody or binding a fragment thereof, particularly wherein the antibody or fragment is neutralizing, may be combined with agents or drugs to form an antibody-drug or antibody-agent conjugate for respiratory tract or airway administration, including inhalation or intranasal administration, for use in embodiments disclosed herein. The drug or agent combined with or conjugated to the antibody or fragment may be a virus neutralizing drug or agent.

Alternatively, the antibody or combination may be administered along with an antiviral agent, antiviral therapeutic, an anti-influenza drug or agent, particularly including an oral anti-influenza drug. An anti-influenza agent may be a neuraminidase inhibitor. The anti-influenza agent may be selected from Tamiflu and Relenza. An anti-influenza agent may be an M2 inhibitor, such as amantadine or rimantadine. Additional agents for combination may be selected from an antiviral therapeutic, viral replication inhibitor, protease inhibitor, polymerase inhibitor, hemagglutinin inhibitor, bronchodilator (e.g., albuterol, levalbuterol, salmeterol), or inhaled corticosteroid. The antiviral agent may be a viral binding agent or viral binding inhibitor. In an aspect thereof, the viral binding inhibitor may be an antibody capable of binding influenza virus and inhibiting influenza by binding and not a more traditional neutralization means. TRL809 and TRL832 represent exemplary binding antibodies that may be suitable or effective in combination with the cocktail to provide enhanced efficacy or synergy, particularly via airway administration. Other agents effective by airway administration, particularly in combination with the antibody cocktail disclosed herein, may include surfactants or airway lining modulators, such as surfactant nano-emulsions and cationic airway lining modulators. Agents that modulate or alleviate airway inflammation may also be effective or useful in combination with the present antibody cocktails.

In some embodiments, the therapeutic compositions, particularly pulmonary compositions, may further include an effective amount of the neutralizing antibody or fragment thereof, and one or more of the following active ingredients: an antibiotic, an antiviral agent, a steroid, an anti-inflammatory. In a particular aspect, the compositions include an antiviral therapeutic. The compositions may include an anti-influenza agent. In some embodiments methods and compositions are provided for improving efficacy by combining the inventive mAb therapy with other anti-viral treatments, such as an antiviral therapeutic such as a neuraminidase inhibitors (e.g. oseltamivir [TAMIFLU™], zanamivir [RELENZA™]), RNA polymerase inhibitors (e.g. favipiravir, VX-787), immune modulators (e.g. inhaled Interferon beta 1a), host-cell targeting agents (e.g. Das 181[Fludase™], Radavirsen), ion-channel inhibitors (e.g. amantidine), or other antivirals.

Any such anti-influenza agents may also be compounded or combined as part of the compositions provided herein or administered in conjunction with or separately to the antibodies or active fragments hereof. The anti-influenza agents may be administered via the same or alternative means (such as via inhalation or via oral (e.g. pills) means) as the antibodies or fragments thereof or the inhalation or intranasal compositions of the invention. Thus, the antibody combination(s) of the present disclosure and the present inhalation or intranasal compositions may further comprise or may be administered in combination with or sequentially after or before an anti-influenza agent or antiviral agent, such as for instance a neuraminidase inhibitor, including an agent selected from Tamiflu and Relenza.

As used herein, "pg" means picogram, "ng" means nanogram, "ug" or "μg" mean microgram. "mg" means milligram, "ul" or "μl" mean microliter, "ml" means milliliter, "l" means liter.

Compositions may be formulated in nasal sprays or inhalation solutions or suspensions using approaches known and acceptable in the art and in the medical field and clinical practice. The FDA provides guideline and guidance with regard to such sprays, solutions and suspensions and spray drug products, including in Guidance for Industry documents available at fda.gov. An exemplary July 2002 Guidance for Industry document entitled Nasal Spray and Inhalation Solution, Suspension and Spray Drug Products—Chemistry, Manufacturing and Controls Documentation includes details regarding formulation components and compositions, specifications therefore, manufacturing, and closed container systems.

Nasal Sprays are drug products that contain active ingredients dissolved or suspended in a formulation, typically aqueous-based, which can contain other excipients and are intended for use by nasal inhalation. Container closure systems for nasal sprays include the container and all components that are responsible for metering, atomization, and delivery of the formulation to the patient. Nasal spray drug products contain therapeutically active ingredients (drug substances) dissolved or suspended in solutions or mixtures of excipients (e.g., preservatives, viscosity modifiers, emulsifiers, buffering agents) in nonpressurized dispensers that deliver a spray containing a metered dose of the active ingredient. The dose can be metered by the spray pump or could have been premetered during manufacture. A nasal spray unit can be designed for unit dosing or can discharge numerous metered sprays of formulation containing the drug substance. Nasal sprays are applied to the nasal cavity for local and/or systemic effects.

Inhalation solution and suspension drug products are typically aqueous-based formulations that contain therapeutically active ingredients and can also contain additional excipients. Aqueous-based oral inhalation solutions and suspension must be sterile (21 CFR 200.51). Inhalation solutions and suspensions are intended for delivery to the lungs by oral inhalation for local and/or systemic effects and are to be used with a specified nebulizer. An inhalation spray drug product consists of the formulation and the container closure system. The formulations are typically aqueous based and do not contain any propellant.

Current container closure system designs for inhalation spray drug products include both premetered and device-metered presentations using mechanical or power assistance and/or energy from patient inspiration for production of the spray plume. Premetered presentations contain previously measured doses or a dose fraction in some type of units (e.g., single or multiple blisters or other cavities) that are subsequently inserted into the device during manufacture or by the patient before use. Typical device-metered units have a reservoir containing formulation sufficient for multiple doses that are delivered as metered sprays by the device itself when activated by the patient.

A prolonged residence time in the nasal cavity may also be achieved by using bioadhesive polymers, microspheres, chitosan or by increasing the viscosity of the formulation. Nasal mucociliary clearance can also be stimulated or inhibited by drugs, excipients, preservatives and/or absorption enhancers and thus affect drug delivery to the absorption site.

Microsphere technology is one of the specialized systems being utilized for designing nasal products. Microspheres may provide more prolonged contact with the nasal mucosa and thus enhance absorption or efficacy. Microspheres for nasal applications have been prepared using biocompatible materials, such as starch, albumin, dextran and gelatin (Bjork E, Edman P (1990) Int J Pharm 62:187-192).

Aqueous solubility of drug may be a relevant parameter limitation for nasal drug delivery in solution. Conventional solvents or co-solvents such as glycols, small quantities of alcohol, Transcutol (diethylene glycol monoethyl ether), medium chain glycerides and Labrasol (saturated polyglycolyzed $C_8$-$C_{10}$ glyceride) can be used to enhance the solubility of drugs. Other options include the use of surfactants or cyclodextrins such as HP-beta-Cyclodextrin that serve as a biocompatible solubilizer and stabilizer in combination with lipophilic absorption enhancers. In such cases, their impact on nasal irritancy should be considered.

Most nasal formulations are aqueous based and need preservatives to prevent microbial growth. Parabens, benzalkonium chloride, phenyl ethyl alcohol, EDTA and benzoyl alcohol are some of the commonly used preservatives in nasal formulations. Mercury-containing preservatives have a fast and irreversible effect on ciliary movement and are not recommended for use in nasal systems.

A small quantity of antioxidants may be required to prevent drug oxidation. Commonly used antioxidants are sodium metabisulfite, sodium bisulfite, butylated hydroxytoluene and tocopherol. Usually, antioxidants do not affect drug absorption or cause nasal irritation. Chemical/physical interaction of antioxidants and preservatives with drugs, excipients, manufacturing equipment and packaging components should be considered as part of the formulation development program.

Many allergic and chronic diseases are often connected with crusts and drying of mucous membrane. Certain preservatives/antioxidants among other excipients are also likely to cause nasal irritation especially when used in higher quantities. Adequate intranasal moisture is essential for preventing dehydration. Therefore, humectants can be added especially in gel-based nasal products. Humectants avoid nasal irritation and are not likely to affect drug absorption. Common examples include glycerin, sorbitol and mannitol.

The selection of delivery system depends upon the drug being used, proposed indication, patient population and last but not least, marketing preferences. Some of these delivery systems include nasal drops, nasal sprays, nasal gels, and nasal powders.

In some embodiments, compositions are provided for administration via a nebulizer for intranasal and inhalation delivery. A nebulizer is a drug delivery device used to administer medication in the form of a mist inhaled into the respiratory tract. Nebulizers can be used for intransal and inhalation delivery of mAbs through the mouth and nasal passage and are effective devices for delivery of mAbs to the upper and/or lower respiratory track. Nebulizers use oxygen, compressed air or ultrasonic power to break up medical solutions and suspensions into small aerosol droplets that can be directly inhaled from the mouthpiece of the device. An aerosol is a mixture of gas and liquid particles, and the best example of a naturally occurring aerosol is mist, formed when small vaporized water particles mixed with hot ambient air are cooled down and condense into a fine cloud of visible airborne water droplets. A metered-dose inhaler (MDI) is a device that delivers a specific amount of medication to the lungs, in the form of a short burst of aerosolized medicine that is usually self-administered by the patient via inhalation. Dry powder inhalers involve micronised powder often packaged in single dose quantities in blisters or gel capsules containing the powdered medication to be drawn into the lungs by the user's own breath. A new significant innovation was made in the nebulizer market with creation of the ultrasonic Vibrating Mesh Technology (VMT). With this technology a mesh/membrane with 1000-7000 laser drilled holes vibrates at the top of the liquid reservoir, and thereby pressures out a mist of very fine droplets through the holes. This technology is more efficient than having a vibrating piezoclectric element at the bottom of the liquid reservoir, and thereby shorter treatment times are also achieved. Available VMT nebulizers include Pari eFlow Respironics i-Neb, Omron MicroAir, Beurer Nebulizer IH50, and Aerogen Aeroneb.

In another embodiment, the composition is prepared as a lyophilized powder for reconstitution, or a preserved or non-preserved sterile liquid composition for administration intranasally by a mucosal atomization device (MAD). A mucosal atomization device (MAD) is attached via luer lock to a syringe comprising the anti-viral composition. The syringe plunger is briskly compressed to create a rapid intranasal mist spray of about 0.01, 0.05, 0.1, 0.2, 0.3, 0.4, 0.5, 0.6, 0.7, 0.8, 0.9, or 1 mL per dose. In some cases, the entire dose is administered to a single nostril, or the dose may be split between nostrils, in one or in multiple sprays per dose.

The pH of a nasal formulation is important for stability of the antibodies, and to avoid irritation of nasal mucosa, to allow the antibodies to be available in an optimal form for absorption, to prevent growth of pathogenic bacteria in the nasal passage, to maintain functionality of excipients such as preservatives, and to sustain normal physiological ciliary movement. In some embodiments, the composition is prepared with a pH within 4.5-8.2, 5.2-7.9, or 4.5 to 6.5, keeping in mind the physicochemical properties of the antibody cocktail, drug or active ingredient. Nasal formulations are generally administered in small volumes ranging from 25 to 200 µL with 100 µL being the most common dose volume.

Administration

It is again noted that normal and reasonably expected antibody therapy doses are well-established to be IV or IP doses in the mg range. This is based on research and clinical experience to date with numerous recombinant antibodies. To date, over twenty (20) monoclonal antibodies have been clinically approved in the United States (see e.g Newsome B W and Emstoff M S (2008) Br J Clin Pharmacol 66(1): 6-19). Clinically approved antibodies presently in use are all utilized and administered IP or IV in the mg/kg range.

No influenza monoclonal antibody has been clinically approved to date. All trials in progress or reported currently utilize intravenous delivery as the standard. In particular, TheraClone Sciences antibody TCN-032 was assessed in a single dose-escalation ranging from 1-40 mg/kg (NCT01390025, clinical trails.gov). The TCN-032 antibody is a human antibody that binds to a conserved epitope of the amino-terminal extracellular domain (M2e) of the influenza matrix protein (M2) (Grandea A G et al (2010) PNAS USA 107(28):12658-12663; Epub 2010 Jul. 1). The antibodies CR6261 and CR8020 are being similarly assessed in safety and tolerability studies using escalating doses from 2 mg/kg to 50 mg/kg administered IV over 2 hours (Crucell Holland BV clinical trials NCT01406418 and NCT01756950 respectively).

Influenza vaccines are administered by injection. One exception in influenza vaccines is the FluMist live influenza vaccine (MedImmune) which is administered intranasally. FluMist is a combination of three live flu strains—an A/H1N1 strain, an A/H3N2 strain, and a B strain, and is administered in a 0.2 ml dose using a suspension supplied in a single dose pre-filled intranasal sprayer. In addition to the virus strains, each dose also contains monosodium glutamate, hydrolyzed porcine gelatin, arginine, sucrose, dibasic potassium phosphate and monobasic potassium phosphate, with no preservatives (FluMist Highlights of Prescribing Information, 2012-2013 Formula, MedImmune, RAL-FLUV12, Component No.: 11294).

The present disclosure provides a novel and efficacious mode of administration of a combination of antibodies and antibody administration protocol for treatment and prophylaxis of viral infection, particularly viruses which infect or transmit via the respiratory route, including particularly influenza virus. Thus the disclosure provides for treatment, prophylaxis or alleviation of virus infection, particularly influenza virus, by pulmonary administration of a combination of antibodies capable of neutralizing any relevant or circulating influenza virus. The antibody combination may be administered by a single IN dose or may be given in multiple individual doses at the same time or essentially simultaneously. Additional combination or individual doses may be administered subsequently, each administration separated by minutes, hours, or days.

In a particular aspect, the present disclosure provides for treatment, prophylaxis or alleviation of virus infection, particularly influenza virus, by pulmonary administration of a combination of antibodies directed against circulating strains of influenza. Thus, treatment, prophylaxis or alleviation of virus infection, particularly influenza virus, is provided and achieved in accordance with the disclosure by pulmonary administration of a combination of antibodies directed against influenza B and circulating influenza A viruses, particularly in an aspect thereof a combination of anti-influenza B antibody, anti-Group 1 influenza A antibody, such as anti-H1 antibody, and anti-Group 2 influenza A antibody, such as anti-H3 antibody. In accordance with the present disclosure, intranasal administration of a combination of anti-influenza B antibody, anti-Group 1 influenza A antibody, such as anti-H1 antibody, and anti-Group 2 influenza A antibody, such as anti-H3 antibody, is effective in preventing infection or treating influenza infection by an influenza B or influenza A virus. To the extent that antibodies are available, and herein tested and demonstrated, to be effective and directed against more than one subtype or strain of virus, the combinations provided and contemplated herein serve as a universal cocktail or combination effective against numerous strains and/or subtypes of virus, particularly influenza virus, including known and circulating strains or subtypes, emerging strains or subtypes and unknown, unanticipated and variant strains or subtypes.

Antibody of use in embodiments disclosed herein may be administered intranasally or by inhalation, followed by or along with, including at the same time, in combination, or sequentially or separately, systemic administration of another or the same antibody, particularly IP or IV administration. Thus, a combination administration protocol or method is contemplated and provided herein, wherein intranasal and IP (or IV) administration is combined for enhanced efficacy against an agent, particularly virus, particularly influenza virus. Indeed, the studies provided herein demonstrate that using combined dosing of intranasal with alternative administration (IP or IV) the combined efficacy is synergistic and low doses both IN and IP as an example can be utilized.

Airway administration provides for the unique opportunity to deliver an effective low dose and low cost therapy that would therefore not require confirmation by a diagnostic assay. Presentation of symptoms during the influenza season would be sufficient for physicians to administer this low dose cocktail, for example as a dry-powder-inhaler or as a nebulizer or other airway delivery method. This diagnostic-free standard of care is the current practice for Tamiflu and Relenza, but would not be possible with expensive intravenous antibody therapy, which would not be practical and is cost prohibitive. Upon follow-up with diagnosis, administration of high dose antibody could be administered either through intravenous route or through the airway, and could be composed as a cocktail or as a stand-alone that is specific for the influenza type.

The present disclosure provides a method for treatment or prophylaxis of viral infection in a mammal exposed to, at risk of exposure, having contracted, clinically presenting symptoms or suffering from a respiratory virus comprising administering intranasally (IN) or via inhalation to said mammal a combination or cocktail of antibodies as provided herein. The cocktail or combination of antibodies may particularly all be IgG antibodies.

Antibody combination can be administered post infection or after presumed infection. In an aspect thereof, the antibody combination can be administered in a time period up to 8 hours post infection (hpi), including 2 hpi, 4 hpi, 6 hpi, 8 hpi. Alternatively, the antibody combination is administered in a time period up to 24 hours post infection, including 4 hpi, 8 hpi, 12 hpi, 18 hpi, 24 hpi. In a further alternative, the antibody is administered in a time period up to 48 hours post infection, including 12 hpi, 24 hpi, 36 hpi. 48 hpi. In a still further alternative, the antibody is administered in a time period up to 72 hours post infection, including 24 hpi, 36 hpi, 48 hpi, 60 hpi, 72 hpi. Antibody may be administered days post infection, or after presumed infection, or after presentation of clinical symptoms, such as fever, aches, joint pain, lethargy. Antibody may be administered 1 day post infection, 2 days post infection, 3 days post infection, 4 days post infection, 5 days post infection, 6 days post infection, 7 days post infection, 10 days post infection, 12 days post infection, 14 days post infection. Antibody may be administered weeks after infection or presumed infection, including 1 week after, 2 weeks after, 3 weeks after, 4 weeks after, a month after.

Antibody combination can be administered before infection or in order to reduce or prevent transmission, or before any clinical indication of illness, disease or infection. In an aspect thereof, the antibody can be administered in a time period days before infection or before possible or presumed exposure or risk of exposure as a prophylactic. Antibody combination may be administered a day prior or before, 2 days before or prior, 3 days prior or before, 4 days prior or before, 5 days prior or before, 6 days prior or before, 7 days prior or before, a week prior or before, more than 7 days prior or before, more than a week prior or before, up to 9 days prior or before, up to 10 days prior or before. Antibody may be administered one or more times prior or before in one or more doses, separated by hours, days or weeks.

The antibody combination may be administered in one single dose or in repeated multiple combination doses. In any preferred aspect each antibody in the combination or cocktail is administered in the same relative amount. Each dose may be identical in unit or mg/kg amount or may be different in amount. For example an initial dose may be a higher relative dose, such as for example but not by limitation about 1 mg/kg, greater than 1 mg/kg, less than 1 mg/kg, or about the maximum or near maximum tolerated dose, or one half maximum tolerated dose for the mammal being administered. Subsequent doses may be the same as the initial dose or may be less than or greater than the initial dose, and may depend on the reaction or response in the subject or patient or the alleviation or degree of clinical symptoms.

The multiple doses, of the same or different amounts each or any dose, may be administered hours, minutes, days or weeks apart. The timing may vary and may be shortened or lengthened depending on response and symptoms. Doses, for example and not by limitation, may be at least 2 hours apart, at least 4 hours apart, at least 6 hours apart, at least 8 hours apart, at least 24 hours apart, at least 48 hours apart, at least 72 hours apart. The antibody dose or doses may be administered post infection or post presumed infection and up to 2, 4, 6, 8, 12, 24, 36, 48, 72 hours after, up to 1 day, 2 days, 3 days, 4 days, 5 days, 6 days, 7 days, a week, 2 weeks, 3 weeks, 4 weeks, a month or longer.

The method may comprise additional administration IP or IV of a virus specific monoclonal antibody wherein the antibody additionally administered is a neutralizing or non-neutralizing antibody. The antibody additionally administered IP or IV may be the same antibody as administered IN or via inhalation. The antibody additionally administered IP or IV may be administered simultaneously, sequentially, or subsequently to the IN or inhalation administered antibody. Any such subsequent administration may be hours later and may be 2, 4, 6, 8, 12, 24, 36, 48, 72 or more hours later. Subsequent administration may be days later and may be 1 day, 2 days, 3 days, 4 days, 5 days, 6 days 7 days later. Subsequent administration may be weeks later and may be 1, 2, 3, 4 or 5 weeks later.

An inhalation or intransal dose may be used to boost response or efficacy in a patient or subject that is particularly ill or continuing to demonstrate symptoms of infection or illness after an initial IN or IP or IV or combined dose.

In a further aspect, the present disclosure provides a protocol for administration of monoclonal antibody cocktail or combination against influenza virus comprising administering a first intranasal or inhalation dose of antibody combination and subsequently or simultaneously administering a second dose of antibody intraperitoneally or intravenously, or again intranasally or by inhalation, wherein the antibody combination of the second dose is the same or a different antibody combination as the antibody combination of the first dose. The antibody of the second dose, or any additional dose, may be a neutralizing or a non-neutralizing antibody.

The embodiments disclosed herein may be better understood by reference to the following non-limiting Examples, which are provided as exemplary of the invention. The following examples are presented in order to more fully illustrate the preferred or specific embodiments and should in no way be construed, however, as limiting the broad scope of the.

Antibody Structures

Certain heavy and light chain amino acid sequences of the mAbs of the invention are provided below and in the accompanying Sequence Listing.

TRL 784

EXAMPLES

The following Materials and Methods are employed for the Examples provided herein.

Antibodies:

In some cases Mabs were isolated using phage display as described below. Mabs CR8020 and CR6261 are well characterized broadly-reactive antibodies against group 2 and group 1 viruses, respectively (Throsby M et al (2008) PLOS ONE 3:e3942; Eckert D C et al (2009) Science 324:246-251; Friesen RHE et al (2010) PLoS ONE 5(2):e1906; U.S. Pat. No. 8,192,927; Eckert D C et al (2011) Science 333:843-850). Antibody CR9114 binds a conserved epitope in the HA stem and protects against lethal challenge with influenza A and B viruses when administered IV (Dreyfus C et al (2012) Science Express 9 Aug. 2012 10.1126/science. 1222908). These neutralizing antibodies were cloned in our hands by synthesizing the variable region and subcloned into mouse IgG2a expression vectors. The variable region of CR8020 was cloned using the published heavy chain GI: 339779688 and light chain GI: 339832448. The variable region of CR6261 was cloned using the published heavy chain GI: 313742594 and light chain GI: 313742595. The variable region of CR9114 was cloned using the Genbank sequence heavy chain accession JX213639 and light chain accession JX213640. CR6261, CR8020 and CR9114 antibodies utilized in these studies are cloned into IgG expression vectors containing the human variable regions fused to mouse IgG2a. The chimeric antibodies for mouse antibodies CR6261. CR8020 and CR9114 are referenced as CA6261, CA8020 and CA9114 herein respectively. Mab 5A7 binds to a common epitope on B virus HA and neutralizes virus, and protects mice from lethal challenge when given IP (Yasugi M et al (2013) PLoS Pathog 9(2): e1003150, doi: 10.1371/journal.ppat.1003150).

Human antibody Mab53 (also denoted TRL053) is described in US2012/0020971 and WO2011/160083, each of which is incorporated by reference herein, and is effective in neutralizing Group 1 and 2 H1, H9, H7 and H5 subtypes.

The antibody Mab579 (also denoted TRL579) is described in WO2013/086052 which is incorporated by reference herein, and is effective in neutralizing H3 and H7.

Published sequences including antibody heavy and light chain variable regions sequences, and particularly heavy and light chain CDR domain (CDR1, CDR2 and CDR3) sequences of above noted and exemplified antibodies herein, particularly including CR6261, CR8020, CR9114, 5A7, Mab53 and Mab579, are known and publicly available, including in references noted above and incorporated herein by reference.

Fab Validation:

Fab encoding phage lysates were screened by ELISA against recombinant HA. Single colonies picked into 384 well plates containing 2XYT/Cam/Glc media were grown overnight at 30° C. TG1 cells in 384 well plates were replicated into 384 well expression plates containing 2XYT/Cam with low glucose using Qpix. Plates were grown for 2-4 hrs at 30'C and 400 rpm. Fab expression was induced with 0.5 mM IPTG and grown overnight at 22° C. and 400 rpm. Fab-containing cells were lysed with BEL buffer containing Benzonase at 22'C and 400 rpm for 1 hr. Fab-containing lysates were blocked with 12.5% MPBST for 30 min at 400 rmp and 22° C. Lysates were added to HA-coated ELISA plates for 1 hr at RT. Plates were washed five times with PBST and then incubated with anti-Fab IgG conjugated to alkaline phosphatase for 1 hr at RT. Plates were washed five times with TBST and developed with AutoPhos (Roche, N.J.). Plates were read using an Infinite Pro F200. Positive phage lysates were sequenced and the unique Fabs were subcloned into Fab expression constructs containing a c-myc and his tag for further characterization.

Fab Expression:

Fab expression plasmids were electroporated into TG1 F-cells and plated onto LB/Cam agar plates. Plates were incubated at 37° C. overnight. 5 ml of 2XYT/Cam/Glc were inoculated with a single colony and grown overnight at 30'C and 350 rpm. 500 ml of 2XYT/Cam/low Glc were inoculated with 2 ml of overnight culture and shaken at 30'C and 180 rpm until an OD600 nm of 0.5 was reached. Fab expression as induced by addition of IPTG at a final concentration of 0.75 mM. Cultures were shaken at 30° C. and 160 rpm overnight. Cultures were centrifuged for 30 min at 5,000 g and 4° C., Bacterial pellets were frozen at −80'C for least 2 hrs. Cells were lysed and filtered on 0.22 um filter and subjected to IMAC purification and a size exclusion step.

Cloning and Expression of Antibodies:

Fab encoding phage were sequenced and subcloned into IgG expression plasmids for the respective heavy and light chains. IgGs were produced in Invitrogen 293F or Invitrogen 293Expi cells in shaker flasks. Cells were transfected with expression plasmids for the heavy and light chains. Culture supernatants were harvested six days post-transfection and purified using Protein A affinity chromatography and a buffer exchange step.

Therapeutic Efficacy Studies in Mice:

Female 6-7 weeks old BALB/c mice were used in experiments. All mice were acclimated and maintained for a period of at least three days prior to the start of the experiment. Mice were weighed on the day of virus challenge and then daily for 2 weeks. A clinical scoring system was used as criteria for clinical endpoint and removal from the study. Clinical signs were scored as follows: hunched posture=3, piloerrection=3, no eating or drinking=2, weight loss ≥30%=10, neurological symptoms=10. Mice were removed from the study and euthanized when reaching a score of 16 or more. Animal studies were conducted per approved Institutional Animal Care and Use Committee protocols. Therapeutic treatment of mice was performed on indicated days post infection. Mice were first anesthetized with a ketamine/xylazine mixture prior to intranasal administration of virus, Mab, or Fab in 50 ul of volume per mouse. Peritoneal administration of Mab or Fab was given in 100 ul volume. Mean body weight was determined for each day during the 14 day study period and shown relative to the mean body weight on day 0.

Viruses:

Strains of influenza virus (including A/California/7/09, A/Victoria/11, B/Malaysia/2506/2004, B/Florida/04/2006) were mouse-adapted according to Cottey, Rowe, and Bender (Current Protocols in Immunology, 2001). Three rounds of mouse adaptation were performed followed by one round of propagation of virus in embryonated eggs. In brief, three 6-8 week old mice were anesthetized and infected intranasally with 20 ul of virus. Three days post infection, mice were euthanized and lungs were removed. Lungs were mechanically homogenized, clarified, and centrifuged to remove large pieces of debris. Additional passaging into naïve mice of 20 ul of lung homogenate were performed for three rounds.

REFERENCES

Huber V C, Lynch J M, Bucher D J, Le J, Metzger D W: Fc receptor-mediated phagocytosis makes a significant contribution to clearance of influenza virus infections. J Immunol 2001, 166:7381-7388.

Jegerlehner A, Schmitz N, Storni T, Bachmann M F: Influenza A vaccine based on the extracellular domain of M2: weak protection mediated via antibody-dependent N K cell activity. J Immunol 2004, 172:5598-5605.

Feng J, Mozdzanowska K, Gerhard W: Complement component C1q enhances the biological activity of influenza virus hemagglutinin-specific antibodies depending on their fine antigen specificity and heavy chain isotype. J Virol 2002, 76:1369-1378.

Mozdzanowska K, Feng J, Eid M, Zharikova D, Gerhard W: Enhancement of neutralizing activity of influenza virus-specific antibodies by serum components. Virology 2006, 352:418-426.

The following examples are offered to illustrate but not to limit the invention.

Example 1. Affinity of Monoclonal Antibodies

Primary screening using the CELLSPOT™ technology is inherently biased for discovery of high affinity mAbs since the antigens are bound to beads which are not retained during washing if the antigen-antibody interaction is too weak. The sensor instrument used for measuring the affinity of the cloned mAbs was a FORTEBIO™ Octet. Measuring affinity as the ratio of on and off rates becomes less accurate as the off rate becomes very slow. To get a better estimate, varying concentrations of the antibody were flowed across the antigen fixed to the sensor surface. Table 5 shows the suite of influenza B mAbs along with their KDs determined in this manner.

TABLE 5

| KD of mAbs against influenza B. | | |
|---|---|---|
| mAb | Florida Ag Affinity (nM) | Malaysia Affinity Ag (nM) |
| TRL 784 | 0.7 | 7 |
| TRL 798 | ND | ND |
| TRL 809 | 0.18 | 0.2 |
| TRL 823 | 2 | 0.3 |
| TRL 832 | 1.7 | 0.2 |
| TRL 833 | 2.9 | 0.2 |

TABLE 5-continued

KD of mAbs against influenza B.

| mAb | Florida Ag Affinity (nM) | Malaysia Affinity Ag (nM) |
|---|---|---|
| TRL 834 | ND | ND |
| TRL 835 | 0.6 | 2.3 |
| TRL 837 | 0.3 | 1.0 |
| TRL 841 | ND | ND |
| TRL 842 | 2.5 | <1.0 |
| TRL 845 | 5.2 | <1.0 |
| TRL 847 | 0.7 | <1.0 |
| TRL 848 | 3.9 | <1.0 |
| TRL 849 | 0.2 | <1.0 |
| TRL 851 | ND | ND |

The biosensor (BIACORE™) determined affinity for HA (KD) of 5A7 described by Yasugi, et al., (paragraph 0008) is ~5 nM. Invention mAb TRL 835 competes for binding with 5A7, but has a substantially tighter KD at 0.6 nM as shown.

Example 2. Binding to Recombinant Influenza B HAs by mAbs

Antibody binding was determined by ELISA. 384 well ELISA plates were coated with 20 ng per well of rHA protein in DPBS, pH 7.4. After overnight coating of the plates at 4° C., plates were washed twice with PBS with 0.01% TWEEN™20(polysorbate 20), (PBS-T). The plates were then blocked with 5% fat free Milk in PBS-T (M-PBS-T) for one hour, and washed two times in PBS-T. Purified antibodies were diluted in PBS and probed against each antigen with 20 ng per well. Plates were washed five times with PBS-T, and probed with a secondary antibody conjugated to Alkaline Phosphatase. Plates were then washed five times with PBS-T and developed with AttoPhos AP fluorescent substrate (Promega S1000). Plates were continuously read until background signal from the negative control wells began to provide fluorescent signal.

Results of certain ELISA assays are shown in FIG. 3 Recombinant HA ELISA data illustrating reactivity of several anti-influenza B mAbs and two anti-influenza A mAbs to influenza A and B strains. Recombinant HA ELISAs were performed in triplicate and the average fold reactivity over background is shown. FIG. 3 shows each of the anti-B mAbs TRL809. TRL812, TRL813; TRL832, TRL841, TRL842, TRL845, TRL846, TRL847, TRL848. TRL849. TRL854, and TRL856 are broadly cross-reactive against both lineages of influenza B viruses including B/Florida/06, B/Mass/12, and B/Wisconsin/10 of the Yamagata clade, and B/Brisbane/08, B/Malaysia/04, and B/Victoria/87 of the Victoria clade. The anti-influenza A mAbs CF401 (=mAb 53, TRL053) and CF402 (=mAb 579, TRL579) are reactive to members of the influenza A H1 (A/California/09) and H3 (A/Sydney/97) subtypes, but not to the influenza B strains.

Example 3. Neutralization of Influenza B Viruses by mAbs

Antibodies were incubated with 200 PFU of viruses at 37° C. for 1 hour. Then, MDCK cells were adsorbed with the mixtures at 37° C. for 1 hour. MDCK cells were overlaid with Avicel-containing media for plaque assay development. Plaques were determined after two days of incubation. Identified broadly reactive influenza B mAbs are capable of neutralizing both Yamagata and Victoria lineages with high potency. After incubation for 12 hours, the cells were fixed and subjected to immunofluorescene for detection of infected cells. Control anti-B mAb 5A7 showed neutralization of both Yamagata and Malaysia lineage strains, data not shown. However, the invention mAbs exhibited greater potency, as shown in Table 8 at FIG. 4.

Results of Neutralization assays for selected anti-influenza B antibodies are shown in FIG. 4 for anti-influenza B antibodies TRL845, TRL848, TRL849. TRL854, TRL832 and TRL809. The IC50s are the concentrations that inhibit the virus in this particular neutralization assay. The mAbs each neutralize a representative member of each of the Yamagata lineage and the Victoria lineage. Definitive strains for these lineages were used in this experiment, but mAbs also neutralized all B viruses tested.

Example 4. In Vivo Efficacy in Mouse Influenza Infection Model

In general, except where noted otherwise, mAbs were evaluated for enhanced efficacy in the pulmonary delivery model. Mice were infected with 10×LD50 and treated 24 hpi at 1 mg/kg administered by pulmonary delivery via the intranasal route. Body weight and survival were monitored to assess the relative efficacies.

FIGS. 6A-D shows in vivo activities of inventive anti-influenza B mAbs against 10×LD50 virus at 1 Day post-infection in murine model following 1 mg/kg by IN route with assessment of mouse body weight at up to 14 days post-infection, with PBS and no virus as controls. Animals were monitored for body weight daily for 14 days post infection and percent body weight of original day 0 weight is plotted.

FIG. 6A shows 1 mg/kg of mAbs TRL845, TRL847, TRL 848, TRL849, and 5A7 by IN route provides protection from disease in mice infected with B/Malaysia/2506/04, representative of the Victoria clade.

FIG. 6B shows 1 mg/kg of mAbs TRL845, TRL847, TRL 848, TRL849, and 5A7 by IN route provides protection from disease in mice infected with B/Florida/04/2006, representative of the Yamagata clade.

FIG. 6C shows 1 mg/kg of mAbs TRL849, TRL846, TRL854, TRL 856, TRL847, and 5A7 by IN route provides protection from disease in mice infected with B/Malaysia/2506/04, representative of the Victoria clade.

FIG. 6D shows 1 mg/kg of mAbs TRL849, TRL846, TRL854, TRL 856, TRL847, and 5A7 by IN route provides protection from disease in mice infected with B/Florida/04/2006, representative of the Yamagata clade.

Example 5. In Vivo Efficacy Enhancement by Pulmonary Delivery

To assess the potential for efficacy enhancement through an alternate delivery method, mAbs were tested for in vivo efficacy. Mice were infected with 10×LD50 and treated 24 hpi at 10.1, and 0.1 mg/kg using conventional systemic delivery via intraperitoneal administration as compared to the mAb at 1.0 and 0.1 mg/kg administered by pulmonary delivery via the intranasal route. Both survival and body weight were then compared. Survival and weight loss (a measure of the severity of the infection) were used to assess the relative activities. FIGS. 5A and 5B show mAb 5A7 is shown as an example to illustrate the enhanced efficacy through pulmonary delivery.

FIG. 5A shows in vivo activity of anti-influenza B antibody 5A7 in mice as percent body weight following intranasal (IN) vs. intraperitoneal (IP) administration of 5A7 in mice infected with 10×LD50 of B/Florida (Yamagata lineage). Mice were treated 24 hpi with mAb by either the IN or IP route and body weight was measured daily as an indication of disease severity, with PBS and no virus as controls. Animals were monitored for body weight daily for 14 days post infection and percent body weight of original day 0 weight is plotted. Mice that lost >30% body weight were euthanized. 1 mg/kg IN provides complete protection from weight loss, whereas 1 mg/kg by IP route has some weight loss. Enhanced efficiency of IN over IP route of administration is demonstrated.

Figure 5A:
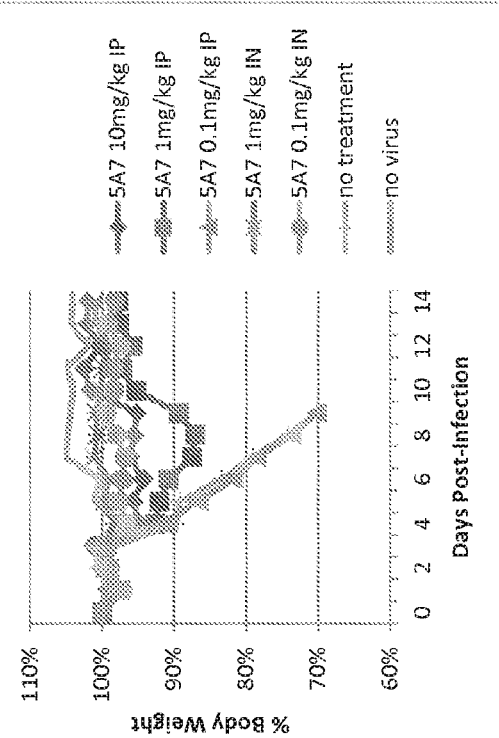
FIG. 5A shows in vivo activity of anti-influenza B antibody 5A7 in mice as percent body weight following intranasal (IN) vs. intraperitoneal (IP) administration of 5A7 in mice infected with 10×LD50 of B/Florida (Yamagata lineage). Mice were treated 24 hours post-infection (24 hpi) with mAb by either the IN or IP route and body weight was measured daily as an indication of disease severity, with PBS and no virus as controls. Animals were monitored for body weight daily for 14 days post infection and percent body weight of original day 0 weight is plotted. Mice that lost >30% body weight were euthanized. 1 mg/kg IN provides complete protection from weight loss, whereas 1 mg/kg by IP route has some weight loss. Enhanced efficacy of IN over IP route of administration is demonstrated.
Figure 5B:
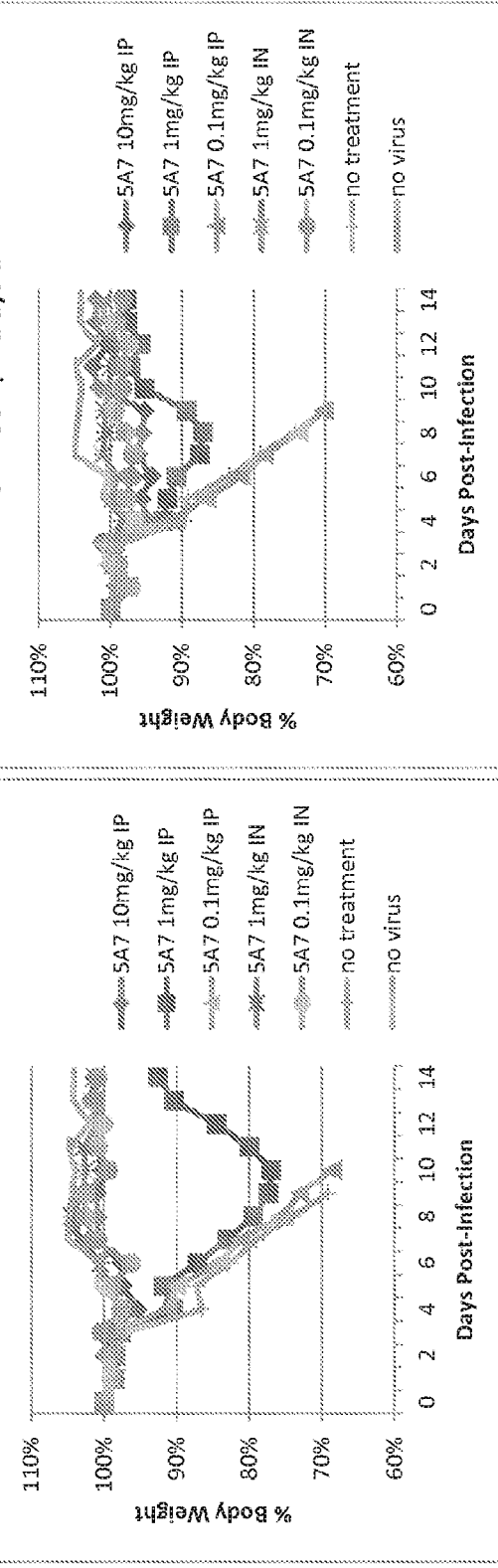
FIG. 5B shows in vivo activity of anti-influenza B antibody 5A7 in mice as percent body weight following IN vs. IP administration of 5A7 infected with 10×LD50 of B/Malaysia (Victoria lineage). Mice were treated 24 hpi with mAb by either the IN our IP route and body weight was measured daily as an indication of disease severity. Mice that lost >30% body weight were euthanizcd. 1 mg/kg IN provides complete protection from weight loss, whereas 1 mg/kg by IP route has some weight loss. Enhanced efficacy of IN over IP route of administration is demonstrated.
Figure 6A:
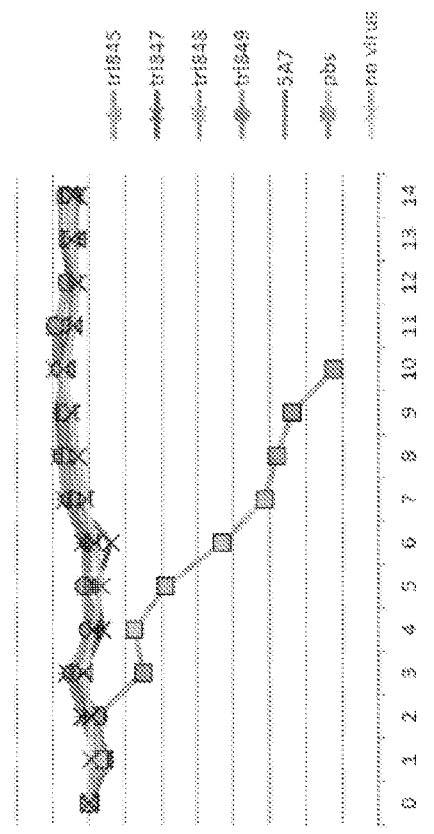
FIGS. 6A-D shows in vivo activities of inventive anti-influenza B mAbs against 10×LD50 (dose causing 50% lethality) virus at 1 Day post-infection in murine model following 1 mg/kg by IN route with assessment of mouse body weight at up to 14 days post-infection, with PBS and no virus as controls. Animals were monitored for body weight daily, for 14 days post infection and percent body weight of original day 0 weight is plotted.
Figure 6B:
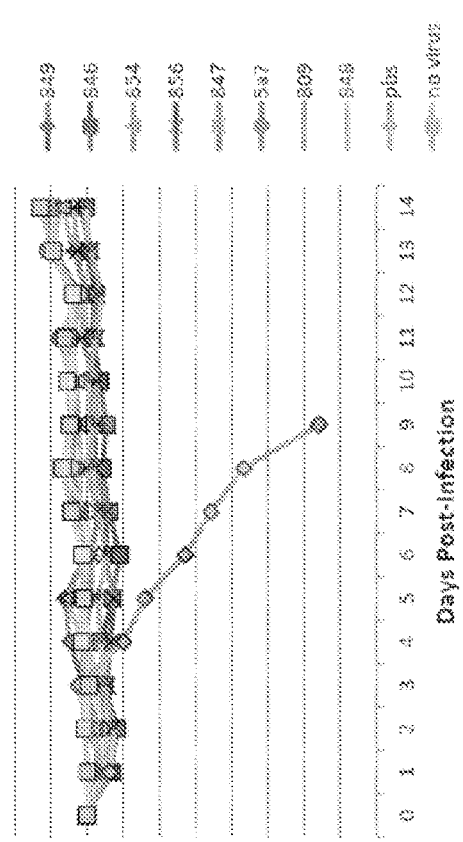
Figure 6C:
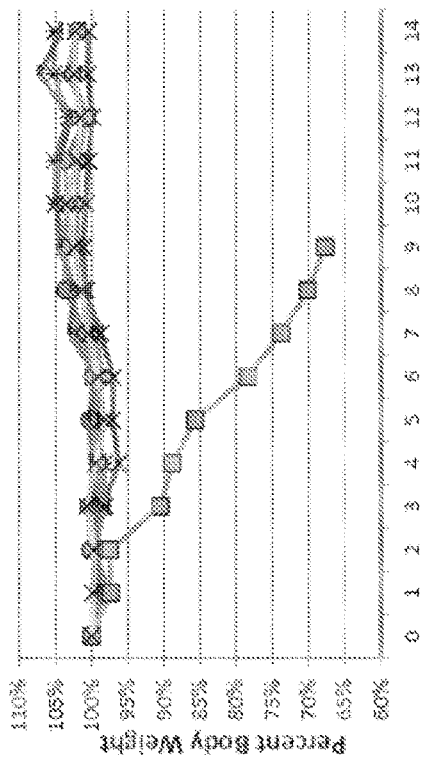
Figure 6D:
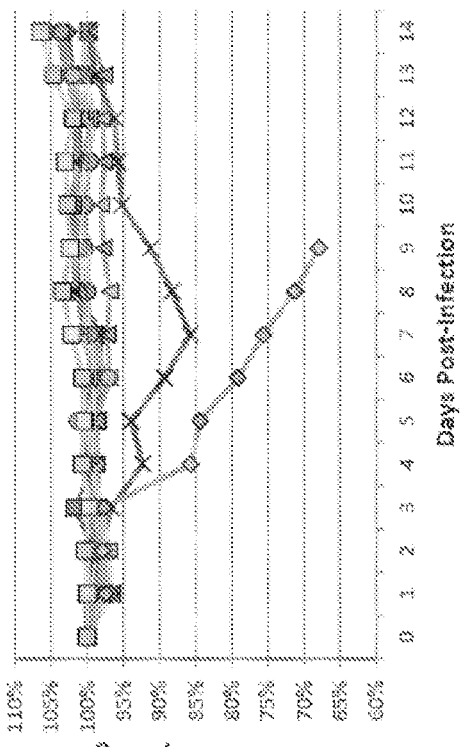

FIG. 5B shows in vivo activity of anti-influenza B antibody 5A7 in mice as percent body weight following IN vs. IP administration of 5A7 infected with 10×LD50 of B/Malaysia (Victoria lineage). Mice were treated 24 hpi with mAb by either the IN our IP route and body weight was measured daily as an indication of disease severity. Mice that lost >30% body weight were euthanized. 1 mg/kg IN provides complete protection from weight loss, whereas 1 mg/kg by IP route has some weight loss. Enhanced efficiency of IN over IP route of administration is demonstrated.

Example 6. In Vivo Efficacy is Unaffected by the Presence of Anti-Influenza Group A mAbs Efficacy of administration to the airway, using intranasal administration, was assessed with additional alternative influenza antibodies. Human monoclonal antibodies have been previously isolated that neutralize and have efficacy against both Group 1 and Group 2 influenza A viruses. The human antibody Mab53 (also denoted TRL053) is described in US2012/0020971 and WO2011/160083 and is effective in neutralizing Group 1 and 2 H1, H9, H7 and H5 subtypes. The antibody Mab579 (also denoted TRL579) is described in WO2013/086052 and is effective in neutralizing H3 and H7. As provided herein, these mAbs were prepared and optimized to provide anti-H1 CF-401(=mAb 53, TRL053), anti-H3 CF-402(=mAb 579, TRL579), used in the present studies.

The Mab579 and Mab53 antibodies were tested in the mouse model for therapeutic efficacy against influenza A virus infection. Mab579 was tested against H3 influenza and Mab53 was tested against H1 influenza. IN and IP dosing were compared, with IN dosing at 1 mg/kg and IP dosing tenfold higher at 10 mg/kg. Antibody Mab579 was administered 24 hours post infection (24 hpi) for treatment efficacy against 10×LD50 of 1H3 influenza virus Vic11 (data not shown and FIG. 12B). Antibody Mab53 was administered 24 hours post infection (24 hpi) for treatment efficacy against 10×LD50 of H1 influenza virus Cal09 and PR8 (data not shown and FIG. 11B). IN administration was more effective than IP administration, even with IP administration at a 10 fold higher dose in the same experiment.

Comparable survival and weight loss data were obtained for both the individual anti-B mAbs and mixtures of the same mAbs with anti-H1 and anti-H3 mAbs in a cocktail format, establishing that the mAbs do not interfere with each other's activity.

FIGS. 7A-7D show co-administration of three anti-influenza mAbs does not interfere with anti-B mAb efficiency. Mice were infected with 10×LD50 virus and treated 24 hpi with 3 mg/kg triple mAb cocktail comprised of anti-H1 CF-401(=mAb 53, TRL053), anti-H3 CF-402(=mAb 579, TRL579), and either anti-B TRL845 (Cocktail 1), anti-B TRL847 (Cocktail 2), or anti-B TRL849 (Cocktail 3), with PBS and no virus as controls. Animals were monitored for body weight daily for 14 days post infection and percent body weight of original day 0 weight is plotted.

FIGS. 7A-7D together demonstrate that the cocktail will provide the expected level of protection without interference from the other mabs in the cocktail against representative strains from all seasonal influenza subtypes (H1N1, H3N2, and both lineages of B).

Figure 7A:
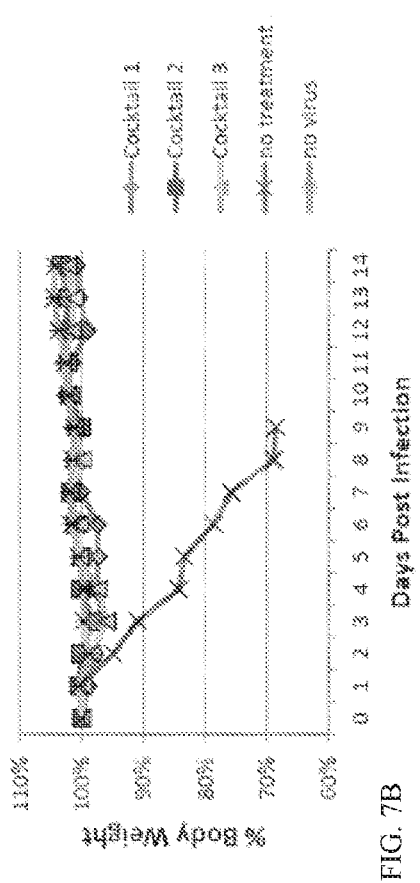
FIGS. 7A-7D show co-administration of three anti-influenza mAbs does not interfere with anti-B mAb efficiency. Mice were infected with 10×LD50 virus and treated 24 hpi with 3 mg/kg triple mAb cocktail comprised of anti-H1 CF-401, anti-H3 CF-402, and either anti-B TRL845 (Cocktail 1), anti-B TRL847 (Cocktail 2), or anti-B TRL849 (Cocktail 3), with PBS and no virus as controls. Animals were monitored for body weight daily for 14 days post infection and percent body weight of original day 0 weight is plotted.

FIG. 7A shows in vivo protection of mice infected with 10×LD50 H1N1 and treated 24 hpi with 3 mg/kg triple mAb cocktail comprised of anti-H1 CF-401, anti-H3 CF-402, and either anti-B TRL845 (Cocktail 1), anti-B TRL847 (Cocktail 2), or anti-B TRL849 (Cocktail 3).

Figure 7B:
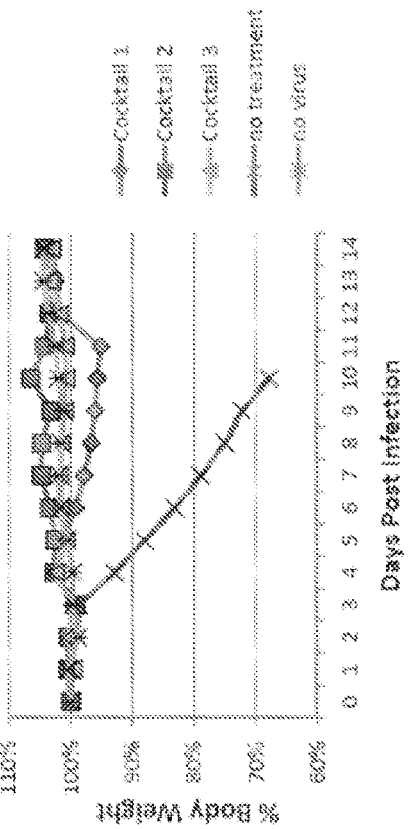

FIG. 7B shows in vivo protection of mice infected with 10×LD50 H3N2 and treated 24 hpi with 3 mg/kg triple mAb cocktail comprised of anti-H1 CF-401, anti-H3 CF-402, and either anti-B TRL845 (Cocktail 1), anti-B TRL847 (Cocktail 2), or anti-B TRL849 (Cocktail 3).

Figure 7C:
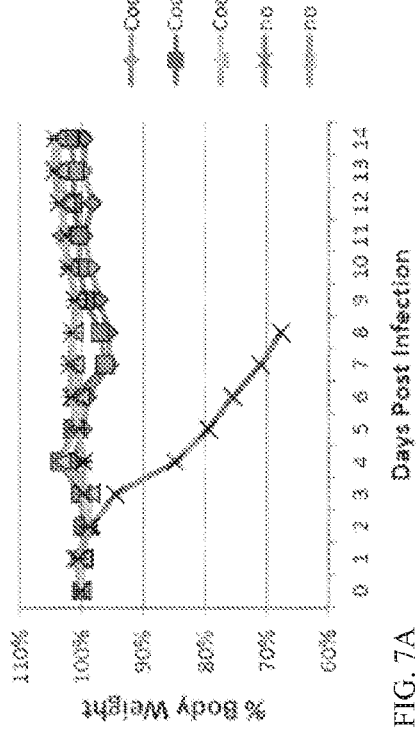

FIG. 7C shows in vivo protection of mice infected with 10×LD50 B/Yamagata lineage and treated 24 hpi with 3 mg/kg triple mAb cocktail comprised of anti-H1 CF-401, anti-H3 CF-402, and either anti-B TRL845 (Cocktail 1), anti-B TRL847 (Cocktail 2), or anti-B TRL849 (Cocktail 3).

Figure 7D:
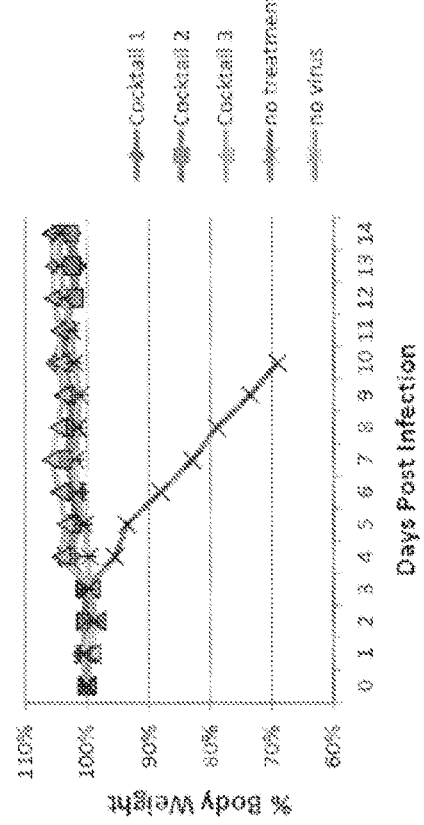

FIG. 7D shows in vivo protection of mice infected with 10×LD50 B/Victoria lineage and treated 24 hpi with 3 mg/kg triple mAb cocktail comprised of anti-H1 CF-401, anti-H3 CF-402, and either anti-B TRL845 (Cocktail 1), anti-B TRL847 (Cocktail 2), or anti-B TRL849 (Cocktail 3).

Example 7. Epitope Mapping of Anti-B mAbs Using PEPSCAN™

Epitopes of anti-B mAbs were mapped using the Pepscan CLIPS™ technique where various immobilized linear and constrained peptides corresponding to segments of stalk region of influenza B hemagglutinin were scored for binding to the different anti-B mAbs. The stalk sequence of influenza B strain B Lee was chosen as it is a progenitor of both the Victoria and Yamagata lineages. Peptides that bind to the mAbs are considered epitopes. For each mAb tested, a unique pattern of discontinuous epitopes was delineated. The results are summarized in FIGS. 8 and 9. FIG. 8 shows the peptide array that was made by PEPSCAN™ of B/Lee/1940/HA protein (SEQ ID NO: 291) (upper panel). Shaded regions of B/Lee/1940/HA protein correspond to residues used to generate peptide arrays from aa_15-65 (SEQ ID NO: 292), aa_300-359 (SEQ ID NO:293), and aa_362-481 (SEQ ID NO: 294). The Table (lower panel) shows mAb 5A7 epitope 1-aa_333-338 (SEQ ID NO: 304), epitope 2-aa_342-346 (SEQ ID NO: 305), and epitope 3-aa_457-463 (SEQ ID NO:306); mAb TRL845 epitope-aa_455-463 (SEQ ID NO:307); TRL848 epitope 1-aa_64-71 (SEQ ID NO: 308); epitope 2-aa_336-348 (SEQ ID NO: 309); epitope 3-aa_424-428 (SEQ ID NO: 310); mAb 849 epitope 1-aa_317-323 (SEQ ID NO: 311), epitope 2-aa_344-349312), epitope 3-aa_378-383 (SEQ ID NO: 313); mAb 854 epitope 1-aa_457-463 (SEQ ID NO: 314). The drawing at lower right shows the region mapped out onto the stalk of the HA in dark grey.

Figure 9:
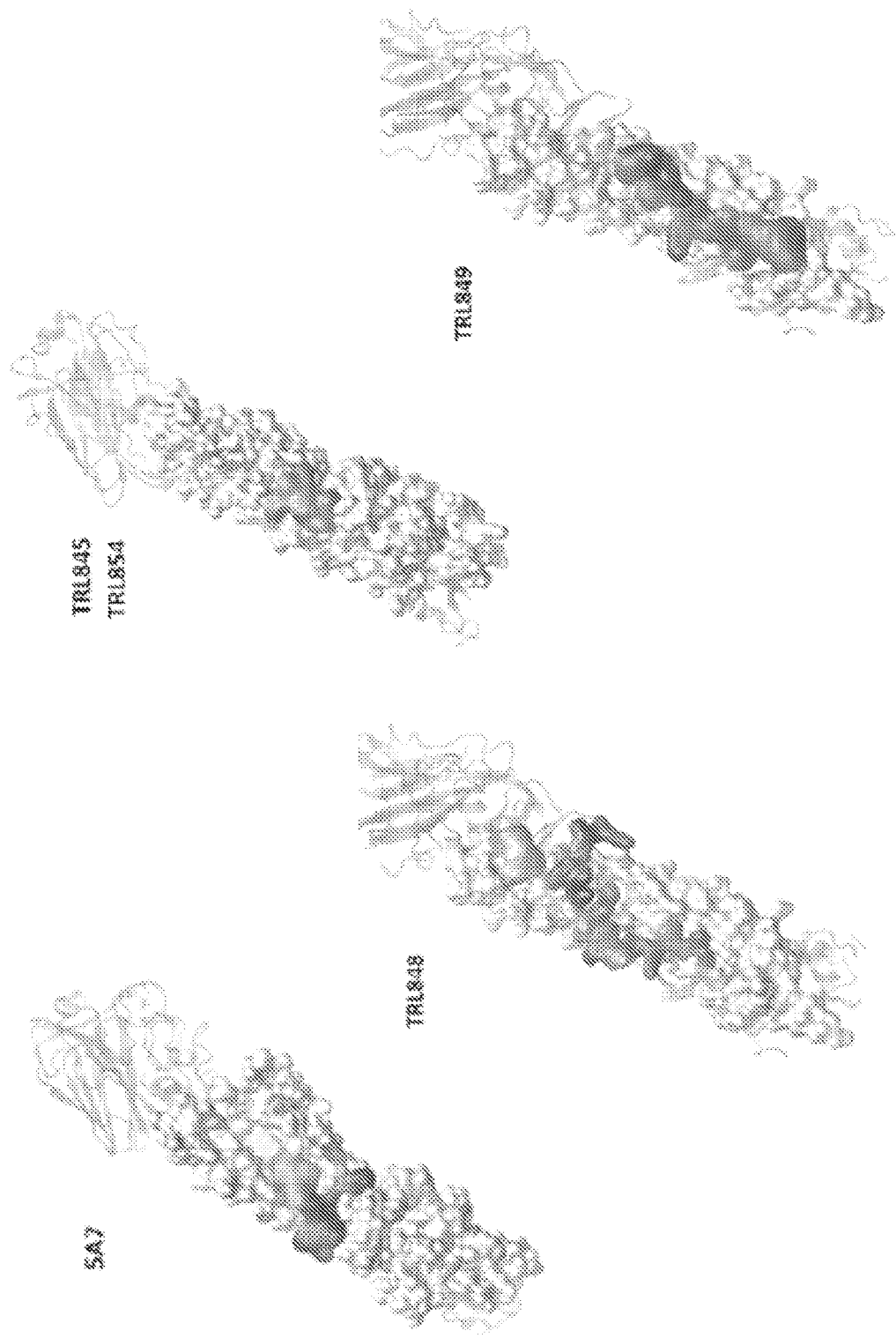
FIG. 9 illustrates that epitope mapping by PEPSCAN™ analysis along the stalk of HA protein. The shaded regions depict the epitope that each mAb binds to. mAbs TRL848, TRL845, TRL854, and TRL849 recognize discontinuous epitopes that partially overlap along the stalk of HA. Control mAb 5A7 derived from published sequence yielded similar but unique epitopes.

FIG. 9 illustrates epitope mapping by PEPSCAN™ analysis along the stalk of HA protein. The shaded regions depict the epitope that each mAb binds to. mAbs TRL848, TRL845, TRL854, and TRL849 recognize discontinuous epitopes that partially overlap along the stalk of HA. Control mAb 5A7 derived from published sequence yielded similar but unique epitopes.

Example 8. In Vivo Expression of mAbs

In some embodiment, the mAbs of the invention are targeted for in vivo expression. Several delivery systems have been described for transfer of genetic information for a mAb into host cells for in situ production of mAb. In one embodiment, the encoding DNA is encapsulated into a lentiviral particle that contains a fusogenic protein on its surface combined with a tissue targeting antibody, as described by David Baltimore's laboratory: *Proc. Nat'l Acad. Sci. USA* 103(31):11479-11484 (2006). The targeting antibody can bind CD20, for example, thereby achieving preferential delivery of the vector to B-cells for optimal production of antibodies. Alternatively, an AAV vector (adeno associated virus) is used as described by Johnson, P. R., et al., *Nature Medicine* (2009) 15:901-906. Other methods include encapsulation of encoding mRNA into a liposome or lipid particle to facilitate cellular uptake.

Example 9. Melting Curve Assays

Figure 10F:
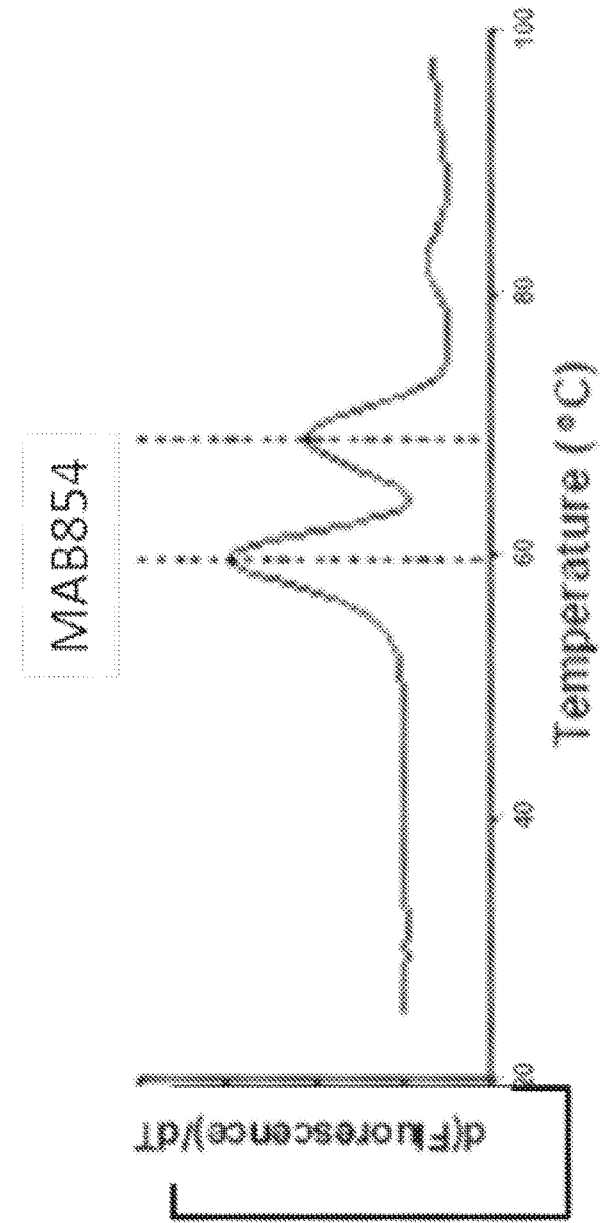

Melting curve assays were performed at a concentration of 2 μg/mL in PBS with PCR STEPONE PLUS™ instrument heating from 15° C. to 99° C. at 1.58° C./min with continuous fluorescence measurement. FIGS. 10A-10F show melting curve assays for mAbs TRL845, TRL847, TRL848, TRL849, and TRL854. Each mAb exhibited high thermal stability. FIG. 10A shows a melting curve for TRL845 exhibiting two melting temperatures (Tm1, Tm2), at 58.3° C. and 68.7° C., respectively. FIG. 10B shows a Table of melting temperatures (Tms) for mAbs TRL845, TRL847, TRL848, TRL849, and TRL854, as shown in FIGS. 10A and 10C-10F, respectively. Exhibition of two melting temperatures (Tm1, Tm2) was likely due to Fc and Fab domains denaturing separately for those mAbs. FIG. 10C shows melting curve for TRL847, exhibiting a melting temperature (Tm1) of 70.3° C. FIG. 10D shows melting curve for TRL848, exhibiting a melting temperature (Tm1) of 70.1° C. FIG. 10E shows melting curve for TRL849 exhibiting two melting temperatures (Tm1, Tm2), at 70° C. and 81.8° C., respectively. FIG. 10F shows melting curve for TRL854 exhibiting two melting temperatures (Tm1, Tm2), at 59.7° C. and 68.9° C. Antibodies TRL053, comprising HC/LC amino acid sequences of SEQ ID NO: 17/18, and TRL597 comprising HC/LC amino acid sequences of SEQ ID NO: 27/28, each exhibited melting temperatures as shown in Table 6.

TABLE 6

Melting Temperatures for mAbs.

| mAb | Tm1 | Tm2 |
|---|---|---|
| TRL053 | 70.1 | 76.5 |
| TRL579 | 70.5 | |

Exhibition of two melting temperatures (Tm1, Tm2) for some antibodies was likely due to Fc and Fab domains denaturing separately for those mAbs. Thus the antibodies used in particular combinations and compositions provided herein are stable and exhibit melting temperatures of greater than 55° C., or in some cases greater than 65° C.

Figure 24:
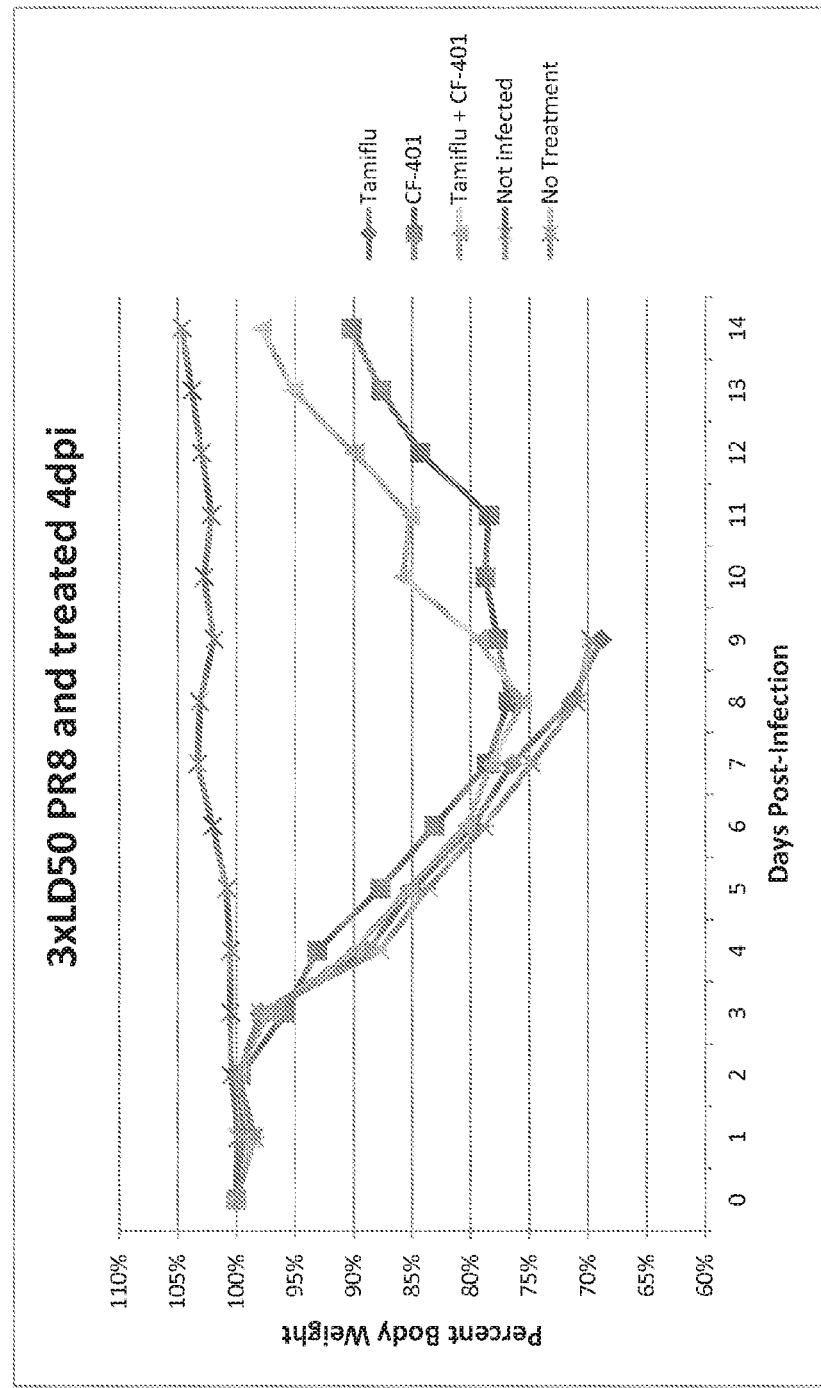
FIG. 24 shows animal studies wherein 100% of mice survive challenged from a lethal dose of H1N1 when treated 4 days post infection with a single administration of CF-401 at 1 mg/kg. Administration of standard of care Tamiflu is not protective, but in addition to CF-401 mAb therapy provides additional protection from weight loss. 10 mg/kg Tamiflu was administered orally on days 4-8 BID. The data show that standard of care (Tamiflu) plus mAb therapy is effective when administered at late time points.

Example 10. Anti-Influenza mAbs Provide Protection when Delivered Via the Pulmonary Route To study the effect of combining CF-401 (mAb 053) with the neuraminidase inhibitor oseltamivir for the treatment of H1N1 infection, mice were challenged with 3×LD50 H1N1 virus and were treated on the fourth day with either a single intranasal dose of 1 mg/kg mAb CF-401, 10 mg/kg bid oral oseltamivir treatment for four days, or a combination of both treatments. As shown in FIG. 24, 100% of mice survived the challenge when treated with a single administration of CF-401 at 1 mg/kg. Standard of care oseltamivir is not protective (0% survival) when administered at these late time points post-infection, but when combined with CF-401 mAb therapy it provided additional protection from weight loss compared to mAb therapy alone. Results are shown in FIG. 24 wherein 100% of mice survive challenged from a lethal dose of H1N1N1 when treated 4 days post infection with a single administration of CF-401 at 1 mg/kg. Administration of standard of care Tamiflu is not protective, but in addition to CF-401 mAb therapy provides additional protection from weight loss. 10 mg/kg Tamiflu was administered orally on days 4-8 BID. The data show that standard of care (Tamiflu) plus mAb therapy is effective when administered at late time points.

Anti-influenza mAbs provide protection when delivered via the pulmonary route. In some embodiments, efficacy can be improved by combining the inventive mAb therapy with other anti-viral treatments, such as neuraminidase inhibitors (e.g. oseltamivir [TAMIFLU™], zanamivir [RELENZA™]), RNA polymerase inhibitors (e.g. favipiravir, VX-787), immune modulators (e.g. inhaled Interferon beta 1a), host-cell targeting agents (e.g. DAS181 [FLUDASE™], Radavirsen), ion-channel inhibitors (e.g. amantidine), or other antivirals.

Example 11. Neutralizing Antibodies are Effective Intranasally

The therapeutic efficacy of systemically delivered antibodies is not solely reliant on neutralization capability, as both neutralizing and non-neutralizing antibodies given by IP route exhibit similar effects in treating and preventing lethal infection. Neutralizing and non-neutralizing antibodies were similarly effective when administered IP. This brings into question whether neutralization contributes significantly to therapeutic efficacy during systemic delivery. Delivery of non-neutralizing antibodies by IV or IP route did not result in significant efficacy differences (data not shown).

Figures 11A, 11B:
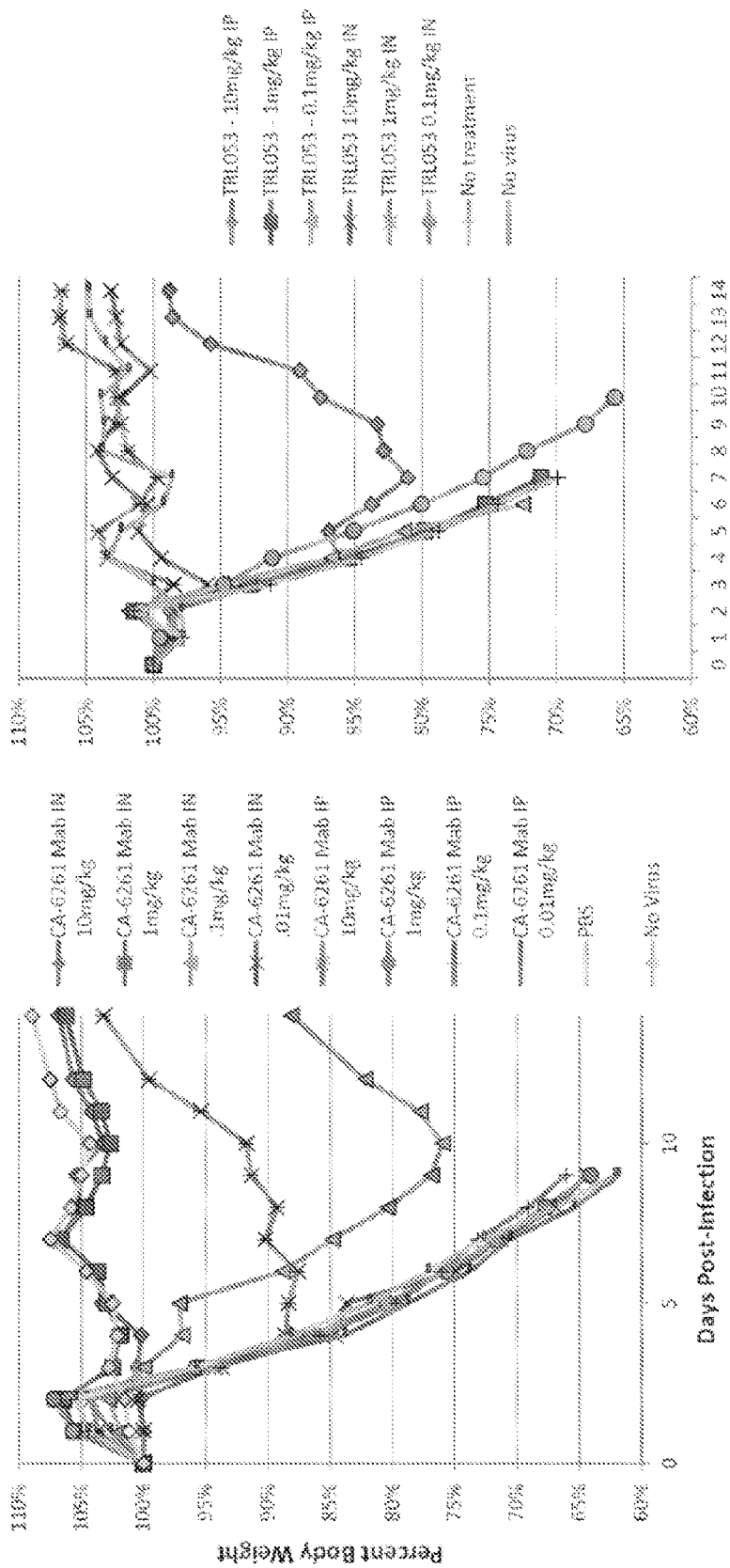
FIG. 11A shows IN and IP administration at comparable doses and shows that Mab IN is between 10 and 100 fold more potent than the same Mab administered IP. Animals were inoculated with 10×LD50 of H1 influenza virus (A/Puerto Rico/8/1934) and treated IN or IP 24 hpi with 10 mg/kg, 1 mg/kg and 0.1 mg/kg of neutralizing CA6261 Mab, with PBS and no virus as controls. Animals were monitored for body weight daily for 14 days post infection and percent body weight of original day 0 weight is plotted. The data shows IN delivery of neutralizing antibodies significantly enhanced their therapeutic efficacy compared to systemic delivery.
FIG. 11B shows evaluation of IN and IP administration of antibody MAb53 (TRL053) in therapeutic efficacy against H1 virus. Animals were inoculated with 10×LD50 of H1 influenza virus A/Puerto Rico/8/1934 (PR8) and treated 24 hpi with 10 mg/kg, 1 mg/kg and 0.1 mg/kg of neutralizing antibody TRL053 (MAb53) administered IN or IP, with PBS treatment and no virus as controls. Animals were monitored for body weight daily for 14 days post infection and percent body weight of original day 0 weight is plotted. IN administered TRL053 demonstrated greater efficacy that IP dosing. TRL053 was somewhat effective only at an IP dose of 10 mg/kg. IN doses were effective at 10 mg/kg and 1 mg/kg.
Figures 12A, 12B:
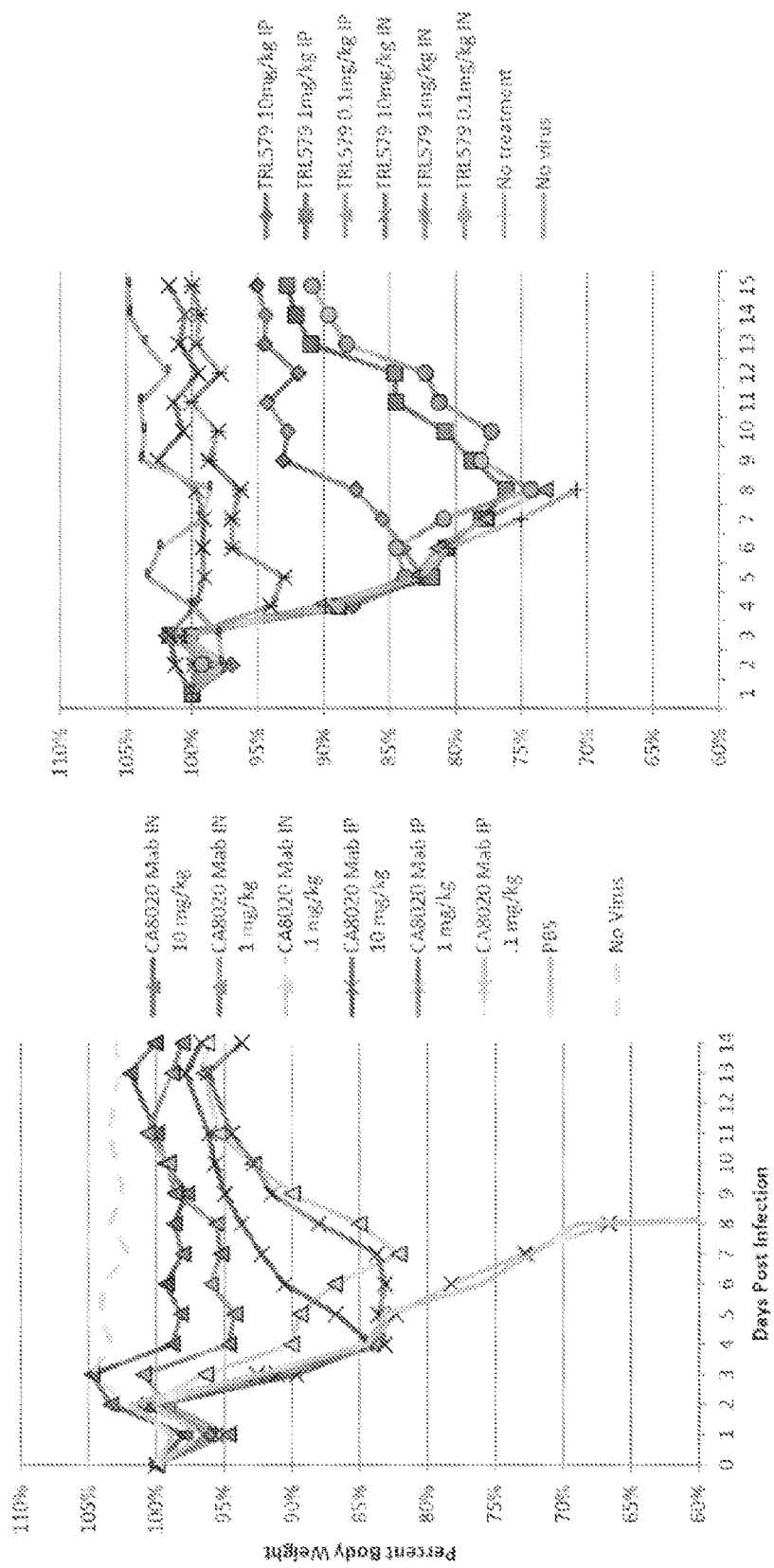
FIG. 12A shows IN and IP comparison at comparable doses and shows that Mab CA8020 IN is between 10 and 100 fold more potent than the same Mab administered IP. Animals were inoculated with 10×LD50 of H3 influenza virus and treated IN or IP 24 hpi with 10 mg/kg, 1 mg/kg and 0.1 mg/kg of neutralizing CA8020 Mab, with PBS and no virus as controls. Animals were monitored for body weight daily for 14 days post infection and percent body weight of original day 0 weight is plotted.
FIG. 12B shows evaluation of IN and IP administration of antibody MAb579 (TRL579) in therapeutic efficacy against H3 virus. Animals were inoculated with 10×LD50 of Vic/11 H3 virus and treated 24 hpi with 10 mg/kg, 1 mg/kg and 0.1 mg/kg of antibody TRL579 administered IN or IP. Animals were monitored for body weight daily for 14 days post infection. TRL579 is effective IP or IN, however, IN administered TRL579 demonstrated greater efficacy that IP dosing. TRL579 was somewhat effective only at an IP dose of 10 mg/kg. IN doses in this study were effective at 10 mg/kg and 1 mg/kg.
Figure 13:
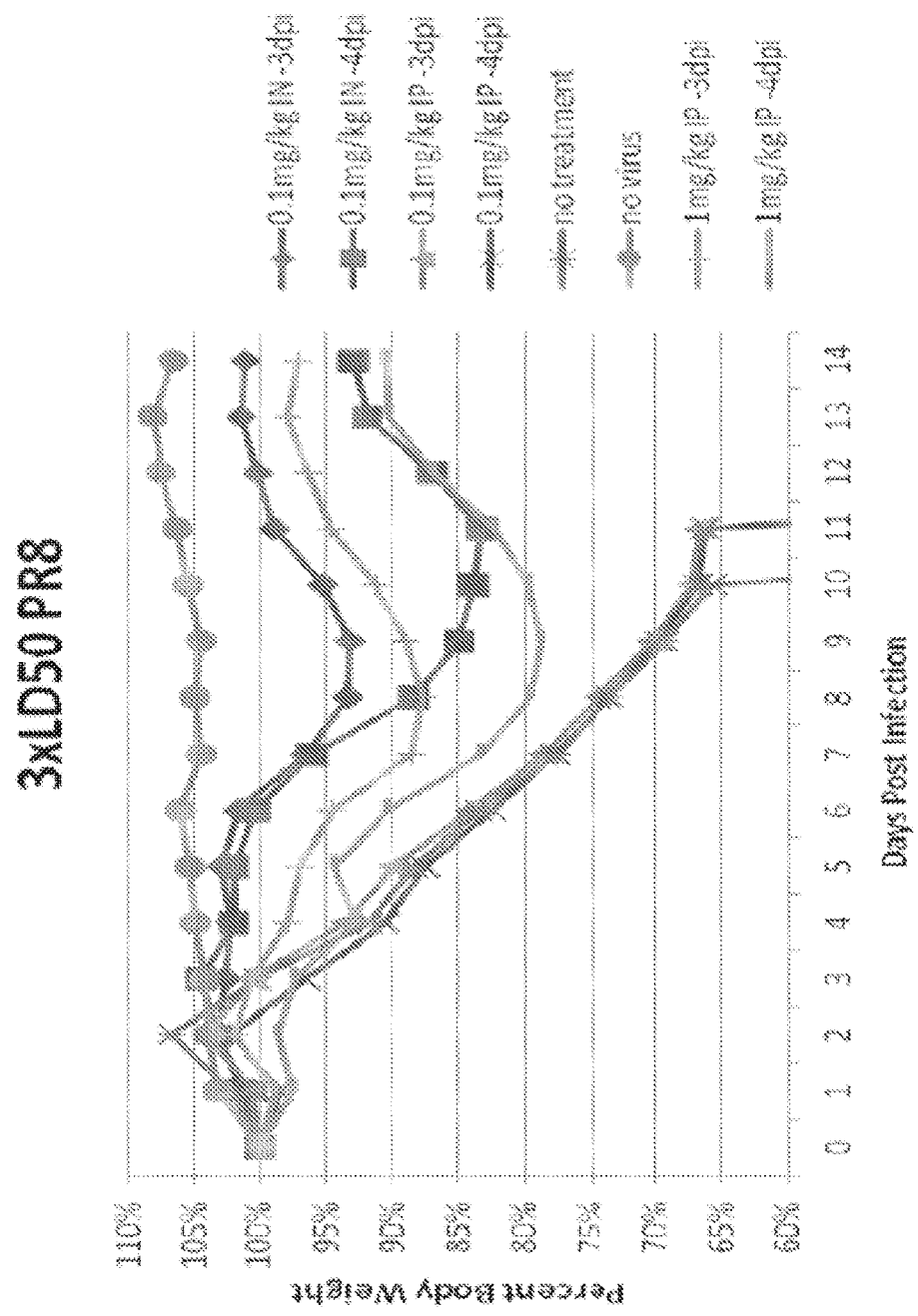
FIG. 13 shows IN and IP administration prophylactically 3 or 4 days prior to infection with virus. Antibody CA6261 was administered IN or IP 3 or 4 days before challenge with 3×LD50 of H1 influenza virus A/Puerto Rico/8/1934 (denoted PR8). CA6261 antibody was administered IN (0.1 mg/kg) or IP (0.1 mg/kg and 1 mg/kg) 3 days prior to infection (−3 dpi) or 4 days prior to infection (−4 dpi) and challenge with H1 influenza virus. Controls were no virus and no treatment. Animals were monitored for body weight daily for 14 days post infection and percent body weight of original day 0 weight is plotted.

In contrast, IN delivery of neutralizing antibodies significantly enhanced their therapeutic efficacy compared to systemic delivery (FIG. 11A). This boost in therapeutic efficacy is specific to neutralizing antibodies, as established non-neutralizing antibodies do not display a similar enhanced therapeutic efficacy. Unlike IP delivery, IN delivery of neutralizing antibodies offers significant therapeutic benefit compared to non-neutralizing antibodies. This enhanced efficacy of IN therapy correlates with the ability of an antibody to neutralize, as non-neutralizing antibodies did not exhibit improved therapeutic efficacy IN. IN enhanced efficacy is demonstrated by broadly recognizing antibodies against H1 virus CA6261 (an IgG2a antibody binding the short α helix of HA2 subunit) (FIG. 11A). Further validating the IN efficacy effect, we have evaluated another cross-protective antibody CR9114 and shown it to be highly effective IN (data not shown and FIG. 24). CR9114 binds a conserved epitope in the HA stem and protects against lethal challenge with influenza A and B viruses when administered IV (Dreyfus C et al (2012) Science Express 9 Aug. 2012 10.1126/science.1222908).

We have not observed a significant difference in IN efficacy with regard to antibodies having distinct antibody isotypes. Isotype differences have been observed in IP dosing, suggesting that effector function may be relevant.

Also, single neutralizing antibodies were effective in blocking infection against multiple strains of their target H1 or H3 virus, indicating that efficacy is not strain specific or limited. Thus, IN administration provides a viable and indeed more effective alternative for neutralizing antibodies directed against influenza virus.

Example 12. Neutralizing Fabs are Effective Intranasally

A study was performed to evaluate whether removal of the Fc will abrogate therapeutic efficacy of IP or IN administered neutralizing and non-neutralizing Fabs. As seen in FIG. 25, IP administration of a model Fab (CA6261 antibody Fab) does not provide therapeutic efficacy against H1 virus at 10 mg/kg or lower. Mice treated with Fab IP all succumbed to infection similar to PBS treated mice. In contrast, mice treated IN with neutralizing Fab at a dose of 10 mg/kg and 1 mg/kg were able to survive lethal infection (FIG. 25). All doses administered IN (even to 0.1 mg/kg) showed greater efficacy than any IP dose administered. Comparable results were observed comparing CA6261 Fab IN versus IP or IV in the same experiment, where Fab CA6261 was not protective or efficacious when administered either IP or IV, but showed significant efficacy (animals retained 95% or greater body weight) when the same dose (5 mg/kg) was administered IN (data not shown). These data demonstrate that Fabs are effective to block or treat viral infection intranasally for neutralizing antibodies. The data further indicate that systemic Mab delivery requires Fc effector function for therapeutic efficacy because Fabs were ineffective.

Model Fabs from non-neutralizing antibodies did not retain therapeutic efficacy when administered by either IN or IP route. Mice infected with an H3 virus were treated by IN delivery of purified Fab of exemplary prior art antibodies CA8020 (neutralizing) and a non-neutralizing antibody (data not shown). While neutralizing Fabs are able to show therapeutic efficacy, non-neutralizing Fabs are not capable of protecting mice from lethal challenge. Antibody fragments, particularly Fabs, from non-neutralizing antibodies do not exhibit therapeutic efficacy when administered IN.

Example 13. IN Delivery is 10-100 Fold More Potent than IP Delivery

Intranasal (IN) delivery of neutralizing antibodies is between 10-100 fold more potent than intraperitoneal (IP) delivery. Mice were infected with 10×LD50 of PR8 virus (H1 virus) and at 24 hpi were treated with antibody (FIG. 11A). Neutralizing antibody CA6261 was ten-fold serially diluted and administered either by IN or IP route (FIG. 11A). Mice treated by IN route exhibited less disease severity as indicated by weight loss and were 100% protected from lethal infection at all dilutions. In comparison, only mice treated IP at the highest dose (10 mg/kg) exhibited transient weight loss and protection from lethal infection. All lower dilutions did not protect mice when administered IP. In contrast, IN treatment with a dose of 0.1 mg/kg resulted in transient weight loss and survival of all mice. Mice treated by IN delivery with a dose of 10 mg/kg and 1 mg/kg were protected from detectable weight loss at all times post infection. Antibodies given by IP route at all doses exhibited some degree of weight loss, and only mice treated at the highest dose of 10 mg/kg survived infection.

We confirmed that intranasal delivery of neutralizing antibodies similarly results in enhanced therapeutic efficacy against H3 viruses. Mice were infected with an H3 virus and treated 24 hpi (FIG. 12A). Neutralizing antibody CA8020 was ten-fold serially diluted and administered by IN or IP. As observed in our studies with H1 virus, antibody administered by the IN route provided 100% survival at all dilutions against H3 virus, and exhibited less weight loss than antibodies administered by IP route.

Together these data demonstrate that neutralization is essential for enhanced therapeutic efficacy when delivered IN. Furthermore, therapeutic efficacy of systemically delivered antibodies is not dependent on neutralization, as similar levels of efficacy can be observed for both neutralizing and non-neutralizing antibodies. Supporting this observation, the therapeutic efficacy of a neutralizing Fab is abolished when administered IP, but neutralizing Fab display efficacy when delivered IN. Neutralizing Fabs administered IN display similar improved efficacy compared to IP administration as IN delivery of their full Mab counterpart.

Example 14. Prophylaxis Studies with IN Antibodies

Given the remarkable efficacy of intranasal administration of neutralizing antibodies after infection, studies were undertaken to evaluate efficacy of intranasal administration prophylactically and prior to infection with virus. These studies serve to assess and demonstrate the applicability of intranasal administration in instances where an individual is exposed to influenza virus and as an effective approach to prevent or reduce transmission within an exposed or at risk population, or clinically in patients where infection or illness would be an overall greater health risk. The Group 1 (H1) antibody CA6261 was evaluated for administration days prior to influenza virus infection in the mouse animal model. Administration of CA6261 was evaluated 3, 4, 5, 6, and 7 days prior to infection challenge and IN and IP dosing at different doses were directly compared.

In the first studies, antibody CA6261 was administered IN or IP and the mice were then challenged with 3×LD50 dose of H1 PR8 virus. FIG. 13 depicts studies of IN and IP administration prophylactically 3 or 4 days prior to infection with virus. Antibody CA6261 was administered IN or IP 3 or 4 days before challenge with 3×LD50 PR8. CA6261 antibody was administered IN (0.1 mg/kg) or IP (0.1 mg/kg and 1 mg/kg). IN administration up to 4 days prior to infection (−4 dpi) (assessed at 0.1 mg/kg) protected mice from virus challenge. IP administration 3 or 4 days prior to infection at the same dose (0.1 mg/kg) was completely ineffective. IP administration at 3 or 4 days pre-infection was effective at 1 mg/kg. On comparing the IN (0.1 mg/kg) and IP (1 mg/kg) administrations at −3 dpi and −4 dpi, in both instances, the tenfold lower IN dose was more effective than IP.

Prophylactic efficacy was then evaluated 5, 6 and 7 days prior to virus infection. A tenfold higher dose IP was evaluated versus IN administration. Antibody CA6261 was administered IP (at 1 mg/kg) or IN (at 0.1 mg/kg) either 5, 6 or 7 days before challenge with 3×LD50 of H1 influenza virus PR8 (data not shown). Tamiflu administration (10 mg/kg orally, twice a day for five days) was also assessed for comparison. Efficacy was demonstrated at 0.1 mg/kg IN administration at −5 dpi. Not all mice survived with 0.1 mg/kg IN administration 6 or 7 days prior to virus challenge. The tenfold higher IP dose (10 mg/kg) was effective at 5, 6 or 7 days prior to challenge. Administration of antibody IN at 0.1 mg/kg 5 days prior to challenge was at least as effective as IP administration of a tenfold higher 1 mg/kg dose 7 days prior to challenge.

Figure 14:
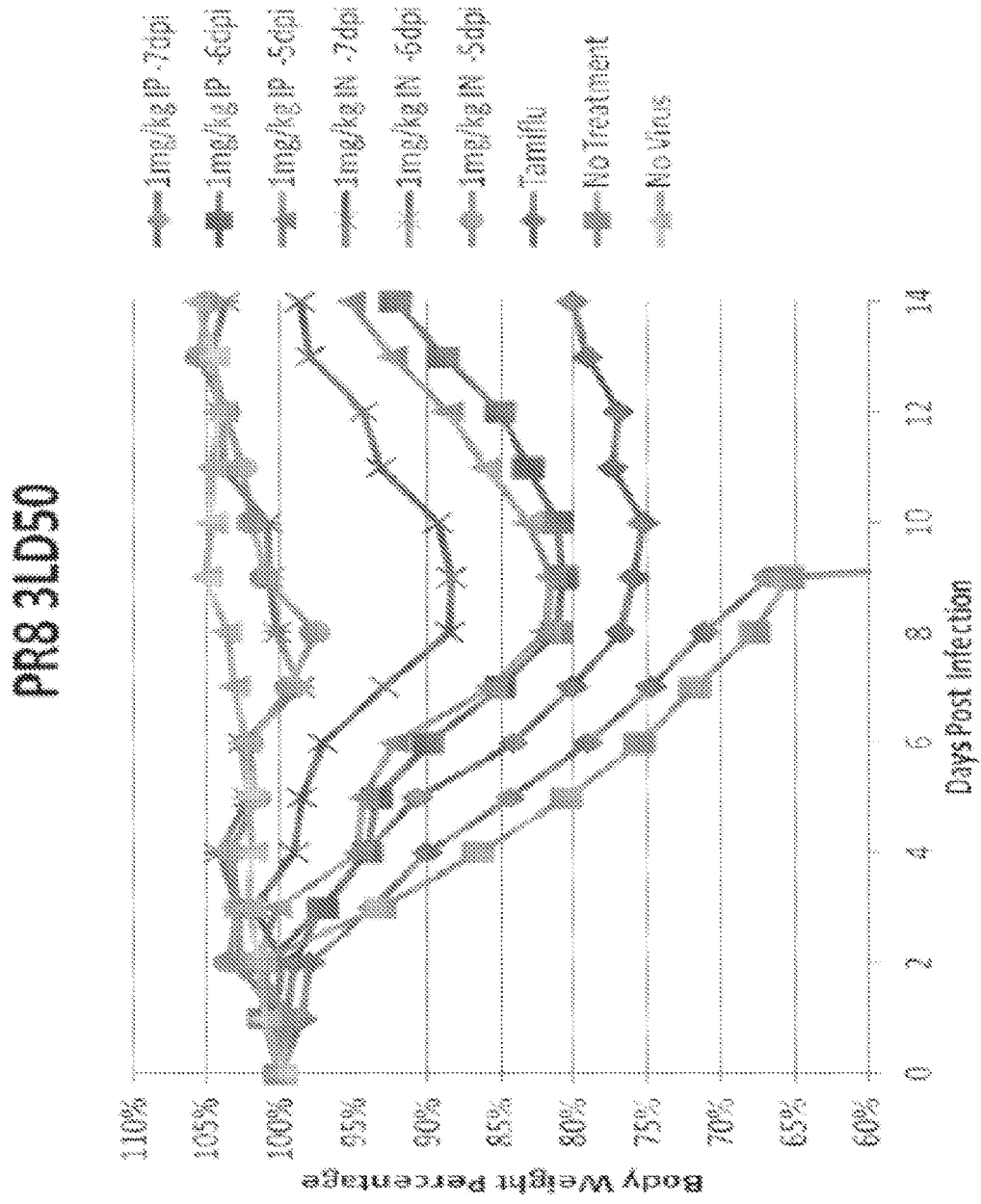
FIG. 14 shows IN and IP administration prophylactically 5, 6 or 7 days prior to infection with virus. Antibody CA6261 was administered IP (at 1 mg/kg) or IN (at 1 mg/kg) 5, 6 or 7 days before challenge with 3×LD50 of H1 influenza virus PR8. Controls were Tamiflu (10 mg/kg given orally, twice a day for five days), no treatment and no virus. Animals were monitored for body weight daily for 14 days post infection and percent body weight of original day 0 weight is plotted. In all instances, antibody was more effective than Tamiflu.
Figure 15:
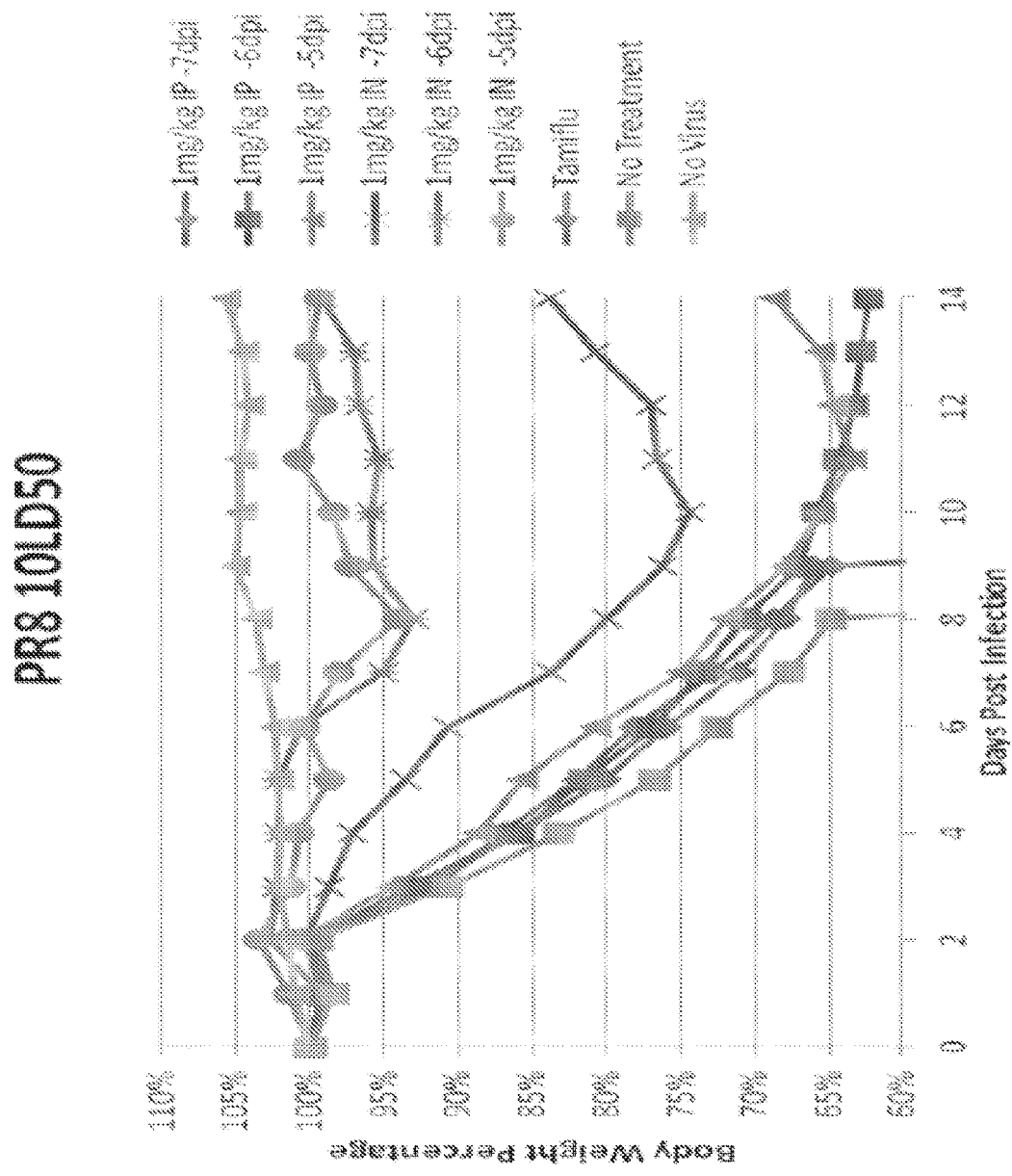
FIG. 15 shows IN and IP administration prophylactically 5, 6 or 7 days prior to infection with virus, with virus challenge at higher dose of 10×LD50. Antibody CA6261 was administered IP (at 1 mg/kg) or IN (at 1 mg/kg) 5, 6 or 7 days before challenge with 10×LD50 of H1 influenza virus PR8. Controls were Tamiflu (10 mg/kg given orally, twice a day for five days), no treatment and no virus. Animals were monitored for body weight daily for 14 days post infection and percent body weight of original day 0 weight is plotted. In this study, only animals administered antibody to the airway (via intranasal administration) completely survived virus challenge. Mice treated with 1 mg/kg of antibody administered 5, 6 or 7 days prior to virus challenge were not fully protected and mice died from the infection. Tamiflu was completely ineffective in protection. Mice treated with 0.1 mg/kg antibody intranasally either 5 or 6 days prior to virus infection survived virus challenge nearly as well as control animals that were not infected.
Figure 18:
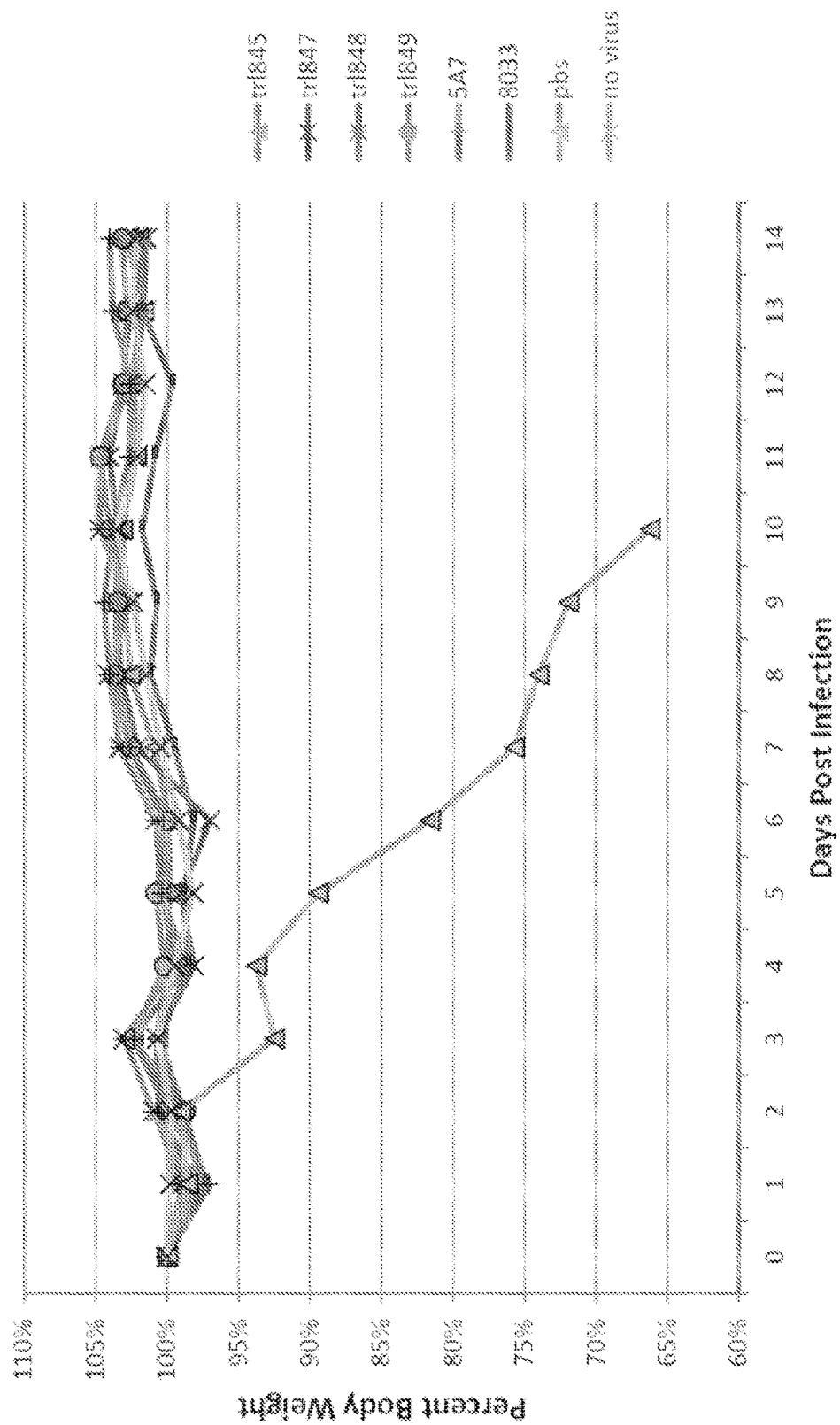
FIG. 18 shows animal efficacy studies with various influenza B antibodies administered 24 hpi with B/Florida (Yamagata lineage) virus. All antibodies were administered IN at 1 mg/kg 24 hpi with 10×LD50 virus. Antibodies tested were TRL845, TRL847, TRL848, TRL849, 5A7 and CA8033. PBS and no virus were controls. Animals were monitored for body weight daily for 14 days post infection and percent body weight of original day 0 weight is plotted. IN administered anti-influenza B antibodies demonstrated efficacy against infection with Yamagata lineage virus at a 10×LD50 dose, with several antibodies showing antibody-treated infected animals retaining 100% body weight.
Figure 19:
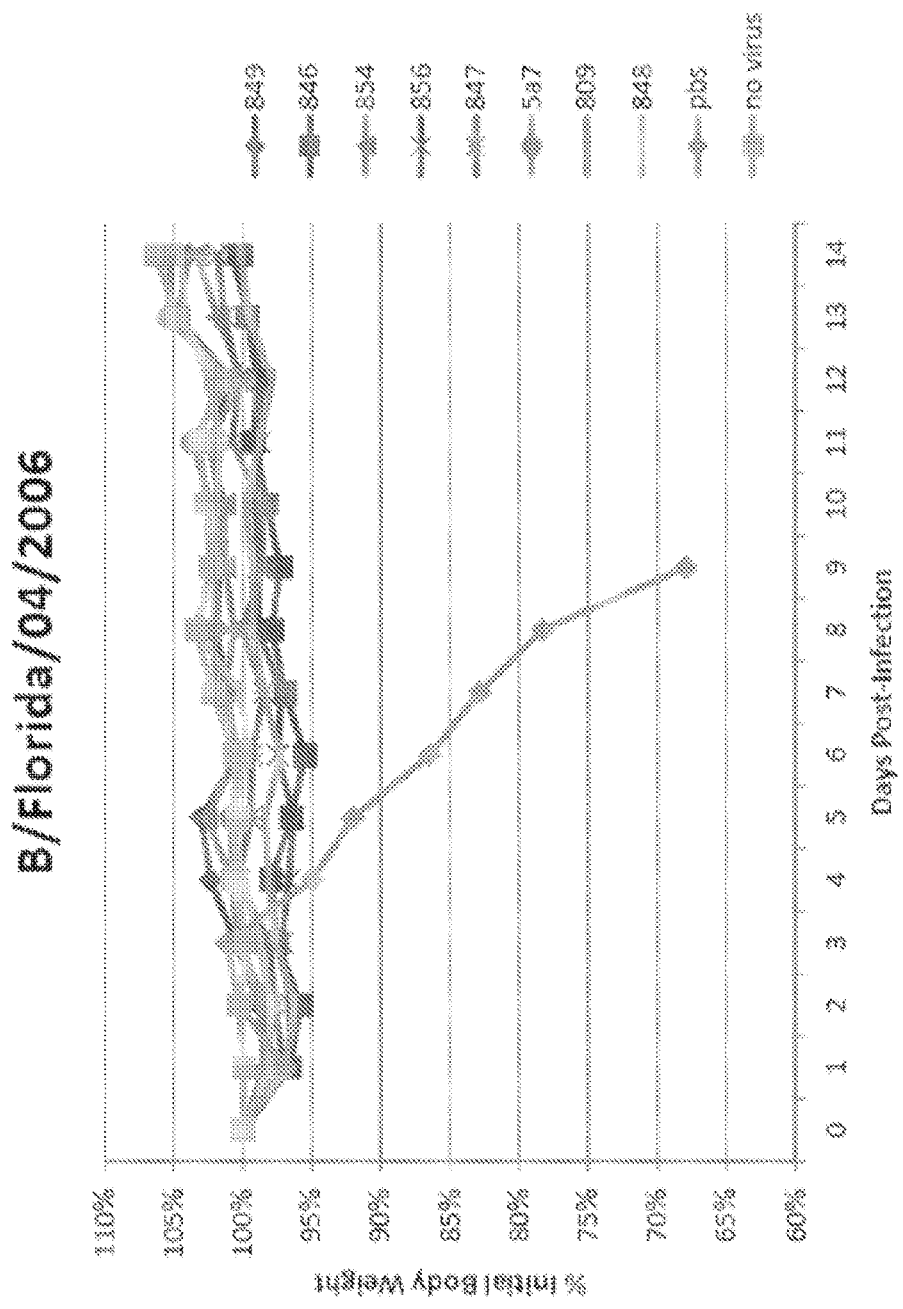
FIG. 19 shows animal efficacy studies with various influenza B antibodies administered 24 hpi with B/Florida (Yamagata lineage) virus. All antibodies were administered IN at 1 mg/kg 24 hpi with 10×LD50 virus. Antibodies tested were TRL849, TRL846, TRL854, TRL856, TRL847, 5A7, TRL809 and TRL848. PBS and no virus were controls. Animals were monitored for body weight daily for 14 days post infection and percent body weight of original day 0 weight is plotted. IN administered anti-influenza B antibodies demonstrated efficacy against infection with Yamagata lineage virus at a 10×LD50 dose, with several antibodies showing antibody-treated infected animals retaining 100% body weight.
Figure 20:
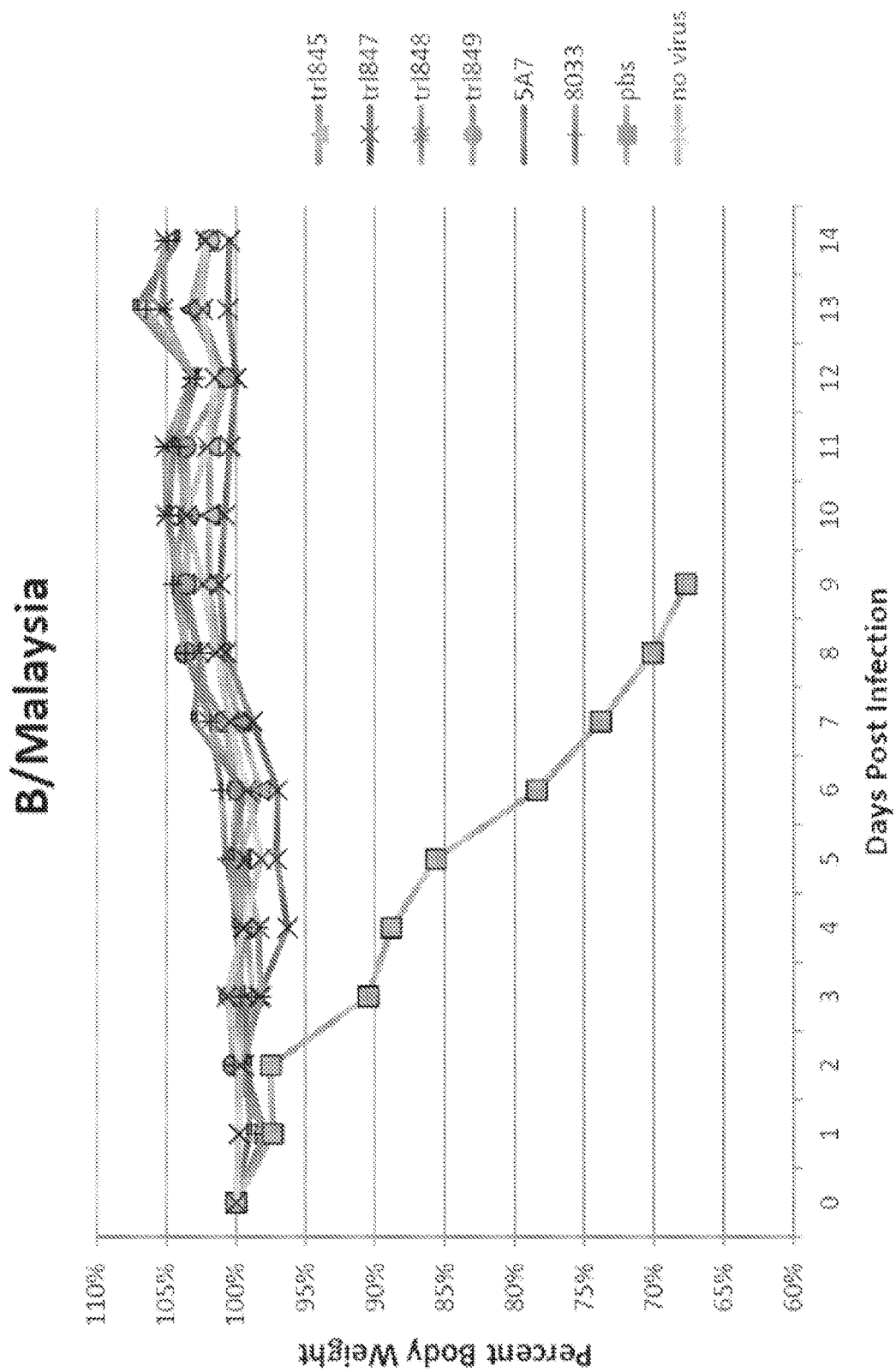
FIG. 20 shows animal efficacy studies with various influenza B antibodies administered 24 hpi with B/Malaysia (Victoria lineage) virus. All antibodies were administered IN at 1 mg/kg 24 hpi with 10×LD50 virus. Antibodies tested were TRL845, TRL847, TRL848, TRL849, 5A7 and CA8033. PBS and no virus were controls. Animals were monitored for body weight daily for 14 days post infection and percent body weight of original day 0 weight is plotted. IN administered anti-influenza B antibodies demonstrated efficacy against infection with Victoria lineage virus at a 10×LD50 dose, with several antibodies showing antibody-treated infected animals retaining 100% body weight.
Figure 21:
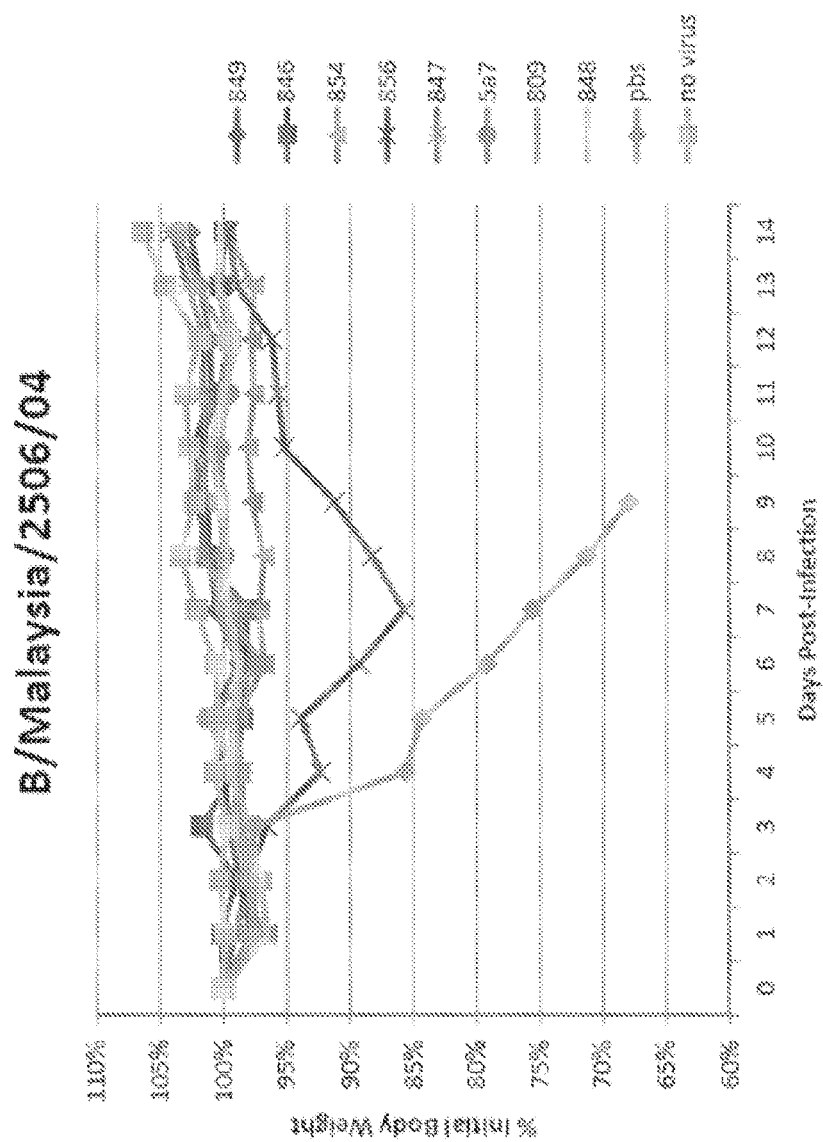
FIG. 21 shows animal efficacy studies with various influenza B antibodies administered 24 hpi with B/Malaysia (Victoria lineage) virus. All antibodies were administered IN at 1 mg/kg 24 hpi with 10×LD50 virus. Antibodies tested were TRL849, TRL846, TRL854, TRL856, TRL847, 5A7, TRL809 and TRL848. PBS and no virus were controls. Animals were monitored for body weight daily for 14 days post infection and percent body weight of original day 0 weight is plotted. IN administered anti-influenza B antibodies demonstrated efficacy against infection with Victoria lineage virus at a 10×LD50 dose, with several antibodies showing antibody-treated infected animals retaining 100% body weight.
Figures 22A, 22B:
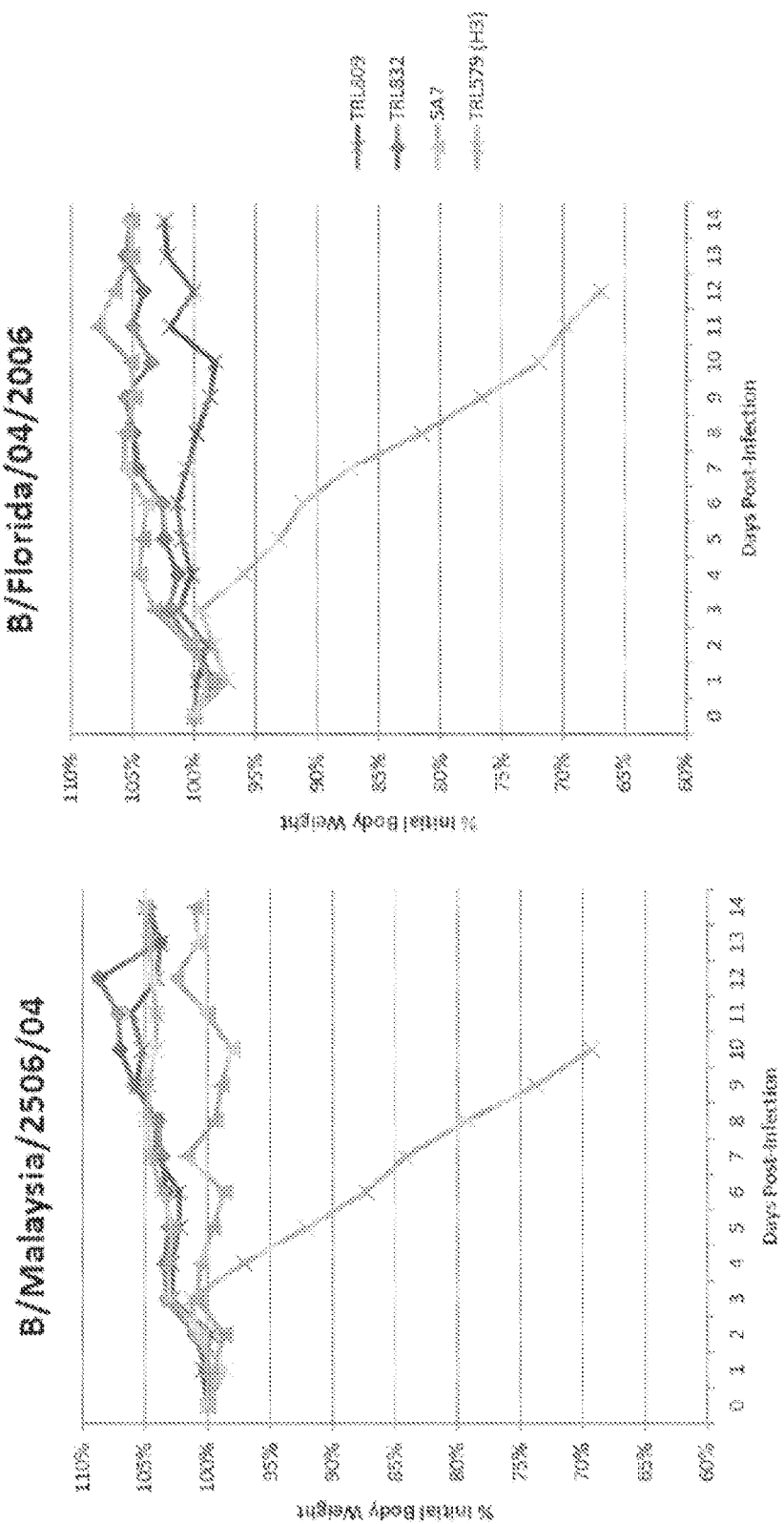
FIGS. 22A and 22B show anti-influenza B antibody efficacy assessment in animal studies with (FIG. 22A) Victoria lineage virus B/Malaysia and (FIG. 22B) Yamagata lineage virus B/Florida. Mice were infected with 10×LD50 of virus and treated IN 24 hpi with antibody at 1 mg/kg dose. Animals were monitored for body weight daily for 14 days post infection and percent body weight of original day 0 weight is plotted. Antibodies tested were TRL809, TRL832, antibody 5A7 and TRL579 as indicated. TRL579 is an anti-H3 antibody and served as a negative control. TRL809 and TRL832 neutralize influenza by blocking virus binding. IN administered anti-influenza B antibodies TRL809, TRL832 and 5A7 exhibited efficacy against infection with Victoria lineage virus at a 10×LD50 dose, showing antibody-treated infected animals retaining ~100% body weight.

Higher IN doses at 1 mg/kg were then evaluated 5, 6 and 7 days prior to virus challenge. FIG. 14 depicts studies of IN versus IP administration with antibody CA6261 administered IP or IN at 1 mg/kg 5, 6 or 7 days before challenge with 3×LD50 virus PR8. IN administration of 1 mg/kg antibody was effective prophylactically up to 7 days prior to virus challenge, and in each instance IN was more effective than the same amount of antibody administered IP. IN fact, IN administration at any time (5, 6 or 7 days prior to challenge) was more effective than any IP administration, even if IP was administered closer to virus challenge. In all instances, antibody was more effective than Tamiflu.

The above studies demonstrate that IN administration is in fact superior to IP administration for prophylactic protection. IN administration of 0.1 mg/kg antibody is protective against challenge (3×LD50) up to 5 days pre-infection (−5 dpi). The same dose 0.1 mg/kg administered IP at any of 3-7 days before virus infection does not protect animal (against the same 3×LD50 dose of virus). At higher doses of IN administered antibody (1 mg/kg was evaluated), IN administered antibody can protect against challenge if administered at least up to 7 days in advance. IN administration more than 7 days in advance was not evaluated but may be efficacious.

Repeated dosing post infection is efficacious and lower doses intranasally are effective when multi-dosed hours apart (8 hours, 32 hours, 52 hours)(data not shown). Similarly, repeated dosing prior to virus infection or exposure is predicted to be effective and may permit lower IN prophylactic dosing.

Prophylactic efficacy was evaluated at higher doses of virus challenge, particularly administering the CA2621 antibody days before challenging with 10×LD50 of H1 virus PR8. Three and four days before challenge with 10×LD50 of PR8 H1 subtype virus, animals were administered 0.1 mg/kg CA6261 antibody either IN or IP (data not shown). IP administration of 0.1 mg/kg antibody 3 or 4 days before virus challenge was completely ineffective, with the IP treated animals succumbing to virus infections similar to animals who received no treatment. In contrast, animals administered 0.1 mg/kg antibody intranasally either 3 or 4 days prior to high titer virus challenge were protected from infection.

Antibody administration 5, 6 and 7 days prior to high titer challenge was evaluated, with antibody administered at 1 mg/kg either IN or IP (FIG. 15). In this study, only animals administered antibody to the airway (via intranasal administration) completely survived virus challenge. Mice treated with 1 mg/kg of antibody administered 5, 6 or 7 days prior to virus challenge were not fully protected and mice died from the infection. Tamiflu was completely ineffective in protection. Mice treated with 0.1 mg/kg antibody intranasally either 5 or 6 days prior to virus infection survived virus challenge nearly as well as control animals that were not infected.

Thus, intranasal administration of anti-influenza antibodies is an effective protocol and method for prophylaxis against antibody infection. Influenza neutralizing antibody administered intranasally at least up to 7 days prior to virus infection was protective against virus challenge. Protection via intranasal administration at least as much as 7 days in advance was demonstrated for high titer virus, higher even than might be reasonably expected to represent a human's exposure to virus. The level of protection observed in these studies indicates that intranasal antibody administration will be effective in a human subject to protect against virus challenge and to block or reduce virus transmission. Pulmonary administered antibody is protective under conditions and in instances where systemic administration is ineffective.

Example 16. Combinations for Influenza Therapy or Prophylaxis

A combination of antibodies cross-reacting with the three principal strains of influenza (H1, H3 and B) is desirable, in order that any anticipated circulating influenza can be treated or prevented in a single dose or combination of doses. This could circumvent the need to characterize an infective virus in detail prior to administering an antibody or antibody mixture. Diagnostics to determine influenza strain necessitate available clinical laboratory facilities and typically require a 12-24 minimum turnaround time, resulting in unfavorable delay in treatment if determination of flu strain is needed before selecting the appropriate directed therapy. With a broadly reactive composition against influenza A and B strains, prior strain diagnosis is not necessary prior to treatment. Additionally, antibodies, particularly neutralizing antibodies, have an immediate treatment effect that cannot be obtained by vaccination, which only acts prophylactically and typically requires weeks to become effective We sought to evaluate and identify a therapeutic combination of monoclonal antibodies (mAbs) covering influenza Types A and Type B. In particular, a suitable and valuable combination includes antibodies effective against Type A Group 1, Type A Group 2, and influenza B viruses. This provides for a combination effective against relevant and circulating influenza and can be administered prior to or without diagnostic evaluation or assessment of virus type. Criteria for a therapeutic combination included: effective neutralizing antibodies; antibodies having efficacy in combination against the relevant circulating influenza viruses, particularly influenza A H1 and H3, and influenza B; efficacy in combination against either influenza A or influenza B challenge; absence of notable interaction or competition between antibodies; antibodies effective IP, IV and IN, or via an airway route as well as systemically. Preferably, mAbs to be included in the cocktail have compatible biophysical properties such that they can be readily coformulated. Matching of pI values may be desirable. The therapeutic combination would be effective against any relevant circulating influenza virus, without requiring diagnostic evaluation or characterization of influenza in a patient or subject. Human monoclonal antibodies, or at least antibodies comprising human variable region, particularly at least human complementarity determining regions (CDRs) in heavy and light chains are preferred and utilized.

Suitable anti-influenza A antibodies were evaluated. The anti-H1 antibody TRL053 (MAb53) is effective in neutralizing Group 1 influenza viruses, including H1, in vitro and in vivo. TRL-053 was isolated from a human antibody phage library and is described in US2012/0020971 and WO2011/160083 and is effective in neutralizing Group 1 and 2 H1, H9, H7 and H5 subtypes. TRL053 exhibits binding affinity Kd to influenza H1 and H5 virus strains in the nM or sub nM range and exhibits an isoelectric point (pI) of 8.54. The heavy and light chain variable region CDR sequences for TRL053 are provided in the accompanying sequence listing, with full variable region amino acid sequences indicated above. TRL053 was evaluated in vivo for efficacy against Ill virus PR8 (FIG. 11B). Animals were inoculated with 10×LD50 of H1 influenza virus PR8 and treated 24 hpi with 10 mg/kg, 1 mg/kg and 0.1 mg/kg of antibody TRL053 (MAb53) administered IN or IP. Animals were monitored for body weight daily for 14 days post infection. TRL053 is effective IP or IN, however. IN administered TRL053 demonstrated greater efficacy that IP dosing. TRL053 was somewhat effective only at an IP dose of 10 mg/kg. IN doses in this study were effective at 10 mg/kg and 1 mg/kg.

Figure 23:
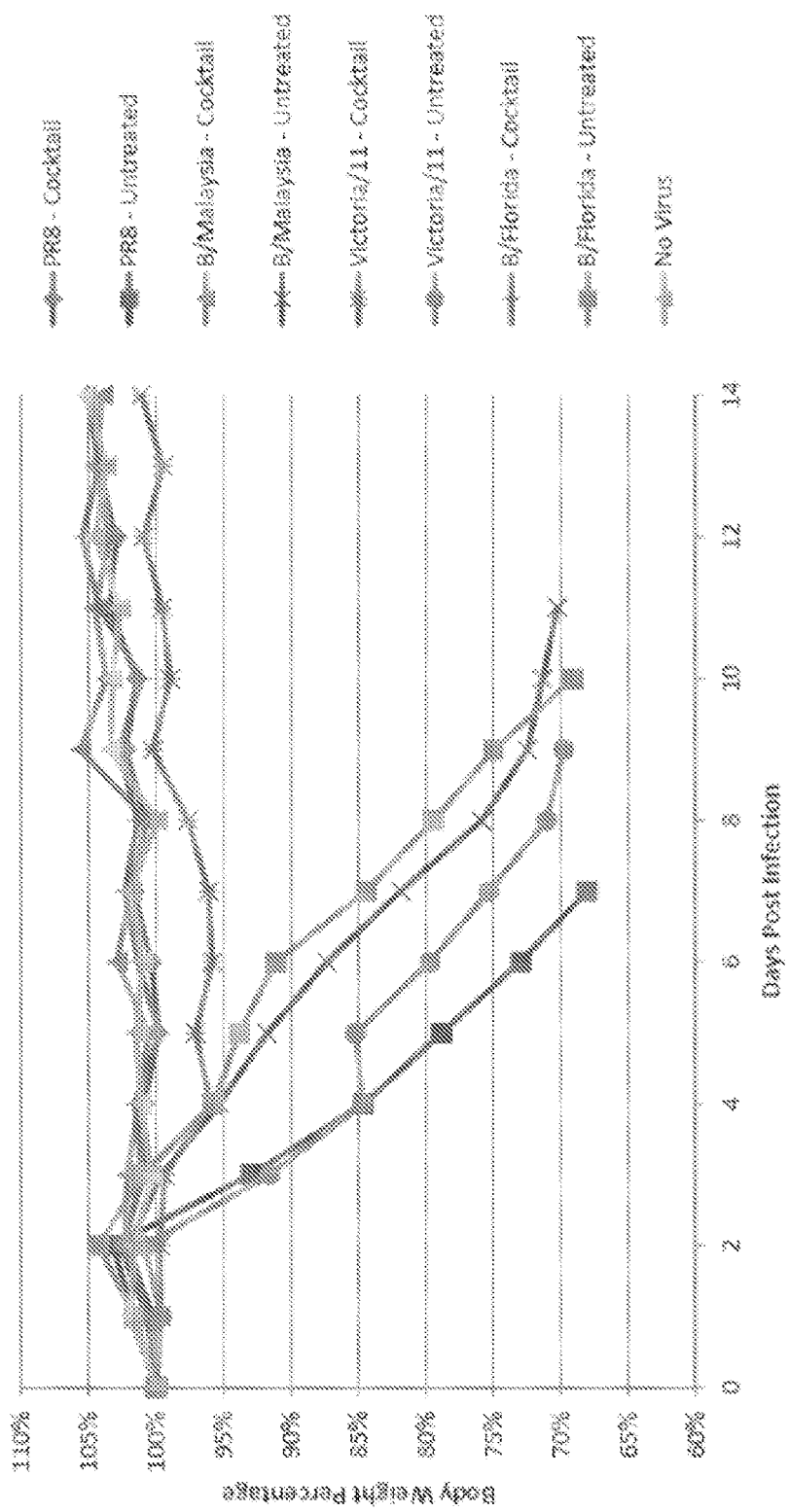
FIG. 23 shows animal studies evaluating antiviral efficacy using IN administration of a combination of antibodies TRL053, TRL579 and 5A7 against influenza A or influenza B viruses. Animals were infected with either H1 virus PR8, H3 virus Victoria/11, influenza B virus B/Malaysia or influenza B virus B/Florida and then left untreated or treated with a cocktail of the three antibodies. Each antibody was included at a dose of 1 mg/kg, providing a total antibody dosage of 3 mg/kg. For cocktail treated animals, the combination antibody was dosed at 24 hpi with 10×LD50 of viruses as indicated. No virus is depicted as a control. Animals were monitored for body weight daily for 14 days post infection and percent body weight of original day 0 weight is plotted.

The anti-H antibody TRL579 (MAb579) is effective in neutralizing Group 2 influenza viruses in vitro and in vivo. TRL-579 was isolated from a human antibody phage library and is described in WO2013/086-52 and is effective in neutralizing H3 and H7. TRL579 exhibits binding affinity Kd to influenza H3 and H7 virus strains in the nM or sub nM range and exhibits an isoelectric point (pI) of 8.60. The heavy and light chain variable region CDR sequences for TRL-579 are provided in the accompanying sequence listing, with full variable region amino acid sequences indicated above. TRL579 was evaluated in vivo for efficacy against H3 virus Vic/11 (FIG. 12B). Animals were inoculated with 10×LD50 of virus and treated 24 hpi with 10 mg/kg, 1 mg/kg and 0.1 mg/kg of antibody TRL579 administered IN or IP. Animals were monitored for body weight daily for 14 days post infection. TRL579 is effective IP or IN, however, IN administered TRL579 demonstrated greater efficacy that IP dosing. TRL579 was somewhat effective only at an IP dose of 10 mg/kg. IN doses in this study were effective at 10 mg/kg and 1 mg/kg.

To provide a suitable anti-B antibody in an effective combination, antibodies directed against influenza B were isolated. Human antibodies binding hemagglutinin protein (HA) of influenza and effective in neutralizing influenza B viruses of the B/Yamagata and B/Victoria clades were identified using CellSpot (U.S. Pat. No. 7,413,868) to identify high affinity binding antibodies and initially described in U.S. Ser. No. 61/935,746 filed Feb. 4, 2014. A listing of B specific antibodies and their sequences, particularly monoclonal antibody heavy and light chain CDR sequences for various B antibodies, are depicted in the Sequence Listing. The CDR1, CDR2 and CDR3 for the heavy and light chain is indicated, as determined by IMGT criteria (international ImMunoGeneTics database imgt; Ehrenmann F., Kaas Q. and Lefranc M.-P. (2010) Nucleic Acids Res., 38, D301-307.

The B antibodies were constructed and isolated to have identical heavy chain constant region sequences. The constant regions are codon optimized for expression in human cells. The heavy chain IgG1 constant region sequence is provided above (SEQ ID NO: 297). The light chain constant region for kappa light chain antibodies (TRL845, 846, 847, 809, 849 and 854) is provided above (SEQ ID NO: 295). Antibody TRL848 and 832 have a lambda light chain constant region as indicated below (SEQ ID NO: 296).

Heavy and light chain variable region sequences for the B antibodies are indicated above and in the accompanying Sequence Listing.

Example 17. Characterization of B Antibodies

In order to identify and characterize a monoclonal antibody suitable in a broadly efficacious antibody combination, human antibodies directed against influenza B were evaluated for efficacy against influenza B viruses. FIG. 16 provides a tabulation of evaluative studies assessing hemagglutination inhibition, classical neutralization in vitro, and in vivo administration for various anti-B antibodies. The antibodies were assessed against both B lineages, Yamagata and Victoria. In vivo results are provided as a summary of three different studies in each instance, evaluating percent of original body weight in animals inoculated with 10×LD50 of virus and administered denoted TRL antibody IN at 1 mg/kg 24 hpi. Animal body weight was observed for 14 days and the lowest body weight observed is indicated. Each of TRL845, TRL847, TRL848. TRL849 and TRL854 were effective to maintain at least 96% of original animal body weight throughout efficacy evaluations in vivo.

The affinity of B antibodies for influenza virus was evaluated to serve as an indicator aspect of relative efficacy. Certain data is provided in FIG. 17. Isoelectric points of the antibodies are noted. The isoeelectric point (pI) for TRL053 is 8.54, and pI for TRL579 is 8.60. Affinity was evaluated against B/Florida (Yamagata lineage) and B/Malaysia (Victoria lineage) influenza virus strains and $K_D$ in nM is tabulated. The B antibodies exhibit nM or subnM affinity for B/Florida strains. Affinity of each of TRL845, TRL847, TRL848, TRL849 and TRL854 for B/Malaysia was sub-nM (<1.0 nM) in each instance (data not shown).

Monoclonal influenza B antibodies were tested for efficacy in animals infected with B/Florida or B/Malaysia virus, representing the Yamagata and Victoria lineages respectively. Antibodies were evaluated by administration IN at 1 mg/kg 24 hpi with 10×LD50 of virus. B/Florida virus efficacy results are provided in FIG. 18, FIG. 19, and FIG. 22B. B/Malaysia virus efficacy results are provided in FIG. 20, FIG. 21, and FIG. 22A. IN administered anti-influenza B antibodies demonstrated efficacy against infection with either B lineage virus at a 10×LD50 dose, with several antibodies showing antibody-treated infected animals retaining 100% body weight. Antibodies TRL847, TRL845, TRL849, TRL848, TRL84, TRL854 and also TRL809 and TRL832 are selected as preferred antibodies based on efficacy in vivo and affinity studies.

These studies provide several B antibodies particularly effective for use in combination with an anti-H1 and anti-H3 antibody to provide a combination of antibodies cross-reactive and efficacious against the principal influenza strains in the human population. A combination of anti-H1 antibody TRL53, anti-H3 antibody TRL579 and anti-B antibody was tested as a cocktail. B antibody 5A7 is described above in prior examples and is effective to treat B/Florida or B/Malaysia at 24 hpi with IP or IN administration (FIG. 5). Pulmonary administration demonstrates greater efficacy, effective at least at 1 mg/kg or 0.1 mg/kg, while higher doses are required for comparable efficacy with systemic delivery.

Example 18. Cocktails, Combinations, and Compositions

Administration of multiple antibodies each 10 mg/kg in a combination is a significant protein antibody dose load and may not be well tolerated or justified, particularly in ill or at risk patients. An antibody combination or cocktail comprising antibodies at lower doses, particularly in the range of Img/kg is feasible. IN administration of antibodies is demonstrated herein to be effective at 1 mg/kg or less, even if given prophylactically. A cocktail comprising anti-influenza A antibodies effective against Group 1 and Group 2 viruses, particularly an anti-H1 and an anti-H3 antibody, as well as an anti-B influenza antibody provides a combination of antibodies against all relevant influenza strains and types in the human population in a single dose or combination. A cocktail of TRL053, TRL579 and 5A7, each at 1 mg/kg, with a total of 3 mg/kg antibody, was evaluated in vivo for protection from weight loss with virus infection. The antibody cocktail was administered as a single mixed dose 24 hours post infection with 10×LD50 virus. The cocktail showed efficacy against infection with each or any of H1 virus, H3 virus, B/Yamagata lineage virus and B/Victoria lineage virus (FIG. 23).

Combinations of anti-H1 antibody TRL053, anti-H3 antibody TRL579 and anti-B TRL antibodies were evaluated as antibody cocktails. These combinations comprise antibodies effective against the relevant influenza types or strains and that are compatible and efficacious when combined. They are constructed with the same subtype backbone, have similar pIs, do not interact or compete, and neutralize their target influenza virus without interference or concentration effects in the presence of the other antibody(ies). A cocktail of TRL053, TRL579 and each candidate B TRL antibody, each at 1 mg/kg, with a total of 3 mg/kg antibody, administered post infection was evaluated in vivo for protection from weight loss with virus infection. Efficacy against infection with each or any of H1 virus, H3 virus, B/Yamagata lineage virus and B/Victoria lineage virus was demonstrated. FIGS. 7 A-D depict results of studies of IN administration of various cocktails. Complete protection against infection with an H1 virus, an H3 virus and B/Yamagata and B/Victoria lineage viruses is achieved with the combination of antibodies. The results from three exemplary cocktails—TRL053, TRL579 and TRL845(c) (Cocktail 1), TRL053, TRL579 and TRL847 (Cocktail 2), and TRL053, TRL579 and TRL849 (Cocktail 3)—are provided in FIG. 7A-7D.

FIGS. 7A-7D show co-administration of three anti-influenza mAbs does not interfere with anti-B mAb efficiency. Mice were infected with 10×LD50 virus and treated 24 hpi with 3 mg/kg triple mAb cocktail comprised of anti-H1 CF-401, anti-H3 CF-402, and either anti-B TRL845 (Cocktail 1), anti-B TRL847 (Cocktail 2), or anti-B TRL849 (Cocktail 3), with PBS and no virus as controls. Animals were monitored for body weight daily for 14 days post infection and percent body weight of original day 0 weight is plotted.

FIGS. 7A-7D together demonstrate that the cocktail will provide the expected level of protection without interference from the other mabs in the cocktail against representative strains from all seasonal influenza subtypes (H1N1, H3N2, and both lineages of B).

FIG. 7A shows in vivo protection of mice infected with 10×LD50 H1N1 and treated 24 hpi with 3 mg/kg triple mAb cocktail comprised of anti-H1 CF-401, anti-H3 CF-402, and either anti-B TRL845 (Cocktail 1), anti-B TRL847 (Cocktail 2), or anti-B TRL849 (Cocktail 3).

FIG. 7B shows in vivo protection of mice infected with 10×LD50 H3N2 and treated 24 hpi with 3 mg/kg triple mAb cocktail comprised of anti-H1 CF-401, anti-H3 CF-402, and either anti-B TRL845 (Cocktail 1), anti-B TRL847 (Cocktail 2), or anti-B TRL849 (Cocktail 3).

FIG. 7C shows in vivo protection of mice infected with 10×LD50 B/Yamagata lineage and treated 24 hpi with 3 mg/kg triple mAb cocktail comprised of anti-H1 CF-401, anti-H3 CF-402, and either anti-B TRL845 (Cocktail 1), anti-B TRL847 (Cocktail 2), or anti-B TRL849 (Cocktail 3).

FIG. 7D shows in vivo protection of mice infected with 10×LD50 B/Victoria lineage and treated 24 hpi with 3 mg/kg triple mAb cocktail comprised of anti-H1 CF-401, anti-H3 CF-402, and either anti-B TRL845 (Cocktail 1), anti-B TRL847 (Cocktail 2), or anti-B TRL849 (Cocktail 3).

The data demonstrate that a cocktail composition combining three novel and unique antibodies is effective against influenza infection by any relevant or circulating virus strain or type. Combination antibodies are effective against Group 1 and Group 2 influenza A viruses and also influenza B viruses. Protection against any challenge is achieved with a combination of antibodies administered in a single dose. In order for a single dose combination to be effective and tolerated, and without the need for antibody doses which are cost-prohibitive or excessive, low doses are achieved in a combination which is administered as a cocktail directly to the airways, such as by intranasal administration. Efficacy of a combination of antibodies each in dose ranges of about 1 mg/kg or less has not been previously achieved with a combination of antibodies against all relevant influenza A and B viruses. The combination of antibodies described and provided herein collectively neutralize all relevant influenza viruses and are designed to be particularly capable in combination. The antibodies have compatible biophysical properties. The antibodies in the combination fail to compete or significantly interfere with one another and are each equivalently active in the combination as they are alone. The antibodies have similar isoelectric points and express similarly in cell culture. In an aspect herein, the antibodies are built on the same IgG backbones and share constant region sequences, each recombinantly expressed with the same heavy and light chain constant region sequences or related sequences.

This invention may be embodied in other forms or carried out in other ways without departing from the spirit or essential characteristics thereof. The present disclosure is therefore to be considered as in all aspects illustrate and not restrictive, the scope of the invention being indicated by the appended Claims, and all changes which come within the meaning and range of equivalency are intended to be embraced therein.

Various references are cited throughout this Specification, each of which is incorporated herein by reference in its entirety.

The invention claimed is:

1. An isolated human antibody, or antigen-binding fragment thereof that binds to one or more strains of each of influenza B Yamagata and influenza B Victoria clades, comprising:
   (a) a heavy chain amino acid sequence comprising a heavy chain variable region (HCVR) comprising:
   a heavy chain complementarity determining region 1 (HCDR1) comprising the amino acid sequence of SEQ ID NO: 201, a heavy chain complementarity determining region 2 (HCDR2) comprising the amino acid sequence of SEQ ID NO:202, and a heavy chain complementarity determining region 3 (HCDR3) comprising the amino acid sequence of SEQ ID NO: 203 and
   a light chain amino acid sequence comprising a light chain variable region (LCVR) comprising:
   a light chain complementarity determining region 1 (LCDR1) comprising the amino acid sequence of SEQ ID NO: 204, a light chain complementarity determining region 2 (LCDR2) comprising the amino acid sequence of SEQ ID NO: 205, and a light chain complementarity determining region 3 (LCDR3) comprising the amino acid sequence of SEQ ID NO: 206;

(b) a heavy chain amino acid sequence comprising a HCVR comprising:
a HCDR1 comprising the amino acid sequence of SEQ ID NO:221, a HCDR2 comprising the amino acid sequence of SEQ ID NO: 222, and a HCDR3 comprising the amino acid sequence of SEQ ID NO: 223 and
a light chain amino acid sequence comprising a LCVR comprising:
a LCDR1 comprising the amino acid sequence of SEQ ID NO: 224, a LCDR2 comprising the amino acid sequence of SEQ ID NO: 225, and a LCDR3 comprising the amino acid sequence of SEQ ID NO: 226;
(c) a heavy chain amino acid sequence comprising a HCVR comprising:
a HCDR1 comprising the amino acid sequence of SEQ ID NO:231, a HCDR2 comprising the amino acid sequence of SEQ ID NO: 232, and a HCDR3 comprising the amino acid sequence of SEQ ID NO: 233 and
a light chain amino acid sequence comprising a LCVR comprising:
a LCDR1 comprising the amino acid sequence of SEQ ID NO: 234, a LCDR2 comprising the amino acid sequence of SEQ ID NO: 235, and a LCDR3 comprising the amino acid sequence of SEQ ID NO: 236;
(d) a heavy chain amino acid sequence comprising a HCVR comprising:
a HCDR1 comprising the amino acid sequence of SEQ ID NO:241, a HCDR2 comprising the amino acid sequence of SEQ ID NO: 242, and a HCDR3 comprising the amino acid sequence of SEQ ID NO: 243 and
a light chain amino acid sequence comprising a LCVR comprising:
a LCDR1 comprising the amino acid sequence of SEQ ID NO: 244, a LCDR2 comprising the amino acid sequence of SEQ ID NO: 245, and a LCDR3 comprising the amino acid sequence of SEQ ID NO: 246; or
(e) a heavy chain amino acid sequence comprising a HCVR comprising:
a HCDR1 comprising the amino acid sequence of SEQ ID NO:261, a HCDR2 comprising the amino acid sequence of SEQ ID NO: 262, and a HCDR3 comprising the amino acid sequence of SEQ ID NO: 263 and
a light chain amino acid sequence comprising a LCVR comprising:
a LCDR1 comprising the amino acid sequence of SEQ ID NO: 264, a LCDR2 comprising the amino acid sequence of SEQ ID NO: 265, and a LCDR3 comprising the amino acid sequence of SEQ ID NO: 266.

2. An isolated human antibody or antigen binding-fragment thereof that binds to one or more strains of each of influenza B Yamagata and influenza B Victoria clades, comprising a heavy chain variable region and a light chain variable sequence sequence pair selected from the group consisting of:
(i) SEQ ID NOs: 209 and 210;
(ii) SEQ ID NOs: 229 and 230;
(iii) SEQ ID NOs: 239 and 240;
(iv) SEQ ID NOs: 249 and 250; and
(v) SEQ ID NOs: 269 and 270.

3. The antibody or antigen binding fragment of claim 1, that binds to one or more epitopes selected from the group consisting of SEQ ID NO: 307, 308, 309, 310, 311, 312, and 313, or a discontinuous epitope thereof.

4. An isolated codon optimized nucleic acid molecule encoding the antibody of claim 1.

5. An expression vector comprising the nucleic acid molecule of claim 4.

6. A host cell for expression of a recombinant polypeptide comprising the expression vector of claim 5.

7. A method of producing an anti-influenza B antibody or antigen-binding fragment thereof, comprising growing the host cell of claim 6 under conditions permitting production of the antibody or fragment thereof, and recovering the antibody or fragment thereof so produced.

8. A pharmaceutical composition comprising the antibody or antigen-binding fragment of claim 1 and a pharmaceutically acceptable carrier.

9. The pharmaceutical composition of claim 8, wherein said antibody or fragment exhibits a first melting temperature (Tm1) as measured in phosphate buffered saline (PBS) of greater than or equal to 55° C.

10. The pharmaceutical composition of claim 9, further comprising one or more human antibodies or antigen-binding fragments thereof with binding specificity to at least one strain of influenza A.

11. The pharmaceutical composition of claim 10, wherein the antibody or antigen-binding fragment with specificity to influenza A includes specificity to one or more strains of both Group 1 and Group 2.

12. A pharmaceutical composition comprising:
(a) a first antibody or antigen-binding fragment thereof that binds to and/or inhibits influenza virus comprising:
a heavy chain amino acid sequence comprising a heavy chain variable region (HCVR) comprising a heavy chain complementarity determining region 1 (HCDR1) comprising the amino acid sequence of SEQ ID NO: 11, a heavy chain complementarity determining region 2 (HCDR2) comprising the amino acid sequence of SEQ ID NO: 12 and a heavy chain complementarity determining region 3 (HCDR3) comprising the amino acid sequence of SEQ ID NO:13 and a light chain amino acid sequence comprising a light chain variable region (LCVR) comprising a light chain complementarity determining region 1 (LCDR1) comprising the amino acid sequence of SEQ ID NO: 14, a light chain complementarity determining region 2 (LCDR2) comprising the amino acid sequence of SEQ ID NO: 15, and a light chain complementarity determining region 3 (LCDR3) comprising the amino acid sequence of SEQ ID NO: 16; a HCDR1 of SEQ ID NO: 11, a HCDR2 of SEQ ID NO: 12, and a HCDR3 of SEQ ID NO:
(b) a second antibody or antigen-binding fragment thereof that binds to and/or inhibits influenza virus comprising:
a heavy chain amino acid sequence comprising a HCVR comprising a HCDR1 comprising the amino acid sequence of SEQ ID NO: 21, a HCDR2 comprising the amino acid sequence of SEQ ID NO: 22, and a HCDR3 comprising the amino acid sequence of SEQ ID NO: 23 and a light chain amino acid sequence comprising a LCVR comprising a LCDR1 comprising the amino acid sequence of SEQ ID NO: 24, a LCDR2 comprising the amino acid sequence of SEQ ID NO: 25, and a LCDR3 comprising the amino acid sequence of SEQ ID NO: 26; said; and
(c) a third antibody or antigen-binding fragment thereof that binds to one or more strains of each of influenza B Yamagata and influenza B Victoria clades comprising:
(i) a heavy chain amino acid sequence comprising a HCVR comprising:
a HCDR1 comprising the amino acid sequence of SEQ ID NO: 201, a HCDR2 comprising the amino acid sequence of SEQ ID NO:202, and a HCDR3 comprising the amino acid sequence of SEQ ID NO: 203 and a light chain amino acid sequence comprising a LCVR comprising: a LCDR1 comprising the amino acid sequence of SEQ ID NO: 204, a LCDR2 comprising the amino acid sequence of SEQ ID NO: 205, and a LCDR3 comprising the amino acid sequence of SEQ ID NO: 206;

(ii) a heavy chain amino acid sequence comprising a HCVR comprising: a HCDR1 comprising the amino acid sequence of SEQ ID NO:221, a HCDR2 comprising the amino acid sequence of SEQ ID NO: 222, and a HCDR3 comprising the amino acid sequence of SEQ ID NO: 223 and a light chain amino acid sequence comprising a LCVR comprising: a LCDR1 comprising the amino acid sequence of SEQ ID NO: 224, a LCDR2 comprising the amino acid sequence of SEQ ID NO: 225, and a LCDR3 comprising the amino acid sequence of SEQ ID NO: 226;

(iii) a heavy chain amino acid sequence comprising a HCVR comprising: a HCDR1 comprising the amino acid sequence of SEQ ID NO:231, a HCDR2 comprising the amino acid sequence of SEQ ID NO: 232, and a HCDR3 comprising the amino acid sequence of SEQ ID NO: 233 and a light chain amino acid sequence comprising a LCVR comprising: a LCDR1 comprising the amino acid sequence of SEQ ID NO: 234, a LCDR2 comprising the amino acid sequence of SEQ ID NO: 235, and a LCDR3 comprising the amino acid sequence of SEQ ID NO: 236;

(iv) a heavy chain amino acid sequence comprising a HCVR comprising: a HCDR1 comprising the amino acid sequence of SEQ ID NO:241, a HCDR2 comprising the amino acid sequence of SEQ ID NO: 242, and a HCDR3 comprising the amino acid sequence of SEQ ID NO: 243 and a light chain amino acid sequence comprising a LCVR comprising: a LCDR1 comprising the amino acid sequence of SEQ ID NO: 244, a LCDR2 comprising the amino acid sequence of SEQ ID NO: 245, and a LCDR3 comprising the amino acid sequence of SEQ ID NO: 246; or (v) a heavy chain amino acid sequence comprising a HCVR comprising: a HCDR1 comprising the amino acid sequence of SEQ ID NO:261, a HCDR2 comprising the amino acid sequence of SEQ ID NO: 262, and a HCDR3 comprising the amino acid sequence of SEQ ID NO: 263 and a light chain amino acid sequence comprising a LCVR comprising: a LCDR1 comprising the amino acid sequence of SEQ ID NO: 264, a LCDR2 comprising the amino acid sequence of SEQ ID NO: 265, and a LCDR3 comprising the amino acid sequence of SEQ ID NO: 266.

13. The pharmaceutical composition of claim 12, wherein said first antibody or fragment comprises a HCVR/LCVR pair of SEQ ID NOs: 19 and 20.

14. The pharmaceutical composition of claim 12, wherein said second antibody or fragment comprises a HCVR/LCVR pair of SEQ ID NOs: 29 and 30.

15. The pharmaceutical composition of claim 12, wherein each of said first, second and third antibodies or fragments exhibit isoelectric points (pI) all within a 2 pI point range.

16. The pharmaceutical composition of claim 12, wherein said first antibody is TRL053/Mab53 comprising heavy chain (HC)/light chain (LC) amino acid sequences of SEQ ID NOs: 17 and 18, said second antibody is antibody TRL579/Mab579 comprising a HC/LC amino acid sequences of SEQ ID NOs: 27 and 28, and said third antibody is selected from the group consisting of:

(i) TRL845 comprising HC/LC amino acid sequences of SEQ ID NOs: 207 and 208;
(ii) TRL847 comprising HC/LC amino acid sequences of SEQ ID NOs: 227 and 228;
(iii) TRL848 comprising HC/LC amino acid sequences of SEQ ID NOs: 237 and 238;
(iv) TRL849 comprising HC/LC amino acid sequences of SEQ ID NOs: 247 and 248; and
(v) TRL854 comprising HC/LC amino acid sequences of SEQ ID NOs: 267 and 268.

17. The pharmaceutical composition of claim 16, wherein each of said first, second and third antibodies or fragments are formulated in a single dose in an effective amount for treating or preventing influenza A and influenza B infection or disease in a subject in need thereof.

18. The pharmaceutical composition of claim 17, wherein each of said first, second and third antibodies or fragments are each present in the composition in an amount of 100 mg/kg or less of each of said first, second and third antibodies or fragments per dose.

19. The pharmaceutical composition of claim 17, wherein each of said first, second and third antibodies or fragments are each present in the composition in an amount of 10 mg/kg or less of each of said first, second and third antibodies or fragments per dose.

20. The pharmaceutical composition of claim 17, wherein each of said first, second and third antibodies or fragments are each present in the composition in an amount of 1 mg/kg or less of each of said first, second and third antibodies or fragments per dose.

21. The pharmaceutical composition of claim 17, wherein each of said first, second and third antibodies or fragments are each present in the composition in an amount of total antibody or antibody fragment of 10 mg/kg or less per dose.

22. The pharmaceutical composition of claim 17, wherein said carrier comprises a diluent and/or excipient for nasal or pulmonary delivery.

23. The pharmaceutical composition of claim 17, further comprising one or more of an antiviral therapeutic, viral replication inhibitor, protease inhibitor, polymerase inhibitor, hemagglutinin inhibitor, bronchodilator, immune modulator, or inhaled corticosteroid.

24. The pharmaceutical composition of claim 22, wherein one or more of said antibodies or antigen binding fragments thereof is an antibody fragment selected from Fab, Fab', and F(ab')$_2$, scFv, dAb, or a multispecific antibody, comprising:

(a) a heavy chain amino acid sequence comprising a HCVR comprising: a HCDR1 comprising the amino acid sequence of SEQ ID NO: 201, a HCDR2 comprising the amino acid sequence of SEQ ID NO: 202, and a HCDR3 comprising the amino acid sequence of SEQ ID NO: 203 and a light chain amino acid sequence comprising a LCVR comprising: a LCDR1 comprising the amino acid sequence of SEQ ID NO: 204, a LCDR2 comprising the amino acid sequence of SEQ ID NO: 205, and a LCDR3 comprising the amino acid sequence of SEQ ID NO: 206;

(b) a heavy chain amino acid sequence comprising a HCVR comprising: a HCDR1 comprising the amino acid sequence of SEQ ID NO: 221, a HCDR2 comprising the amino acid sequence of SEQ ID NO: 222, and a HCDR3 comprising the amino acid sequence of SEQ ID NO: 223 and a light chain amino acid sequence comprising a LCVR comprising: a LCDR1 comprising the amino acid sequence of SEQ ID NO: 224, a LCDR2 comprising the amino acid sequence of SEQ ID NO: 225, and a LCDR3 comprising the amino acid sequence of SEQ ID NO: 226;
(c) a heavy chain amino acid sequence comprising a HCVR comprising: a HCDR1 comprising the amino acid sequence of SEQ ID NO: 231, a HCDR2 comprising the amino acid sequence of SEQ ID NO: 232, and a HCDR3 comprising the amino acid sequence of SEQ ID NO: 233 and a light chain amino acid sequence comprising a LCVR comprising: a LCDR1 comprising the amino acid sequence of SEQ ID NO: 234, a LCDR2 comprising the amino acid sequence of SEQ ID NO: 235, and a LCDR3 comprising the amino acid sequence of SEQ ID NO: 236;
(d) a heavy chain amino acid sequence comprising a HCVR comprising: a HCDR1 comprising the amino acid sequence of SEQ ID NO: 241, a HCDR2 comprising the amino acid sequence of SEQ ID NO: 242, and a HCDR3 comprising the amino acid sequence of SEQ ID NO: 243 and a light chain amino acid sequence comprising a LCVR comprising: a LCDR1 comprising the amino acid sequence of SEQ ID NO: 244, a LCDR2 comprising the amino acid sequence of SEQ ID NO: 245, and a LCDR3 comprising the amino acid sequence of SEQ ID NO: 246; or
(e) a heavy chain amino acid sequence comprising a HCVR comprising: a HCDR1 comprising the amino acid sequence of SEQ ID NO: 261, a HCDR2 comprising the amino acid sequence of SEQ ID NO: 262, and a HCDR3 comprising the amino acid sequence of SEQ ID NO: 263 and a light chain amino acid sequence comprising a LCVR comprising: a LCDR1 comprising the amino acid sequence of SEQ ID NO: 264, a LCDR2 comprising the amino acid sequence of SEQ ID NO: 265, and a LCDR3 comprising the amino acid sequence of SEQ ID NO: 266.

25. A method for the treatment or prophylaxis of influenza infection in a subject which method comprises administering to a subject the pharmaceutical composition of claim 12.

26. The method of claim 25, wherein influenza infection status of said subject is determined without the need for detailed viral strain determination.

27. The method of claim 25, wherein the subject is protected against influenza infection or disease.

28. The method of claim 25, wherein each of said first, second and third antibodies or fragments are administered simultaneously, or sequentially.

29. The pharmaceutical composition of claim 23, wherein said immune modulator is Interferon beta 1a.

30. The pharmaceutical composition of claim 23, wherein said antiviral therapeutic is a neuraminidase inhibitor selected from the group consisting of Oseltamivir, Zanamivir, Peramivir, and Laninamivir.

31. The pharmaceutical composition of claim 23, wherein said antiviral therapeutic is an RNA polymerase inhibitor selected from the group consisting of Favipiravir (T-705) and VX 787.

32. The pharmaceutical composition of claim 23, wherein said antiviral therapeutic is a host-cell targeting therapeutic selected from the group consisting of Das181 and AB-103 (p2TA).

33. The pharmaceutical composition of claim 23, wherein said antiviral therapeutic is an ion channel inhibitor selected from the group consisting of Ramantadine and Amantadine.

34. The pharmaceutical composition of claim 23, wherein the bronchodilator is selected from albuterol, levalbuterol, or salmeterol.

35. The isolated antibody or fragment of claim 1, that is a recombinant antibody or fragment thereof.

* * * * *

SEQUENCE LISTING

```
<160> NUMBER OF SEQ ID NOS: 314

<210> SEQ ID NO 1
<211> LENGTH: 8
<212> TYPE: PRT
<213> ORGANISM: Artificial Sequence
<220> FEATURE:
<223> OTHER INFORMATION: 5A7 HC CDR1

<400> SEQUENCE: 1

Gly Phe Thr Phe Asn Asn Tyr Gly
1               5
```

-continued

```
<210> SEQ ID NO 2
<211> LENGTH: 8
<212> TYPE: PRT
<213> ORGANISM: Artificial Sequence
<220> FEATURE:
<223> OTHER INFORMATION: 5A7 HC CDR2

<400> SEQUENCE: 2

Val Trp Tyr Asp Gly Leu Ile Lys
1               5

<210> SEQ ID NO 3
<211> LENGTH: 15
<212> TYPE: PRT
<213> ORGANISM: Artificial Sequence
<220> FEATURE:
<223> OTHER INFORMATION: 5A7 HC CDR3

<400> SEQUENCE: 3

Ala Arg Asp Leu Gln Pro Pro His Ser Pro Tyr Gly Met Asp Val
1               5                   10                  15

<210> SEQ ID NO 4
<211> LENGTH: 8
<212> TYPE: PRT
<213> ORGANISM: Artificial Sequence
<220> FEATURE:
<223> OTHER INFORMATION: 5A7 LC CDR1

<400> SEQUENCE: 4

Ser Ser Asn Ile Gly Ser Asn Asp
1               5

<210> SEQ ID NO 5
<211> LENGTH: 3
<212> TYPE: PRT
<213> ORGANISM: Artificial Sequence
<220> FEATURE:
<223> OTHER INFORMATION: 5A7 LC CDR2

<400> SEQUENCE: 5

Asn Asn Asn
1

<210> SEQ ID NO 6
<211> LENGTH: 10
<212> TYPE: PRT
<213> ORGANISM: Artificial Sequence
<220> FEATURE:
<223> OTHER INFORMATION: 5A7 LC CDR3

<400> SEQUENCE: 6

Ala Ala Trp Asp Asp Ser Leu Thr Val Ser
1               5                   10

<210> SEQ ID NO 7
<211> LENGTH: 452
<212> TYPE: PRT
<213> ORGANISM: Artificial Sequence
<220> FEATURE:
<223> OTHER INFORMATION: 5A7 HC

<400> SEQUENCE: 7

Gln Cys Gln Leu Val Glu Ser Gly Gly Asp Val Val Gln Pro Gly Arg
1               5                   10                  15

Ser Leu Arg Leu Ser Cys Ala Ala Ser Gly Phe Thr Phe Asn Asn Tyr
            20                  25                  30
```

-continued

```
Gly Met His Trp Val Arg Gln Ala Pro Gly Lys Gly Leu Glu Trp Val
         35                  40                  45

Ala Val Val Trp Tyr Asp Gly Leu Ile Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Thr Leu Arg Ala Glu Asp Met Gly Val Tyr Tyr Cys
                 85                  90                  95

Ala Arg Asp Leu Gln Pro Pro His Ser Pro Tyr Gly Met Asp Val Trp
             100                 105                 110

Gly Gln Gly Thr Thr Val Thr Val Ser Ser Ala Ser Thr Lys Gly Pro
         115                 120                 125

Ser Val Phe Pro Leu Ala Pro Ser Ser Lys Ser Thr Ser Gly Gly Thr
 130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                 165                 170                 175

Ala Val Leu Gln Ser Ser Gly Leu Tyr Ser Leu Ser Ser Val Val Thr
             180                 185                 190

Val Pro Ser Ser Ser Leu Gly Thr Gln Thr Tyr Ile Cys Asn Val Asn
         195                 200                 205

His Lys Pro Ser Asn Thr Lys Val Asp Lys Lys Val Glu Pro Lys Ser
 210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                 245                 250                 255

Met Ile Ser Arg Thr Pro Glu Val Thr Cys Val Val Val Asp Val Ser
             260                 265                 270

His Glu Asp Pro Glu Val Lys Phe Asn Trp Tyr Val Asp Gly Val Glu
         275                 280                 285

Val His Asn Ala Lys Thr Lys Pro Arg Glu Glu Gln Tyr Asn Ser Thr
 290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                 325                 330                 335

Ile Glu Lys Thr Ile Ser Lys Ala Lys Gly Gln Pro Arg Glu Pro Gln
             340                 345                 350

Val Tyr Thr Leu Pro Pro Ser Arg Asp Glu Leu Thr Lys Asn Gln Val
         355                 360                 365

Ser Leu Thr Cys Leu Val Lys Gly Phe Tyr Pro Ser Asp Ile Ala Val
 370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                 405                 410                 415

Val Asp Lys Ser Arg Trp Gln Gln Gly Asn Val Phe Ser Cys Ser Val
             420                 425                 430
```

```
Met His Glu Ala Leu His Asn His Tyr Thr Gln Lys Ser Leu Ser Leu
            435                 440                 445

Ser Pro Gly Lys
    450

<210> SEQ ID NO 8
<211> LENGTH: 215
<212> TYPE: PRT
<213> ORGANISM: Artificial Sequence
<220> FEATURE:
<223> OTHER INFORMATION: 5A7 LC

<400> SEQUENCE: 8

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Asp Val Tyr Trp Tyr Gln Asn Leu Pro Gly Thr Ala Pro Lys Leu Leu
            35                  40                  45

Ile Tyr Asn Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Thr Val Ser Phe Gly Thr Gly Thr Lys Val Thr Val Leu Gly Gln Pro
            100                 105                 110

Lys Ala Ala Pro Ser Val Thr Leu Phe Pro Pro Ser Ser Glu Glu Leu
            115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Val Pro Ala Glu Cys Ser
    210                 215

<210> SEQ ID NO 9
<211> LENGTH: 122
<212> TYPE: PRT
<213> ORGANISM: Artificial Sequence
<220> FEATURE:
<223> OTHER INFORMATION: 5A7 HCVR

<400> SEQUENCE: 9

Gln Cys Gln Leu Val Glu Ser Gly Gly Asp Val Val Gln Pro Gly Arg
1               5                   10                  15

Ser Leu Arg Leu Ser Cys Ala Ala Ser Gly Phe Thr Phe Asn Asn Tyr
            20                  25                  30

Gly Met His Trp Val Arg Gln Ala Pro Gly Lys Gly Leu Glu Trp Val
            35                  40                  45

Ala Val Val Trp Tyr Asp Gly Leu Ile Lys Tyr Tyr Ala Asp Ser Val
    50                  55                  60
```

-continued

Lys Gly Arg Phe Thr Ile Ser Arg Asp Asn Ser Lys Asn Thr Leu Tyr
 65                  70                  75                  80

Leu Gln Met Asn Thr Leu Arg Ala Glu Asp Met Gly Val Tyr Tyr Cys
                 85                  90                  95

Ala Arg Asp Leu Gln Pro Pro His Ser Pro Tyr Gly Met Asp Val Trp
            100                 105                 110

Gly Gln Gly Thr Thr Val Thr Val Ser Ser
        115                 120

<210> SEQ ID NO 10
<211> LENGTH: 111
<212> TYPE: PRT
<213> ORGANISM: Artificial Sequence
<220> FEATURE:
<223> OTHER INFORMATION: 5A7 LCVR

<400> SEQUENCE: 10

Gln Ser Val Leu Thr Gln Pro Pro Ser Ala Ser Gly Thr Pro Gly Gln
1               5                  10                  15

Arg Val Thr Ile Ser Cys Ser Gly Ser Ser Asn Ile Gly Ser Asn
             20                  25                  30

Asp Val Tyr Trp Tyr Gln Asn Leu Pro Gly Thr Ala Pro Lys Leu Leu
         35                  40                  45

Ile Tyr Asn Asn Asn Gln Arg Pro Ser Gly Val Pro Asp Arg Phe Ser
     50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Ala Ala Trp Asp Asp Ser Leu
                 85                  90                  95

Thr Val Ser Phe Gly Thr Gly Thr Lys Val Thr Val Leu Gly Gln
            100                 105                 110

<210> SEQ ID NO 11
<211> LENGTH: 8
<212> TYPE: PRT
<213> ORGANISM: Artificial Sequence
<220> FEATURE:
<223> OTHER INFORMATION: TRL053 HC CDR1

<400> SEQUENCE: 11

Gly Gly Ile Ile Arg Lys Tyr Ala
1               5

<210> SEQ ID NO 12
<211> LENGTH: 8
<212> TYPE: PRT
<213> ORGANISM: Artificial Sequence
<220> FEATURE:
<223> OTHER INFORMATION: TRL053 HC CDR2

<400> SEQUENCE: 12

Ile Ile Ala Ile Phe Asn Thr Ala
1               5

<210> SEQ ID NO 13
<211> LENGTH: 13
<212> TYPE: PRT
<213> ORGANISM: Artificial Sequence
<220> FEATURE:
<223> OTHER INFORMATION: TRL053 HC CDR3

```
<400> SEQUENCE: 13

Ala Arg Gly Met Asn Tyr Tyr Ser Asp Tyr Phe Asp Tyr
1               5                   10

<210> SEQ ID NO 14
<211> LENGTH: 7
<212> TYPE: PRT
<213> ORGANISM: Artificial Sequence
<220> FEATURE:
<223> OTHER INFORMATION: TRL053 LC CDR1

<400> SEQUENCE: 14

Gln Ser Val Arg Ser Asn Asn
1               5

<210> SEQ ID NO 15
<211> LENGTH: 3
<212> TYPE: PRT
<213> ORGANISM: Artificial Sequence
<220> FEATURE:
<223> OTHER INFORMATION: TRL053 LC CDR2

<400> SEQUENCE: 15

Gly Ala Ser
1

<210> SEQ ID NO 16
<211> LENGTH: 10
<212> TYPE: PRT
<213> ORGANISM: Artificial Sequence
<220> FEATURE:
<223> OTHER INFORMATION: TRL053 LC CDR3

<400> SEQUENCE: 16

Gln Gln Tyr Gly Ser Ser Pro Ala Leu Thr
1               5                   10

<210> SEQ ID NO 17
<211> LENGTH: 450
<212> TYPE: PRT
<213> ORGANISM: Artificial Sequence
<220> FEATURE:
<223> OTHER INFORMATION: TRL053 HC

<400> SEQUENCE: 17

Gln Val Gln Leu Val Gln Ser Gly Ala Glu Val Arg Lys Pro Gly Ser
1               5                   10                  15

Ser Val Lys Val Ser Cys Lys Val Ser Gly Gly Ile Ile Arg Lys Tyr
                20                  25                  30

Ala Ile Asn Trp Val Arg Gln Ala Pro Gly Gln Gly Leu Glu Trp Met
            35                  40                  45

Gly Gly Ile Ile Ala Ile Phe Asn Thr Ala Asn Tyr Ala Gln Lys Phe
        50                  55                  60

Gln Gly Arg Val Thr Ile Thr Ala Asp Glu Ser Thr Ser Thr Val Tyr
65                  70                  75                  80

Met Glu Leu Ser Ser Leu Arg Ser Glu Asp Thr Ala Leu Tyr Tyr Cys
                85                  90                  95

Ala Arg Gly Met Asn Tyr Tyr Ser Asp Tyr Phe Asp Tyr Trp Gly Gln
                100                 105                 110

Gly Ser Leu Val Thr Val Ser Pro Ala Ser Thr Lys Gly Pro Ser Val
            115                 120                 125
```

```
Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 18
<211> LENGTH: 216
<212> TYPE: PRT
<213> ORGANISM: Artificial Sequence
<220> FEATURE:
<223> OTHER INFORMATION: TRL053 LC

<400> SEQUENCE: 18

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Arg Ser Asn
            20                  25                  30
```

```
Asn Leu Ala Trp Tyr Gln His Lys Pro Gly Gln Ala Pro Arg Leu Leu
            35                  40                  45

Ile Phe Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                 85                  90                  95

Ala Leu Thr Phe Gly Gly Gly Thr Lys Val Glu Ile Lys Arg Thr Val
            100                 105                 110

Ala Ala Pro Ser Val Phe Ile Phe Pro Pro Ser Asp Glu Gln Leu Lys
            115                 120                 125

Ser Gly Thr Ala Ser Val Val Cys Leu Leu Asn Asn Phe Tyr Pro Arg
130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
            195                 200                 205

Lys Ser Phe Asn Arg Gly Glu Cys
            210                 215

<210> SEQ ID NO 19
<211> LENGTH: 120
<212> TYPE: PRT
<213> ORGANISM: Artificial Sequence
<220> FEATURE:
<223> OTHER INFORMATION: TRL053 HCVR

<400> SEQUENCE: 19

Gln Val Gln Leu Val Gln Ser Gly Ala Glu Val Arg Lys Pro Gly Ser
1               5                   10                  15

Ser Val Lys Val Ser Cys Lys Val Ser Gly Gly Ile Ile Arg Lys Tyr
            20                  25                  30

Ala Ile Asn Trp Val Arg Gln Ala Pro Gly Gln Gly Leu Glu Trp Met
            35                  40                  45

Gly Gly Ile Ile Ala Ile Phe Asn Thr Ala Asn Tyr Ala Gln Lys Phe
 50                  55                  60

Gln Gly Arg Val Thr Ile Thr Ala Asp Glu Ser Thr Ser Thr Val Tyr
 65                  70                  75                  80

Met Glu Leu Ser Ser Leu Arg Ser Glu Asp Thr Ala Leu Tyr Tyr Cys
                 85                 90                   95

Ala Arg Gly Met Asn Tyr Tyr Ser Asp Tyr Phe Asp Tyr Trp Gly Gln
            100                 105                 110

Gly Ser Leu Val Thr Val Ser Pro
            115                 120

<210> SEQ ID NO 20
<211> LENGTH: 111
<212> TYPE: PRT
<213> ORGANISM: Artificial Sequence
<220> FEATURE:
<223> OTHER INFORMATION: TRL053 LCVR
```

-continued

```
<400> SEQUENCE: 20

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Arg Ser Asn
            20                  25                  30

Asn Leu Ala Trp Tyr Gln His Lys Pro Gly Gln Ala Pro Arg Leu Leu
        35                  40                  45

Ile Phe Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Ala Leu Thr Phe Gly Gly Gly Thr Lys Val Glu Ile Lys Arg Thr
            100                 105                 110

<210> SEQ ID NO 21
<211> LENGTH: 8
<212> TYPE: PRT
<213> ORGANISM: Artificial Sequence
<220> FEATURE:
<223> OTHER INFORMATION: TRL579 HC CDR1

<400> SEQUENCE: 21

Gly Tyr Thr Phe Thr Ala Tyr Thr
1               5

<210> SEQ ID NO 22
<211> LENGTH: 8
<212> TYPE: PRT
<213> ORGANISM: Artificial Sequence
<220> FEATURE:
<223> OTHER INFORMATION: TRL579 HC CDR2

<400> SEQUENCE: 22

Ile Asn Ala Gly Asn Gly His Thr
1               5

<210> SEQ ID NO 23
<211> LENGTH: 25
<212> TYPE: PRT
<213> ORGANISM: Artificial Sequence
<220> FEATURE:
<223> OTHER INFORMATION: TRL579 HC CDR3

<400> SEQUENCE: 23

Ala Arg Gly Pro Glu Thr Tyr Tyr Tyr Asp Lys Thr Asn Trp Leu Asn
1               5                   10                  15

Ser His Pro Asp Glu Tyr Phe Gln His
            20                  25

<210> SEQ ID NO 24
<211> LENGTH: 6
<212> TYPE: PRT
<213> ORGANISM: Artificial Sequence
<220> FEATURE:
<223> OTHER INFORMATION: TRL579 LC CDR1

<400> SEQUENCE: 24

Gln Thr Ile Asn Asn Tyr
1               5
```

```
<210> SEQ ID NO 25
<211> LENGTH: 3
<212> TYPE: PRT
<213> ORGANISM: Artificial Sequence
<220> FEATURE:
<223> OTHER INFORMATION: TRL579 LC CDR2

<400> SEQUENCE: 25

Lys Ala Ser
1

<210> SEQ ID NO 26
<211> LENGTH: 10
<212> TYPE: PRT
<213> ORGANISM: Artificial Sequence
<220> FEATURE:
<223> OTHER INFORMATION: TRL579 LC CDR3

<400> SEQUENCE: 26

Gln Glu Tyr Asn Asn Asp Ser Pro Leu Thr
1               5                   10

<210> SEQ ID NO 27
<211> LENGTH: 462
<212> TYPE: PRT
<213> ORGANISM: Artificial Sequence
<220> FEATURE:
<223> OTHER INFORMATION: TRL579 HC

<400> SEQUENCE: 27

Gln Val Gln Leu Val Gln Ser Gly Ala Glu Val Lys Lys Pro Gly Ala
1               5                   10                  15

Ser Val Lys Val Ser Cys Lys Thr Ser Gly Tyr Thr Phe Thr Ala Tyr
            20                  25                  30

Thr Ile His Trp Val Arg Gln Ala Pro Gly Gln Arg Leu Glu Trp Met
        35                  40                  45

Gly Trp Ile Asn Ala Gly Asn Gly His Thr Lys Tyr Ser Gln Arg Phe
    50                  55                  60

Lys Gly Arg Val Thr Ile Thr Arg Asp Thr Ser Ala Arg Thr Thr Tyr
65                  70                  75                  80

Met Glu Leu Arg Ser Leu Thr Ser Glu Asp Thr Ala Leu Tyr Phe Cys
                85                  90                  95

Ala Arg Gly Pro Glu Thr Tyr Tyr Tyr Asp Lys Thr Asn Trp Leu Asn
            100                 105                 110

Ser His Pro Asp Glu Tyr Phe Gln His Trp Gly His Gly Thr Gln Val
        115                 120                 125

Thr Val Ser Ser Ala Ser Thr Lys Gly Pro Ser Val Phe Pro Leu Ala
    130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Gln Thr Tyr Ile Cys Asn Val Asn His Lys Pro Ser Asn Thr
    210                 215                 220

Lys Val Asp Lys Lys Val Glu Pro Lys Ser Cys Asp Lys Thr His Thr
225                 230                 235                 240
```

```
Cys Pro Pro Cys Pro Ala Pro Glu Leu Leu Gly Gly Pro Ser Val Phe
            245                 250                 255

Leu Phe Pro Pro Lys Pro Lys Asp Thr Leu Met Ile Ser Arg Thr Pro
        260                 265                 270

Glu Val Thr Cys Val Val Val Asp Val Ser His Glu Asp Pro Glu Val
            275                 280                 285

Lys Phe Asn Trp Tyr Val Asp Gly Val Glu Val His Asn Ala Lys Thr
        290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
            325                 330                 335

Lys Val Ser Asn Lys Ala Leu Pro Ala Pro Ile Glu Lys Thr Ile Ser
        340                 345                 350

Lys Ala Lys Gly Gln Pro Arg Glu Pro Gln Val Tyr Thr Leu Pro Pro
        355                 360                 365

Ser Arg Asp Glu Leu Thr Lys Asn Gln Val Ser Leu Thr Cys Leu Val
    370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
            405                 410                 415

Gly Ser Phe Phe Leu Tyr Ser Lys Leu Thr Val Asp Lys Ser Arg Trp
        420                 425                 430

Gln Gln Gly Asn Val Phe Ser Cys Ser Val Met His Glu Ala Leu His
        435                 440                 445

Asn His Tyr Thr Gln Lys Ser Leu Ser Leu Ser Pro Gly Lys
    450                 455                 460

<210> SEQ ID NO 28
<211> LENGTH: 215
<212> TYPE: PRT
<213> ORGANISM: Artificial Sequence
<220> FEATURE:
<223> OTHER INFORMATION: TRL579 LC

<400> SEQUENCE: 28

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Thr Ile Asn Asn Tyr
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Glu Tyr Asn Asn Asp Ser Pro
            85                  90                  95

Leu Thr Phe Gly Gly Gly Thr Lys Val Glu Ile Lys Arg Thr Val Ala
        100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140
```

```
Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
            165                 170                 175

Ser Ser Thr Leu Thr Leu Ser Lys Ala Asp Tyr Glu Lys His Lys Val
        180                 185                 190

Tyr Ala Cys Glu Val Thr His Gln Gly Leu Ser Ser Pro Val Thr Lys
    195                 200                 205

Ser Phe Asn Arg Gly Glu Cys
    210                 215

<210> SEQ ID NO 29
<211> LENGTH: 132
<212> TYPE: PRT
<213> ORGANISM: Artificial Sequence
<220> FEATURE:
<223> OTHER INFORMATION: TRL579 HCVR

<400> SEQUENCE: 29

Gln Val Gln Leu Val Gln Ser Gly Ala Glu Val Lys Lys Pro Gly Ala
1               5                   10                  15

Ser Val Lys Val Ser Cys Lys Thr Ser Gly Tyr Thr Phe Thr Ala Tyr
            20                  25                  30

Thr Ile His Trp Val Arg Gln Ala Pro Gly Gln Arg Leu Glu Trp Met
        35                  40                  45

Gly Trp Ile Asn Ala Gly Asn Gly His Thr Lys Tyr Ser Gln Arg Phe
    50                  55                  60

Lys Gly Arg Val Thr Ile Thr Arg Asp Thr Ser Ala Arg Thr Thr Tyr
65                  70                  75                  80

Met Glu Leu Arg Ser Leu Thr Ser Glu Asp Thr Ala Leu Tyr Phe Cys
                85                  90                  95

Ala Arg Gly Pro Glu Thr Tyr Tyr Tyr Asp Lys Thr Asn Trp Leu Asn
            100                 105                 110

Ser His Pro Asp Glu Tyr Phe Gln His Trp Gly His Gly Thr Gln Val
        115                 120                 125

Thr Val Ser Ser
    130

<210> SEQ ID NO 30
<211> LENGTH: 110
<212> TYPE: PRT
<213> ORGANISM: Artificial Sequence
<220> FEATURE:
<223> OTHER INFORMATION: TRL579 LCVR

<400> SEQUENCE: 30

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Thr Ile Asn Asn Tyr
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80
```

```
Asp Asp Phe Ala Thr Tyr Tyr Cys Gln Glu Tyr Asn Asn Asp Ser Pro
                85                  90                  95

Leu Thr Phe Gly Gly Gly Thr Lys Val Glu Ile Lys Arg Thr
        100                 105                 110

<210> SEQ ID NO 31
<211> LENGTH: 8
<212> TYPE: PRT
<213> ORGANISM: Artificial Sequence
<220> FEATURE:
<223> OTHER INFORMATION: TRL784 HC CDR1

<400> SEQUENCE: 31

Gly Gly Thr Phe Ile Asn Tyr Ala
1               5

<210> SEQ ID NO 32
<211> LENGTH: 8
<212> TYPE: PRT
<213> ORGANISM: Artificial Sequence
<220> FEATURE:
<223> OTHER INFORMATION: TRL784 HC CDR2

<400> SEQUENCE: 32

Ile Ile Pro Val Tyr Gly Thr Ser
1               5

<210> SEQ ID NO 33
<211> LENGTH: 18
<212> TYPE: PRT
<213> ORGANISM: Artificial Sequence
<220> FEATURE:
<223> OTHER INFORMATION: TRL784 HC CDR3

<400> SEQUENCE: 33

Ala Ala Ser Thr Ala Thr Ser Gly Thr Tyr Tyr Ala Met Arg Pro Phe
1               5                   10                  15

Asp Phe

<210> SEQ ID NO 34
<211> LENGTH: 6
<212> TYPE: PRT
<213> ORGANISM: Artificial Sequence
<220> FEATURE:
<223> OTHER INFORMATION: TRL784 LC CDR1

<400> SEQUENCE: 34

Asn Met Gly Pro Thr Ser
1               5

<210> SEQ ID NO 35
<211> LENGTH: 3
<212> TYPE: PRT
<213> ORGANISM: Artificial Sequence
<220> FEATURE:
<223> OTHER INFORMATION: TRL784 LC CDR2

<400> SEQUENCE: 35

Asp Asp Ser
1

<210> SEQ ID NO 36
<211> LENGTH: 11
<212> TYPE: PRT
<213> ORGANISM: Artificial Sequence
```

<220> FEATURE:
<223> OTHER INFORMATION: TRL784 LC CDR3

<400> SEQUENCE: 36

Gln Val Trp Asp Met Ser Ser Asp Arg Arg Val
1               5                   10

<210> SEQ ID NO 37
<211> LENGTH: 455
<212> TYPE: PRT
<213> ORGANISM: Artificial Sequence
<220> FEATURE:
<223> OTHER INFORMATION: TRL784 HC

<400> SEQUENCE: 37

Gln Val Gln Leu Val Gln Ser Gly Pro Glu Leu Lys Lys Pro Gly Ser
1               5                   10                  15

Ser Val Lys Leu Ser Cys Met Ala Thr Gly Gly Thr Phe Ile Asn Tyr
            20                  25                  30

Ala Phe Ser Trp Val Arg Gln Ala Pro Gly Gln Gly Leu Glu Trp Leu
        35                  40                  45

Gly Gly Ile Ile Pro Val Tyr Gly Thr Ser Asn His Val Glu Lys Leu
    50                  55                  60

Gln Gly Arg Val Thr Ile Thr Ala Asp Ala Ser Thr Asn Thr Ala Tyr
65                  70                  75                  80

Met Glu Leu Ser Gly Leu Arg Phe Asp Asp Thr Ala Val Tyr Phe Cys
                85                  90                  95

Ala Ala Ser Thr Ala Thr Ser Gly Thr Tyr Tyr Ala Met Arg Pro Phe
            100                 105                 110

Asp Phe Trp Gly Gln Gly Thr Leu Val Ser Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

```
Trp Leu Asn Gly Lys Glu Tyr Lys Cys Lys Val Ser Asn Lys Ala Leu
            325                 330                 335
Pro Ala Pro Ile Glu Lys Thr Ile Ser Lys Ala Lys Gly Gln Pro Arg
            340                 345                 350
Glu Pro Gln Val Tyr Thr Leu Pro Pro Ser Arg Asp Glu Leu Thr Lys
            355                 360                 365
Asn Gln Val Ser Leu Thr Cys Leu Val Lys Gly Phe Tyr Pro Ser Asp
        370                 375                 380
Ile Ala Val Glu Trp Glu Ser Asn Gly Gln Pro Glu Asn Asn Tyr Lys
385                 390                 395                 400
Thr Thr Pro Pro Val Leu Asp Ser Asp Gly Ser Phe Phe Leu Tyr Ser
                405                 410                 415
Lys Leu Thr Val Asp Lys Ser Arg Trp Gln Gln Gly Asn Val Phe Ser
            420                 425                 430
Cys Ser Val Met His Glu Ala Leu His Asn His Tyr Thr Gln Lys Ser
        435                 440                 445
Leu Ser Leu Ser Pro Gly Lys
    450                 455

<210> SEQ ID NO 38
<211> LENGTH: 214
<212> TYPE: PRT
<213> ORGANISM: Artificial Sequence
<220> FEATURE:
<223> OTHER INFORMATION: TRL784 LC

<400> SEQUENCE: 38

Asp Ile Glu Leu Thr Gln Asp Pro Ser Val Ser Val Ala Pro Gly Gln
1               5                   10                  15
Thr Ala Arg Ile Pro Cys Val Arg Phe Asn Met Gly Pro Thr Ser Val
            20                  25                  30
His Trp Tyr Gln Gln Lys Pro Gly Gln Ala Pro Val Leu Val Val Tyr
        35                  40                  45
Asp Asp Ser Asp Arg Pro Ser Gly Ile Pro Glu Arg Phe Ser Gly Ser
    50                  55                  60
Asn Ser Gly Asp Ser Ala Thr Leu Thr Ile Ser Arg Val Glu Ala Gly
65                  70                  75                  80
Asp Glu Ala Asp Tyr Tyr Cys Gln Val Trp Asp Met Ser Ser Asp Arg
                85                  90                  95
Arg Val Phe Gly Gly Gly Thr Thr Leu Thr Val Leu Gly Gln Pro Lys
            100                 105                 110
Ala Ala Pro Ser Val Thr Leu Phe Pro Pro Ser Ser Glu Glu Leu Gln
        115                 120                 125
Ala Asn Lys Ala Thr Leu Val Cys Leu Ile Ser Asp Phe Tyr Pro Gly
    130                 135                 140
Ala Val Thr Val Ala Trp Lys Ala Asp Ser Ser Pro Val Lys Ala Gly
145                 150                 155                 160
Val Glu Thr Thr Thr Pro Ser Lys Gln Ser Asn Asn Lys Tyr Ala Ala
                165                 170                 175
Ser Ser Tyr Leu Ser Leu Thr Pro Glu Gln Trp Lys Ser His Arg Ser
            180                 185                 190
Tyr Ser Cys Gln Val Thr His Glu Gly Ser Thr Val Glu Lys Thr Val
        195                 200                 205
Val Pro Ala Glu Cys Ser
    210
```

-continued

```
<210> SEQ ID NO 39
<211> LENGTH: 125
<212> TYPE: PRT
<213> ORGANISM: Artificial Sequence
<220> FEATURE:
<223> OTHER INFORMATION: TRL784 HCVR

<400> SEQUENCE: 39

Gln Val Gln Leu Val Gln Ser Gly Pro Glu Leu Lys Lys Pro Gly Ser
1               5                   10                  15

Ser Val Lys Leu Ser Cys Met Ala Thr Gly Thr Phe Ile Asn Tyr
            20                  25                  30

Ala Phe Ser Trp Val Arg Gln Ala Pro Gly Gln Gly Leu Glu Trp Leu
        35                  40                  45

Gly Gly Ile Ile Pro Val Tyr Gly Thr Ser Asn His Val Glu Lys Leu
    50                  55                  60

Gln Gly Arg Val Thr Ile Thr Ala Asp Ala Ser Thr Asn Thr Ala Tyr
65                  70                  75                  80

Met Glu Leu Ser Gly Leu Arg Phe Asp Asp Thr Ala Val Tyr Phe Cys
                85                  90                  95

Ala Ala Ser Thr Ala Thr Ser Gly Thr Tyr Tyr Ala Met Arg Pro Phe
            100                 105                 110

Asp Phe Trp Gly Gln Gly Thr Leu Val Ser Val Ser Ser
        115                 120                 125

<210> SEQ ID NO 40
<211> LENGTH: 110
<212> TYPE: PRT
<213> ORGANISM: Artificial Sequence
<220> FEATURE:
<223> OTHER INFORMATION: TRL784 LCVR

<400> SEQUENCE: 40

Asp Ile Glu Leu Thr Gln Asp Pro Ser Val Ser Val Ala Pro Gly Gln
1               5                   10                  15

Thr Ala Arg Ile Pro Cys Val Arg Phe Asn Met Gly Pro Thr Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asp Ser Ala Thr Leu Thr Ile Ser Arg Val Glu Ala Gly
65                  70                  75                  80

Asp Glu Ala Asp Tyr Tyr Cys Gln Val Trp Asp Met Ser Ser Asp Arg
                85                  90                  95

Arg Val Phe Gly Gly Gly Thr Thr Leu Thr Val Leu Gly Gln
            100                 105                 110

<210> SEQ ID NO 41
<211> LENGTH: 8
<212> TYPE: PRT
<213> ORGANISM: Artificial Sequence
<220> FEATURE:
<223> OTHER INFORMATION: TRL794 HC CDR1

<400> SEQUENCE: 41

Gly Phe Thr Phe Arg Ser His Ala
1               5
```

```
<210> SEQ ID NO 42
<211> LENGTH: 8
<212> TYPE: PRT
<213> ORGANISM: Artificial Sequence
<220> FEATURE:
<223> OTHER INFORMATION: TRL794 HC CDR2

<400> SEQUENCE: 42

Ile Ser Tyr Asp Glu Val Asn Lys
1               5

<210> SEQ ID NO 43
<211> LENGTH: 13
<212> TYPE: PRT
<213> ORGANISM: Artificial Sequence
<220> FEATURE:
<223> OTHER INFORMATION: TRL794 HC CDR3

<400> SEQUENCE: 43

Ala Arg Gly His Ser Gly Ser Tyr Arg Leu Phe Asp Phe
1               5                   10

<210> SEQ ID NO 44
<211> LENGTH: 6
<212> TYPE: PRT
<213> ORGANISM: Artificial Sequence
<220> FEATURE:
<223> OTHER INFORMATION: TRL794 LC CDR1

<400> SEQUENCE: 44

Gln Val Val Gly Thr Asn
1               5

<210> SEQ ID NO 45
<211> LENGTH: 3
<212> TYPE: PRT
<213> ORGANISM: Artificial Sequence
<220> FEATURE:
<223> OTHER INFORMATION: TRL794 LC CDR2

<400> SEQUENCE: 45

Ala Ala Ser
1

<210> SEQ ID NO 46
<211> LENGTH: 9
<212> TYPE: PRT
<213> ORGANISM: Artificial Sequence
<220> FEATURE:
<223> OTHER INFORMATION: TRL794 LC CDR3

<400> SEQUENCE: 46

Gln Gln Tyr Asn Asn Trp Pro Leu Ser
1               5

<210> SEQ ID NO 47
<211> LENGTH: 450
<212> TYPE: PRT
<213> ORGANISM: Artificial Sequence
<220> FEATURE:
<223> OTHER INFORMATION: TRL794 HC

<400> SEQUENCE: 47

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Arg Ser His
                20                  25                  30
```

```
Ala Met His Trp Val Arg Gln Ala Pro Gly Lys Gly Pro Glu Trp Val
         35                  40                  45

Ala Leu Ile Ser Tyr Asp Glu Val Asn Lys Phe Tyr Ala Asp Ser Val
     50                  55                  60

Lys Gly Arg Phe Thr Ile Ser Arg Asp Val Ser Lys Asn Thr Val Phe
 65                  70                  75                  80

Leu Gln Met Asn Ser Leu Ser Ala Asp Asp Thr Ala Val Tyr Tyr Cys
                 85                  90                  95

Ala Arg Gly His Ser Gly Ser Tyr Arg Leu Phe Asp Phe Trp Gly Gln
             100                 105                 110

Gly Thr Leu Val Thr Val Ser Ser Ala Ser Thr Lys Gly Pro Ser Val
             115                 120                 125

Phe Pro Leu Ala Pro Ser Ser Lys Ser Thr Ser Gly Gly Thr Ala Ala
         130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                 165                 170                 175

Leu Gln Ser Ser Gly Leu Tyr Ser Leu Ser Ser Val Val Thr Val Pro
             180                 185                 190

Ser Ser Ser Leu Gly Thr Gln Thr Tyr Ile Cys Asn Val Asn His Lys
             195                 200                 205

Pro Ser Asn Thr Lys Val Asp Lys Lys Val Glu Pro Lys Ser Cys Asp
         210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                 245                 250                 255

Ser Arg Thr Pro Glu Val Thr Cys Val Val Val Asp Val Ser His Glu
             260                 265                 270

Asp Pro Glu Val Lys Phe Asn Trp Tyr Val Asp Gly Val Glu Val His
             275                 280                 285

Asn Ala Lys Thr Lys Pro Arg Glu Glu Gln Tyr Asn Ser Thr Tyr Arg
         290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                 325                 330                 335

Lys Thr Ile Ser Lys Ala Lys Gly Gln Pro Arg Glu Pro Gln Val Tyr
             340                 345                 350

Thr Leu Pro Pro Ser Arg Asp Glu Leu Thr Lys Asn Gln Val Ser Leu
             355                 360                 365

Thr Cys Leu Val Lys Gly Phe Tyr Pro Ser Asp Ile Ala Val Glu Trp
         370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                 405                 410                 415

Lys Ser Arg Trp Gln Gln Gly Asn Val Phe Ser Cys Ser Val Met His
             420                 425                 430
```

-continued

```
Glu Ala Leu His Asn His Tyr Thr Gln Lys Ser Leu Ser Leu Ser Pro
            435                 440                 445

Gly Lys
    450

<210> SEQ ID NO 48
<211> LENGTH: 214
<212> TYPE: PRT
<213> ORGANISM: Artificial Sequence
<220> FEATURE:
<223> OTHER INFORMATION: TRL794 LC

<400> SEQUENCE: 48

Asp Ile Val Met Thr Gln Ser Pro Ala Thr Leu Ser Val Ser Pro Gly
1               5                   10                  15

Glu Arg Ala Thr Leu Ser Cys Arg Ala Ser Gln Val Val Gly Thr Asn
            20                  25                  30

Leu Ala Trp Tyr Gln Gln Lys Pro Gly Gln Ala Pro Arg Leu Leu Ile
        35                  40                  45

Tyr Ala Ala Ser Thr Arg Ala Thr Gly Ile Pro Ala Arg Phe Ser Gly
    50                  55                  60

Ser Gly Phe Gly Thr Asp Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Leu
                85                  90                  95

Ser Phe Gly Gly Gly Thr Lys Val Glu Ile Arg Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 49
<211> LENGTH: 120
<212> TYPE: PRT
<213> ORGANISM: Artificial Sequence
<220> FEATURE:
<223> OTHER INFORMATION: TRL794 HCVR

<400> SEQUENCE: 49

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Arg Ser His
            20                  25                  30

Ala Met His Trp Val Arg Gln Ala Pro Gly Lys Gly Pro Glu Trp Val
        35                  40                  45

Ala Leu Ile Ser Tyr Asp Glu Val Asn Lys Phe Tyr Ala Asp Ser Val
    50                  55                  60
```

-continued

Lys Gly Arg Phe Thr Ile Ser Arg Asp Val Ser Lys Asn Thr Val Phe
 65                  70                  75                  80

Leu Gln Met Asn Ser Leu Ser Ala Asp Asp Thr Ala Val Tyr Tyr Cys
                 85                  90                  95

Ala Arg Gly His Ser Gly Ser Tyr Arg Leu Phe Asp Phe Trp Gly Gln
            100                 105                 110

Gly Thr Leu Val Thr Val Ser Ser
            115                 120

<210> SEQ ID NO 50
<211> LENGTH: 109
<212> TYPE: PRT
<213> ORGANISM: Artificial Sequence
<220> FEATURE:
<223> OTHER INFORMATION: TRL794 LCVR

<400> SEQUENCE: 50

Asp Ile Val Met Thr Gln Ser Pro Ala Thr Leu Ser Val Ser Pro Gly
 1               5                  10                  15

Glu Arg Ala Thr Leu Ser Cys Arg Ala Ser Gln Val Val Gly Thr Asn
             20                  25                  30

Leu Ala Trp Tyr Gln Gln Lys Pro Gly Gln Ala Pro Arg Leu Leu Ile
         35                  40                  45

Tyr Ala Ala Ser Thr Arg Ala Thr Gly Ile Pro Ala Arg Phe Ser Gly
     50                  55                  60

Ser Gly Phe Gly Thr Asp Phe Thr Leu Thr Ile Ser Ser Leu Gln Ser
 65                  70                  75                  80

Glu Asp Phe Ala Val Tyr Tyr Cys Gln Gln Tyr Asn Asn Trp Pro Leu
                 85                  90                  95

Ser Phe Gly Gly Gly Thr Lys Val Glu Ile Arg Arg Thr
            100                 105

<210> SEQ ID NO 51
<211> LENGTH: 8
<212> TYPE: PRT
<213> ORGANISM: Artificial Sequence
<220> FEATURE:
<223> OTHER INFORMATION: TRL798 HC CDR1

<400> SEQUENCE: 51

Gly Tyr Asn Phe Ala Ala Tyr Tyr
 1               5

<210> SEQ ID NO 52
<211> LENGTH: 8
<212> TYPE: PRT
<213> ORGANISM: Artificial Sequence
<220> FEATURE:
<223> OTHER INFORMATION: TRL798 HC CDR2

<400> SEQUENCE: 52

Ser Asn Pro Asn Thr Gly Gly Ala
 1               5

<210> SEQ ID NO 53
<211> LENGTH: 22
<212> TYPE: PRT
<213> ORGANISM: Artificial Sequence
<220> FEATURE:
<223> OTHER INFORMATION: TRL798 HC CDR3

```
<400> SEQUENCE: 53

Ala Arg Val Pro Arg Asp Arg Leu Leu Thr Leu Tyr Tyr Glu Ser Ser
1               5                   10                  15

Thr Tyr Gly Phe Asp Tyr
            20

<210> SEQ ID NO 54
<211> LENGTH: 6
<212> TYPE: PRT
<213> ORGANISM: Artificial Sequence
<220> FEATURE:
<223> OTHER INFORMATION: TRL798 LC CDR1

<400> SEQUENCE: 54

Gln Gly Ile Asn Thr His
1               5

<210> SEQ ID NO 55
<211> LENGTH: 3
<212> TYPE: PRT
<213> ORGANISM: Artificial Sequence
<220> FEATURE:
<223> OTHER INFORMATION: TRL798 LC CDR2

<400> SEQUENCE: 55

Ser Ala Ser
1

<210> SEQ ID NO 56
<211> LENGTH: 9
<212> TYPE: PRT
<213> ORGANISM: Artificial Sequence
<220> FEATURE:
<223> OTHER INFORMATION: TRL798 LC CDR3

<400> SEQUENCE: 56

Gln Gln Ser Tyr Asn Tyr Pro Arg Thr
1               5

<210> SEQ ID NO 57
<211> LENGTH: 459
<212> TYPE: PRT
<213> ORGANISM: Artificial Sequence
<220> FEATURE:
<223> OTHER INFORMATION: TRL798 HC

<400> SEQUENCE: 57

Gln Val Gln Leu Val Glu Ser Gly Ala Glu Val Lys Lys Pro Gly Ala
1               5                   10                  15

Ser Val Lys Leu Ser Cys Thr Ala Ser Gly Tyr Asn Phe Ala Ala Tyr
            20                  25                  30

Tyr Ile His Trp Val Arg Gln Ala Pro Gly Gln Gly Leu Glu Trp Met
        35                  40                  45

Gly Trp Ser Asn Pro Asn Thr Gly Gly Ala Asn Tyr Ala Gln Asp Phe
    50                  55                  60

Gln Gly Arg Val Thr Met Thr Ala Val Thr Ser Thr Ser Thr Ala Tyr
65                  70                  75                  80

Met Glu Leu Ser Arg Leu Thr Ser Asp Asp Thr Ala Leu Tyr Phe Cys
                85                  90                  95

Ala Arg Val Pro Arg Asp Arg Leu Leu Thr Leu Tyr Tyr Glu Ser Ser
            100                 105                 110
```

Thr Tyr Gly Phe Asp Tyr Trp Gly Gln Gly Thr Leu Val Thr Val Ser
            115                 120                 125

Ser Ala Ser Thr Lys Gly Pro Ser Val Phe Pro Leu Ala Pro Ser Ser
        130                 135                 140

Lys Ser Thr Ser Gly Gly Thr Ala Ala Leu Gly Cys Leu Val Lys Asp
145                 150                 155                 160

Tyr Phe Pro Glu Pro Val Thr Val Ser Trp Asn Ser Gly Ala Leu Thr
                165                 170                 175

Ser Gly Val His Thr Phe Pro Ala Val Leu Gln Ser Ser Gly Leu Tyr
            180                 185                 190

Ser Leu Ser Ser Val Val Thr Val Pro Ser Ser Ser Leu Gly Thr Gln
        195                 200                 205

Thr Tyr Ile Cys Asn Val Asn His Lys Pro Ser Asn Thr Lys Val Asp
210                 215                 220

Lys Lys Val Glu Pro Lys Ser Cys Asp Lys Thr His Thr Cys Pro Pro
225                 230                 235                 240

Cys Pro Ala Pro Glu Leu Leu Gly Gly Pro Ser Val Phe Leu Phe Pro
                245                 250                 255

Pro Lys Pro Lys Asp Thr Leu Met Ile Ser Arg Thr Pro Glu Val Thr
            260                 265                 270

Cys Val Val Val Asp Val Ser His Glu Asp Pro Glu Val Lys Phe Asn
        275                 280                 285

Trp Tyr Val Asp Gly Val Glu Val His Asn Ala Lys Thr Lys Pro Arg
            290                 295                 300

Glu Glu Gln Tyr Asn Ser Thr Tyr Arg Val Val Ser Val Leu Thr Val
305                 310                 315                 320

Leu His Gln Asp Trp Leu Asn Gly Lys Glu Tyr Lys Cys Lys Val Ser
                325                 330                 335

Asn Lys Ala Leu Pro Ala Pro Ile Glu Lys Thr Ile Ser Lys Ala Lys
            340                 345                 350

Gly Gln Pro Arg Glu Pro Gln Val Tyr Thr Leu Pro Pro Ser Arg Asp
        355                 360                 365

Glu Leu Thr Lys Asn Gln Val Ser Leu Thr Cys Leu Val Lys Gly Phe
            370                 375                 380

Tyr Pro Ser Asp Ile Ala Val Glu Trp Glu Ser Asn Gly Gln Pro Glu
385                 390                 395                 400

Asn Asn Tyr Lys Thr Thr Pro Pro Val Leu Asp Ser Asp Gly Ser Phe
                405                 410                 415

Phe Leu Tyr Ser Lys Leu Thr Val Asp Lys Ser Arg Trp Gln Gln Gly
            420                 425                 430

Asn Val Phe Ser Cys Ser Val Met His Glu Ala Leu His Asn His Tyr
        435                 440                 445

Thr Gln Lys Ser Leu Ser Leu Ser Pro Gly Lys
    450                 455

<210> SEQ ID NO 58
<211> LENGTH: 214
<212> TYPE: PRT
<213> ORGANISM: Artificial Sequence
<220> FEATURE:
<223> OTHER INFORMATION: TRL798 LC

<400> SEQUENCE: 58

Asp Ile Gln Met Thr Gln Ser Pro Ser Ser Leu Ser Ala Ser Val Gly
1               5                   10                  15

Asp Arg Val Thr Ile Val Cys Arg Ala Ser Gln Gly Ile Asn Thr His
            20                  25                  30

Leu His Trp Tyr Gln Gln Lys Pro Gly Lys Ala Pro Lys Leu Leu Ile
        35                  40                  45

Tyr Ser Ala Ser Thr Leu His Thr Gly Val Pro Ser Arg Leu Ser Gly
    50                  55                  60

Ser Gly Ser Gly Thr Asp Phe Thr Leu Ser Ile Ser Ser Leu Gln Pro
65                  70                  75                  80

Glu Asp Phe Ala Thr Tyr Tyr Cys Gln Gln Ser Tyr Asn Tyr Pro Arg
                85                  90                  95

Thr Phe Gly Gln Gly Thr Asn Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 59
<211> LENGTH: 129
<212> TYPE: PRT
<213> ORGANISM: Artificial Sequence
<220> FEATURE:
<223> OTHER INFORMATION: TRL798 HCVR

<400> SEQUENCE: 59

Gln Val Gln Leu Val Glu Ser Gly Ala Glu Val Lys Lys Pro Gly Ala
1               5                   10                  15

Ser Val Lys Leu Ser Cys Thr Ala Ser Gly Tyr Asn Phe Ala Ala Tyr
            20                  25                  30

Tyr Ile His Trp Val Arg Gln Ala Pro Gly Gln Gly Leu Glu Trp Met
        35                  40                  45

Gly Trp Ser Asn Pro Asn Thr Gly Gly Ala Asn Tyr Ala Gln Asp Phe
    50                  55                  60

Gln Gly Arg Val Thr Met Thr Ala Val Thr Ser Thr Ser Thr Ala Tyr
65                  70                  75                  80

Met Glu Leu Ser Arg Leu Thr Ser Asp Thr Ala Leu Tyr Phe Cys
                85                  90                  95

Ala Arg Val Pro Arg Asp Arg Leu Leu Thr Leu Tyr Tyr Glu Ser Ser
            100                 105                 110

Thr Tyr Gly Phe Asp Tyr Trp Gly Gln Gly Thr Leu Val Thr Val Ser
        115                 120                 125

Ser

```
<210> SEQ ID NO 60
<211> LENGTH: 109
<212> TYPE: PRT
<213> ORGANISM: Artificial Sequence
<220> FEATURE:
<223> OTHER INFORMATION: TRL798 LCVR

<400> SEQUENCE: 60

Asp Ile Gln Met Thr Gln Ser Pro Ser Ser Leu Ser Ala Ser Val Gly
1               5                   10                  15

Asp Arg Val Thr Ile Val Cys Arg Ala Ser Gln Gly Ile Asn Thr His
            20                  25                  30

Leu His Trp Tyr Gln Gln Lys Pro Gly Lys Ala Pro Lys Leu Leu Ile
        35                  40                  45

Tyr Ser Ala Ser Thr Leu His Thr Gly Val Pro Ser Arg Leu Ser Gly
    50                  55                  60

Ser Gly Ser Gly Thr Asp Phe Thr Leu Ser Ile Ser Ser Leu Gln Pro
65                  70                  75                  80

Glu Asp Phe Ala Thr Tyr Tyr Cys Gln Gln Ser Tyr Asn Tyr Pro Arg
                85                  90                  95

Thr Phe Gly Gln Gly Thr Asn Val Asp Ile Lys Arg Thr
            100                 105

<210> SEQ ID NO 61
<211> LENGTH: 8
<212> TYPE: PRT
<213> ORGANISM: Artificial Sequence
<220> FEATURE:
<223> OTHER INFORMATION: TRL799 HC CDR1

<400> SEQUENCE: 61

Gly Tyr Thr Leu Ile Asp Tyr Tyr
1               5

<210> SEQ ID NO 62
<211> LENGTH: 8
<212> TYPE: PRT
<213> ORGANISM: Artificial Sequence
<220> FEATURE:
<223> OTHER INFORMATION: TRL799 HC CDR2

<400> SEQUENCE: 62

Ile Asn Pro Ile Asn Gly Gly Thr
1               5

<210> SEQ ID NO 63
<211> LENGTH: 17
<212> TYPE: PRT
<213> ORGANISM: Artificial Sequence
<220> FEATURE:
<223> OTHER INFORMATION: TRL799 HC CDR3

<400> SEQUENCE: 63

Thr Arg Gly Arg Pro Ile Gly Arg Asn Trp Glu Pro Arg Asp Lys Asp
1               5                   10                  15

Tyr

<210> SEQ ID NO 64
<211> LENGTH: 11
<212> TYPE: PRT
<213> ORGANISM: Artificial Sequence
<220> FEATURE:
<223> OTHER INFORMATION: TRL799 LC CDR1
```

<400> SEQUENCE: 64

Gln Ser Leu Leu His Ser Asn Gly Tyr Asn Tyr
1               5                   10

<210> SEQ ID NO 65
<211> LENGTH: 3
<212> TYPE: PRT
<213> ORGANISM: Artificial Sequence
<220> FEATURE:
<223> OTHER INFORMATION: TRL799 LC CDR2

<400> SEQUENCE: 65

Leu Gly Ser
1

<210> SEQ ID NO 66
<211> LENGTH: 9
<212> TYPE: PRT
<213> ORGANISM: Artificial Sequence
<220> FEATURE:
<223> OTHER INFORMATION: TRL799 LC CDR3

<400> SEQUENCE: 66

Met Gln Gly Leu Gln Thr Pro Tyr Thr
1               5

<210> SEQ ID NO 67
<211> LENGTH: 454
<212> TYPE: PRT
<213> ORGANISM: Artificial Sequence
<220> FEATURE:
<223> OTHER INFORMATION: TRL799 HC

<400> SEQUENCE: 67

Gln Val Gln Leu Val Glu Ser Gly Ala Glu Val Lys Lys Phe Gly Ala
1               5                   10                  15

Ser Val Lys Val Ser Cys Lys Ala Ser Gly Tyr Thr Leu Ile Asp Tyr
                20                  25                  30

Tyr Met His Trp Val Arg Val Ala Pro Gly Gln Gly Leu Glu Trp Met
            35                  40                  45

Gly Trp Ile Asn Pro Ile Asn Gly Gly Thr Asn Tyr Ala Gln Lys Phe
    50                  55                  60

Gln Gly Arg Val Thr Met Thr Arg Asp Thr Ser Ile Asn Thr Ala Tyr
65                  70                  75                  80

Met Asp Leu Ser Ser Leu Arg Ser Asp Asp Thr Ala Met Tyr Tyr Cys
                85                  90                  95

Thr Arg Gly Arg Pro Ile Gly Arg Asn Trp Glu Pro Arg Asp Lys Asp
                100                 105                 110

Tyr Trp Gly Gln Gly Thr Pro Val Thr Val Ser Ser Ala Ser Thr Lys
            115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Val Glu Pro
210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
            245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
            275                 280                 285

Val Glu Val His Asn Ala Lys Thr Lys Pro Arg Glu Glu Gln Tyr Asn
290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
            325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Asp Glu Leu Thr Lys Asn
            355                 360                 365

Gln Val Ser Leu Thr Cys Leu Val Lys Gly Phe Tyr Pro Ser Asp Ile
370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
            405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
            435                 440                 445

Ser Leu Ser Pro Gly Lys
    450

<210> SEQ ID NO 68
<211> LENGTH: 219
<212> TYPE: PRT
<213> ORGANISM: Artificial Sequence
<220> FEATURE:
<223> OTHER INFORMATION: TRL799 LC

<400> SEQUENCE: 68

Asp Ile Glu Met Thr Gln Ser Pro Leu Ser Leu Pro Val Thr Pro Gly
1               5                   10                  15

Glu Ser Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Ser Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
            85                  90                  95

Leu Gln Thr Pro Tyr Thr Phe Gly Gln Gly Thr Lys Leu Glu Ile Lys
            100                 105                 110

```
Arg Thr Val Ala Ala Pro Ser Val Phe Ile Phe Pro Ser Asp Glu
            115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 69
<211> LENGTH: 124
<212> TYPE: PRT
<213> ORGANISM: Artificial Sequence
<220> FEATURE:
<223> OTHER INFORMATION: TRL799 HCVR

<400> SEQUENCE: 69

Gln Val Gln Leu Val Glu Ser Gly Ala Glu Val Lys Lys Phe Gly Ala
1               5                   10                  15

Ser Val Lys Val Ser Cys Lys Ala Ser Gly Tyr Thr Leu Ile Asp Tyr
            20                  25                  30

Tyr Met His Trp Val Arg Val Ala Pro Gly Gln Gly Leu Glu Trp Met
        35                  40                  45

Gly Trp Ile Asn Pro Ile Asn Gly Gly Thr Asn Tyr Ala Gln Lys Phe
    50                  55                  60

Gln Gly Arg Val Thr Met Thr Arg Asp Thr Ser Ile Asn Thr Ala Tyr
65                  70                  75                  80

Met Asp Leu Ser Ser Leu Arg Ser Asp Thr Ala Met Tyr Tyr Cys
                85                  90                  95

Thr Arg Gly Arg Pro Ile Gly Arg Asn Trp Glu Pro Arg Asp Lys Asp
            100                 105                 110

Tyr Trp Gly Gln Gly Thr Pro Val Thr Val Ser Ser
        115                 120

<210> SEQ ID NO 70
<211> LENGTH: 114
<212> TYPE: PRT
<213> ORGANISM: Artificial Sequence
<220> FEATURE:
<223> OTHER INFORMATION: TRL799 LCVR

<400> SEQUENCE: 70

Asp Ile Glu Met Thr Gln Ser Pro Leu Ser Leu Pro Val Thr Pro Gly
1               5                   10                  15

Glu Ser Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Ser Arg Ala Ser Gly Val Pro
    50                  55                  60

Asp Arg Phe Ser Gly Ser Gly Ser Gly Thr Asp Phe Thr Leu Lys Ile
65                  70                  75                  80
```

```
Ser Arg Val Glu Ala Glu Asp Val Gly Val Tyr Tyr Cys Met Gln Gly
                85                  90                  95

Leu Gln Thr Pro Tyr Thr Phe Gly Gln Gly Thr Lys Leu Glu Ile Lys
            100                 105                 110

Arg Thr

<210> SEQ ID NO 71
<211> LENGTH: 8
<212> TYPE: PRT
<213> ORGANISM: Artificial Sequence
<220> FEATURE:
<223> OTHER INFORMATION: TRL809 HC CDR1

<400> SEQUENCE: 71

Gly Phe Thr Phe Ser Ala Tyr Ala
1               5

<210> SEQ ID NO 72
<211> LENGTH: 8
<212> TYPE: PRT
<213> ORGANISM: Artificial Sequence
<220> FEATURE:
<223> OTHER INFORMATION: TRL809 HC CDR2

<400> SEQUENCE: 72

Thr Ser Tyr Asp Gly Arg Asp Ser
1               5

<210> SEQ ID NO 73
<211> LENGTH: 19
<212> TYPE: PRT
<213> ORGANISM: Artificial Sequence
<220> FEATURE:
<223> OTHER INFORMATION: TRL809 HC CDR3

<400> SEQUENCE: 73

Ala Lys Val Gly Pro Tyr Thr Gly Tyr Asp Asp Tyr Asn Tyr Tyr Gly
1               5                   10                  15

Met Asp Val

<210> SEQ ID NO 74
<211> LENGTH: 12
<212> TYPE: PRT
<213> ORGANISM: Artificial Sequence
<220> FEATURE:
<223> OTHER INFORMATION: TRL809 LC CDR1

<400> SEQUENCE: 74

Gln Ser Val Leu Ser Asn Ser Lys Asn Leu Asn Tyr
1               5                   10

<210> SEQ ID NO 75
<211> LENGTH: 3
<212> TYPE: PRT
<213> ORGANISM: Artificial Sequence
<220> FEATURE:
<223> OTHER INFORMATION: TRL809 LC CDR2

<400> SEQUENCE: 75

Trp Ala Ser
1
```

```
<210> SEQ ID NO 76
<211> LENGTH: 9
<212> TYPE: PRT
<213> ORGANISM: Artificial Sequence
<220> FEATURE:
<223> OTHER INFORMATION: TRL809 LC CDR3

<400> SEQUENCE: 76

Gln Gln His Tyr Ser Ile Pro Leu Thr
1               5

<210> SEQ ID NO 77
<211> LENGTH: 456
<212> TYPE: PRT
<213> ORGANISM: Artificial Sequence
<220> FEATURE:
<223> OTHER INFORMATION: TRL809 HC

<400> SEQUENCE: 77

Gln Val Gln Leu Leu Glu Ser Gly Gly Gly Val Val Arg Pro Gly Arg
1               5                   10                  15

Ser Leu Arg Leu Ala Cys Ala Gly Ser Gly Phe Thr Phe Ser Ala Tyr
            20                  25                  30

Ala Met His Trp Val Arg Gln Ala Pro Gly Lys Gly Leu Glu Trp Val
        35                  40                  45

Ala His Thr Ser Tyr Asp Gly Arg Asp Ser Tyr Tyr Val Asp Ser Val
    50                  55                  60

Lys Gly Arg Phe Thr Ile Ser Arg Asp Asp Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Lys Val Gly Pro Tyr Thr Gly Tyr Asp Asp Tyr Asn Tyr Tyr Gly
            100                 105                 110

Met Asp Val Trp Gly His Gly Thr Thr Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Lys Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300
```

| Tyr | Asn | Ser | Thr | Tyr | Arg | Val | Val | Ser | Val | Leu | Thr | Val | Leu | His | Gln |
| 305 | | | | 310 | | | | | 315 | | | | | 320 | |

Asp Trp Leu Asn Gly Lys Glu Tyr Lys Cys Lys Val Ser Asn Lys Ala
            325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Asp Glu Leu Thr
            355                 360                 365

Lys Asn Gln Val Ser Leu Thr Cys Leu Val Lys Gly Phe Tyr Pro Ser
            370                 375             380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
            435                 440                 445

Ser Leu Ser Leu Ser Pro Gly Lys
            450                 455

<210> SEQ ID NO 78
<211> LENGTH: 220
<212> TYPE: PRT
<213> ORGANISM: Artificial Sequence
<220> FEATURE:
<223> OTHER INFORMATION: TRL809 LC

<400> SEQUENCE: 78

Asp Ile Val Leu Thr Gln Ser Pro Val Ser Leu Ala Val Ser Leu Gly
1               5                   10                  15

Glu Ser Ala Thr Val Asn Cys Lys Ser Ser Gln Ser Val Leu Ser Asn
            20                  25                  30

Ser Lys Asn Leu Asn Tyr Leu Ala Trp Tyr Gln His Lys Pro Gly Gln
            35                  40                  45

Pro Pro Lys Leu Leu Ile Tyr Trp Ala Ser Thr Arg Glu Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
            85                  90                  95

His Tyr Ser Ile Pro Leu Thr Phe Gly Pro Gly Thr Lys Val Asp Ile
            100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
        130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
            165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
    210                 215                 220

<210> SEQ ID NO 79
<211> LENGTH: 126
<212> TYPE: PRT
<213> ORGANISM: Artificial Sequence
<220> FEATURE:
<223> OTHER INFORMATION: TRL809 HCVR

<400> SEQUENCE: 79

Gln Val Gln Leu Leu Glu Ser Gly Gly Gly Val Arg Pro Gly Arg
1               5                   10                  15

Ser Leu Arg Leu Ala Cys Ala Gly Ser Gly Phe Thr Phe Ser Ala Tyr
            20                  25                  30

Ala Met His Trp Val Arg Gln Ala Pro Gly Lys Gly Leu Glu Trp Val
        35                  40                  45

Ala His Thr Ser Tyr Asp Gly Arg Asp Ser Tyr Tyr Val Asp Ser Val
    50                  55                  60

Lys Gly Arg Phe Thr Ile Ser Arg Asp Asp Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Lys Val Gly Pro Tyr Thr Gly Tyr Asp Asp Tyr Asn Tyr Tyr Gly
            100                 105                 110

Met Asp Val Trp Gly His Gly Thr Thr Val Thr Val Ser Ser
        115                 120                 125

<210> SEQ ID NO 80
<211> LENGTH: 115
<212> TYPE: PRT
<213> ORGANISM: Artificial Sequence
<220> FEATURE:
<223> OTHER INFORMATION: TRL809 LCVR

<400> SEQUENCE: 80

Asp Ile Val Leu Thr Gln Ser Pro Val Ser Leu Ala Val Ser Leu Gly
1               5                   10                  15

Glu Ser Ala Thr Val Asn Cys Lys Ser Ser Gln Ser Val Leu Ser Asn
            20                  25                  30

Ser Lys Asn Leu Asn Tyr Leu Ala Trp Tyr Gln His Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

His Tyr Ser Ile Pro Leu Thr Phe Gly Pro Gly Thr Lys Val Asp Ile
            100                 105                 110

Lys Arg Thr
        115

<210> SEQ ID NO 81
<211> LENGTH: 8
<212> TYPE: PRT
<213> ORGANISM: Artificial Sequence

<220> FEATURE:
<223> OTHER INFORMATION: TRL811 HC CDR1

<400> SEQUENCE: 81

Gly Phe Thr Phe Thr Asn Tyr Ala
1               5

<210> SEQ ID NO 82
<211> LENGTH: 8
<212> TYPE: PRT
<213> ORGANISM: Artificial Sequence
<220> FEATURE:
<223> OTHER INFORMATION: TRL811 HC CDR2

<400> SEQUENCE: 82

Ile Ser Phe Asp Glu Asp Asn Lys
1               5

<210> SEQ ID NO 83
<211> LENGTH: 14
<212> TYPE: PRT
<213> ORGANISM: Artificial Sequence
<220> FEATURE:
<223> OTHER INFORMATION: TRL811 HC CDR3

<400> SEQUENCE: 83

Ala Arg Gly Pro Glu Gly Val Trp Gly Arg Ser Ile Asp Ser
1               5                   10

<210> SEQ ID NO 84
<211> LENGTH: 6
<212> TYPE: PRT
<213> ORGANISM: Artificial Sequence
<220> FEATURE:
<223> OTHER INFORMATION: TRL811 LC CDR1

<400> SEQUENCE: 84

Gln Asp Ile Arg Asn Arg
1               5

<210> SEQ ID NO 85
<211> LENGTH: 3
<212> TYPE: PRT
<213> ORGANISM: Artificial Sequence
<220> FEATURE:
<223> OTHER INFORMATION: TRL811 LC CDR2

<400> SEQUENCE: 85

Ala Ala Ser
1

<210> SEQ ID NO 86
<211> LENGTH: 9
<212> TYPE: PRT
<213> ORGANISM: Artificial Sequence
<220> FEATURE:
<223> OTHER INFORMATION: TRL811 LC CDR3

<400> SEQUENCE: 86

Leu Gln His Asn Ser Tyr Pro Trp Thr
1               5

<210> SEQ ID NO 87
<211> LENGTH: 451
<212> TYPE: PRT
<213> ORGANISM: Artificial Sequence

<220> FEATURE:
<223> OTHER INFORMATION: TRL811 HC

<400> SEQUENCE: 87

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Thr Asn Tyr
            20                  25                  30

Ala Met His Trp Val Arg Gln Ala Pro Gly Lys Gly Leu Glu Trp Val
        35                  40                  45

Ala Val Ile Ser Phe Asp Glu Asp Asn Lys Ser Tyr Ala Asp Tyr Val
    50                  55                  60

Lys Gly Arg Phe Thr Ile Ser Arg Asp Asn Ser Asn Asn Arg Leu Tyr
65                  70                  75                  80

Leu Gln Met Asn Ser Leu Arg Ala Glu Asp Thr Ala Val Tyr Tyr Cys
                85                  90                  95

Ala Arg Gly Pro Glu Gly Val Trp Gly Arg Ser Ile Asp Ser Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400
```

Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
      450

<210> SEQ ID NO 88
<211> LENGTH: 214
<212> TYPE: PRT
<213> ORGANISM: Artificial Sequence
<220> FEATURE:
<223> OTHER INFORMATION: TRL811 LC

<400> SEQUENCE: 88

Asp Ile Leu Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Arg
            20                  25                  30

Leu Ala Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
50                  55                  60

Ser Gly Ser Gly Thr Glu Phe Thr Leu Thr Ile Asn Ser Leu Gln Pro
65                  70                  75                  80

Glu Asp Phe Ala Thr Tyr Tyr Cys Leu Gln His Asn Ser Tyr Pro Trp
                85                  90                  95

Thr Phe Gly Pro Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 89
<211> LENGTH: 121
<212> TYPE: PRT
<213> ORGANISM: Artificial Sequence
<220> FEATURE:
<223> OTHER INFORMATION: TRL811 HCVR

<400> SEQUENCE: 89

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Thr Asn Tyr
            20                  25                  30

```
Ala Met His Trp Val Arg Gln Ala Pro Gly Lys Gly Leu Glu Trp Val
            35                  40                  45

Ala Val Ile Ser Phe Asp Glu Asp Asn Lys Ser Tyr Ala Asp Tyr Val
 50                  55                  60

Lys Gly Arg Phe Thr Ile Ser Arg Asp Asn Ser Asn Asn Arg Leu Tyr
 65                  70                  75                  80

Leu Gln Met Asn Ser Leu Arg Ala Glu Asp Thr Ala Val Tyr Tyr Cys
            85                  90                  95

Ala Arg Gly Pro Glu Gly Val Trp Gly Arg Ser Ile Asp Ser Trp Gly
            100                 105                 110

Gln Gly Thr Leu Val Thr Val Ser Ser
            115                 120

<210> SEQ ID NO 90
<211> LENGTH: 109
<212> TYPE: PRT
<213> ORGANISM: Artificial Sequence
<220> FEATURE:
<223> OTHER INFORMATION: TRL811 LCVR

<400> SEQUENCE: 90

Asp Ile Leu Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Arg
            20                  25                  30

Leu Ala Trp Tyr Gln Gln Lys Pro Gly Lys Ala Pro Lys Arg Leu Ile
            35                  40                  45

Tyr Ala Ala Ser Ser Leu Gln Ser Gly Val Pro Ser Arg Phe Ser Gly
 50                  55                  60

Ser Gly Ser Gly Thr Glu Phe Thr Leu Thr Ile Asn Ser Leu Gln Pro
 65                  70                  75                  80

Glu Asp Phe Ala Thr Tyr Tyr Cys Leu Gln His Asn Ser Tyr Pro Trp
            85                  90                  95

Thr Phe Gly Pro Gly Thr Lys Val Glu Ile Lys Arg Thr
            100                 105

<210> SEQ ID NO 91
<211> LENGTH: 8
<212> TYPE: PRT
<213> ORGANISM: Artificial Sequence
<220> FEATURE:
<223> OTHER INFORMATION: TRL812 HC CDR1

<400> SEQUENCE: 91

Gly Phe Asn Phe Ser Ser Tyr Gly
1               5

<210> SEQ ID NO 92
<211> LENGTH: 8
<212> TYPE: PRT
<213> ORGANISM: Artificial Sequence
<220> FEATURE:
<223> OTHER INFORMATION: TRL812 HC CDR2

<400> SEQUENCE: 92

Ile Trp Ser Gly Gly Ser Asn Lys
1               5
```

```
<210> SEQ ID NO 93
<211> LENGTH: 15
<212> TYPE: PRT
<213> ORGANISM: Artificial Sequence
<220> FEATURE:
<223> OTHER INFORMATION: TRL812 HC CDR3

<400> SEQUENCE: 93

Ala Arg Ala His Thr Ala Leu Thr Arg Phe Arg Trp Leu Asp Pro
1               5                   10                  15

<210> SEQ ID NO 94
<211> LENGTH: 6
<212> TYPE: PRT
<213> ORGANISM: Artificial Sequence
<220> FEATURE:
<223> OTHER INFORMATION: TRL812 LC CDR1

<400> SEQUENCE: 94

Gln Gly Ile Gly Ser Asn
1               5

<210> SEQ ID NO 95
<211> LENGTH: 3
<212> TYPE: PRT
<213> ORGANISM: Artificial Sequence
<220> FEATURE:
<223> OTHER INFORMATION: TRL812 LC CDR2

<400> SEQUENCE: 95

Ala Ala Ser
1

<210> SEQ ID NO 96
<211> LENGTH: 9
<212> TYPE: PRT
<213> ORGANISM: Artificial Sequence
<220> FEATURE:
<223> OTHER INFORMATION: TRL812 LC CDR3

<400> SEQUENCE: 96

Gln Gln Tyr Asn Thr Trp Pro Leu Thr
1               5

<210> SEQ ID NO 97
<211> LENGTH: 452
<212> TYPE: PRT
<213> ORGANISM: Artificial Sequence
<220> FEATURE:
<223> OTHER INFORMATION: TRL812 HC

<400> SEQUENCE: 97

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Asn Phe Ser Ser Tyr
            20                  25                  30

Gly Met His Trp Val Arg Gln Ala Pro Gly Lys Gly Leu Glu Trp Leu
        35                  40                  45

Ser Val Ile Trp Ser Gly Gly Ser Asn Lys Tyr Tyr Ala Asp Ser Val
    50                  55                  60

Lys Gly Arg Phe Thr Ile Ser Arg Asp Asp Ser Lys Asn Thr Val Tyr
65                  70                  75                  80

Leu Gln Met Asn Ser Leu Arg Asp Glu Asp Thr Ala Val Tyr Tyr Cys
                85                  90                  95
```

Ala Arg Ala His Thr Ala Leu Thr Arg Phe Arg Trp Leu Asp Pro Trp
            100                 105                 110

Gly Gln Gly Ile Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

```
<210> SEQ ID NO 98
<211> LENGTH: 214
<212> TYPE: PRT
<213> ORGANISM: Artificial Sequence
<220> FEATURE:
<223> OTHER INFORMATION: TRL812 LC
```

-continued

<400> SEQUENCE: 98

Asp Ile Val Met Thr Gln Ser Pro Ala Thr Leu Ser Val Ser Pro Gly
1               5                   10                  15

Glu Gly Ala Thr Leu Ser Cys Arg Ala Ser Gln Gly Ile Gly Ser Asn
            20                  25                  30

Leu Ala Trp Tyr Gln His Lys Pro Gly Gln Ala Pro Arg Leu Leu Ile
        35                  40                  45

Tyr Ala Ala Ser Thr Arg Ala Thr Gly Val Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Leu Ala Val Tyr Phe Cys Gln Gln Tyr Asn Thr Trp Pro Leu
                85                  90                  95

Thr Phe Gly Gly Gly Thr Lys Val Glu Ile Ile Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 99
<211> LENGTH: 122
<212> TYPE: PRT
<213> ORGANISM: Artificial Sequence
<220> FEATURE:
<223> OTHER INFORMATION: TRL812 HCVR

<400> SEQUENCE: 99

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Asn Phe Ser Ser Tyr
            20                  25                  30

Gly Met His Trp Val Arg Gln Ala Pro Gly Lys Gly Leu Glu Trp Leu
        35                  40                  45

Ser Val Ile Trp Ser Gly Gly Ser Asn Lys Tyr Tyr Ala Asp Ser Val
    50                  55                  60

Lys Gly Arg Phe Thr Ile Ser Arg Asp Asp Ser Lys Asn Thr Val Tyr
65                  70                  75                  80

Leu Gln Met Asn Ser Leu Arg Asp Glu Asp Thr Ala Val Tyr Tyr Cys
                85                  90                  95

Ala Arg Ala His Thr Ala Leu Thr Arg Phe Arg Trp Leu Asp Pro Trp
            100                 105                 110

Gly Gln Gly Ile Leu Val Thr Val Ser Ser
        115                 120

```
<210> SEQ ID NO 100
<211> LENGTH: 109
<212> TYPE: PRT
<213> ORGANISM: Artificial Sequence
<220> FEATURE:
<223> OTHER INFORMATION: TRL812 LCVR

<400> SEQUENCE: 100

Asp Ile Val Met Thr Gln Ser Pro Ala Thr Leu Ser Val Ser Pro Gly
1               5                   10                  15

Glu Gly Ala Thr Leu Ser Cys Arg Ala Ser Gln Gly Ile Gly Ser Asn
            20                  25                  30

Leu Ala Trp Tyr Gln His Lys Pro Gly Gln Ala Pro Arg Leu Leu Ile
        35                  40                  45

Tyr Ala Ala Ser Thr Arg Ala Thr Gly Val Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Leu Ala Val Tyr Phe Cys Gln Gln Tyr Asn Thr Trp Pro Leu
                85                  90                  95

Thr Phe Gly Gly Gly Thr Lys Val Glu Ile Ile Arg Thr
            100                 105

<210> SEQ ID NO 101
<211> LENGTH: 8
<212> TYPE: PRT
<213> ORGANISM: Artificial Sequence
<220> FEATURE:
<223> OTHER INFORMATION: TRL813 HC CDR1

<400> SEQUENCE: 101

Gly Phe Ile Phe Gly Asp Phe Ala
1               5

<210> SEQ ID NO 102
<211> LENGTH: 10
<212> TYPE: PRT
<213> ORGANISM: Artificial Sequence
<220> FEATURE:
<223> OTHER INFORMATION: TRL813 HC CDR2

<400> SEQUENCE: 102

Ile Arg Ser Gly Leu Asn Arg Phe Glu Thr
1               5                   10

<210> SEQ ID NO 103
<211> LENGTH: 11
<212> TYPE: PRT
<213> ORGANISM: Artificial Sequence
<220> FEATURE:
<223> OTHER INFORMATION: TRL813 HC CDR3

<400> SEQUENCE: 103

Thr Tyr Leu Val Gly Ala Val Gly Phe Gln His
1               5                   10

<210> SEQ ID NO 104
<211> LENGTH: 6
<212> TYPE: PRT
<213> ORGANISM: Artificial Sequence
<220> FEATURE:
<223> OTHER INFORMATION: TRL813 LC CDR1
```

<400> SEQUENCE: 104

Gln Thr Ile Tyr Arg Trp
1               5

<210> SEQ ID NO 105
<211> LENGTH: 3
<212> TYPE: PRT
<213> ORGANISM: Artificial Sequence
<220> FEATURE:
<223> OTHER INFORMATION: TRL813 LC CDR2

<400> SEQUENCE: 105

Lys Ala Ser
1

<210> SEQ ID NO 106
<211> LENGTH: 9
<212> TYPE: PRT
<213> ORGANISM: Artificial Sequence
<220> FEATURE:
<223> OTHER INFORMATION: TRL813 LC CDR3

<400> SEQUENCE: 106

Gln Gln Tyr Asn Ser Phe Pro Tyr Arg
1               5

<210> SEQ ID NO 107
<211> LENGTH: 450
<212> TYPE: PRT
<213> ORGANISM: Artificial Sequence
<220> FEATURE:
<223> OTHER INFORMATION: TRL813 HC

<400> SEQUENCE: 107

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Ile Phe Gly Asp Phe
                20                  25                  30

Ala Ile His Trp Val Arg Gln Ala Ser Gly Lys Gly Leu Glu Trp Val
            35                  40                  45

Ala Arg Ile Arg Ser Gly Leu Asn Arg Phe Glu Thr Ala Tyr Ala Ala
        50                  55                  60

Ser Val Glu Gly Arg Leu Thr Ile Ser Arg Asp Asp Ser Lys Ser Met
65                  70                  75                  80

Ala Tyr Leu Gln Met Asn Asn Val Lys Ala Glu Asp Thr Ala Val Tyr
                85                  90                  95

Leu Cys Thr Tyr Leu Val Gly Ala Val Gly Phe Gln His Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 108
<211> LENGTH: 214
<212> TYPE: PRT
<213> ORGANISM: Artificial Sequence
<220> FEATURE:
<223> OTHER INFORMATION: TRL813 LC

<400> SEQUENCE: 108

Asp Ile Val Met Thr Gln Ser Pro Ser Thr Leu Ser Ala Ser Val Gly
1               5                   10                  15

Asp Arg Val Thr Ile Thr Cys Arg Ala Ser Gln Thr Ile Tyr Arg Trp
            20                  25                  30

Leu Ala Trp Tyr Gln Gln Lys Pro Gly Lys Ala Pro Lys Val Leu Ile
        35                  40                  45

Tyr Lys Ala Ser Thr Leu Glu Ser Gly Val Pro Ser Arg Phe Ser Gly
    50                  55                  60

Ser Gly Ser Gly Thr Glu Phe Thr Leu Ala Ile Ser Ser Leu Gln Pro
65                  70                  75                  80

Asp Asp Phe Ala Thr Tyr Tyr Cys Gln Gln Tyr Asn Ser Phe Pro Tyr
                85                  90                  95

Arg Phe Gly Gln Gly Thr Lys Val Glu Ile Lys Arg Thr Val Ala Ala
            100                 105                 110

```
Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 109
<211> LENGTH: 120
<212> TYPE: PRT
<213> ORGANISM: Artificial Sequence
<220> FEATURE:
<223> OTHER INFORMATION: TRL813 HCVR

<400> SEQUENCE: 109

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Ile Phe Gly Asp Phe
            20                  25                  30

Ala Ile His Trp Val Arg Gln Ala Ser Gly Lys Gly Leu Glu Trp Val
        35                  40                  45

Ala Arg Ile Arg Ser Gly Leu Asn Arg Phe Glu Thr Ala Tyr Ala Ala
    50                  55                  60

Ser Val Glu Gly Arg Leu Thr Ile Ser Arg Asp Asp Ser Lys Ser Met
65                  70                  75                  80

Ala Tyr Leu Gln Met Asn Asn Val Lys Ala Glu Asp Thr Ala Val Tyr
                85                  90                  95

Leu Cys Thr Tyr Leu Val Gly Ala Val Gly Phe Gln His Trp Gly Gln
            100                 105                 110

Gly Thr Leu Val Thr Val Ser Ser
        115                 120
```

<210> SEQ ID NO 110
<211> LENGTH: 109
<212> TYPE: PRT
<213> ORGANISM: Artificial Sequence
<220> FEATURE:
<223> OTHER INFORMATION: TRL813 LCVR

<400> SEQUENCE: 110

```
Asp Ile Val Met Thr Gln Ser Pro Ser Thr Leu Ser Ala Ser Val Gly
1               5                   10                  15

Asp Arg Val Thr Ile Thr Cys Arg Ala Ser Gln Thr Ile Tyr Arg Trp
            20                  25                  30

Leu Ala Trp Tyr Gln Gln Lys Pro Gly Lys Ala Pro Lys Val Leu Ile
        35                  40                  45

Tyr Lys Ala Ser Thr Leu Glu Ser Gly Val Pro Ser Arg Phe Ser Gly
    50                  55                  60

Ser Gly Ser Gly Thr Glu Phe Thr Leu Ala Ile Ser Ser Leu Gln Pro
65                  70                  75                  80
```

```
Asp Asp Phe Ala Thr Tyr Tyr Cys Gln Gln Tyr Asn Ser Phe Pro Tyr
            85                  90                  95

Arg Phe Gly Gln Gly Thr Lys Val Glu Ile Lys Arg Thr
            100                 105

<210> SEQ ID NO 111
<211> LENGTH: 8
<212> TYPE: PRT
<213> ORGANISM: Artificial Sequence
<220> FEATURE:
<223> OTHER INFORMATION: TRL823 HC CDR1

<400> SEQUENCE: 111

Gly Phe Asn Phe Asp Glu Tyr Val
1               5

<210> SEQ ID NO 112
<211> LENGTH: 8
<212> TYPE: PRT
<213> ORGANISM: Artificial Sequence
<220> FEATURE:
<223> OTHER INFORMATION: TRL823 HC CDR2

<400> SEQUENCE: 112

Ile Gly Ala Asp Gly Arg Gly Thr
1               5

<210> SEQ ID NO 113
<211> LENGTH: 19
<212> TYPE: PRT
<213> ORGANISM: Artificial Sequence
<220> FEATURE:
<223> OTHER INFORMATION: TRL823 HC CDR3

<400> SEQUENCE: 113

Ala Lys Val Glu Arg Ser Phe Tyr Asp Gly Ser Gly Tyr Gly Asp Ala
1               5                   10                  15

Leu Glu Ile

<210> SEQ ID NO 114
<211> LENGTH: 6
<212> TYPE: PRT
<213> ORGANISM: Artificial Sequence
<220> FEATURE:
<223> OTHER INFORMATION: TRL823 LC CDR1

<400> SEQUENCE: 114

Gln Thr Ile Thr Arg Phe
1               5

<210> SEQ ID NO 115
<211> LENGTH: 3
<212> TYPE: PRT
<213> ORGANISM: Artificial Sequence
<220> FEATURE:
<223> OTHER INFORMATION: TRL823 LC CDR2

<400> SEQUENCE: 115

Ala Ala Ser
1

<210> SEQ ID NO 116
<211> LENGTH: 9
<212> TYPE: PRT
<213> ORGANISM: Artificial Sequence
```

-continued

```
<220> FEATURE:
<223> OTHER INFORMATION: TRL823 LC CDR3

<400> SEQUENCE: 116

Gln Gln Ser Tyr Ser Ala Pro Phe Thr
1               5

<210> SEQ ID NO 117
<211> LENGTH: 456
<212> TYPE: PRT
<213> ORGANISM: Artificial Sequence
<220> FEATURE:
<223> OTHER INFORMATION: TRL823 HC

<400> SEQUENCE: 117

Gln Val Gln Leu Val Glu Ser Gly Gly Gly Val Val Gln Pro Gly Gly
1               5                   10                  15

Ser Leu Arg Leu Ser Cys Ala Ala Ser Gly Phe Asn Phe Asp Glu Tyr
            20                  25                  30

Val Met Tyr Trp Val Arg Gln Ser Pro Gly Lys Gly Leu Glu Trp Val
        35                  40                  45

Ser Leu Ile Gly Ala Asp Gly Arg Gly Thr Tyr Asn Ser Asp Ser Val
    50                  55                  60

Lys Gly Arg Phe Thr Ile Ser Arg Asp Asn Arg Lys Asn Ser Leu Tyr
65                  70                  75                  80

Leu Gln Met Asn Ser Leu Arg Ser Asp Asp Thr Ala Leu Tyr Tyr Cys
                85                  90                  95

Ala Lys Val Glu Arg Ser Phe Tyr Asp Gly Ser Gly Tyr Gly Asp Ala
            100                 105                 110

Leu Glu Ile Trp Gly Gln Gly Thr Met Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Leu Gly Thr Gln Thr Tyr Ile
        195                 200                 205

Cys Asn Val Asn His Lys Pro Ser Asn Thr Lys Val Asp Lys Lys Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320
```

```
Asp Trp Leu Asn Gly Lys Glu Tyr Lys Cys Lys Val Ser Asn Lys Ala
            325                 330                 335

Leu Pro Ala Pro Ile Glu Lys Thr Ile Ser Lys Ala Lys Gly Gln Pro
        340                 345                 350

Arg Glu Pro Gln Val Tyr Thr Leu Pro Pro Ser Arg Asp Glu Leu Thr
        355                 360                 365

Lys Asn Gln Val Ser Leu Thr Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
                420                 425                 430

Ser Cys Ser Val Met His Glu Ala Leu His Asn His Tyr Thr Gln Lys
            435                 440                 445

Ser Leu Ser Leu Ser Pro Gly Lys
        450                 455

<210> SEQ ID NO 118
<211> LENGTH: 214
<212> TYPE: PRT
<213> ORGANISM: Artificial Sequence
<220> FEATURE:
<223> OTHER INFORMATION: TRL823 LC

<400> SEQUENCE: 118

Asp Ile Val Met Thr Gln Ser Pro Ser Ser Leu Ser Ala Ser Val Gly
1               5                   10                  15

Asp Arg Val Ser Ile Thr Cys Arg Ala Ser Gln Thr Ile Thr Arg Phe
            20                  25                  30

Leu Asn Trp Tyr Gln Gln Lys Pro Gly Lys Gly Pro Lys Leu Leu Ile
        35                  40                  45

Tyr Ala Ala Ser Thr Val His Arg Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Ala Pro Phe
                85                  90                  95

Thr Phe Gly Pro Gly Thr Thr Val Asp Ile Arg Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

```
<210> SEQ ID NO 119
<211> LENGTH: 126
<212> TYPE: PRT
<213> ORGANISM: Artificial Sequence
<220> FEATURE:
<223> OTHER INFORMATION: TRL823 HCVR

<400> SEQUENCE: 119

Gln Val Gln Leu Val Glu Ser Gly Gly Gly Val Val Gln Pro Gly Gly
1               5                   10                  15

Ser Leu Arg Leu Ser Cys Ala Ala Ser Gly Phe Asn Phe Asp Glu Tyr
            20                  25                  30

Val Met Tyr Trp Val Arg Gln Ser Pro Gly Lys Gly Leu Glu Trp Val
        35                  40                  45

Ser Leu Ile Gly Ala Asp Gly Arg Gly Thr Tyr Asn Ser Asp Ser Val
    50                  55                  60

Lys Gly Arg Phe Thr Ile Ser Arg Asp Asn Lys Asn Ser Leu Tyr
65                  70                  75                  80

Leu Gln Met Asn Ser Leu Arg Ser Asp Asp Thr Ala Leu Tyr Tyr Cys
            85                  90                  95

Ala Lys Val Glu Arg Ser Phe Tyr Asp Gly Ser Gly Tyr Gly Asp Ala
            100                 105                 110

Leu Glu Ile Trp Gly Gln Gly Thr Met Val Thr Val Ser Ser
        115                 120                 125

<210> SEQ ID NO 120
<211> LENGTH: 109
<212> TYPE: PRT
<213> ORGANISM: Artificial Sequence
<220> FEATURE:
<223> OTHER INFORMATION: TRL823 LCVR

<400> SEQUENCE: 120

Asp Ile Val Met Thr Gln Ser Pro Ser Ser Leu Ser Ala Ser Val Gly
1               5                   10                  15

Asp Arg Val Ser Ile Thr Cys Arg Ala Ser Gln Thr Ile Thr Arg Phe
            20                  25                  30

Leu Asn Trp Tyr Gln Gln Lys Pro Gly Lys Gly Pro Lys Leu Leu Ile
        35                  40                  45

Tyr Ala Ala Ser Thr Val His Arg Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Ala Pro Phe
            85                  90                  95

Thr Phe Gly Pro Gly Thr Thr Val Asp Ile Arg Arg Thr
            100                 105

<210> SEQ ID NO 121
<211> LENGTH: 8
<212> TYPE: PRT
<213> ORGANISM: Artificial Sequence
<220> FEATURE:
<223> OTHER INFORMATION: TRL832 HC CDR1

<400> SEQUENCE: 121

Gly Gly Ser Val Ser Asn Tyr Tyr
1               5
```

<210> SEQ ID NO 122
<211> LENGTH: 10
<212> TYPE: PRT
<213> ORGANISM: Artificial Sequence
<220> FEATURE:
<223> OTHER INFORMATION: TRL832 HC CDR2

<400> SEQUENCE: 122

Val Phe Tyr Ser Gly Ser Ser Asn Tyr Asn
1               5                   10

<210> SEQ ID NO 123
<211> LENGTH: 19
<212> TYPE: PRT
<213> ORGANISM: Artificial Sequence
<220> FEATURE:
<223> OTHER INFORMATION: TRL832 HC CDR3

<400> SEQUENCE: 123

Tyr Cys Ala Arg Gly Arg Val Asn Ser Gly Tyr Asp Trp Gly Pro Asn
1               5                   10                  15
Phe Asp Ser

<210> SEQ ID NO 124
<211> LENGTH: 6
<212> TYPE: PRT
<213> ORGANISM: Artificial Sequence
<220> FEATURE:
<223> OTHER INFORMATION: TRL832 LC CDR1

<400> SEQUENCE: 124

Arg Leu Gly Glu Lys Phe
1               5

<210> SEQ ID NO 125
<211> LENGTH: 3
<212> TYPE: PRT
<213> ORGANISM: Artificial Sequence
<220> FEATURE:
<223> OTHER INFORMATION: TRL832 LC CDR2

<400> SEQUENCE: 125

Glu Asp Ser
1

<210> SEQ ID NO 126
<211> LENGTH: 9
<212> TYPE: PRT
<213> ORGANISM: Artificial Sequence
<220> FEATURE:
<223> OTHER INFORMATION: TRL832 LC CDR3

<400> SEQUENCE: 126

Gln Ala Trp Asp Ser Ser Thr Val Val
1               5

<210> SEQ ID NO 127
<211> LENGTH: 458
<212> TYPE: PRT
<213> ORGANISM: Artificial Sequence
<220> FEATURE:
<223> OTHER INFORMATION: TRL832 HC

<400> SEQUENCE: 127

Gln Val Gln Leu Val Glu Ser Gly Pro Gly Leu Met Lys Pro Ser Glu
1               5                   10                  15

Thr Leu Ser Leu Thr Cys Thr Val Ser Gly Gly Ser Val Ser Asn Tyr
            20                  25                  30

Tyr Trp Ser Trp Ile Arg Gln Pro Pro Gly Lys Gly Leu Glu Trp Ile
        35                  40                  45

Gly Tyr Val Phe Tyr Ser Gly Ser Ser Asn Tyr Asn Pro Ser Leu Asn
    50                  55                  60

Asn Pro Ser Leu Lys Ser Arg Val Thr Ile Ser Ile Asp Thr Ser Asn
65                  70                  75                  80

Asn Gln Phe Ser Leu Lys Leu Ser Ser Val Thr Ala Ala Asp Thr Ala
                85                  90                  95

Val Tyr Tyr Cys Ala Arg Gly Arg Val Asn Ser Gly Tyr Asp Trp Gly
            100                 105                 110

Pro Asn Phe Asp Ser Trp Gly Gln Gly Ala Leu Val Thr Val Ser Ser
        115                 120                 125

Ala Ser Thr Lys Gly Pro Ser Val Phe Pro Leu Ala Pro Ser Ser Lys
    130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Gln Thr
        195                 200                 205

Tyr Ile Cys Asn Val Asn His Lys Pro Ser Asn Thr Lys Val Asp Lys
    210                 215                 220

Lys Val Glu Pro Lys Ser Cys Asp Lys Thr His Thr Cys Pro Pro Cys
225                 230                 235                 240

Pro Ala Pro Glu Leu Leu Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
    290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
            340                 345                 350

Gln Pro Arg Glu Pro Gln Val Tyr Thr Leu Pro Pro Ser Arg Asp Glu
        355                 360                 365

Leu Thr Lys Asn Gln Val Ser Leu Thr Cys Leu Val Lys Gly Phe Tyr
    370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

-continued

Leu Tyr Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
        435                 440                 445

Gln Lys Ser Leu Ser Leu Ser Pro Gly Lys
    450                 455

<210> SEQ ID NO 128
<211> LENGTH: 212
<212> TYPE: PRT
<213> ORGANISM: Artificial Sequence
<220> FEATURE:
<223> OTHER INFORMATION: TRL832 LC

<400> SEQUENCE: 128

Asp Ile Val Leu Thr Gln Ala Pro Ser Val Ser Val Ser Pro Gly Gln
1               5                   10                  15

Thr Ala Ser Ile Thr Cys Ser Gly Asp Arg Leu Gly Glu Lys Phe Ala
            20                  25                  30

Ser Trp Tyr Gln Gln Lys Pro Gly Gln Ser Pro Val Leu Val Ile Tyr
        35                  40                  45

Glu Asp Ser Lys Arg Pro Ser Gly Ile Pro Asp Arg Phe Ser Gly Ser
    50                  55                  60

Asn Ser Gly Asn Thr Ala Thr Leu Thr Ile Ser Gly Thr Gln Ile Met
65                  70                  75                  80

Asp Glu Gly Asp Phe Phe Cys Gln Ala Trp Asp Ser Ser Thr Val Val
                85                  90                  95

Phe Gly Gly Gly Thr Lys Leu Thr Val Leu Gly Gln Pro Lys Ala Ala
            100                 105                 110

Pro Ser Val Thr Leu Phe Pro Pro Ser Ser Glu Glu Leu Gln Ala Asn
        115                 120                 125

Lys Ala Thr Leu Val Cys Leu Ile Ser Asp Phe Tyr Pro Gly Ala Val
    130                 135                 140

Thr Val Ala Trp Lys Ala Asp Ser Ser Pro Val Lys Ala Gly Val Glu
145                 150                 155                 160

Thr Thr Thr Pro Ser Lys Gln Ser Asn Asn Lys Tyr Ala Ala Ser Ser
                165                 170                 175

Tyr Leu Ser Leu Thr Pro Glu Gln Trp Lys Ser His Arg Ser Tyr Ser
            180                 185                 190

Cys Gln Val Thr His Glu Gly Ser Thr Val Glu Lys Thr Val Val Pro
        195                 200                 205

Ala Glu Cys Ser
    210

<210> SEQ ID NO 129
<211> LENGTH: 128
<212> TYPE: PRT
<213> ORGANISM: Artificial Sequence
<220> FEATURE:
<223> OTHER INFORMATION: TRL832 HCVR

<400> SEQUENCE: 129

Gln Val Gln Leu Val Glu Ser Gly Pro Gly Leu Met Lys Pro Ser Glu
1               5                   10                  15

Thr Leu Ser Leu Thr Cys Thr Val Ser Gly Gly Ser Val Ser Asn Tyr
            20                  25                  30

Tyr Trp Ser Trp Ile Arg Gln Pro Pro Gly Lys Gly Leu Glu Trp Ile
        35                  40                  45

```
Gly Tyr Val Phe Tyr Ser Gly Ser Ser Asn Tyr Asn Pro Ser Leu Asn
        50                  55                  60

Asn Pro Ser Leu Lys Ser Arg Val Thr Ile Ser Ile Asp Thr Ser Asn
 65                  70                  75                  80

Asn Gln Phe Ser Leu Lys Leu Ser Ser Val Thr Ala Ala Asp Thr Ala
                 85                  90                  95

Val Tyr Tyr Cys Ala Arg Gly Arg Val Asn Ser Gly Tyr Asp Trp Gly
            100                 105                 110

Pro Asn Phe Asp Ser Trp Gly Gln Gly Ala Leu Val Thr Val Ser Ser
        115                 120                 125
```

<210> SEQ ID NO 130
<211> LENGTH: 108
<212> TYPE: PRT
<213> ORGANISM: Artificial Sequence
<220> FEATURE:
<223> OTHER INFORMATION: TRL832 LCVR

<400> SEQUENCE: 130

```
Asp Ile Val Leu Thr Gln Ala Pro Ser Val Ser Val Ser Pro Gly Gln
 1               5                  10                  15

Thr Ala Ser Ile Thr Cys Ser Gly Asp Arg Leu Gly Glu Lys Phe Ala
                20                  25                  30

Ser Trp Tyr Gln Gln Lys Pro Gly Gln Ser Pro Val Leu Val Ile Tyr
            35                  40                  45

Glu Asp Ser Lys Arg Pro Ser Gly Ile Pro Asp Arg Phe Ser Gly Ser
        50                  55                  60

Asn Ser Gly Asn Thr Ala Thr Leu Thr Ile Ser Gly Thr Gln Ile Met
 65                  70                  75                  80

Asp Glu Gly Asp Phe Phe Cys Gln Ala Trp Asp Ser Ser Thr Val Val
                 85                  90                  95

Phe Gly Gly Gly Thr Lys Leu Thr Val Leu Gly Gln
            100                 105
```

<210> SEQ ID NO 131
<211> LENGTH: 10
<212> TYPE: PRT
<213> ORGANISM: Artificial Sequence
<220> FEATURE:
<223> OTHER INFORMATION: TRL833 HC CDR1

<400> SEQUENCE: 131

```
Gly Ala Ser Ile Ser Thr Gly Gly Asn Tyr
 1               5                  10
```

<210> SEQ ID NO 132
<211> LENGTH: 10
<212> TYPE: PRT
<213> ORGANISM: Artificial Sequence
<220> FEATURE:
<223> OTHER INFORMATION: TRL833 HC CDR2

<400> SEQUENCE: 132

```
Ile Phe Tyr Ser Gly Thr Thr Lys Tyr Asn
 1               5                  10
```

<210> SEQ ID NO 133
<211> LENGTH: 19
<212> TYPE: PRT
<213> ORGANISM: Artificial Sequence
<220> FEATURE:
<223> OTHER INFORMATION: TRL833 HC CDR3

```
<400> SEQUENCE: 133

Phe Cys Ala Arg Gly Ser Pro Asn Ser Gly Tyr Asp Trp Pro His
1               5                   10                  15
Phe Asp Tyr

<210> SEQ ID NO 134
<211> LENGTH: 6
<212> TYPE: PRT
<213> ORGANISM: Artificial Sequence
<220> FEATURE:
<223> OTHER INFORMATION: TRL833 LC CDR1

<400> SEQUENCE: 134

Lys Leu Gly Asp Lys Phe
1               5

<210> SEQ ID NO 135
<211> LENGTH: 3
<212> TYPE: PRT
<213> ORGANISM: Artificial Sequence
<220> FEATURE:
<223> OTHER INFORMATION: TRL833 LC CDR2

<400> SEQUENCE: 135

Gln Asp Asp
1

<210> SEQ ID NO 136
<211> LENGTH: 9
<212> TYPE: PRT
<213> ORGANISM: Artificial Sequence
<220> FEATURE:
<223> OTHER INFORMATION: TRL833 LC CDR3

<400> SEQUENCE: 136

Gln Ala Trp Asp Ser Thr Thr Val Val
1               5

<210> SEQ ID NO 137
<211> LENGTH: 460
<212> TYPE: PRT
<213> ORGANISM: Artificial Sequence
<220> FEATURE:
<223> OTHER INFORMATION: TRL833 HC

<400> SEQUENCE: 137

Gln Val Gln Leu Leu Glu Ser Gly Pro Gly Leu Val Lys Pro Ser Gln
1               5                   10                  15

Thr Leu Leu Leu Thr Cys Thr Val Ser Gly Ala Ser Ile Ser Thr Gly
                20                  25                  30

Gly Asn Tyr Trp Ser Trp Ile Arg Gln His Pro Gly Lys Asp Leu Glu
            35                  40                  45

Trp Ile Gly Tyr Ile Phe Tyr Ser Gly Thr Thr Lys Tyr Asn Pro Ser
        50                  55                  60

Val Asp Asn Pro Ser Leu Lys Ser Arg Val Thr Met Ser Val Asp Thr
65                  70                  75                  80

Ser Glu Asn Gln Phe Ser Leu Lys Leu Ser Ser Val Thr Ala Ala Asp
                85                  90                  95

Thr Ala Val Tyr Phe Cys Ala Arg Gly Ser Pro Asn Ser Gly Tyr Asp
            100                 105                 110

Trp Gly Pro His Phe Asp Tyr Trp Gly Gln Gly Thr Leu Val Thr Val
        115                 120                 125
```

Ser Ser Ala Ser Thr Lys Gly Pro Ser Val Phe Pro Leu Ala Pro Ser
    130                 135                 140

Ser Lys Ser Thr Ser Gly Gly Thr Ala Ala Leu Gly Cys Leu Val Lys
145                 150                 155                 160

Asp Tyr Phe Pro Glu Pro Val Thr Val Ser Trp Asn Ser Gly Ala Leu
                165                 170                 175

Thr Ser Gly Val His Thr Phe Pro Ala Val Leu Gln Ser Ser Gly Leu
            180                 185                 190

Tyr Ser Leu Ser Ser Val Val Thr Val Pro Ser Ser Ser Leu Gly Thr
        195                 200                 205

Gln Thr Tyr Ile Cys Asn Val Asn His Lys Pro Ser Asn Thr Lys Val
    210                 215                 220

Asp Lys Lys Val Glu Pro Lys Ser Cys Asp Lys Thr His Thr Cys Pro
225                 230                 235                 240

Pro Cys Pro Ala Pro Glu Leu Leu Gly Gly Pro Ser Val Phe Leu Phe
                245                 250                 255

Pro Pro Lys Pro Lys Asp Thr Leu Met Ile Ser Arg Thr Pro Glu Val
            260                 265                 270

Thr Cys Val Val Val Asp Val Ser His Glu Asp Pro Glu Val Lys Phe
        275                 280                 285

Asn Trp Tyr Val Asp Gly Val Glu Val His Asn Ala Lys Thr Lys Pro
    290                 295                 300

Arg Glu Glu Gln Tyr Asn Ser Thr Tyr Arg Val Val Ser Val Leu Thr
305                 310                 315                 320

Val Leu His Gln Asp Trp Leu Asn Gly Lys Glu Tyr Lys Cys Lys Val
                325                 330                 335

Ser Asn Lys Ala Leu Pro Ala Pro Ile Glu Lys Thr Ile Ser Lys Ala
            340                 345                 350

Lys Gly Gln Pro Arg Glu Pro Gln Val Tyr Thr Leu Pro Pro Ser Arg
        355                 360                 365

Asp Glu Leu Thr Lys Asn Gln Val Ser Leu Thr Cys Leu Val Lys Gly
    370                 375                 380

Phe Tyr Pro Ser Asp Ile Ala Val Glu Trp Glu Ser Asn Gly Gln Pro
385                 390                 395                 400

Glu Asn Asn Tyr Lys Thr Thr Pro Pro Val Leu Asp Ser Asp Gly Ser
                405                 410                 415

Phe Phe Leu Tyr Ser Lys Leu Thr Val Asp Lys Ser Arg Trp Gln Gln
            420                 425                 430

Gly Asn Val Phe Ser Cys Ser Val Met His Glu Ala Leu His Asn His
        435                 440                 445

Tyr Thr Gln Lys Ser Leu Ser Leu Ser Pro Gly Lys
    450                 455                 460

<210> SEQ ID NO 138
<211> LENGTH: 212
<212> TYPE: PRT
<213> ORGANISM: Artificial Sequence
<220> FEATURE:
<223> OTHER INFORMATION: TRL833 LC

<400> SEQUENCE: 138

Asp Ile Glu Leu Thr Gln Ser Pro Ser Val Ser Val Ser Pro Gly Gln
1               5                   10                  15

Thr Ala Ser Ile Thr Cys Ser Gly Asp Lys Leu Gly Asp Lys Phe Val
            20                  25                  30

```
Cys Trp Tyr Gln Gln Lys Ala Gly Gln Ser Pro Ile Val Val Ile Tyr
         35                  40                  45

Gln Asp Asp Lys Arg Pro Ser Gly Ile Pro Glu Arg Phe Ser Gly Ser
 50                  55                  60

Asn Ser Gly Asn Thr Ala Thr Leu Thr Ile Ser Gly Thr Gln Ala Met
 65                  70                  75                  80

Asp Glu Ala Asp Tyr Phe Cys Gln Ala Trp Asp Ser Thr Thr Val Val
                 85                  90                  95

Phe Gly Gly Gly Thr Lys Leu Thr Val Leu Gly Gln Pro Lys Ala Ala
            100                 105                 110

Pro Ser Val Thr Leu Phe Pro Pro Ser Ser Glu Glu Leu Gln Ala Asn
            115                 120                 125

Lys Ala Thr Leu Val Cys Leu Ile Ser Asp Phe Tyr Pro Gly Ala Val
130                 135                 140

Thr Val Ala Trp Lys Ala Asp Ser Ser Pro Val Lys Ala Gly Val Glu
145                 150                 155                 160

Thr Thr Thr Pro Ser Lys Gln Ser Asn Asn Lys Tyr Ala Ala Ser Ser
                165                 170                 175

Tyr Leu Ser Leu Thr Pro Glu Gln Trp Lys Ser His Arg Ser Tyr Ser
            180                 185                 190

Cys Gln Val Thr His Glu Gly Ser Thr Val Glu Lys Thr Val Val Pro
        195                 200                 205

Ala Glu Cys Ser
        210

<210> SEQ ID NO 139
<211> LENGTH: 130
<212> TYPE: PRT
<213> ORGANISM: Artificial Sequence
<220> FEATURE:
<223> OTHER INFORMATION: TRL833 HCVR

<400> SEQUENCE: 139

Gln Val Gln Leu Leu Glu Ser Gly Pro Gly Leu Val Lys Pro Ser Gln
1                5                  10                  15

Thr Leu Leu Leu Thr Cys Thr Val Ser Gly Ala Ser Ile Ser Thr Gly
             20                  25                  30

Gly Asn Tyr Trp Ser Trp Ile Arg Gln His Pro Gly Lys Asp Leu Glu
         35                  40                  45

Trp Ile Gly Tyr Ile Phe Tyr Ser Gly Thr Thr Lys Tyr Asn Pro Ser
 50                  55                  60

Val Asp Asn Pro Ser Leu Lys Ser Arg Val Thr Met Ser Val Asp Thr
 65                  70                  75                  80

Ser Glu Asn Gln Phe Ser Leu Lys Leu Ser Ser Val Thr Ala Ala Asp
                 85                  90                  95

Thr Ala Val Tyr Phe Cys Ala Arg Gly Ser Pro Asn Ser Gly Tyr Asp
            100                 105                 110

Trp Gly Pro His Phe Asp Tyr Trp Gly Gln Gly Thr Leu Val Thr Val
            115                 120                 125

Ser Ser
130

<210> SEQ ID NO 140
<211> LENGTH: 108
<212> TYPE: PRT
<213> ORGANISM: Artificial Sequence
```

<220> FEATURE:
<223> OTHER INFORMATION: TRL833 LCVR

<400> SEQUENCE: 140

Asp Ile Glu Leu Thr Gln Ser Pro Ser Val Ser Val Ser Pro Gly Gln
1               5                   10                  15

Thr Ala Ser Ile Thr Cys Ser Gly Asp Lys Leu Gly Asp Lys Phe Val
            20                  25                  30

Cys Trp Tyr Gln Gln Lys Ala Gly Gln Ser Pro Ile Val Val Ile Tyr
        35                  40                  45

Gln Asp Asp Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Phe Cys Gln Ala Trp Asp Ser Thr Val Val
                85                  90                  95

Phe Gly Gly Gly Thr Lys Leu Thr Val Leu Gly Gln
            100                 105

<210> SEQ ID NO 141
<211> LENGTH: 8
<212> TYPE: PRT
<213> ORGANISM: Artificial Sequence
<220> FEATURE:
<223> OTHER INFORMATION: TRL834 HC CDR1

<400> SEQUENCE: 141

Gly Gly Thr Phe Ser Tyr Tyr Ala
1               5

<210> SEQ ID NO 142
<211> LENGTH: 8
<212> TYPE: PRT
<213> ORGANISM: Artificial Sequence
<220> FEATURE:
<223> OTHER INFORMATION: TRL834 HC CDR2

<400> SEQUENCE: 142

Ile Ile Pro Ile Val Gly Thr Ala
1               5

<210> SEQ ID NO 143
<211> LENGTH: 21
<212> TYPE: PRT
<213> ORGANISM: Artificial Sequence
<220> FEATURE:
<223> OTHER INFORMATION: TRL834 HC CDR3

<400> SEQUENCE: 143

Ala Arg Ala Ala Asp Glu Ser Val Glu Ser Leu Thr Ile Lys Ala Phe
1               5                   10                  15

Arg Thr Asn Tyr His
            20

<210> SEQ ID NO 144
<211> LENGTH: 8
<212> TYPE: PRT
<213> ORGANISM: Artificial Sequence
<220> FEATURE:
<223> OTHER INFORMATION: TRL834 LC CDR1

<400> SEQUENCE: 144

Thr Ser Asn Ile Gly Ser Asn Thr
1               5

<210> SEQ ID NO 145
<211> LENGTH: 3
<212> TYPE: PRT
<213> ORGANISM: Artificial Sequence
<220> FEATURE:
<223> OTHER INFORMATION: TRL834 LC CDR2

<400> SEQUENCE: 145

Thr Asp Asn
1

<210> SEQ ID NO 146
<211> LENGTH: 11
<212> TYPE: PRT
<213> ORGANISM: Artificial Sequence
<220> FEATURE:
<223> OTHER INFORMATION: TRL834 LC CDR3

<400> SEQUENCE: 146

Ala Ala Trp Asp Asp Ser Leu Asn Gly Trp Val
1               5                   10

<210> SEQ ID NO 147
<211> LENGTH: 458
<212> TYPE: PRT
<213> ORGANISM: Artificial Sequence
<220> FEATURE:
<223> OTHER INFORMATION: TRL834 HC

<400> SEQUENCE: 147

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Tyr Tyr
            20                  25                  30

Ala Ile Ser Trp Val Arg Gln Ala Pro Gly Gln Gly Leu Glu Trp Met
        35                  40                  45

Gly Gly Ile Ile Pro Ile Val Gly Thr Ala His Tyr Thr Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Ala Ala Asp Glu Ser Val Glu Ser Leu Thr Ile Lys Ala Phe
            100                 105                 110

Arg Thr Asn Tyr His Trp Gly Gln Gly Thr Leu Val Thr Val Ser Ser
        115                 120                 125

Ala Ser Thr Lys Gly Pro Ser Val Phe Pro Leu Ala Pro Ser Ser Lys
    130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Gln Thr
        195                 200                 205

Tyr Ile Cys Asn Val Asn His Lys Pro Ser Asn Thr Lys Val Asp Lys
    210                 215                 220
Lys Val Glu Pro Lys Ser Cys Asp Lys Thr His Thr Cys Pro Pro Cys
225                 230                 235                 240
Pro Ala Pro Glu Leu Leu Gly Gly Pro Ser Val Phe Leu Phe Pro Pro
            245                 250                 255
Lys Pro Lys Asp Thr Leu Met Ile Ser Arg Thr Pro Glu Val Thr Cys
        260                 265                 270
Val Val Val Asp Val Ser His Glu Asp Pro Glu Val Lys Phe Asn Trp
    275                 280                 285
Tyr Val Asp Gly Val Glu Val His Asn Ala Lys Thr Lys Pro Arg Glu
290                 295                 300
Glu Gln Tyr Asn Ser Thr Tyr Arg Val Val Ser Val Leu Thr Val Leu
305                 310                 315                 320
His Gln Asp Trp Leu Asn Gly Lys Glu Tyr Lys Cys Lys Val Ser Asn
            325                 330                 335
Lys Ala Leu Pro Ala Pro Ile Glu Lys Thr Ile Ser Lys Ala Lys Gly
        340                 345                 350
Gln Pro Arg Glu Pro Gln Val Tyr Thr Leu Pro Pro Ser Arg Asp Glu
    355                 360                 365
Leu Thr Lys Asn Gln Val Ser Leu Thr Cys Leu Val Lys Gly Phe Tyr
370                 375                 380
Pro Ser Asp Ile Ala Val Glu Trp Glu Ser Asn Gly Gln Pro Glu Asn
385                 390                 395                 400
Asn Tyr Lys Thr Thr Pro Pro Val Leu Asp Ser Asp Gly Ser Phe Phe
            405                 410                 415
Leu Tyr Ser Lys Leu Thr Val Asp Lys Ser Arg Trp Gln Gln Gly Asn
        420                 425                 430
Val Phe Ser Cys Ser Val Met His Glu Ala Leu His Asn His Tyr Thr
    435                 440                 445
Gln Lys Ser Leu Ser Leu Ser Pro Gly Lys
450                 455

<210> SEQ ID NO 148
<211> LENGTH: 216
<212> TYPE: PRT
<213> ORGANISM: Artificial Sequence
<220> FEATURE:
<223> OTHER INFORMATION: TRL834 LC

<400> SEQUENCE: 148

Asp Ile Glu Leu Thr Gln Glu Pro Ser Ala Ser Gly Thr Pro Gly Gln
1               5                   10                  15
Arg Val Thr Ile Ser Cys Ser Gly Asp Thr Ser Asn Ile Gly Ser Asn
            20                  25                  30
Thr Val Ser Trp Phe Gln Leu Leu Pro Gly Thr Ala Pro Lys Leu Leu
        35                  40                  45
Ile Phe Thr Asp Asn Gln Arg Pro Ser Gly Val Pro Gly Arg Phe Ser
    50                  55                  60
Gly Ser Lys Ser Gly Thr Ser Ala Ser Leu Ala Ile Ser Gly Leu Gln
65                  70                  75                  80
Ser Glu Asp Glu Thr Asp Tyr Tyr Cys Ala Ala Trp Asp Asp Ser Leu
            85                  90                  95
Asn Gly Trp Val Phe Gly Gly Gly Thr Lys Leu Thr Val Leu Gly Gln
            100                 105                 110

```
Pro Lys Ala Ala Pro Ser Val Thr Leu Phe Pro Ser Ser Glu Glu
            115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
            195                 200                 205

Thr Val Val Pro Ala Glu Cys Ser
    210                 215

<210> SEQ ID NO 149
<211> LENGTH: 128
<212> TYPE: PRT
<213> ORGANISM: Artificial Sequence
<220> FEATURE:
<223> OTHER INFORMATION: TRL834 HCVR

<400> SEQUENCE: 149

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Tyr Tyr
            20                  25                  30

Ala Ile Ser Trp Val Arg Gln Ala Pro Gly Gln Gly Leu Glu Trp Met
        35                  40                  45

Gly Gly Ile Ile Pro Ile Val Gly Thr Ala His Tyr Thr Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Ala Ala Asp Glu Ser Val Glu Ser Leu Thr Ile Lys Ala Phe
            100                 105                 110

Arg Thr Asn Tyr His Trp Gly Gln Gly Thr Leu Val Thr Val Ser Ser
        115                 120                 125

<210> SEQ ID NO 150
<211> LENGTH: 112
<212> TYPE: PRT
<213> ORGANISM: Artificial Sequence
<220> FEATURE:
<223> OTHER INFORMATION: TRL834 LCVR

<400> SEQUENCE: 150

Asp Ile Glu Leu Thr Gln Glu Pro Ser Ala Ser Gly Thr Pro Gly Gln
1               5                   10                  15

Arg Val Thr Ile Ser Cys Ser Gly Asp Thr Ser Asn Ile Gly Ser Asn
            20                  25                  30

Thr Val Ser Trp Phe Gln Leu Leu Pro Gly Thr Ala Pro Lys Leu Leu
        35                  40                  45

Ile Phe Thr Asp Asn Gln Arg Pro Ser Gly Val Pro Gly Arg Phe Ser
    50                  55                  60

Gly Ser Lys Ser Gly Thr Ser Ala Ser Leu Ala Ile Ser Gly Leu Gln
65                  70                  75                  80
```

```
Ser Glu Asp Glu Thr Asp Tyr Tyr Cys Ala Ala Trp Asp Asp Ser Leu
                85                  90                  95

Asn Gly Trp Val Phe Gly Gly Gly Thr Lys Leu Thr Val Leu Gly Gln
            100                 105                 110
```

<210> SEQ ID NO 151
<211> LENGTH: 8
<212> TYPE: PRT
<213> ORGANISM: Artificial Sequence
<220> FEATURE:
<223> OTHER INFORMATION: TRL835 HC CDR1

<400> SEQUENCE: 151

```
Gly Tyr Asn Phe Pro Lys Tyr Trp
1               5
```

<210> SEQ ID NO 152
<211> LENGTH: 8
<212> TYPE: PRT
<213> ORGANISM: Artificial Sequence
<220> FEATURE:
<223> OTHER INFORMATION: TRL835 HC CDR2

<400> SEQUENCE: 152

```
Ile Tyr Pro Gly Asp Ser Asp Val
1               5
```

<210> SEQ ID NO 153
<211> LENGTH: 20
<212> TYPE: PRT
<213> ORGANISM: Artificial Sequence
<220> FEATURE:
<223> OTHER INFORMATION: TRL835 HC CDR3

<400> SEQUENCE: 153

```
Ala Arg His Leu Gly Gln Gln Leu Val Ser Asn Thr Tyr Tyr Tyr Tyr
1               5                   10                  15

Gly Met Asp Val
            20
```

<210> SEQ ID NO 154
<211> LENGTH: 11
<212> TYPE: PRT
<213> ORGANISM: Artificial Sequence
<220> FEATURE:
<223> OTHER INFORMATION: TRL835 LC CDR1

<400> SEQUENCE: 154

```
Gln Ser Leu Leu Asp Ser Asn Gly Tyr Asn Tyr
1               5                   10
```

<210> SEQ ID NO 155
<211> LENGTH: 3
<212> TYPE: PRT
<213> ORGANISM: Artificial Sequence
<220> FEATURE:
<223> OTHER INFORMATION: TRL835 LC CDR2

<400> SEQUENCE: 155

```
Leu Ala Ser
1
```

<210> SEQ ID NO 156
<211> LENGTH: 11
<212> TYPE: PRT
<213> ORGANISM: Artificial Sequence

<220> FEATURE:
<223> OTHER INFORMATION: TRL835 LC CDR3

<400> SEQUENCE: 156

Met Gln Ala Leu Gln Thr Pro Pro Met Tyr Thr
1               5                   10

<210> SEQ ID NO 157
<211> LENGTH: 457
<212> TYPE: PRT
<213> ORGANISM: Artificial Sequence
<220> FEATURE:
<223> OTHER INFORMATION: TRL835 HC

<400> SEQUENCE: 157

Gln Val Gln Leu Val Gln Ser Gly Ala Glu Val Arg Lys Pro Gly Glu
1               5                   10                  15

Ser Leu Arg Ile Ser Cys Arg Gly Ser Gly Tyr Asn Phe Pro Lys Tyr
                20                  25                  30

Trp Ile Gly Trp Val Arg Gln Met Pro Gly Lys Gly Leu Glu Trp Met
            35                  40                  45

Gly Met Ile Tyr Pro Gly Asp Ser Asp Val Arg Tyr Asn Pro Ser Phe
    50                  55                  60

Gln Gly Gln Val Thr Ile Ser Ala Asp Glu Ser Ile Asn Thr Ala Tyr
65                  70                  75                  80

Leu Gln Trp Ser Ser Leu Arg Thr Ser Asp Thr Ala Arg Tyr Tyr Cys
                85                  90                  95

Ala Arg His Leu Gly Gln Gln Leu Val Ser Asn Thr Tyr Tyr Tyr Tyr
            100                 105                 110

Gly Met Asp Val Trp Gly Gln Gly Thr Thr Val Thr Val Ser Ser Ala
        115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
        195                 200                 205

Ile Cys Asn Val Asn His Lys Pro Ser Asn Thr Lys Val Asp Lys Lys
    210                 215                 220

Val Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
        275                 280                 285

Val Asp Gly Val Glu Val His Asn Ala Lys Thr Lys Pro Arg Glu Glu
    290                 295                 300

Gln Tyr Asn Ser Thr Tyr Arg Val Val Ser Val Leu Thr Val Leu His
305                 310                 315                 320

```
Gln Asp Trp Leu Asn Gly Lys Glu Tyr Lys Cys Lys Val Ser Asn Lys
                325                 330                 335

Ala Leu Pro Ala Pro Ile Glu Lys Thr Ile Ser Lys Ala Lys Gly Gln
            340                 345                 350

Pro Arg Glu Pro Gln Val Tyr Thr Leu Pro Pro Ser Arg Asp Glu Leu
        355                 360                 365

Thr Lys Asn Gln Val Ser Leu Thr Cys Leu Val Lys Gly Phe Tyr Pro
    370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
            405                 410                 415

Tyr Ser Lys Leu Thr Val Asp Lys Ser Arg Trp Gln Gln Gly Asn Val
        420                 425                 430

Phe Ser Cys Ser Val Met His Glu Ala Leu His Asn His Tyr Thr Gln
    435                 440                 445

Lys Ser Leu Ser Leu Ser Pro Gly Lys
    450                 455

<210> SEQ ID NO 158
<211> LENGTH: 221
<212> TYPE: PRT
<213> ORGANISM: Artificial Sequence
<220> FEATURE:
<223> OTHER INFORMATION: TRL835 LC

<400> SEQUENCE: 158

Asp Ile Val Leu Thr Gln Ser Pro Leu Ser Leu Pro Val Thr Pro Gly
1               5                   10                  15

Glu Pro Ala Ser Ile Ser Cys Arg Ser Ser Gln Ser Leu Leu Asp Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Ala Ser Tyr Arg Ala Pro Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Leu Tyr Tyr Cys Met Gln Ala
                85                  90                  95

Leu Gln Thr Pro Pro Met Tyr Thr Phe Gly Gln Gly Thr Lys Leu Glu
            100                 105                 110

Ile Lys Arg Thr Val Ala Ala Pro Ser Val Phe Ile Phe Pro Pro Ser
        115                 120                 125

Asp Glu Gln Leu Lys Ser Gly Thr Ala Ser Val Val Cys Leu Leu Asn
    130                 135                 140

Asn Phe Tyr Pro Arg Glu Ala Lys Val Gln Trp Lys Val Asp Asn Ala
145                 150                 155                 160

Leu Gln Ser Gly Asn Ser Gln Glu Ser Val Thr Glu Gln Asp Ser Lys
                165                 170                 175

Asp Ser Thr Tyr Ser Leu Ser Ser Thr Leu Thr Leu Ser Lys Ala Asp
            180                 185                 190

Tyr Glu Lys His Lys Val Tyr Ala Cys Glu Val Thr His Gln Gly Leu
        195                 200                 205

Ser Ser Pro Val Thr Lys Ser Phe Asn Arg Gly Glu Cys
    210                 215                 220
```

```
<210> SEQ ID NO 159
<211> LENGTH: 127
<212> TYPE: PRT
<213> ORGANISM: Artificial Sequence
<220> FEATURE:
<223> OTHER INFORMATION: TRL835 HCVR

<400> SEQUENCE: 159

Gln Val Gln Leu Val Gln Ser Gly Ala Glu Val Arg Lys Pro Gly Glu
1               5                   10                  15

Ser Leu Arg Ile Ser Cys Arg Gly Ser Gly Tyr Asn Phe Pro Lys Tyr
            20                  25                  30

Trp Ile Gly Trp Val Arg Gln Met Pro Gly Lys Gly Leu Glu Trp Met
        35                  40                  45

Gly Met Ile Tyr Pro Gly Asp Ser Asp Val Arg Tyr Asn Pro Ser Phe
    50                  55                  60

Gln Gly Gln Val Thr Ile Ser Ala Asp Glu Ser Ile Asn Thr Ala Tyr
65                  70                  75                  80

Leu Gln Trp Ser Ser Leu Arg Thr Ser Asp Thr Ala Arg Tyr Tyr Cys
                85                  90                  95

Ala Arg His Leu Gly Gln Gln Leu Val Ser Asn Thr Tyr Tyr Tyr Tyr
            100                 105                 110

Gly Met Asp Val Trp Gly Gln Gly Thr Thr Val Thr Val Ser Ser
        115                 120                 125

<210> SEQ ID NO 160
<211> LENGTH: 116
<212> TYPE: PRT
<213> ORGANISM: Artificial Sequence
<220> FEATURE:
<223> OTHER INFORMATION: TRL835 LCVR

<400> SEQUENCE: 160

Asp Ile Val Leu Thr Gln Ser Pro Leu Ser Leu Pro Val Thr Pro Gly
1               5                   10                  15

Glu Pro Ala Ser Ile Ser Cys Arg Ser Ser Gln Ser Leu Leu Asp Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Ala Ser Tyr Arg Ala Pro Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Leu Tyr Tyr Cys Met Gln Ala
                85                  90                  95

Leu Gln Thr Pro Pro Met Tyr Thr Phe Gly Gln Gly Thr Lys Leu Glu
            100                 105                 110

Ile Lys Arg Thr
        115

<210> SEQ ID NO 161
<211> LENGTH: 8
<212> TYPE: PRT
<213> ORGANISM: Artificial Sequence
<220> FEATURE:
<223> OTHER INFORMATION: TRL837 HC CDR1

<400> SEQUENCE: 161

Gly His Thr Phe Ile Ser Tyr Ala
1               5
```

<210> SEQ ID NO 162
<211> LENGTH: 8
<212> TYPE: PRT
<213> ORGANISM: Artificial Sequence
<220> FEATURE:
<223> OTHER INFORMATION: TRL837 HC CDR2

<400> SEQUENCE: 162

Ile Val Pro Ile Phe Gly Thr Val
1               5

<210> SEQ ID NO 163
<211> LENGTH: 17
<212> TYPE: PRT
<213> ORGANISM: Artificial Sequence
<220> FEATURE:
<223> OTHER INFORMATION: TRL837 HC CDR3

<400> SEQUENCE: 163

Ala Arg Glu Ala Gly Tyr His Ser Ser Phe Ser Gly Val Tyr Phe Asp
1               5                   10                  15

Tyr

<210> SEQ ID NO 164
<211> LENGTH: 7
<212> TYPE: PRT
<213> ORGANISM: Artificial Sequence
<220> FEATURE:
<223> OTHER INFORMATION: TRL837 LC CDR1

<400> SEQUENCE: 164

Gln Ser Val Arg Ser Gly Tyr
1               5

<210> SEQ ID NO 165
<211> LENGTH: 3
<212> TYPE: PRT
<213> ORGANISM: Artificial Sequence
<220> FEATURE:
<223> OTHER INFORMATION: TRL837 LC CDR2

<400> SEQUENCE: 165

Asp Ala Ser
1

<210> SEQ ID NO 166
<211> LENGTH: 9
<212> TYPE: PRT
<213> ORGANISM: Artificial Sequence
<220> FEATURE:
<223> OTHER INFORMATION: TRL837 LC CDR3

<400> SEQUENCE: 166

Leu Gln Tyr Gly Ser Ser Pro Arg Thr
1               5

<210> SEQ ID NO 167
<211> LENGTH: 454
<212> TYPE: PRT
<213> ORGANISM: Artificial Sequence
<220> FEATURE:
<223> OTHER INFORMATION: TRL837 HC -continued

```
<400> SEQUENCE: 167

Gln Val Gln Leu Val Gln Ser Gly Ala Glu Val Lys Lys Pro Gly Ser
1               5                   10                  15

Ser Val Thr Val Ser Cys Lys Thr Ser Gly His Thr Phe Ile Ser Tyr
            20                  25                  30

Ala Ile Ser Trp Leu Arg Gln Ala Pro Gly Gln Gly Leu Glu Trp Met
        35                  40                  45

Gly Gly Ile Val Pro Ile Phe Gly Thr Val Asn Tyr Thr Gln Lys Phe
    50                  55                  60

Gln Gly Arg Leu Thr Ile Thr Ala Asp Glu Ser Thr Ser Thr Ala Tyr
65                  70                  75                  80

Met Asp Leu Ser Arg Leu Thr Phe Glu Asp Thr Ala Ile Tyr Phe Cys
                85                  90                  95

Ala Arg Glu Ala Gly Tyr His Ser Ser Phe Ser Gly Val Tyr Phe Asp
            100                 105                 110

Tyr Trp Gly Gln Gly Thr Leu Leu Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Asp Glu Leu Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415
```

-continued

Leu Thr Val Asp Lys Ser Arg Trp Gln Gln Gly Asn Val Phe Ser Cys
                420                 425                 430

Ser Val Met His Glu Ala Leu His Asn His Tyr Thr Gln Lys Ser Leu
            435                 440                 445

Ser Leu Ser Pro Gly Lys
        450

<210> SEQ ID NO 168
<211> LENGTH: 215
<212> TYPE: PRT
<213> ORGANISM: Artificial Sequence
<220> FEATURE:
<223> OTHER INFORMATION: TRL837 LC

<400> SEQUENCE: 168

Asp Ile Val Met Thr Gln Ser Pro Gly Thr Leu Ser Leu Ser Pro Gly
1               5                   10                  15

Glu Arg Ala Thr Leu Tyr Cys Arg Ala Ser Gln Ser Val Arg Ser Gly
            20                  25                  30

Tyr Leu Ala Trp Tyr Gln His Lys Pro Gly Gln Ala Pro Leu Leu Leu
        35                  40                  45

Phe Tyr Asp Ala Ser Gly Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Leu Gln Tyr Gly Ser Ser Pro
                85                  90                  95

Arg Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 169
<211> LENGTH: 124
<212> TYPE: PRT
<213> ORGANISM: Artificial Sequence
<220> FEATURE:
<223> OTHER INFORMATION: TRL837 HCVR

<400> SEQUENCE: 169

Gln Val Gln Leu Val Gln Ser Gly Ala Glu Val Lys Lys Pro Gly Ser
1               5                   10                  15

Ser Val Thr Val Ser Cys Lys Thr Ser Gly His Thr Phe Ile Ser Tyr
            20                  25                  30

Ala Ile Ser Trp Leu Arg Gln Ala Pro Gly Gln Gly Leu Glu Trp Met
        35                  40                  45

Gly Gly Ile Val Pro Ile Phe Gly Thr Val Asn Tyr Thr Gln Lys Phe
        50                  55                  60

Gln Gly Arg Leu Thr Ile Thr Ala Asp Glu Ser Thr Ser Thr Ala Tyr
65                  70                  75                  80

Met Asp Leu Ser Arg Leu Thr Phe Glu Asp Thr Ala Ile Tyr Phe Cys
                85                  90                  95

Ala Arg Glu Ala Gly Tyr His Ser Ser Phe Ser Gly Val Tyr Phe Asp
                100                 105                 110

Tyr Trp Gly Gln Gly Thr Leu Leu Thr Val Ser Ser
            115                 120

<210> SEQ ID NO 170
<211> LENGTH: 110
<212> TYPE: PRT
<213> ORGANISM: Artificial Sequence
<220> FEATURE:
<223> OTHER INFORMATION: TRL837 LCVR

<400> SEQUENCE: 170

Asp Ile Val Met Thr Gln Ser Pro Gly Thr Leu Ser Leu Ser Pro Gly
1               5                   10                  15

Glu Arg Ala Thr Leu Tyr Cys Arg Ala Ser Gln Ser Val Arg Ser Gly
            20                  25                  30

Tyr Leu Ala Trp Tyr Gln His Lys Pro Gly Gln Ala Pro Leu Leu Leu
        35                  40                  45

Phe Tyr Asp Ala Ser Gly Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Leu Gln Tyr Gly Ser Ser Pro
                85                  90                  95

Arg Thr Phe Gly Gln Gly Thr Lys Val Glu Ile Lys Arg Thr
            100                 105                 110

<210> SEQ ID NO 171
<211> LENGTH: 8
<212> TYPE: PRT
<213> ORGANISM: Artificial Sequence
<220> FEATURE:
<223> OTHER INFORMATION: TRL839 HC CDR1

<400> SEQUENCE: 171

Gly Phe Thr Phe Arg Thr Tyr Gly
1               5

<210> SEQ ID NO 172
<211> LENGTH: 8
<212> TYPE: PRT
<213> ORGANISM: Artificial Sequence
<220> FEATURE:
<223> OTHER INFORMATION: TRL839 HC CDR2

<400> SEQUENCE: 172

Ile Ser Tyr Asp Gly Thr Asn Lys
1               5

<210> SEQ ID NO 173
<211> LENGTH: 15
<212> TYPE: PRT
<213> ORGANISM: Artificial Sequence
<220> FEATURE:
<223> OTHER INFORMATION: TRL839 HC CDR3

-continued

<400> SEQUENCE: 173

Ala Ser Leu Asp Tyr Asp Phe Ser Tyr Tyr Tyr His Arg Asp Val
1               5                   10                  15

<210> SEQ ID NO 174
<211> LENGTH: 9
<212> TYPE: PRT
<213> ORGANISM: Artificial Sequence
<220> FEATURE:
<223> OTHER INFORMATION: TRL839 LC CDR1

<400> SEQUENCE: 174

Ser Ser Asp Val Gly Gly Tyr Asp Tyr
1               5

<210> SEQ ID NO 175
<211> LENGTH: 3
<212> TYPE: PRT
<213> ORGANISM: Artificial Sequence
<220> FEATURE:
<223> OTHER INFORMATION: TRL839 LC CDR2

<400> SEQUENCE: 175

Glu Val Arg
1

<210> SEQ ID NO 176
<211> LENGTH: 10
<212> TYPE: PRT
<213> ORGANISM: Artificial Sequence
<220> FEATURE:
<223> OTHER INFORMATION: TRL839 LC CDR3

<400> SEQUENCE: 176

Ala Ser Tyr Ala Gly Thr Tyr Ile His Leu
1               5                   10

<210> SEQ ID NO 177
<211> LENGTH: 452
<212> TYPE: PRT
<213> ORGANISM: Artificial Sequence
<220> FEATURE:
<223> OTHER INFORMATION: TRL839 HC

<400> SEQUENCE: 177

Gln Val Gln Leu Val Gln Ser Gly Gly Gly Val Val Gln Arg Gly Arg
1               5                   10                  15

Ser Leu Arg Leu Ser Cys Ala Ala Ser Gly Phe Thr Phe Arg Thr Tyr
            20                  25                  30

Gly Met His Trp Val Arg Gln Ala Pro Gly Lys Gly Leu Glu Cys Val
        35                  40                  45

Ala Leu Ile Ser Tyr Asp Gly Thr Asn Lys Tyr Ala Asp Ser Val
    50                  55                  60

Lys Gly Arg Phe Thr Ile Ser Arg Asp Asn Ser Lys Asp Thr Leu Tyr
65                  70                  75                  80

Leu Gln Met Asn Ser Leu Arg Ala Glu Asp Thr Gly Val Tyr Tyr Cys
                85                  90                  95

Ala Ser Leu Asp Tyr Asp Phe Ser Tyr Tyr Tyr His Arg Asp Val Trp
            100                 105                 110

Gly Pro Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Val Glu Pro Lys Ser
210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 178
<211> LENGTH: 216
<212> TYPE: PRT
<213> ORGANISM: Artificial Sequence
<220> FEATURE:
<223> OTHER INFORMATION: TRL839 LC

<400> SEQUENCE: 178

Asp Ile Val Leu Thr Gln Ser Pro Ser Ala Ser Gly Ser Pro Gly Gln
1               5                   10                  15

Ser Val Thr Ile Ser Cys Thr Gly Thr Ser Ser Asp Val Gly Gly Tyr
            20                  25                  30

```
Asp Tyr Val Ser Trp Tyr Gln Gln His Pro Gly Lys Ala Pro Lys Leu
            35                  40                  45

Met Ile Tyr Glu Val Arg Lys Arg Pro Ser Gly Val Pro Asp Arg Phe
 50                  55                  60

Ser Gly Ser Lys Ser Gly Asn Thr Ala Ser Leu Thr Val Ser Gly Leu
 65                  70                  75                  80

Gln Ala Glu Asp Glu Ala Tyr Tyr Cys Ala Ser Tyr Ala Gly Thr
                85                  90                  95

Tyr Ile His Leu Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
            115                 120                 125

Leu Gln Ala Asn Lys Ala Thr Leu Val Cys Leu Ile Ser Asp Phe Tyr
130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Val Pro Ala Glu Cys Ser
        210                 215

<210> SEQ ID NO 179
<211> LENGTH: 122
<212> TYPE: PRT
<213> ORGANISM: Artificial Sequence
<220> FEATURE:
<223> OTHER INFORMATION: TRL839 HCVR

<400> SEQUENCE: 179

Gln Val Gln Leu Val Gln Ser Gly Gly Gly Val Val Gln Arg Gly Arg
1               5                   10                  15

Ser Leu Arg Leu Ser Cys Ala Ala Ser Gly Phe Thr Phe Arg Thr Tyr
            20                  25                  30

Gly Met His Trp Val Arg Gln Ala Pro Gly Lys Gly Leu Glu Cys Val
        35                  40                  45

Ala Leu Ile Ser Tyr Asp Gly Thr Asn Lys Tyr Tyr Ala Asp Ser Val
 50                  55                  60

Lys Gly Arg Phe Thr Ile Ser Arg Asp Asn Ser Lys Asp Thr Leu Tyr
 65                  70                  75                  80

Leu Gln Met Asn Ser Leu Arg Ala Glu Asp Thr Gly Val Tyr Tyr Cys
                85                  90                  95

Ala Ser Leu Asp Tyr Asp Phe Ser Tyr Tyr Tyr His Arg Asp Val Trp
            100                 105                 110

Gly Pro Gly Thr Thr Val Thr Val Ser Ser
        115                 120

<210> SEQ ID NO 180
<211> LENGTH: 112
<212> TYPE: PRT
<213> ORGANISM: Artificial Sequence
<220> FEATURE:
<223> OTHER INFORMATION: TRL839 LCVR
```

-continued

<400> SEQUENCE: 180

Asp Ile Val Leu Thr Gln Ser Pro Ala Ser Gly Ser Pro Gly Gln
1               5                   10                  15

Ser Val Thr Ile Ser Cys Thr Gly Thr Ser Ser Asp Val Gly Gly Tyr
            20                  25                  30

Asp Tyr Val Ser Trp Tyr Gln Gln His Pro Gly Lys Ala Pro Lys Leu
        35                  40                  45

Met Ile Tyr Glu Val Arg Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Tyr Tyr Cys Ala Ser Tyr Ala Gly Thr
                85                  90                  95

Tyr Ile His Leu Phe Gly Gly Gly Thr Lys Leu Thr Val Leu Gly Gln
            100                 105                 110

<210> SEQ ID NO 181
<211> LENGTH: 8
<212> TYPE: PRT
<213> ORGANISM: Artificial Sequence
<220> FEATURE:
<223> OTHER INFORMATION: TRL841 HC CDR1

<400> SEQUENCE: 181

Gly Phe Thr Phe Ser Ser Tyr Gly
1               5

<210> SEQ ID NO 182
<211> LENGTH: 8
<212> TYPE: PRT
<213> ORGANISM: Artificial Sequence
<220> FEATURE:
<223> OTHER INFORMATION: TRL841 HC CDR2

<400> SEQUENCE: 182

Ile Ser Tyr Asp Glu Ile Asn Lys
1               5

<210> SEQ ID NO 183
<211> LENGTH: 13
<212> TYPE: PRT
<213> ORGANISM: Artificial Sequence
<220> FEATURE:
<223> OTHER INFORMATION: TRL841 HC CDR3

<400> SEQUENCE: 183

Ala Lys Pro Leu Arg Gly Ser Tyr Arg Tyr Phe Asp Leu
1               5                   10

<210> SEQ ID NO 184
<211> LENGTH: 6
<212> TYPE: PRT
<213> ORGANISM: Artificial Sequence
<220> FEATURE:
<223> OTHER INFORMATION: TRL841 LC CDR1

<400> SEQUENCE: 184

Gln Gly Leu Gly Ser Asn
1               5

```
<210> SEQ ID NO 185
<211> LENGTH: 3
<212> TYPE: PRT
<213> ORGANISM: Artificial Sequence
<220> FEATURE:
<223> OTHER INFORMATION: TRL841 LC CDR2

<400> SEQUENCE: 185

Ala Ala Ser
1

<210> SEQ ID NO 186
<211> LENGTH: 9
<212> TYPE: PRT
<213> ORGANISM: Artificial Sequence
<220> FEATURE:
<223> OTHER INFORMATION: TRL841 LC CDR3

<400> SEQUENCE: 186

Gln Gln Tyr Thr Tyr Trp Pro Leu Thr
1               5

<210> SEQ ID NO 187
<211> LENGTH: 450
<212> TYPE: PRT
<213> ORGANISM: Artificial Sequence
<220> FEATURE:
<223> OTHER INFORMATION: TRL841 HC

<400> SEQUENCE: 187

Gln Val Gln Leu Val Glu Ser Gly Gly Gly Val Val Gln Pro Gly Arg
1               5                  10                  15

Ser Leu Arg Leu Ser Cys Ala Ala Ser Gly Phe Thr Phe Ser Ser Tyr
                20                  25                  30

Gly Ile Tyr Trp Val Arg Gln Ala Pro Gly Lys Gly Leu Glu Trp Val
            35                  40                  45

Ala Phe Ile Ser Tyr Asp Glu Ile Asn Lys Phe Tyr Ala Asp Ser Val
        50                  55                  60

Lys Gly Arg Phe Thr Ile Ser Arg Asp Asn Ser Lys Asn Thr Val Phe
65                  70                  75                  80

Leu Gln Met Asn Ser Leu Arg Asp Glu Asp Thr Ala Val Tyr Tyr Cys
                85                  90                  95

Ala Lys Pro Leu Arg Gly Ser Tyr Arg Tyr Phe Asp Leu Trp Gly Arg
            100                 105                 110

Gly Thr Val Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240
```

Pro Ser Val Phe Leu Phe Pro Lys Pro Lys Asp Thr Leu Met Ile
            245                 250                 255

Ser Arg Thr Pro Glu Val Thr Cys Val Val Asp Val Ser His Glu
        260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly Lys
    450

<210> SEQ ID NO 188
<211> LENGTH: 214
<212> TYPE: PRT
<213> ORGANISM: Artificial Sequence
<220> FEATURE:
<223> OTHER INFORMATION: TRL841 LC

<400> SEQUENCE: 188

Asp Ile Val Met Thr Gln Pro Pro Ala Thr Leu Ser Val Ser Pro Gly
1               5                   10                  15

Glu Arg Ala Thr Leu Ser Cys Gly Ala Ser Gln Gly Leu Gly Ser Asn
            20                  25                  30

Leu Ala Trp Tyr Gln Gln Lys Pro Gly Gln Ala Pro Arg Leu Leu Ile
        35                  40                  45

Tyr Ala Ala Ser Thr Arg Ala Thr Gly Ile Thr Ala Arg Phe Ser Gly
    50                  55                  60

Ser Gly Ser Gly Thr Glu Phe Thr Leu Thr Ile Asn Ser Leu Gln Ser
65                  70                  75                  80

Glu Asp Phe Ala Leu Tyr Tyr Cys Gln Gln Tyr Thr Tyr Trp Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

```
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 189
<211> LENGTH: 120
<212> TYPE: PRT
<213> ORGANISM: Artificial Sequence
<220> FEATURE:
<223> OTHER INFORMATION: TRL841 HCVR

<400> SEQUENCE: 189

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Ile Tyr Trp Val Arg Gln Ala Pro Gly Lys Gly Leu Glu Trp Val
        35                  40                  45

Ala Phe Ile Ser Tyr Asp Glu Ile Asn Lys Phe Tyr Ala Asp Ser Val
    50                  55                  60

Lys Gly Arg Phe Thr Ile Ser Arg Asp Asn Lys Asn Thr Val Phe
65                  70                  75                  80

Leu Gln Met Asn Ser Leu Arg Asp Glu Asp Thr Ala Val Tyr Tyr Cys
                85                  90                  95

Ala Lys Pro Leu Arg Gly Ser Tyr Arg Tyr Phe Asp Leu Trp Gly Arg
            100                 105                 110

Gly Thr Val Val Thr Val Ser Ser
        115                 120
```

<210> SEQ ID NO 190
<211> LENGTH: 109
<212> TYPE: PRT
<213> ORGANISM: Artificial Sequence
<220> FEATURE:
<223> OTHER INFORMATION: TRL841 LCVR

<400> SEQUENCE: 190

```
Asp Ile Val Met Thr Gln Pro Pro Ala Thr Leu Ser Val Ser Pro Gly
1               5                   10                  15

Glu Arg Ala Thr Leu Ser Cys Gly Ala Ser Gln Gly Leu Gly Ser Asn
            20                  25                  30

Leu Ala Trp Tyr Gln Gln Lys Pro Gly Gln Ala Pro Arg Leu Leu Ile
        35                  40                  45

Tyr Ala Ala Ser Thr Arg Ala Thr Gly Ile Thr Ala Arg Phe Ser Gly
    50                  55                  60

Ser Gly Ser Gly Thr Glu Phe Thr Leu Thr Ile Asn Ser Leu Gln Ser
65                  70                  75                  80

Glu Asp Phe Ala Leu Tyr Tyr Cys Gln Gln Tyr Thr Tyr Trp Pro Leu
                85                  90                  95

Thr Phe Gly Gly Gly Thr Lys Val Glu Ile Lys Arg Thr
            100                 105
```

```
<210> SEQ ID NO 191
<211> LENGTH: 8
<212> TYPE: PRT
<213> ORGANISM: Artificial Sequence
<220> FEATURE:
<223> OTHER INFORMATION: TRL842 HC CDR1

<400> SEQUENCE: 191

Gly Phe Ser Leu Trp Thr Ser Gly
1               5

<210> SEQ ID NO 192
<211> LENGTH: 8
<212> TYPE: PRT
<213> ORGANISM: Artificial Sequence
<220> FEATURE:
<223> OTHER INFORMATION: TRL842 HC CDR2

<400> SEQUENCE: 192

Met Ser Tyr Asp Glu Thr Lys Lys
1               5

<210> SEQ ID NO 193
<211> LENGTH: 16
<212> TYPE: PRT
<213> ORGANISM: Artificial Sequence
<220> FEATURE:
<223> OTHER INFORMATION: TRL842 HC CDR3

<400> SEQUENCE: 193

Ala Lys Pro Arg Leu Asp Tyr Leu Asp Tyr Phe His Ala Ala Asp Ser
1               5                   10                  15

<210> SEQ ID NO 194
<211> LENGTH: 6
<212> TYPE: PRT
<213> ORGANISM: Artificial Sequence
<220> FEATURE:
<223> OTHER INFORMATION: TRL842 LC CDR1

<400> SEQUENCE: 194

Tyr Ile Gly Ser Lys Ser
1               5

<210> SEQ ID NO 195
<211> LENGTH: 3
<212> TYPE: PRT
<213> ORGANISM: Artificial Sequence
<220> FEATURE:
<223> OTHER INFORMATION: TRL842 LC CDR2

<400> SEQUENCE: 195

Asp Asp Ser
1

<210> SEQ ID NO 196
<211> LENGTH: 12
<212> TYPE: PRT
<213> ORGANISM: Artificial Sequence
<220> FEATURE:
<223> OTHER INFORMATION: TRL842 LC CDR3

<400> SEQUENCE: 196

Cys Gln Val Trp Glu Thr Ser Glu Asp Leu Trp Val
1               5                   10
```

-continued

```
<210> SEQ ID NO 197
<211> LENGTH: 453
<212> TYPE: PRT
<213> ORGANISM: Artificial Sequence
<220> FEATURE:
<223> OTHER INFORMATION: TRL842 HC

<400> SEQUENCE: 197

Gln Val Gln Leu Leu Glu Ser Gly Gly Asp Val Val Gln Pro Gly Thr
1               5                   10                  15

Ser Leu Arg Leu Ser Cys Ala Ala Ser Gly Phe Ser Leu Trp Thr Ser
            20                  25                  30

Gly Met His Trp Val Arg Gln Ala Pro Gly Lys Gly Leu Glu Trp Val
        35                  40                  45

Ala Val Met Ser Tyr Asp Glu Thr Lys Lys Tyr Tyr Ala Asp Ser Val
    50                  55                  60

Arg Gly Arg Phe Ser Ile Ser Arg Asp Asn Ser Arg Asn Thr Leu Tyr
65                  70                  75                  80

Leu Gln Met Asn Ser Leu Arg Val Glu Asp Thr Ala Val Tyr Phe Cys
                85                  90                  95

Ala Lys Pro Arg Leu Asp Tyr Leu Asp Tyr Phe His Ala Ala Asp Ser
            100                 105                 110

Trp Gly Gln Gly Thr Leu Val Ser Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365
```

```
Val Ser Leu Thr Cys Leu Val Lys Gly Phe Tyr Pro Ser Asp Ile Ala
            370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
            435                 440                 445

Leu Ser Pro Gly Lys
            450

<210> SEQ ID NO 198
<211> LENGTH: 217
<212> TYPE: PRT
<213> ORGANISM: Artificial Sequence
<220> FEATURE:
<223> OTHER INFORMATION: TRL842 LC

<400> SEQUENCE: 198

Asp Ile Val Leu Thr Gln Pro Pro Ser Val Ser Val Ala Pro Gly Gln
1               5                   10                  15

Thr Ala Thr Ile Thr Cys Gly Gly Asn Tyr Ile Gly Ser Lys Ser Val
            20                  25                  30

Asn Trp Tyr Gln Gln Arg Pro Gly His Ala Pro Val Leu Val Val Tyr
            35                  40                  45

Asp Asp Ser Asp Arg Pro Ser Gly Ile Pro Asp Arg Phe Ser Gly Ser
50                  55                  60

Asn Ser Arg Ser Thr Ala Thr Thr Ala Thr Leu Thr Ile Ser Arg Val
65                  70                  75                  80

Glu Ala Gly Asp Glu Ala Asp Tyr Tyr Cys Gln Val Trp Glu Thr Ser
            85                  90                  95

Glu Asp Leu Trp Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
            115                 120                 125

Glu Leu Gln Ala Asn Lys Ala Thr Leu Val Cys Leu Ile Ser Asp Phe
130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
            195                 200                 205

Lys Thr Val Val Pro Ala Glu Cys Ser
        210                 215

<210> SEQ ID NO 199
<211> LENGTH: 123
<212> TYPE: PRT
<213> ORGANISM: Artificial Sequence
<220> FEATURE:
<223> OTHER INFORMATION: TRL842 HCVR
```

<400> SEQUENCE: 199

Gln Val Gln Leu Leu Glu Ser Gly Gly Asp Val Val Gln Pro Gly Thr
1               5                   10                  15

Ser Leu Arg Leu Ser Cys Ala Ala Ser Gly Phe Ser Leu Trp Thr Ser
            20                  25                  30

Gly Met His Trp Val Arg Gln Ala Pro Gly Lys Gly Leu Glu Trp Val
        35                  40                  45

Ala Val Met Ser Tyr Asp Glu Thr Lys Lys Tyr Ala Asp Ser Val
    50                  55                  60

Arg Gly Arg Phe Ser Ile Ser Arg Asp Asn Ser Arg Asn Thr Leu Tyr
65                  70                  75                  80

Leu Gln Met Asn Ser Leu Arg Val Glu Asp Thr Ala Val Tyr Phe Cys
                85                  90                  95

Ala Lys Pro Arg Leu Asp Tyr Leu Asp Tyr Phe His Ala Ala Asp Ser
            100                 105                 110

Trp Gly Gln Gly Thr Leu Val Ser Val Ser Ser
        115                 120

<210> SEQ ID NO 200
<211> LENGTH: 113
<212> TYPE: PRT
<213> ORGANISM: Artificial Sequence
<220> FEATURE:
<223> OTHER INFORMATION: TRL842 LCVR

<400> SEQUENCE: 200

Asp Ile Val Leu Thr Gln Pro Pro Ser Val Ser Val Ala Pro Gly Gln
1               5                   10                  15

Thr Ala Thr Ile Thr Cys Gly Gly Asn Tyr Ile Gly Ser Lys Ser Val
            20                  25                  30

Asn Trp Tyr Gln Gln Arg Pro Gly His Ala Pro Val Leu Val Val Tyr
        35                  40                  45

Asp Asp Ser Asp Arg Pro Ser Gly Ile Pro Asp Arg Phe Ser Gly Ser
    50                  55                  60

Asn Ser Arg Ser Thr Ala Thr Thr Ala Thr Leu Thr Ile Ser Arg Val
65                  70                  75                  80

Glu Ala Gly Asp Glu Ala Asp Tyr Tyr Cys Gln Val Trp Glu Thr Ser
                85                  90                  95

Glu Asp Leu Trp Val Phe Gly Gly Gly Thr Lys Leu Thr Val Leu Gly
            100                 105                 110

Gln

<210> SEQ ID NO 201
<211> LENGTH: 8
<212> TYPE: PRT
<213> ORGANISM: Artificial Sequence
<220> FEATURE:
<223> OTHER INFORMATION: TRL845 HC CDR1

<400> SEQUENCE: 201

Gly Phe Thr Phe Ser Arg Tyr Ser
1               5

<210> SEQ ID NO 202
<211> LENGTH: 8
<212> TYPE: PRT
<213> ORGANISM: Artificial Sequence
<220> FEATURE:
<223> OTHER INFORMATION: TRL845 HC CDR2

```
<400> SEQUENCE: 202

Ile Ser Asp Thr Ser Arg Thr Ile
1               5

<210> SEQ ID NO 203
<211> LENGTH: 14
<212> TYPE: PRT
<213> ORGANISM: Artificial Sequence
<220> FEATURE:
<223> OTHER INFORMATION: TRL845 HC CDR3

<400> SEQUENCE: 203

Ala Arg Asp Pro Asp Thr Pro Phe Val Arg Ala Phe Asp Ser
1               5                   10

<210> SEQ ID NO 204
<211> LENGTH: 6
<212> TYPE: PRT
<213> ORGANISM: Artificial Sequence
<220> FEATURE:
<223> OTHER INFORMATION: TRL845 LC CDR1

<400> SEQUENCE: 204

Gln Leu Ile Ser Ser Tyr
1               5

<210> SEQ ID NO 205
<211> LENGTH: 3
<212> TYPE: PRT
<213> ORGANISM: Artificial Sequence
<220> FEATURE:
<223> OTHER INFORMATION: TRL845 LC CDR2

<400> SEQUENCE: 205

Ala Ala Ser
1

<210> SEQ ID NO 206
<211> LENGTH: 10
<212> TYPE: PRT
<213> ORGANISM: Artificial Sequence
<220> FEATURE:
<223> OTHER INFORMATION: TRL845 LC CDR3

<400> SEQUENCE: 206

Gln Gln Leu Asn Ser Tyr Pro Pro Ile Thr
1               5                   10

<210> SEQ ID NO 207
<211> LENGTH: 451
<212> TYPE: PRT
<213> ORGANISM: Artificial Sequence
<220> FEATURE:
<223> OTHER INFORMATION: TRL845 HC

<400> SEQUENCE: 207

Gln Val Gln Leu Val Gln Ser Gly Gly Asp Leu Val Gln Pro Gly Gly
1               5                   10                  15

Ser Leu Arg Leu Ser Cys Ala Ala Ser Gly Phe Thr Phe Ser Arg Tyr
            20                  25                  30

Ser Met Asn Trp Val Arg Gln Ala Pro Gly Met Gly Leu Glu Trp Val
        35                  40                  45

Ala Tyr Ile Ser Asp Thr Ser Arg Thr Ile Tyr Tyr Ala Asp Ser Val
    50                  55                  60
```

```
Lys Gly Arg Phe Thr Ile Ser Arg Asp Asn Ala Lys Asn Ser Leu Tyr
 65                  70                  75                  80

Leu Gln Met Lys Ser Leu Arg Asp Glu Asp Thr Ala Val Tyr Tyr Cys
             85                  90                  95

Ala Arg Asp Pro Asp Thr Pro Phe Val Arg Ala Phe Asp Ser Trp Gly
            100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
            130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
450
```

```
<210> SEQ ID NO 208
<211> LENGTH: 215
<212> TYPE: PRT
<213> ORGANISM: Artificial Sequence
<220> FEATURE:
<223> OTHER INFORMATION: TRL845 LC

<400> SEQUENCE: 208

Asp Ile Val Leu Thr Gln Ser Pro Ser Phe Leu Ser Ala Ser Val Gly
1               5                   10                  15

Asp Arg Val Thr Ile Thr Cys Arg Ala Ser Gln Leu Ile Ser Ser Tyr
            20                  25                  30

Phe Ala Trp Tyr Gln Gln Lys Pro Gly Lys Pro Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Gln Phe Ser Leu Thr Ile Ser Ser Leu Gln Pro
65                  70                  75                  80

Glu Asp Phe Ala Thr Tyr Tyr Cys Gln Gln Leu Asn Ser Tyr Pro Pro
                85                  90                  95

Ile Thr Phe Gly Gln Gly Thr Arg Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 209
<211> LENGTH: 121
<212> TYPE: PRT
<213> ORGANISM: Artificial Sequence
<220> FEATURE:
<223> OTHER INFORMATION: TRL845 HCVR

<400> SEQUENCE: 209

Gln Val Gln Leu Val Gln Ser Gly Gly Asp Leu Val Gln Pro Gly Gly
1               5                   10                  15

Ser Leu Arg Leu Ser Cys Ala Ala Ser Gly Phe Thr Phe Ser Arg Tyr
            20                  25                  30

Ser Met Asn Trp Val Arg Gln Ala Pro Gly Met Gly Leu Glu Trp Val
        35                  40                  45

Ala Tyr Ile Ser Asp Thr Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Lys Ser Leu Arg Asp Glu Asp Thr Ala Val Tyr Tyr Cys
                85                  90                  95
```

Ala Arg Asp Pro Asp Thr Pro Phe Val Arg Ala Phe Asp Ser Trp Gly
            100                 105                 110
Gln Gly Thr Leu Val Thr Val Ser Ser
        115                 120

<210> SEQ ID NO 210
<211> LENGTH: 110
<212> TYPE: PRT
<213> ORGANISM: Artificial Sequence
<220> FEATURE:
<223> OTHER INFORMATION: TRL845 LCVR

<400> SEQUENCE: 210

Asp Ile Val Leu Thr Gln Ser Pro Ser Phe Leu Ser Ala Ser Val Gly
1               5                   10                  15
Asp Arg Val Thr Ile Thr Cys Arg Ala Ser Gln Leu Ile Ser Ser Tyr
            20                  25                  30
Phe Ala Trp Tyr Gln Gln Lys Pro Gly Lys Pro Pro Lys Leu Leu Ile
        35                  40                  45
Tyr Ala Ala Ser Thr Leu Gln Ser Gly Val Pro Ser Arg Phe Ser Gly
    50                  55                  60
Ser Gly Ser Gly Thr Gln Phe Ser Leu Thr Ile Ser Ser Leu Gln Pro
65                  70                  75                  80
Glu Asp Phe Ala Thr Tyr Tyr Cys Gln Gln Leu Asn Ser Tyr Pro Pro
                85                  90                  95
Ile Thr Phe Gly Gln Gly Thr Arg Leu Glu Ile Lys Arg Thr
            100                 105                 110

<210> SEQ ID NO 211
<211> LENGTH: 8
<212> TYPE: PRT
<213> ORGANISM: Artificial Sequence
<220> FEATURE:
<223> OTHER INFORMATION: TRL846 HC CDR1

<400> SEQUENCE: 211

Gly Phe Thr Phe Asn Ser Tyr Ala
1               5

<210> SEQ ID NO 212
<211> LENGTH: 8
<212> TYPE: PRT
<213> ORGANISM: Artificial Sequence
<220> FEATURE:
<223> OTHER INFORMATION: TRL846 HC CDR2

<400> SEQUENCE: 212

Ile Arg Gly Ser Gly Glu Asn Thr
1               5

<210> SEQ ID NO 213
<211> LENGTH: 22
<212> TYPE: PRT
<213> ORGANISM: Artificial Sequence
<220> FEATURE:
<223> OTHER INFORMATION: TRL846 HC CDR3

<400> SEQUENCE: 213

Ala Arg Lys Trp Gly Arg Met Thr Val Phe Gly Val Ala Thr Asp Gln
1               5                   10                  15
Leu Tyr Tyr Phe Asp Tyr
            20

```
<210> SEQ ID NO 214
<211> LENGTH: 6
<212> TYPE: PRT
<213> ORGANISM: Artificial Sequence
<220> FEATURE:
<223> OTHER INFORMATION: TRL846 LC CDR1

<400> SEQUENCE: 214

Gln Ser Val Ser Ser Asn
1               5

<210> SEQ ID NO 215
<211> LENGTH: 3
<212> TYPE: PRT
<213> ORGANISM: Artificial Sequence
<220> FEATURE:
<223> OTHER INFORMATION: TRL846 LC CDR2

<400> SEQUENCE: 215

Gly Ala Ser
1

<210> SEQ ID NO 216
<211> LENGTH: 10
<212> TYPE: PRT
<213> ORGANISM: Artificial Sequence
<220> FEATURE:
<223> OTHER INFORMATION: TRL846 LC CDR3

<400> SEQUENCE: 216

Gln Gln Phe Asn Asp Trp Pro Phe Leu Thr
1               5                   10

<210> SEQ ID NO 217
<211> LENGTH: 459
<212> TYPE: PRT
<213> ORGANISM: Artificial Sequence
<220> FEATURE:
<223> OTHER INFORMATION: TRL846 HC

<400> SEQUENCE: 217

Gln Val Gln Leu Val Glu Ser Gly Gly Gly Leu Val Gln Pro Gly Gly
1               5                   10                  15

Ser Leu Arg Leu Ser Cys Thr Val Ser Gly Phe Thr Phe Asn Ser Tyr
            20                  25                  30

Ala Met Asn Trp Val Arg Gln Ala Pro Gly Lys Gly Leu Glu Trp Val
        35                  40                  45

Ser Gly Ile Arg Gly Ser Gly Glu Asn Thr Tyr Tyr Ala Glu Thr Val
    50                  55                  60

Lys Gly Arg Phe Thr Ile Ser Arg Asp Asn Ser Lys Asn Thr Leu Tyr
65                  70                  75                  80

Leu Glu Met Asn Ser Leu Arg Ala Glu Asp Thr Ala Val Tyr Tyr Cys
                85                  90                  95

Ala Arg Lys Trp Gly Arg Met Thr Val Phe Gly Val Ala Thr Asp Gln
            100                 105                 110

Leu Tyr Tyr Phe Asp Tyr Trp Gly Gln Gly Thr Leu Val Thr Val Ser
        115                 120                 125

Ser Ala Ser Thr Lys Gly Pro Ser Val Phe Pro Leu Ala Pro Ser Ser
    130                 135                 140

Lys Ser Thr Ser Gly Gly Thr Ala Ala Leu Gly Cys Leu Val Lys Asp
145                 150                 155                 160
```

Tyr Phe Pro Glu Pro Val Thr Val Ser Trp Asn Ser Gly Ala Leu Thr
                165                 170                 175

Ser Gly Val His Thr Phe Pro Ala Val Leu Gln Ser Ser Gly Leu Tyr
            180                 185                 190

Ser Leu Ser Ser Val Val Thr Val Pro Ser Ser Ser Leu Gly Thr Gln
        195                 200                 205

Thr Tyr Ile Cys Asn Val Asn His Lys Pro Ser Asn Thr Lys Val Asp
    210                 215                 220

Lys Lys Val Glu Pro Lys Ser Cys Asp Lys Thr His Thr Cys Pro Pro
225                 230                 235                 240

Cys Pro Ala Pro Glu Leu Leu Gly Gly Pro Ser Val Phe Leu Phe Pro
                245                 250                 255

Pro Lys Pro Lys Asp Thr Leu Met Ile Ser Arg Thr Pro Glu Val Thr
            260                 265                 270

Cys Val Val Val Asp Val Ser His Glu Asp Pro Glu Val Lys Phe Asn
        275                 280                 285

Trp Tyr Val Asp Gly Val Glu Val His Asn Ala Lys Thr Lys Pro Arg
    290                 295                 300

Glu Glu Gln Tyr Asn Ser Thr Tyr Arg Val Val Ser Val Leu Thr Val
305                 310                 315                 320

Leu His Gln Asp Trp Leu Asn Gly Lys Glu Tyr Lys Cys Lys Val Ser
                325                 330                 335

Asn Lys Ala Leu Pro Ala Pro Ile Glu Lys Thr Ile Ser Lys Ala Lys
            340                 345                 350

Gly Gln Pro Arg Glu Pro Gln Val Tyr Thr Leu Pro Pro Ser Arg Asp
        355                 360                 365

Glu Leu Thr Lys Asn Gln Val Ser Leu Thr Cys Leu Val Lys Gly Phe
    370                 375                 380

Tyr Pro Ser Asp Ile Ala Val Glu Trp Glu Ser Asn Gly Gln Pro Glu
385                 390                 395                 400

Asn Asn Tyr Lys Thr Thr Pro Pro Val Leu Asp Ser Asp Gly Ser Phe
                405                 410                 415

Phe Leu Tyr Ser Lys Leu Thr Val Asp Lys Ser Arg Trp Gln Gln Gly
            420                 425                 430

Asn Val Phe Ser Cys Ser Val Met His Glu Ala Leu His Asn His Tyr
        435                 440                 445

Thr Gln Lys Ser Leu Ser Leu Ser Pro Gly Lys
    450                 455

<210> SEQ ID NO 218
<211> LENGTH: 215
<212> TYPE: PRT
<213> ORGANISM: Artificial Sequence
<220> FEATURE:
<223> OTHER INFORMATION: TRL846 LC

<400> SEQUENCE: 218

Asp Ile Thr Leu Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Asn Arg Ala Thr Asp Ile Pro Ala Arg Phe Ser Gly
    50                  55                  60

```
Ser Gly Ser Gly Thr Glu Phe Thr Leu Thr Ile Ser Ser Leu Gln Ser
 65                  70                  75                  80

Glu Asp Phe Ala Val Tyr Tyr Cys Gln Gln Phe Asn Asp Trp Pro Phe
                 85                  90                  95

Leu Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 219
<211> LENGTH: 129
<212> TYPE: PRT
<213> ORGANISM: Artificial Sequence
<220> FEATURE:
<223> OTHER INFORMATION: TRL846 HCVR

<400> SEQUENCE: 219

Gln Val Gln Leu Val Glu Ser Gly Gly Gly Leu Val Gln Pro Gly Gly
 1               5                  10                  15

Ser Leu Arg Leu Ser Cys Thr Val Ser Gly Phe Thr Phe Asn Ser Tyr
            20                  25                  30

Ala Met Asn Trp Val Arg Gln Ala Pro Gly Lys Gly Leu Glu Trp Val
        35                  40                  45

Ser Gly Ile Arg Gly Ser Gly Glu Asn Thr Tyr Tyr Ala Glu Thr Val
    50                  55                  60

Lys Gly Arg Phe Thr Ile Ser Arg Asp Asn Ser Lys Asn Thr Leu Tyr
 65                  70                  75                  80

Leu Glu Met Asn Ser Leu Arg Ala Glu Asp Thr Ala Val Tyr Tyr Cys
                 85                  90                  95

Ala Arg Lys Trp Gly Arg Met Thr Val Phe Gly Val Ala Thr Asp Gln
            100                 105                 110

Leu Tyr Tyr Phe Asp Tyr Trp Gly Gln Gly Thr Leu Val Thr Val Ser
        115                 120                 125

Ser

<210> SEQ ID NO 220
<211> LENGTH: 110
<212> TYPE: PRT
<213> ORGANISM: Artificial Sequence
<220> FEATURE:
<223> OTHER INFORMATION: TRL846 LCVR
```

<400> SEQUENCE: 220

Asp Ile Thr Leu Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Asn Arg Ala Thr Asp Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Phe Asn Asp Trp Pro Phe
                85                  90                  95

Leu Thr Phe Gly Gly Gly Thr Lys Val Glu Ile Lys Arg Thr
            100                 105                 110

<210> SEQ ID NO 221
<211> LENGTH: 8
<212> TYPE: PRT
<213> ORGANISM: Artificial Sequence
<220> FEATURE:
<223> OTHER INFORMATION: TRL847 HC CDR1

<400> SEQUENCE: 221

Gly Phe Thr Phe Ser Arg Phe Ser
1               5

<210> SEQ ID NO 222
<211> LENGTH: 8
<212> TYPE: PRT
<213> ORGANISM: Artificial Sequence
<220> FEATURE:
<223> OTHER INFORMATION: TRL847 HC CDR2

<400> SEQUENCE: 222

Ile Ser Asp Thr Gly Arg Thr Ile
1               5

<210> SEQ ID NO 223
<211> LENGTH: 14
<212> TYPE: PRT
<213> ORGANISM: Artificial Sequence
<220> FEATURE:
<223> OTHER INFORMATION: TRL847 HC CDR3

<400> SEQUENCE: 223

Ala Arg Asp Pro Asp Thr Pro Phe Val Arg Ala Phe Asp Ser
1               5                   10

<210> SEQ ID NO 224
<211> LENGTH: 6
<212> TYPE: PRT
<213> ORGANISM: Artificial Sequence
<220> FEATURE:
<223> OTHER INFORMATION: TRL847 LC CDR1

<400> SEQUENCE: 224

Gln Val Ile Ser Ser Tyr
1               5

-continued

```
<210> SEQ ID NO 225
<211> LENGTH: 3
<212> TYPE: PRT
<213> ORGANISM: Artificial Sequence
<220> FEATURE:
<223> OTHER INFORMATION: TRL847 LC CDR2

<400> SEQUENCE: 225

Ala Ala Ser
1

<210> SEQ ID NO 226
<211> LENGTH: 10
<212> TYPE: PRT
<213> ORGANISM: Artificial Sequence
<220> FEATURE:
<223> OTHER INFORMATION: TRL847 LC CDR3

<400> SEQUENCE: 226

Gln Gln Leu Thr Thr Tyr Pro Pro Ile Thr
1               5                   10

<210> SEQ ID NO 227
<211> LENGTH: 451
<212> TYPE: PRT
<213> ORGANISM: Artificial Sequence
<220> FEATURE:
<223> OTHER INFORMATION: TRL847 HC

<400> SEQUENCE: 227

Gln Val Gln Leu Val Glu Ser Gly Gly Gly Leu Val Gln Pro Gly Gly
1               5                   10                  15

Ser Leu Arg Leu Ser Cys Val Ala Ser Gly Phe Thr Phe Ser Arg Phe
            20                  25                  30

Ser Met Asn Trp Val Arg Gln Ala Pro Gly Met Gly Leu Glu Trp Val
        35                  40                  45

Ser Tyr Ile Ser Asp Thr Gly Arg Thr Ile Tyr Tyr Ala Asp Ser Val
    50                  55                  60

Lys Gly Arg Phe Thr Ile Ser Arg Asp Asn Asp Lys Asn Thr Leu Tyr
65                  70                  75                  80

Leu Gln Met Lys Ser Leu Arg Asp Glu Asp Ser Ala Phe Tyr Tyr Cys
                85                  90                  95

Ala Arg Asp Pro Asp Thr Pro Phe Val Arg Ala Phe Asp Ser Trp Gly
            100                 105                 110

Gln Gly Val Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
    210                 215                 220

Asp Lys Thr His Thr Cys Pro Pro Cys Pro Ala Pro Glu Leu Leu Gly
225                 230                 235                 240
```

```
Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
            290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
            325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450

<210> SEQ ID NO 228
<211> LENGTH: 215
<212> TYPE: PRT
<213> ORGANISM: Artificial Sequence
<220> FEATURE:
<223> OTHER INFORMATION: TRL847 LC

<400> SEQUENCE: 228

Asp Ile Val Met Thr Gln Ser Pro Ser Phe Leu Ser Ala Ser Val Gly
1               5                   10                  15

Asp Arg Val Thr Ile Thr Cys Arg Thr Ser Gln Val Ile Ser Ser Tyr
            20                  25                  30

Leu Ala Trp Tyr Gln Gln Arg Pro Gly Lys Ala Pro Lys Leu Leu Ile
            35                  40                  45

Tyr Ala Ala Ser Thr Leu Gln Ser Gly Val Pro Ser Arg Phe Ser Gly
        50                  55                  60

Ser Gly Ser Gly Thr Arg Phe Ser Leu Thr Ile Ser Asn Leu Gln Pro
65                  70                  75                  80

Glu Asp Phe Ala Thr Tyr Phe Cys Gln Gln Leu Thr Tyr Pro Pro
            85                  90                  95

Ile Thr Phe Gly Gln Gly Thr Arg Leu Glu Ile Lys Arg Thr Val Ala
            100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
            130                 135                 140
```

```
Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
            165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 229
<211> LENGTH: 121
<212> TYPE: PRT
<213> ORGANISM: Artificial Sequence
<220> FEATURE:
<223> OTHER INFORMATION: TRL847 HCVR

<400> SEQUENCE: 229

Gln Val Gln Leu Val Glu Ser Gly Gly Gly Leu Val Gln Pro Gly Gly
1               5                   10                  15

Ser Leu Arg Leu Ser Cys Val Ala Ser Gly Phe Thr Phe Ser Arg Phe
            20                  25                  30

Ser Met Asn Trp Val Arg Gln Ala Pro Gly Met Gly Leu Glu Trp Val
        35                  40                  45

Ser Tyr Ile Ser Asp Thr Gly Arg Thr Ile Tyr Tyr Ala Asp Ser Val
    50                  55                  60

Lys Gly Arg Phe Thr Ile Ser Arg Asp Asn Lys Asn Thr Leu Tyr
65                  70                  75                  80

Leu Gln Met Lys Ser Leu Arg Asp Glu Asp Ser Ala Phe Tyr Tyr Cys
                85                  90                  95

Ala Arg Asp Pro Asp Thr Pro Phe Val Arg Ala Phe Asp Ser Trp Gly
            100                 105                 110

Gln Gly Val Leu Val Thr Val Ser Ser
        115                 120

<210> SEQ ID NO 230
<211> LENGTH: 110
<212> TYPE: PRT
<213> ORGANISM: Artificial Sequence
<220> FEATURE:
<223> OTHER INFORMATION: TRL847 LCVR

<400> SEQUENCE: 230

Asp Ile Val Met Thr Gln Ser Pro Ser Phe Leu Ser Ala Ser Val Gly
1               5                   10                  15

Asp Arg Val Thr Ile Thr Cys Arg Thr Ser Gln Val Ile Ser Ser Tyr
            20                  25                  30

Leu Ala Trp Tyr Gln Gln Arg Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Arg Phe Ser Leu Thr Ile Ser Asn Leu Gln Pro
65                  70                  75                  80

Glu Asp Phe Ala Thr Tyr Phe Cys Gln Gln Leu Thr Thr Tyr Pro Pro
                85                  90                  95

Ile Thr Phe Gly Gln Gly Thr Arg Leu Glu Ile Lys Arg Thr
            100                 105                 110
```

```
<210> SEQ ID NO 231
<211> LENGTH: 8
<212> TYPE: PRT
<213> ORGANISM: Artificial Sequence
<220> FEATURE:
<223> OTHER INFORMATION: TRL848 HC CDR1

<400> SEQUENCE: 231

Gly Phe Ser Leu Trp Thr Ser Gly
1               5

<210> SEQ ID NO 232
<211> LENGTH: 8
<212> TYPE: PRT
<213> ORGANISM: Artificial Sequence
<220> FEATURE:
<223> OTHER INFORMATION: TRL848 HC CDR2

<400> SEQUENCE: 232

Met Ser Tyr Asp Glu Thr Lys Lys
1               5

<210> SEQ ID NO 233
<211> LENGTH: 16
<212> TYPE: PRT
<213> ORGANISM: Artificial Sequence
<220> FEATURE:
<223> OTHER INFORMATION: TRL848 HC CDR3

<400> SEQUENCE: 233

Ala Lys Pro Arg Leu Asp Tyr Leu Asp Tyr Phe His Ala Ala Asp Ser
1               5                   10                  15

<210> SEQ ID NO 234
<211> LENGTH: 6
<212> TYPE: PRT
<213> ORGANISM: Artificial Sequence
<220> FEATURE:
<223> OTHER INFORMATION: TRL848 LC CDR1

<400> SEQUENCE: 234

Tyr Ile Gly Ser Lys Ser
1               5

<210> SEQ ID NO 235
<211> LENGTH: 3
<212> TYPE: PRT
<213> ORGANISM: Artificial Sequence
<220> FEATURE:
<223> OTHER INFORMATION: TRL848 LC CDR2

<400> SEQUENCE: 235

Asp Asp Ser
1

<210> SEQ ID NO 236
<211> LENGTH: 12
<212> TYPE: PRT
<213> ORGANISM: Artificial Sequence
<220> FEATURE:
<223> OTHER INFORMATION: TRL848 LC CDR3

<400> SEQUENCE: 236

Cys Gln Val Trp Glu Thr Ser Glu Asp Leu Trp Val
1               5                   10
```

```
<210> SEQ ID NO 237
<211> LENGTH: 453
<212> TYPE: PRT
<213> ORGANISM: Artificial Sequence
<220> FEATURE:
<223> OTHER INFORMATION: TRL848 HC

<400> SEQUENCE: 237

Gln Val Gln Leu Leu Glu Ser Gly Gly Asp Val Val Gln Pro Gly Thr
1               5                   10                  15

Ser Leu Arg Leu Ser Cys Ala Ala Ser Gly Phe Ser Leu Trp Thr Ser
            20                  25                  30

Gly Met His Trp Val Arg Gln Ala Pro Gly Lys Gly Leu Glu Trp Val
        35                  40                  45

Ala Val Met Ser Tyr Asp Glu Thr Lys Lys Tyr Tyr Ala Asp Ser Val
    50                  55                  60

Arg Gly Arg Phe Ser Ile Ser Arg Asp Asn Ser Arg Asn Thr Leu Tyr
65                  70                  75                  80

Leu Gln Met Asn Ser Leu Arg Val Glu Asp Thr Ala Val Tyr Phe Cys
                85                  90                  95

Ala Lys Pro Arg Leu Asp Tyr Leu Asp Tyr Phe His Ala Ala Asp Ser
            100                 105                 110

Trp Gly Gln Gly Thr Leu Val Ser Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365
```

-continued

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
        450

<210> SEQ ID NO 238
<211> LENGTH: 217
<212> TYPE: PRT
<213> ORGANISM: Artificial Sequence
<220> FEATURE:
<223> OTHER INFORMATION: TRL848 LC

<400> SEQUENCE: 238

Asp Ile Val Leu Thr Gln Pro Pro Ser Val Ser Val Ala Pro Gly Gln
1               5                   10                  15

Thr Ala Thr Ile Thr Cys Gly Gly Asn Tyr Ile Gly Ser Lys Ser Val
            20                  25                  30

Asn Trp Tyr Gln Gln Arg Pro Gly His Ala Pro Val Leu Val Val Tyr
        35                  40                  45

Asp Asp Ser Asp Arg Pro Ser Gly Ile Pro Asp Arg Phe Ser Gly Ser
    50                  55                  60

Asn Ser Arg Ser Thr Ala Thr Thr Ala Thr Leu Thr Ile Ser Arg Val
65                  70                  75                  80

Glu Ala Gly Asp Glu Ala Asp Tyr Tyr Cys Gln Val Trp Glu Thr Ser
                85                  90                  95

Glu Asp Leu Trp Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Val Pro Ala Glu Cys Ser
    210                 215

<210> SEQ ID NO 239
<211> LENGTH: 123
<212> TYPE: PRT
<213> ORGANISM: Artificial Sequence
<220> FEATURE:
<223> OTHER INFORMATION: TRL848 HCVR -continued

<400> SEQUENCE: 239

Gln Val Gln Leu Leu Glu Ser Gly Gly Asp Val Val Gln Pro Gly Thr
1               5                   10                  15
Ser Leu Arg Leu Ser Cys Ala Ala Ser Gly Phe Ser Leu Trp Thr Ser
            20                  25                  30
Gly Met His Trp Val Arg Gln Ala Pro Gly Lys Gly Leu Glu Trp Val
        35                  40                  45
Ala Val Met Ser Tyr Asp Glu Thr Lys Lys Tyr Tyr Ala Asp Ser Val
    50                  55                  60
Arg Gly Arg Phe Ser Ile Ser Arg Asp Asn Ser Arg Asn Thr Leu Tyr
65                  70                  75                  80
Leu Gln Met Asn Ser Leu Arg Val Glu Asp Thr Ala Val Tyr Phe Cys
                85                  90                  95
Ala Lys Pro Arg Leu Asp Tyr Leu Asp Tyr Phe His Ala Ala Asp Ser
            100                 105                 110
Trp Gly Gln Gly Thr Leu Val Ser Val Ser Ser
        115                 120

<210> SEQ ID NO 240
<211> LENGTH: 113
<212> TYPE: PRT
<213> ORGANISM: Artificial Sequence
<220> FEATURE:
<223> OTHER INFORMATION: TRL848 LCVR

<400> SEQUENCE: 240

Asp Ile Val Leu Thr Gln Pro Pro Ser Val Ser Val Ala Pro Gly Gln
1               5                   10                  15
Thr Ala Thr Ile Thr Cys Gly Gly Asn Tyr Ile Gly Ser Lys Ser Val
            20                  25                  30
Asn Trp Tyr Gln Gln Arg Pro Gly His Ala Pro Val Leu Val Val Tyr
        35                  40                  45
Asp Asp Ser Asp Arg Pro Ser Gly Ile Pro Asp Arg Phe Ser Gly Ser
    50                  55                  60
Asn Ser Arg Ser Thr Ala Thr Thr Ala Thr Leu Thr Ile Ser Arg Val
65                  70                  75                  80
Glu Ala Gly Asp Glu Ala Asp Tyr Tyr Cys Gln Val Trp Glu Thr Ser
                85                  90                  95
Glu Asp Leu Trp Val Phe Gly Gly Gly Thr Lys Leu Thr Val Leu Gly
            100                 105                 110
Gln

<210> SEQ ID NO 241
<211> LENGTH: 10
<212> TYPE: PRT
<213> ORGANISM: Artificial Sequence
<220> FEATURE:
<223> OTHER INFORMATION: TRL849 HC CDR1

<400> SEQUENCE: 241

Gly Gly Ser Ile Ser Asn Gly Gly Tyr His
1               5                   10

<210> SEQ ID NO 242
<211> LENGTH: 7
<212> TYPE: PRT
<213> ORGANISM: Artificial Sequence
<220> FEATURE:
<223> OTHER INFORMATION: TRL849 HC CDR2

```
<400> SEQUENCE: 242

Ile Tyr Tyr Arg Gly Ser Thr
1               5

<210> SEQ ID NO 243
<211> LENGTH: 21
<212> TYPE: PRT
<213> ORGANISM: Artificial Sequence
<220> FEATURE:
<223> OTHER INFORMATION: TRL849 HC CDR3

<400> SEQUENCE: 243

Ala Arg Met Pro Leu Ala Asn Tyr Asp Leu Leu Thr Gly Leu Tyr Ile
1               5                   10                  15

Gly Ala Phe Asp Leu
            20

<210> SEQ ID NO 244
<211> LENGTH: 6
<212> TYPE: PRT
<213> ORGANISM: Artificial Sequence
<220> FEATURE:
<223> OTHER INFORMATION: TRL849 LC CDR1

<400> SEQUENCE: 244

Gln Ser Val Asn Arg Asn
1               5

<210> SEQ ID NO 245
<211> LENGTH: 3
<212> TYPE: PRT
<213> ORGANISM: Artificial Sequence
<220> FEATURE:
<223> OTHER INFORMATION: TRL849 LC CDR2

<400> SEQUENCE: 245

Asp Ala Ser
1

<210> SEQ ID NO 246
<211> LENGTH: 9
<212> TYPE: PRT
<213> ORGANISM: Artificial Sequence
<220> FEATURE:
<223> OTHER INFORMATION: TRL849 LC CDR3

<400> SEQUENCE: 246

Gln Gln Tyr Asp Lys Trp Pro Pro Gly
1               5

<210> SEQ ID NO 247
<211> LENGTH: 459
<212> TYPE: PRT
<213> ORGANISM: Artificial Sequence
<220> FEATURE:
<223> OTHER INFORMATION: TRL849 HC

<400> SEQUENCE: 247

Gln Val Gln Leu Val Glu Ser Gly Pro Gly Leu Val Lys Pro Ser Gln
1               5                   10                  15

Thr Leu Ser Leu Thr Cys Thr Val Ser Gly Gly Ser Ile Ser Asn Gly
            20                  25                  30

Gly Tyr His Trp Ser Trp Ile Arg Gln His Pro Gly Lys Gly Leu Glu
        35                  40                  45
```

-continued

Trp Ile Gly Asn Ile Tyr Tyr Arg Gly Ser Thr Phe Tyr Asp Pro Ser
 50                  55                   60

Leu Lys Ser Arg Val Thr Ile Ser Val Asp Thr Ser Lys Ser Gln Phe
65                   70                  75                   80

Ser Leu Lys Leu Thr Ser Val Thr Ala Ala Asp Thr Ala Val Tyr Tyr
                 85                  90                  95

Cys Ala Arg Met Pro Leu Ala Asn Tyr Asp Leu Leu Thr Gly Leu Tyr
             100                 105                 110

Ile Gly Ala Phe Asp Leu Trp Gly Gln Gly Thr Met Val Thr Val Ser
             115                 120                 125

Ser Ala Ser Thr Lys Gly Pro Ser Val Phe Pro Leu Ala Pro Ser Ser
130                 135                 140

Lys Ser Thr Ser Gly Gly Thr Ala Ala Leu Gly Cys Leu Val Lys Asp
145                 150                 155                 160

Tyr Phe Pro Glu Pro Val Thr Val Ser Trp Asn Ser Gly Ala Leu Thr
                165                 170                 175

Ser Gly Val His Thr Phe Pro Ala Val Leu Gln Ser Ser Gly Leu Tyr
             180                 185                 190

Ser Leu Ser Ser Val Val Thr Val Pro Ser Ser Ser Leu Gly Thr Gln
         195                 200                 205

Thr Tyr Ile Cys Asn Val Asn His Lys Pro Ser Asn Thr Lys Val Asp
         210                 215                 220

Lys Lys Val Glu Pro Lys Ser Cys Asp Lys Thr His Thr Cys Pro Pro
225                 230                 235                 240

Cys Pro Ala Pro Glu Leu Leu Gly Gly Pro Ser Val Phe Leu Phe Pro
                245                 250                 255

Pro Lys Pro Lys Asp Thr Leu Met Ile Ser Arg Thr Pro Glu Val Thr
             260                 265                 270

Cys Val Val Val Asp Val Ser His Glu Asp Pro Glu Val Lys Phe Asn
         275                 280                 285

Trp Tyr Val Asp Gly Val Glu Val His Asn Ala Lys Thr Lys Pro Arg
     290                 295                 300

Glu Glu Gln Tyr Asn Ser Thr Tyr Arg Val Val Ser Val Leu Thr Val
305                 310                 315                 320

Leu His Gln Asp Trp Leu Asn Gly Lys Glu Tyr Lys Cys Lys Val Ser
                325                 330                 335

Asn Lys Ala Leu Pro Ala Pro Ile Glu Lys Thr Ile Ser Lys Ala Lys
             340                 345                 350

Gly Gln Pro Arg Glu Pro Gln Val Tyr Thr Leu Pro Pro Ser Arg Asp
         355                 360                 365

Glu Leu Thr Lys Asn Gln Val Ser Leu Thr Cys Leu Val Lys Gly Phe
         370                 375                 380

Tyr Pro Ser Asp Ile Ala Val Glu Trp Glu Ser Asn Gly Gln Pro Glu
385                 390                 395                 400

Asn Asn Tyr Lys Thr Thr Pro Pro Val Leu Asp Ser Asp Gly Ser Phe
                405                 410                 415

Phe Leu Tyr Ser Lys Leu Thr Val Asp Lys Ser Arg Trp Gln Gln Gly
             420                 425                 430

Asn Val Phe Ser Cys Ser Val Met His Glu Ala Leu His Asn His Tyr
         435                 440                 445

Thr Gln Lys Ser Leu Ser Leu Ser Pro Gly Lys
450                 455

```
<210> SEQ ID NO 248
<211> LENGTH: 214
<212> TYPE: PRT
<213> ORGANISM: Artificial Sequence
<220> FEATURE:
<223> OTHER INFORMATION: TRL849 LC

<400> SEQUENCE: 248
```

Asp Ile Val Leu Thr Gln Ser Pro Ala Thr Leu Ser Val Ser Pro Gly
1               5                   10                  15

Glu Arg Ala Thr Leu Ser Cys Arg Ala Ser Gln Ser Val Asn Arg Asn
            20                  25                  30

Leu Ala Trp Phe Gln Gln Ile Pro Gly Gln Ala Pro Arg Leu Leu Ile
        35                  40                  45

Phe Asp Ala Ser Thr Arg Ala Ala Asp Ile Pro Ala Arg Phe Ser Gly
    50                  55                  60

Gly Gly Ser Gly Ala Glu Phe Thr Leu Thr Val Ser Ser Leu Gln Pro
65                  70                  75                  80

Glu Asp Phe Ala Val Tyr Tyr Cys Gln Gln Tyr Asp Lys Trp Pro Pro
                85                  90                  95

Gly Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

```
<210> SEQ ID NO 249
<211> LENGTH: 129
<212> TYPE: PRT
<213> ORGANISM: Artificial Sequence
<220> FEATURE:
<223> OTHER INFORMATION: TRL849 HCVR

<400> SEQUENCE: 249
```

Gln Val Gln Leu Val Glu Ser Gly Pro Gly Leu Val Lys Pro Ser Gln
1               5                   10                  15

Thr Leu Ser Leu Thr Cys Thr Val Ser Gly Gly Ser Ile Ser Asn Gly
            20                  25                  30

Gly Tyr His Trp Ser Trp Ile Arg Gln His Pro Gly Lys Gly Leu Glu
        35                  40                  45

Trp Ile Gly Asn Ile Tyr Tyr Arg Gly Ser Thr Phe Tyr Asp Pro Ser
    50                  55                  60

Leu Lys Ser Arg Val Thr Ile Ser Val Asp Thr Ser Lys Ser Gln Phe
65                  70                  75                  80

Ser Leu Lys Leu Thr Ser Val Thr Ala Ala Asp Thr Ala Val Tyr Tyr
                85                  90                  95

-continued

```
Cys Ala Arg Met Pro Leu Ala Asn Tyr Asp Leu Leu Thr Gly Leu Tyr
            100                 105                 110

Ile Gly Ala Phe Asp Leu Trp Gly Gln Gly Thr Met Val Thr Val Ser
        115                 120                 125

Ser

<210> SEQ ID NO 250
<211> LENGTH: 109
<212> TYPE: PRT
<213> ORGANISM: Artificial Sequence
<220> FEATURE:
<223> OTHER INFORMATION: TRL849 LCVR

<400> SEQUENCE: 250

Asp Ile Val Leu Thr Gln Ser Pro Ala Thr Leu Ser Val Ser Pro Gly
1               5                   10                  15

Glu Arg Ala Thr Leu Ser Cys Arg Ala Ser Gln Ser Val Asn Arg Asn
            20                  25                  30

Leu Ala Trp Phe Gln Gln Ile Pro Gly Gln Ala Pro Arg Leu Leu Ile
        35                  40                  45

Phe Asp Ala Ser Thr Arg Ala Ala Asp Ile Pro Ala Arg Phe Ser Gly
    50                  55                  60

Gly Gly Ser Gly Ala Glu Phe Thr Leu Thr Val Ser Ser Leu Gln Pro
65                  70                  75                  80

Glu Asp Phe Ala Val Tyr Tyr Cys Gln Gln Tyr Asp Lys Trp Pro Pro
                85                  90                  95

Gly Phe Gly Gln Gly Thr Lys Val Glu Ile Lys Arg Thr
            100                 105

<210> SEQ ID NO 251
<211> LENGTH: 8
<212> TYPE: PRT
<213> ORGANISM: Artificial Sequence
<220> FEATURE:
<223> OTHER INFORMATION: TRL851 HC CDR1

<400> SEQUENCE: 251

Gly Asp Ser Phe Thr Ser Tyr Trp
1               5

<210> SEQ ID NO 252
<211> LENGTH: 8
<212> TYPE: PRT
<213> ORGANISM: Artificial Sequence
<220> FEATURE:
<223> OTHER INFORMATION: TRL851 HC CDR2

<400> SEQUENCE: 252

Ile Tyr Pro Arg Asp Ser Glu Thr
1               5

<210> SEQ ID NO 253
<211> LENGTH: 16
<212> TYPE: PRT
<213> ORGANISM: Artificial Sequence
<220> FEATURE:
<223> OTHER INFORMATION: TRL851 HC CDR3

<400> SEQUENCE: 253

Ala Arg Ser Pro Gly Tyr Ser Gly Tyr Leu Tyr Gly Trp Phe Asp Pro
1               5                   10                  15
```

```
<210> SEQ ID NO 254
<211> LENGTH: 11
<212> TYPE: PRT
<213> ORGANISM: Artificial Sequence
<220> FEATURE:
<223> OTHER INFORMATION: TRL851 LC CDR1

<400> SEQUENCE: 254

Gln Ser Leu Leu His Ser Asn Gly Tyr Asn Tyr
1               5                   10

<210> SEQ ID NO 255
<211> LENGTH: 3
<212> TYPE: PRT
<213> ORGANISM: Artificial Sequence
<220> FEATURE:
<223> OTHER INFORMATION: TRL851 LC CDR2

<400> SEQUENCE: 255

Leu Gly Ser
1

<210> SEQ ID NO 256
<211> LENGTH: 9
<212> TYPE: PRT
<213> ORGANISM: Artificial Sequence
<220> FEATURE:
<223> OTHER INFORMATION: TRL851 LC CDR3

<400> SEQUENCE: 256

Met Gln Gly Leu Gln Thr Pro Tyr Thr
1               5

<210> SEQ ID NO 257
<211> LENGTH: 453
<212> TYPE: PRT
<213> ORGANISM: Artificial Sequence
<220> FEATURE:
<223> OTHER INFORMATION: TRL851 HC

<400> SEQUENCE: 257

Gln Val Gln Leu Val Glu Ser Gly Ala Glu Val Arg Lys Pro Gly Glu
1               5                   10                  15

Ser Leu Arg Ile Ser Cys Lys Ala His Gly Asp Ser Phe Thr Ser Tyr
            20                  25                  30

Trp Ile Gly Trp Val Arg Gln Leu Pro Gly Lys Gly Leu Glu Trp Met
        35                  40                  45

Ala Val Ile Tyr Pro Arg Asp Ser Glu Thr Lys Phe Ser Pro Ala Phe
    50                  55                  60

His Gly Gln Val Ser Ile Ser Val Asp Lys Ser Thr Ser Thr Val His
65                  70                  75                  80

Leu Gln Trp Asn Ser Leu Lys Ala Ser Asp Thr Ala Val Tyr Tyr Cys
                85                  90                  95

Ala Arg Ser Pro Gly Tyr Ser Gly Tyr Leu Tyr Gly Trp Phe Asp Pro
            100                 105                 110

Trp Gly Gln Gly Thr Pro Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160
```

```
Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 258
<211> LENGTH: 219
<212> TYPE: PRT
<213> ORGANISM: Artificial Sequence
<220> FEATURE:
<223> OTHER INFORMATION: TRL851 LC

<400> SEQUENCE: 258

Asp Ile Glu Met Thr Gln Ser Pro Leu Ser Leu Pro Val Thr Pro Gly
1               5                   10                  15

Glu Ser Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Ser Arg Ala Ser Gly Val Pro
    50                  55                  60
```

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Gly
                 85                  90                  95

Leu Gln Thr Pro Tyr Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 259
<211> LENGTH: 123
<212> TYPE: PRT
<213> ORGANISM: Artificial Sequence
<220> FEATURE:
<223> OTHER INFORMATION: TRL851 HCVR

<400> SEQUENCE: 259

Gln Val Gln Leu Val Glu Ser Gly Ala Glu Val Arg Lys Pro Gly Glu
1               5                   10                  15

Ser Leu Arg Ile Ser Cys Lys Ala His Gly Asp Ser Phe Thr Ser Tyr
                20                  25                  30

Trp Ile Gly Trp Val Arg Gln Leu Pro Gly Lys Gly Leu Glu Trp Met
            35                  40                  45

Ala Val Ile Tyr Pro Arg Asp Ser Glu Thr Lys Phe Ser Pro Ala Phe
        50                  55                  60

His Gly Gln Val Ser Ile Ser Val Asp Lys Ser Thr Ser Thr Val His
65                  70                  75                  80

Leu Gln Trp Asn Ser Leu Lys Ala Ser Asp Thr Ala Val Tyr Tyr Cys
                85                  90                  95

Ala Arg Ser Pro Gly Tyr Ser Gly Tyr Leu Tyr Gly Trp Phe Asp Pro
            100                 105                 110

Trp Gly Gln Gly Thr Pro Val Thr Val Ser Ser
        115                 120

<210> SEQ ID NO 260
<211> LENGTH: 114
<212> TYPE: PRT
<213> ORGANISM: Artificial Sequence
<220> FEATURE:
<223> OTHER INFORMATION: TRL851 LCVR

<400> SEQUENCE: 260

Asp Ile Glu Met Thr Gln Ser Pro Leu Ser Leu Pro Val Thr Pro Gly
1               5                   10                  15

Glu Ser Ala Ser Ile Ser Cys Arg Ser Ser Gln Ser Leu Leu His Ser
                20                  25                  30

```
                Asn Gly Tyr Asn Tyr Leu Asp Trp Tyr Leu Gln Lys Pro Gly Gln Ser
                                 35                  40                  45

Pro Gln Leu Leu Ile Tyr Leu Gly Ser Ser Arg Ala Ser Gly Val Pro
                     50                  55                  60

Asp Arg Phe Ser Gly Ser Gly Ser Gly Thr Asp Phe Thr Leu Lys Ile
                65                  70                  75                  80

Ser Arg Val Glu Ala Glu Asp Val Gly Val Tyr Tyr Cys Met Gln Gly
                                 85                  90                  95

Leu Gln Thr Pro Tyr Thr Phe Gly Gln Gly Thr Lys Leu Glu Ile Lys
                                100                 105                 110

Arg Thr
```

<210> SEQ ID NO 261
<211> LENGTH: 8
<212> TYPE: PRT
<213> ORGANISM: Artificial Sequence
<220> FEATURE:
<223> OTHER INFORMATION: TRL854 HC CDR1

<400> SEQUENCE: 261

```
                Gly Tyr Thr Phe Thr Ala Tyr His
                1               5
```

<210> SEQ ID NO 262
<211> LENGTH: 8
<212> TYPE: PRT
<213> ORGANISM: Artificial Sequence
<220> FEATURE:
<223> OTHER INFORMATION: TRL854 HC CDR2

<400> SEQUENCE: 262

```
                Ile Asn Pro Asn Ser Gly Ala Thr
                1               5
```

<210> SEQ ID NO 263
<211> LENGTH: 22
<212> TYPE: PRT
<213> ORGANISM: Artificial Sequence
<220> FEATURE:
<223> OTHER INFORMATION: TRL854 HC CDR3

<400> SEQUENCE: 263

```
                Ala Thr Asp Ile Val Val Glu Arg Asp Ala Ser Leu Gly Gly Phe Asn
                1               5                   10                  15

Ser Tyr Gly Met Asp Val
                                20
```

<210> SEQ ID NO 264
<211> LENGTH: 11
<212> TYPE: PRT
<213> ORGANISM: Artificial Sequence
<220> FEATURE:
<223> OTHER INFORMATION: TRL854 LC CDR1

<400> SEQUENCE: 264

```
                Gln Ser Leu Leu His Ser Asn Gly Tyr Asn His
                1               5                   10
```

<210> SEQ ID NO 265
<211> LENGTH: 3
<212> TYPE: PRT
<213> ORGANISM: Artificial Sequence
<220> FEATURE:
<223> OTHER INFORMATION: TRL854 LC CDR2

```
<400> SEQUENCE: 265

Leu Ala Ser
1

<210> SEQ ID NO 266
<211> LENGTH: 9
<212> TYPE: PRT
<213> ORGANISM: Artificial Sequence
<220> FEATURE:
<223> OTHER INFORMATION: TRL854 LC CDR3

<400> SEQUENCE: 266

Met Gln Ser Leu Gln Thr Ser Ile Thr
1               5

<210> SEQ ID NO 267
<211> LENGTH: 459
<212> TYPE: PRT
<213> ORGANISM: Artificial Sequence
<220> FEATURE:
<223> OTHER INFORMATION: TRL854 HC

<400> SEQUENCE: 267

Gln Val Gln Leu Val Glu Ser Gly Ala Glu Val Lys Lys Pro Gly Ala
1               5                   10                  15

Ser Val Arg Val Ser Cys Lys Gly Ser Gly Tyr Thr Phe Thr Ala Tyr
            20                  25                  30

His Met His Trp Val Arg Gln Ala Pro Gly Gln Gly Phe Glu Trp Val
        35                  40                  45

Gly Trp Ile Asn Pro Asn Ser Gly Ala Thr Tyr Tyr Ser Thr Thr Phe
    50                  55                  60

Glu Gly Arg Val Thr Met Thr Arg Asp Thr Ser Ile Thr Thr Ala Tyr
65                  70                  75                  80

Met Glu Leu Ser Ser Leu Arg Ser Asp Asp Thr Ala Val Tyr Tyr Cys
                85                  90                  95

Ala Thr Asp Ile Val Val Glu Arg Asp Ala Ser Leu Gly Gly Phe Asn
            100                 105                 110

Ser Tyr Gly Met Asp Val Trp Gly Gln Gly Thr Thr Val Thr Val Ser
        115                 120                 125

Ser Ala Ser Thr Lys Gly Pro Ser Val Phe Pro Leu Ala Pro Ser Ser
    130                 135                 140

Lys Ser Thr Ser Gly Gly Thr Ala Ala Leu Gly Cys Leu Val Lys Asp
145                 150                 155                 160

Tyr Phe Pro Glu Pro Val Thr Val Ser Trp Asn Ser Gly Ala Leu Thr
                165                 170                 175

Ser Gly Val His Thr Phe Pro Ala Val Leu Gln Ser Ser Gly Leu Tyr
            180                 185                 190

Ser Leu Ser Ser Val Val Thr Val Pro Ser Ser Ser Leu Gly Thr Gln
        195                 200                 205

Thr Tyr Ile Cys Asn Val Asn His Lys Pro Ser Asn Thr Lys Val Asp
    210                 215                 220

Lys Lys Val Glu Pro Lys Ser Cys Asp Lys Thr His Thr Cys Pro Pro
225                 230                 235                 240

Cys Pro Ala Pro Glu Leu Leu Gly Gly Pro Ser Val Phe Leu Phe Pro
                245                 250                 255

Pro Lys Pro Lys Asp Thr Leu Met Ile Ser Arg Thr Pro Glu Val Thr
            260                 265                 270
```

```
Cys Val Val Asp Val Ser His Glu Asp Pro Glu Val Lys Phe Asn
        275                 280                 285

Trp Tyr Val Asp Gly Val Glu Val His Asn Ala Lys Thr Lys Pro Arg
290                 295                 300

Glu Glu Gln Tyr Asn Ser Thr Tyr Arg Val Val Ser Val Leu Thr Val
305                 310                 315                 320

Leu His Gln Asp Trp Leu Asn Gly Lys Glu Tyr Lys Cys Lys Val Ser
                325                 330                 335

Asn Lys Ala Leu Pro Ala Pro Ile Glu Lys Thr Ile Ser Lys Ala Lys
            340                 345                 350

Gly Gln Pro Arg Glu Pro Gln Val Tyr Thr Leu Pro Pro Ser Arg Asp
        355                 360                 365

Glu Leu Thr Lys Asn Gln Val Ser Leu Thr Cys Leu Val Lys Gly Phe
370                 375                 380

Tyr Pro Ser Asp Ile Ala Val Glu Trp Glu Ser Asn Gly Gln Pro Glu
385                 390                 395                 400

Asn Asn Tyr Lys Thr Thr Pro Pro Val Leu Asp Ser Asp Gly Ser Phe
                405                 410                 415

Phe Leu Tyr Ser Lys Leu Thr Val Asp Lys Ser Arg Trp Gln Gln Gly
            420                 425                 430

Asn Val Phe Ser Cys Ser Val Met His Glu Ala Leu His Asn His Tyr
        435                 440                 445

Thr Gln Lys Ser Leu Ser Leu Ser Pro Gly Lys
    450                 455

<210> SEQ ID NO 268
<211> LENGTH: 219
<212> TYPE: PRT
<213> ORGANISM: Artificial Sequence
<220> FEATURE:
<223> OTHER INFORMATION: TRL854 LC

<400> SEQUENCE: 268

Asp Ile Glu Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn His Leu Ala Trp Tyr Leu Gln Lys Pro Gly Arg Ser
        35                  40                  45

Pro His Leu Leu Ile Tyr Leu Ala Ser Thr Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Ile Tyr Tyr Cys Met Gln Ser
                85                  90                  95

Leu Gln Thr Ser Ile Thr Phe Gly Gln Gly Thr Arg Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175
```

```
Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
            210                 215

<210> SEQ ID NO 269
<211> LENGTH: 129
<212> TYPE: PRT
<213> ORGANISM: Artificial Sequence
<220> FEATURE:
<223> OTHER INFORMATION: TRL854 HCVR

<400> SEQUENCE: 269

Gln Val Gln Leu Val Glu Ser Gly Ala Glu Val Lys Lys Pro Gly Ala
1               5                   10                  15

Ser Val Arg Val Ser Cys Lys Gly Ser Gly Tyr Thr Phe Thr Ala Tyr
            20                  25                  30

His Met His Trp Val Arg Gln Ala Pro Gly Gln Gly Phe Glu Trp Val
        35                  40                  45

Gly Trp Ile Asn Pro Asn Ser Gly Ala Thr Tyr Tyr Thr Ser Thr Phe
    50                  55                  60

Glu Gly Arg Val Thr Met Thr Arg Asp Thr Ser Ile Thr Thr Ala Tyr
65                  70                  75                  80

Met Glu Leu Ser Ser Leu Arg Ser Asp Asp Thr Ala Val Tyr Tyr Cys
                85                  90                  95

Ala Thr Asp Ile Val Val Glu Arg Asp Ala Ser Leu Gly Gly Phe Asn
            100                 105                 110

Ser Tyr Gly Met Asp Val Trp Gly Gln Gly Thr Thr Val Thr Val Ser
        115                 120                 125

Ser

<210> SEQ ID NO 270
<211> LENGTH: 114
<212> TYPE: PRT
<213> ORGANISM: Artificial Sequence
<220> FEATURE:
<223> OTHER INFORMATION: TRL854 LCVR

<400> SEQUENCE: 270

Asp Ile Glu Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn His Leu Ala Trp Tyr Leu Gln Lys Pro Gly Arg Ser
        35                  40                  45

Pro His Leu Leu Ile Tyr Leu Ala Ser Thr Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Ile Tyr Tyr Cys Met Gln Ser
                85                  90                  95

Leu Gln Thr Ser Ile Thr Phe Gly Gln Gly Thr Arg Leu Glu Ile Lys
            100                 105                 110

Arg Thr
```

```
<210> SEQ ID NO 271
<211> LENGTH: 8
<212> TYPE: PRT
<213> ORGANISM: Artificial Sequence
<220> FEATURE:
<223> OTHER INFORMATION: TRL856 HC CDR1

<400> SEQUENCE: 271

Gly Phe Thr Phe Ser Asp Tyr Trp
1               5

<210> SEQ ID NO 272
<211> LENGTH: 8
<212> TYPE: PRT
<213> ORGANISM: Artificial Sequence
<220> FEATURE:
<223> OTHER INFORMATION: TRL856 HC CDR2

<400> SEQUENCE: 272

Ile Ser Ser Asp Gly Ser Thr Thr
1               5

<210> SEQ ID NO 273
<211> LENGTH: 15
<212> TYPE: PRT
<213> ORGANISM: Artificial Sequence
<220> FEATURE:
<223> OTHER INFORMATION: TRL856 HC CDR3

<400> SEQUENCE: 273

Ala Arg Val Ala Thr Pro Tyr Tyr Tyr Glu Ser Gly Phe Asp Tyr
1               5                   10                  15

<210> SEQ ID NO 274
<211> LENGTH: 6
<212> TYPE: PRT
<213> ORGANISM: Artificial Sequence
<220> FEATURE:
<223> OTHER INFORMATION: TRL856 LC CDR1

<400> SEQUENCE: 274

Asp Ile Gly Ser Lys Ser
1               5

<210> SEQ ID NO 275
<211> LENGTH: 3
<212> TYPE: PRT
<213> ORGANISM: Artificial Sequence
<220> FEATURE:
<223> OTHER INFORMATION: TRL856 LC CDR2

<400> SEQUENCE: 275

Asp Asp Arg
1

<210> SEQ ID NO 276
<211> LENGTH: 11
<212> TYPE: PRT
<213> ORGANISM: Artificial Sequence
<220> FEATURE:
<223> OTHER INFORMATION: TRL856 LC CDR3

<400> SEQUENCE: 276

Gln Val Trp Asp Ile Thr Ser Asp Leu Val Val
1               5                   10
```

<210> SEQ ID NO 277
<211> LENGTH: 452
<212> TYPE: PRT
<213> ORGANISM: Artificial Sequence
<220> FEATURE:
<223> OTHER INFORMATION: TRL856 HC

<400> SEQUENCE: 277

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Trp Met Val Trp Val Arg Gln Ala Pro Gly Lys Gly Leu Val Trp Val
        35                  40                  45

Ser Arg Ile Ser Ser Asp Gly Ser Thr Thr Ser Tyr Ala Asp Ser Val
    50                  55                  60

Lys Gly Pro Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Ala Thr Pro Tyr Tyr Tyr Glu Ser Gly Phe Asp Tyr Trp
            100                 105                 110

Gly Gln Gly Ala Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365
```

```
Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
                420                 425                 430

Met His Glu Ala Leu His Asn His Tyr Thr Gln Lys Ser Leu Ser Leu
                435                 440                 445

Ser Pro Gly Lys
    450

<210> SEQ ID NO 278
<211> LENGTH: 214
<212> TYPE: PRT
<213> ORGANISM: Artificial Sequence
<220> FEATURE:
<223> OTHER INFORMATION: TRL856 LC

<400> SEQUENCE: 278

Asp Ile Val Leu Thr Gln Ser Pro Ser Val Ser Val Ala Pro Gly Gln
1               5                   10                  15

Thr Ala Arg Ile Thr Cys Gly Gly Asn Asp Ile Gly Ser Lys Ser Val
                20                  25                  30

His Trp Tyr Gln Gln Lys Pro Gly Gln Ala Pro Val Leu Val Val Phe
            35                  40                  45

Asp Asp Arg Asp Arg Pro Ser Gly Ile Pro Glu Arg Phe Ser Gly Ser
50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ile Thr Ser Asp Leu
                85                  90                  95

Val Val Phe Gly Gly Gly Thr Lys Leu Thr Val Val Gly Gln Pro Lys
                100                 105                 110

Ala Ala Pro Ser Val Thr Leu Phe Pro Pro Ser Ser Glu Glu Leu Gln
            115                 120                 125

Ala Asn Lys Ala Thr Leu Val Cys Leu Ile Ser Asp Phe Tyr Pro Gly
130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
                180                 185                 190

Tyr Ser Cys Gln Val Thr His Glu Gly Ser Thr Val Glu Lys Thr Val
            195                 200                 205

Val Pro Ala Glu Cys Ser
    210

<210> SEQ ID NO 279
<211> LENGTH: 122
<212> TYPE: PRT
<213> ORGANISM: Artificial Sequence
<220> FEATURE:
<223> OTHER INFORMATION: TRL856 HCVR
```

<400> SEQUENCE: 279

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Trp Met Val Trp Val Arg Gln Ala Pro Gly Lys Gly Leu Val Trp Val
        35                  40                  45

Ser Arg Ile Ser Ser Asp Gly Ser Thr Thr Ser Tyr Ala Asp Ser Val
    50                  55                  60

Lys Gly Pro Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Ala Thr Pro Tyr Tyr Tyr Glu Ser Gly Phe Asp Tyr Trp
            100                 105                 110

Gly Gln Gly Ala Leu Val Thr Val Ser Ser
        115                 120

<210> SEQ ID NO 280
<211> LENGTH: 110
<212> TYPE: PRT
<213> ORGANISM: Artificial Sequence
<220> FEATURE:
<223> OTHER INFORMATION: TRL856 LCVR

<400> SEQUENCE: 280

Asp Ile Val Leu Thr Gln Ser Pro Ser Val Ser Val Ala Pro Gly Gln
1               5                   10                  15

Thr Ala Arg Ile Thr Cys Gly Gly Asn Asp Ile Gly Ser Lys Ser Val
            20                  25                  30

His Trp Tyr Gln Gln Lys Pro Gly Gln Ala Pro Val Leu Val Val Phe
        35                  40                  45

Asp Asp Arg Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ile Thr Ser Asp Leu
                85                  90                  95

Val Val Phe Gly Gly Gly Thr Lys Leu Thr Val Val Gly Gln
            100                 105                 110

<210> SEQ ID NO 281
<211> LENGTH: 10
<212> TYPE: PRT
<213> ORGANISM: Artificial Sequence
<220> FEATURE:
<223> OTHER INFORMATION: TRL858 HC CDR1

<400> SEQUENCE: 281

Gly Asp Ser Val Ile Asn Ser Ala Tyr Tyr
1               5                   10

<210> SEQ ID NO 282
<211> LENGTH: 7
<212> TYPE: PRT
<213> ORGANISM: Artificial Sequence
<220> FEATURE:
<223> OTHER INFORMATION: TRL858 HC CDR2

```
<400> SEQUENCE: 282

Val Tyr Tyr Ser Gly Ile Thr
1               5

<210> SEQ ID NO 283
<211> LENGTH: 15
<212> TYPE: PRT
<213> ORGANISM: Artificial Sequence
<220> FEATURE:
<223> OTHER INFORMATION: TRL858 HC CDR3

<400> SEQUENCE: 283

Ala Arg Arg Gly Gly Gly Trp Gln Tyr Tyr Tyr Gly Met Asp Val
1               5                   10                  15

<210> SEQ ID NO 284
<211> LENGTH: 6
<212> TYPE: PRT
<213> ORGANISM: Artificial Sequence
<220> FEATURE:
<223> OTHER INFORMATION: TRL858 LC CDR1

<400> SEQUENCE: 284

Gln Ser Val Ser Thr Asn
1               5

<210> SEQ ID NO 285
<211> LENGTH: 3
<212> TYPE: PRT
<213> ORGANISM: Artificial Sequence
<220> FEATURE:
<223> OTHER INFORMATION: TRL858 LC CDR2

<400> SEQUENCE: 285

Gly Ala Ser
1

<210> SEQ ID NO 286
<211> LENGTH: 10
<212> TYPE: PRT
<213> ORGANISM: Artificial Sequence
<220> FEATURE:
<223> OTHER INFORMATION: TRL858 LC CDR3

<400> SEQUENCE: 286

Gln Gln Tyr Asp Asn Trp Leu Pro Ile Thr
1               5                   10

<210> SEQ ID NO 287
<211> LENGTH: 453
<212> TYPE: PRT
<213> ORGANISM: Artificial Sequence
<220> FEATURE:
<223> OTHER INFORMATION: TRL858 HC

<400> SEQUENCE: 287

Gln Val Gln Leu Val Glu Ser Gly Pro Gly Leu Val Lys Pro Ser Glu
1               5                   10                  15

Thr Leu Ser Leu Thr Cys Thr Val Ser Gly Asp Ser Val Ile Asn Ser
            20                  25                  30

Ala Tyr Tyr Trp Asp Trp Ile Arg Gln Pro Pro Gly Lys Gly Leu Glu
        35                  40                  45

Trp Val Gly Ser Val Tyr Tyr Ser Gly Ile Thr Tyr Tyr Asn Pro Ser
    50                  55                  60
```

-continued

```
Leu Lys Ser Arg Val Thr Ile Ser Val Asp Thr Ser Lys Asn Gln Phe
 65                  70                  75                  80

Ser Leu Arg Leu Ser Tyr Val Thr Ala Ala Asp Thr Ala Leu Tyr Tyr
                 85                  90                  95

Cys Ala Arg Arg Gly Gly Gly Trp Gln Tyr Tyr Gly Met Asp Val
             100                 105                 110

Trp Gly Gln Gly Thr Thr Val Thr Val Ser Ser Ala Ser Thr Lys Gly
             115                 120                 125

Pro Ser Val Phe Pro Leu Ala Pro Ser Ser Lys Ser Thr Ser Gly Gly
             130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                 165                 170                 175

Pro Ala Val Leu Gln Ser Ser Gly Leu Tyr Ser Leu Ser Ser Val Val
                 180                 185                 190

Thr Val Pro Ser Ser Ser Leu Gly Thr Gln Thr Tyr Ile Cys Asn Val
                 195                 200                 205

Asn His Lys Pro Ser Asn Thr Lys Val Asp Lys Lys Val Glu Pro Lys
                 210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                 245                 250                 255

Leu Met Ile Ser Arg Thr Pro Glu Val Thr Cys Val Val Val Asp Val
                 260                 265                 270

Ser His Glu Asp Pro Glu Val Lys Phe Asn Trp Tyr Val Asp Gly Val
                 275                 280                 285

Glu Val His Asn Ala Lys Thr Lys Pro Arg Glu Glu Gln Tyr Asn Ser
                 290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                 325                 330                 335

Pro Ile Glu Lys Thr Ile Ser Lys Ala Lys Gly Gln Pro Arg Glu Pro
                 340                 345                 350

Gln Val Tyr Thr Leu Pro Pro Ser Arg Asp Glu Leu Thr Lys Asn Gln
                 355                 360                 365

Val Ser Leu Thr Cys Leu Val Lys Gly Phe Tyr Pro Ser Asp Ile Ala
                 370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                 405                 410                 415

Thr Val Asp Lys Ser Arg Trp Gln Gln Gly Asn Val Phe Ser Cys Ser
                 420                 425                 430

Val Met His Glu Ala Leu His Asn His Tyr Thr Gln Lys Ser Leu Ser
                 435                 440                 445

Leu Ser Pro Gly Lys
                450
```

```
<210> SEQ ID NO 288
<211> LENGTH: 215
<212> TYPE: PRT
<213> ORGANISM: Artificial Sequence
<220> FEATURE:
<223> OTHER INFORMATION: TRL858 LC

<400> SEQUENCE: 288

Asp Ile Val Met Thr Gln Pro Pro Gly Thr Leu Ser Val Ser Pro Gly
1               5                   10                  15

Glu Arg Ala Thr Leu Ser Cys Arg Ala Ser Gln Ser Val Ser Thr Asn
            20                  25                  30

Leu Ala Trp Tyr Gln Gln Lys Pro Gly Gln Ala Pro Arg Leu Leu Ile
        35                  40                  45

His Gly Ala Ser Thr Arg Ala Thr Gly Ile Pro Ala Arg Phe Ser Gly
    50                  55                  60

Ser Gly Ser Gly Ala Glu Phe Thr Leu Thr Ile Ser Ser Leu Gln Ser
65                  70                  75                  80

Glu Asp Val Ala Val Tyr Tyr Cys Gln Gln Tyr Asp Asn Trp Leu Pro
                85                  90                  95

Ile Thr Phe Gly Pro Gly Thr Lys Val Asp Ile Gln Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 289
<211> LENGTH: 123
<212> TYPE: PRT
<213> ORGANISM: Artificial Sequence
<220> FEATURE:
<223> OTHER INFORMATION: TRL858 HCVR

<400> SEQUENCE: 289

Gln Val Gln Leu Val Glu Ser Gly Pro Gly Leu Val Lys Pro Ser Glu
1               5                   10                  15

Thr Leu Ser Leu Thr Cys Thr Val Ser Gly Asp Ser Val Ile Asn Ser
            20                  25                  30

Ala Tyr Tyr Trp Asp Trp Ile Arg Gln Pro Pro Gly Lys Gly Leu Glu
        35                  40                  45

Trp Val Gly Ser Val Tyr Tyr Ser Gly Ile Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Arg Leu Ser Tyr Val Thr Ala Ala Asp Thr Ala Leu Tyr Tyr
                85                  90                  95
```

Cys Ala Arg Arg Gly Gly Gly Trp Gln Tyr Tyr Gly Met Asp Val
            100                 105                 110

Trp Gly Gln Gly Thr Thr Val Thr Val Ser Ser
        115                 120

<210> SEQ ID NO 290
<211> LENGTH: 110
<212> TYPE: PRT
<213> ORGANISM: Artificial Sequence
<220> FEATURE:
<223> OTHER INFORMATION: TRL858 LCVR

<400> SEQUENCE: 290

Asp Ile Val Met Thr Gln Pro Pro Gly Thr Leu Ser Val Ser Pro Gly
1               5                   10                  15

Glu Arg Ala Thr Leu Ser Cys Arg Ala Ser Gln Ser Val Ser Thr Asn
            20                  25                  30

Leu Ala Trp Tyr Gln Gln Lys Pro Gly Gln Ala Pro Arg Leu Leu Ile
        35                  40                  45

His Gly Ala Ser Thr Arg Ala Thr Gly Ile Pro Ala Arg Phe Ser Gly
    50                  55                  60

Ser Gly Ser Gly Ala Glu Phe Thr Leu Thr Ile Ser Ser Leu Gln Ser
65                  70                  75                  80

Glu Asp Val Ala Val Tyr Tyr Cys Gln Gln Tyr Asp Asn Trp Leu Pro
                85                  90                  95

Ile Thr Phe Gly Pro Gly Thr Lys Val Asp Ile Gln Arg Thr
            100                 105                 110

<210> SEQ ID NO 291
<211> LENGTH: 584
<212> TYPE: PRT
<213> ORGANISM: Influenza B virus
<220> FEATURE:
<221> NAME/KEY: VARIANT
<222> LOCATION: (1)..(584)
<223> OTHER INFORMATION: B/Lee/1940 HA protein Full length
<220> FEATURE:
<221> NAME/KEY: MISC_FEATURE
<222> LOCATION: (486)..(486)
<223> OTHER INFORMATION: Xaa can be any naturally occurring amino acid

<400> SEQUENCE: 291

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
        35                  40                  45

Thr Thr Pro Thr Lys Ser His Phe Ala Asn Leu Lys Gly Thr Gln Thr
    50                  55                  60

Arg Gly Lys Leu Cys Pro Asn Cys Phe Asn Cys Thr Asp Leu Asp Val
65                  70                  75                  80

Ala Leu Gly Arg Pro Lys Cys Met Gly Asn Thr Pro Ser Ala Lys Val
                85                  90                  95

Ser Ile Leu His Glu Val Lys Pro Ala Thr Ser Gly Cys Phe Pro Ile
            100                 105                 110

Met His Asp Arg Thr Lys Ile Arg Gln Leu Pro Asn Leu Leu Arg Gly
        115                 120                 125

Tyr Glu Asn Ile Arg Leu Ser Thr Ser Asn Val Ile Asn Thr Glu Thr
    130                 135                 140

```
Ala Pro Gly Gly Pro Tyr Lys Val Gly Thr Ser Gly Ser Cys Pro Asn
145                 150                 155                 160

Val Ala Asn Gly Asn Gly Phe Phe Asn Thr Met Ala Trp Val Ile Pro
            165                 170                 175

Lys Asp Asn Asn Lys Thr Ala Ile Asn Pro Val Thr Val Glu Val Pro
        180                 185                 190

Tyr Ile Cys Ser Glu Gly Glu Asp Gln Ile Thr Val Trp Gly Phe His
    195                 200                 205

Ser Asp Asp Lys Thr Gln Met Glu Arg Leu Tyr Gly Asp Ser Asn Pro
210                 215                 220

Gln Lys Phe Thr Ser Ser Ala Asn Gly Val Thr Thr His Tyr Val Ser
225                 230                 235                 240

Gln Ile Gly Gly Phe Pro Asn Gln Thr Glu Asp Glu Gly Leu Lys Gln
                245                 250                 255

Ser Gly Arg Ile Val Val Asp Tyr Met Val Gln Lys Pro Gly Lys Thr
            260                 265                 270

Gly Thr Ile Val Tyr Gln Arg Gly Ile Leu Leu Pro Gln Lys Val Trp
        275                 280                 285

Cys Ala Ser Gly Arg Ser Lys Val Ile Lys Gly Ser Leu Pro Leu Ile
    290                 295                 300

Gly Glu Ala Asp Cys Leu His Glu Lys Tyr Gly Gly Leu Asn Lys Ser
305                 310                 315                 320

Lys Pro Tyr Tyr Thr Gly Glu His Ala Lys Ala Ile Gly Asn Cys Pro
                325                 330                 335

Ile Trp Val Lys Thr Pro Leu Lys Leu Ala Asn Gly Thr Lys Tyr Arg
            340                 345                 350

Pro Pro Ala Lys Leu Leu Lys Glu Arg Gly Phe Phe Gly Ala Ile Ala
        355                 360                 365

Gly Phe Leu Glu Gly Gly Trp Glu Gly Met Ile Ala Gly Trp His Gly
370                 375                 380

Tyr Thr Ser His Gly Ala His Gly Val Ala Val Ala Ala Asp Leu Lys
385                 390                 395                 400

Ser Thr Gln Glu Ala Ile Asn Lys Ile Thr Lys Asn Leu Asn Tyr Leu
                405                 410                 415

Ser Glu Leu Glu Val Lys Asn Leu Gln Arg Leu Ser Gly Ala Met Asn
            420                 425                 430

Glu Leu His Asp Glu Ile Leu Glu Leu Asp Lys Val Asp Asp Leu
        435                 440                 445

Arg Ala Asp Thr Ile Ser Ser Gln Ile Glu Leu Ala Val Leu Leu Ser
450                 455                 460

Asn Glu Gly Ile Ile Asn Ser Glu Asp Glu His Leu Leu Ala Leu Glu
465                 470                 475                 480

Arg Lys Leu Lys Lys Xaa Leu Gly Pro Ser Ala Val Glu Ile Gly Asn
                485                 490                 495

Gly Cys Phe Glu Thr Lys His Lys Cys Asn Gln Thr Cys Leu Asp Arg
            500                 505                 510

Ile Ala Ala Gly Thr Phe Asn Ala Gly Asp Phe Ser Leu Pro Thr Phe
        515                 520                 525

Asp Ser Leu Asn Ile Thr Ala Ala Ser Leu Asn Asp Asp Gly Leu Asp
530                 535                 540

Asn His Thr Ile Leu Leu Tyr Tyr Ser Thr Ala Ala Ser Ser Leu Ala
545                 550                 555                 560
```

```
Val Thr Leu Met Ile Ala Ile Phe Ile Val Tyr Met Val Ser Arg Asp
            565                 570                 575

Asn Val Ser Cys Ser Ile Cys Leu
        580

<210> SEQ ID NO 292
<211> LENGTH: 50
<212> TYPE: PRT
<213> ORGANISM: Influenza B virus
<220> FEATURE:
<221> NAME/KEY: VARIANT
<222> LOCATION: (1)..(50)
<223> OTHER INFORMATION: B/Lee/1940 HA protein aa_15-65

<400> SEQUENCE: 292

Asp Arg Ile Cys Thr Gly Ile Thr Ser Ser Asn Ser Pro His Val Val
1               5                   10                  15

Lys Thr Ala Thr Gln Gly Glu Val Asn Val Thr Gly Val Ile Pro Leu
            20                  25                  30

Thr Thr Thr Pro Thr Lys Ser His Phe Ala Asn Leu Lys Gly Thr Gln
        35                  40                  45

Thr Arg
    50

<210> SEQ ID NO 293
<211> LENGTH: 59
<212> TYPE: PRT
<213> ORGANISM: Influenza B virus
<220> FEATURE:
<221> NAME/KEY: VARIANT
<222> LOCATION: (1)..(59)
<223> OTHER INFORMATION: B/Lee/1940 HA protein aa_300-359

<400> SEQUENCE: 293

Leu Pro Leu Ile Gly Glu Ala Asp Cys Leu His Glu Lys Tyr Gly Gly
1               5                   10                  15

Leu Asn Lys Ser Lys Pro Tyr Tyr Thr Gly Glu His Ala Lys Ala Ile
            20                  25                  30

Gly Asn Cys Pro Ile Trp Val Lys Thr Pro Leu Lys Leu Ala Asn Gly
        35                  40                  45

Thr Lys Tyr Arg Pro Pro Ala Lys Leu Leu Lys
    50                  55

<210> SEQ ID NO 294
<211> LENGTH: 120
<212> TYPE: PRT
<213> ORGANISM: Influenza B virus
<220> FEATURE:
<221> NAME/KEY: VARIANT
<222> LOCATION: (1)..(120)
<223> OTHER INFORMATION: B/Lee/1940 HA protein aa_362-481

<400> SEQUENCE: 294

Gly Phe Phe Gly Ala Ile Ala Gly Phe Leu Glu Gly Gly Trp Glu Gly
1               5                   10                  15

Met Ile Ala Gly Trp His Gly Tyr Thr Ser His Gly Ala His Gly Val
            20                  25                  30

Ala Val Ala Ala Asp Leu Lys Ser Thr Gln Glu Ala Ile Asn Lys Ile
        35                  40                  45

Thr Lys Asn Leu Asn Tyr Leu Ser Glu Leu Glu Val Lys Asn Leu Gln
    50                  55                  60
```

Arg Leu Ser Gly Ala Met Asn Glu Leu His Asp Glu Ile Leu Glu Leu
65                  70                  75                  80

Asp Glu Lys Val Asp Asp Leu Arg Ala Asp Thr Ile Ser Ser Gln Ile
                85                  90                  95

Glu Leu Ala Val Leu Leu Ser Asn Glu Gly Ile Ile Asn Ser Glu Asp
            100                 105                 110

Glu His Leu Leu Ala Leu Glu Arg
        115                 120

<210> SEQ ID NO 295
<211> LENGTH: 105
<212> TYPE: PRT
<213> ORGANISM: Homo sapiens
<220> FEATURE:
<221> NAME/KEY: VARIANT
<222> LOCATION: (1)..(105)
<223> OTHER INFORMATION: Human LC Kappa constant  Kappa constant

<400> SEQUENCE: 295

Val Ala Ala Pro Ser Val Phe Ile Phe Pro Pro Ser Asp Glu Gln Leu
1               5                   10                  15

Lys Ser Gly Thr Ala Ser Val Val Cys Leu Leu Asn Asn Phe Tyr Pro
            20                  25                  30

Arg Glu Ala Lys Val Gln Trp Lys Val Asp Asn Ala Leu Gln Ser Gly
        35                  40                  45

Asn Ser Gln Glu Ser Val Thr Glu Gln Asp Ser Lys Asp Ser Thr Tyr
    50                  55                  60

Ser Leu Ser Ser Thr Leu Thr Leu Ser Lys Ala Asp Tyr Glu Lys His
65                  70                  75                  80

Lys Val Tyr Ala Cys Glu Val Thr His Gln Gly Leu Ser Ser Pro Val
                85                  90                  95

Thr Lys Ser Phe Asn Arg Gly Glu Cys
            100                 105

<210> SEQ ID NO 296
<211> LENGTH: 104
<212> TYPE: PRT
<213> ORGANISM: Homo sapiens
<220> FEATURE:
<221> NAME/KEY: VARIANT
<222> LOCATION: (1)..(104)
<223> OTHER INFORMATION: Human LC Lambda constant Lambda constant

<400> SEQUENCE: 296

Pro Lys Ala Ala Pro Ser Val Thr Leu Phe Pro Pro Ser Ser Glu Glu
1               5                   10                  15

Leu Gln Ala Asn Lys Ala Thr Leu Val Cys Leu Ile Ser Asp Phe Tyr
            20                  25                  30

Pro Gly Ala Val Thr Val Ala Trp Lys Ala Asp Ser Ser Pro Val Lys
        35                  40                  45

Ala Gly Val Glu Thr Thr Thr Pro Ser Lys Gln Ser Asn Asn Lys Tyr
    50                  55                  60

Ala Ala Ser Ser Tyr Leu Ser Leu Thr Pro Glu Gln Trp Lys Ser His
65                  70                  75                  80

Arg Ser Tyr Ser Cys Gln Val Thr His Glu Gly Ser Thr Val Glu Lys
                85                  90                  95

Thr Val Val Pro Ala Glu Cys Ser
            100

```
<210> SEQ ID NO 297
<211> LENGTH: 330
<212> TYPE: PRT
<213> ORGANISM: Homo sapiens
<220> FEATURE:
<221> NAME/KEY: VARIANT
<222> LOCATION: (1)..(330)
<223> OTHER INFORMATION: Human IgG1 HC constant region Human HC constant
      region

<400> SEQUENCE: 297

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

-continued

<210> SEQ ID NO 298
<211> LENGTH: 8
<212> TYPE: PRT
<213> ORGANISM: Artificial Sequence
<220> FEATURE:
<223> OTHER INFORMATION: A/H3/HA0 consensus N-terminal

<400> SEQUENCE: 298

Asn Val Pro Glu Lys Gln Thr Arg
1               5

<210> SEQ ID NO 299
<211> LENGTH: 11
<212> TYPE: PRT
<213> ORGANISM: Artificial Sequence
<220> FEATURE:
<223> OTHER INFORMATION: A/H3/HA0 consensus C-terminal

<400> SEQUENCE: 299

Gly Ile Phe Gly Ala Ile Ala Gly Phe Ile Glu
1               5                   10

<210> SEQ ID NO 300
<211> LENGTH: 8
<212> TYPE: PRT
<213> ORGANISM: Artificial Sequence
<220> FEATURE:
<223> OTHER INFORMATION: A/H1/HA0 consensus N-terminal

<400> SEQUENCE: 300

Asn Ile Pro Ser Ile Gln Ser Arg
1               5

<210> SEQ ID NO 301
<211> LENGTH: 11
<212> TYPE: PRT
<213> ORGANISM: Artificial Sequence
<220> FEATURE:
<223> OTHER INFORMATION: A/H1/HA0 consensus C-terminal

<400> SEQUENCE: 301

Gly Leu Phe Gly Ala Ile Ala Gly Phe Ile Glu
1               5                   10

<210> SEQ ID NO 302
<211> LENGTH: 8
<212> TYPE: PRT
<213> ORGANISM: Artificial Sequence
<220> FEATURE:
<223> OTHER INFORMATION: B/HA0 consensus N-terminal

<400> SEQUENCE: 302

Pro Ala Lys Leu Leu Lys Glu Arg
1               5

<210> SEQ ID NO 303
<211> LENGTH: 11
<212> TYPE: PRT
<213> ORGANISM: Artificial Sequence
<220> FEATURE:
<223> OTHER INFORMATION: B/HA0 consensus C-terminal

<400> SEQUENCE: 303

Gly Phe Phe Gly Ala Ile Ala Gly Phe Leu Glu
1               5                   10

```
<210> SEQ ID NO 304
<211> LENGTH: 8
<212> TYPE: PRT
<213> ORGANISM: Artificial Sequence
<220> FEATURE:
<223> OTHER INFORMATION: 5A7 Epitope 1

<400> SEQUENCE: 304

Gly Asn Cys Pro Ile Trp Val Lys
1               5

<210> SEQ ID NO 305
<211> LENGTH: 5
<212> TYPE: PRT
<213> ORGANISM: Artificial Sequence
<220> FEATURE:
<223> OTHER INFORMATION: 5A7 Epitope 2

<400> SEQUENCE: 305

Leu Lys Leu Ala Asn
1               5

<210> SEQ ID NO 306
<211> LENGTH: 7
<212> TYPE: PRT
<213> ORGANISM: Artificial Sequence
<220> FEATURE:
<223> OTHER INFORMATION: 5A7 Epitope 3

<400> SEQUENCE: 306

Ile Glu Leu Ala Val Leu Leu
1               5

<210> SEQ ID NO 307
<211> LENGTH: 9
<212> TYPE: PRT
<213> ORGANISM: Artificial Sequence
<220> FEATURE:
<223> OTHER INFORMATION: TRL845 Epitope 1

<400> SEQUENCE: 307

Ser Gln Ile Glu Leu Ala Val Leu Leu
1               5

<210> SEQ ID NO 308
<211> LENGTH: 7
<212> TYPE: PRT
<213> ORGANISM: Artificial Sequence
<220> FEATURE:
<223> OTHER INFORMATION: TRL848 Epitope 1

<400> SEQUENCE: 308

Ser His Phe Ala Asn Leu Lys
1               5

<210> SEQ ID NO 309
<211> LENGTH: 13
<212> TYPE: PRT
<213> ORGANISM: Artificial Sequence
<220> FEATURE:
<223> OTHER INFORMATION: TRL848 Epitope 2

<400> SEQUENCE: 309

Pro Ile Trp Val Lys Thr Pro Leu Lys Leu Ala Asn Gly
1               5                   10
```

```
<210> SEQ ID NO 310
<211> LENGTH: 4
<212> TYPE: PRT
<213> ORGANISM: Artificial Sequence
<220> FEATURE:
<223> OTHER INFORMATION: TRL848 Epitope 3

<400> SEQUENCE: 310

Arg Leu Ser Gly
1

<210> SEQ ID NO 311
<211> LENGTH: 7
<212> TYPE: PRT
<213> ORGANISM: Artificial Sequence
<220> FEATURE:
<223> OTHER INFORMATION: TRL849 Epitope 1

<400> SEQUENCE: 311

Leu Asn Lys Ser Lys Pro Tyr
1               5

<210> SEQ ID NO 312
<211> LENGTH: 7
<212> TYPE: PRT
<213> ORGANISM: Artificial Sequence
<220> FEATURE:
<223> OTHER INFORMATION: TRL849 Epitope 2

<400> SEQUENCE: 312

Lys Leu Ala Asn Thr Gly Thr
1               5

<210> SEQ ID NO 313
<211> LENGTH: 6
<212> TYPE: PRT
<213> ORGANISM: Artificial Sequence
<220> FEATURE:
<223> OTHER INFORMATION: TRL849 Epitope 3

<400> SEQUENCE: 313

Met Ile Ala Gly Trp His
1               5

<210> SEQ ID NO 314
<211> LENGTH: 7
<212> TYPE: PRT
<213> ORGANISM: Artificial Sequence
<220> FEATURE:
<223> OTHER INFORMATION: TRL854 Epitope 1

<400> SEQUENCE: 314

Ile Glu Leu Ala Val Leu Leu
1               5
```